(12) United States Patent
Gray et al.

(10) Patent No.: US 12,157,741 B2
(45) Date of Patent: Dec. 3, 2024

(54) MACROCYCLIC INHIBITORS OF DYRK1A

(71) Applicants: DANA-FARBER CANCER INSTITUTE, INC., Boston, MA (US); VORONOI INC, Incheon (KR)

(72) Inventors: Nathanael S. Gray, Boston, MA (US); John M. Hatcher, Boston, MA (US); Hwangeun Choi, Seoul (KR)

(73) Assignees: Dana-Farber Cancer Institute, Inc., Boston, MA (US); Voronoi Inc., Incheon (KR)

( * ) Notice: Subject to any disclaimer, the term of this patent is extended or adjusted under 35 U.S.C. 154(b) by 753 days.

(21) Appl. No.: 17/293,292

(22) PCT Filed: Nov. 19, 2019

(86) PCT No.: PCT/US2019/062150
§ 371 (c)(1),
(2) Date: May 12, 2021

(87) PCT Pub. No.: WO2020/106685
PCT Pub. Date: May 28, 2020

(65) Prior Publication Data
US 2022/0112201 A1    Apr. 14, 2022

Related U.S. Application Data

(60) Provisional application No. 62/769,179, filed on Nov. 19, 2018, provisional application No. 62/902,021, filed on Sep. 18, 2019.

(51) Int. Cl.
*C07D 487/22* (2006.01)
*C07D 471/22* (2006.01)

(52) U.S. Cl.
CPC ........ *C07D 487/22* (2013.01); *C07D 471/22* (2013.01)

(58) Field of Classification Search
CPC ............................ C07D 487/22; C07D 471/22
See application file for complete search history.

(56) References Cited

U.S. PATENT DOCUMENTS

| 2015/0183781 A1* | 7/2015 | Gummadi | C07D 471/04 546/113 |
| 2017/0204116 A1 | 7/2017 | Gray et al. | |
| 2017/0334929 A1* | 11/2017 | Cui | C07D 498/18 |

FOREIGN PATENT DOCUMENTS

WO      2017040993 A1    3/2017

OTHER PUBLICATIONS

Neumann, Fernanda, et al., "DYRK1A Inhibition and Cognitive Rescue in a Down Syndrome Mouse Model are Induced by New Fluoro-DANDY Derivatives", Scientific Reports, 2018, vol. 8; pp. 1-12.

* cited by examiner

*Primary Examiner* — Clinton A Brooks
*Assistant Examiner* — Josmalen M. Ramos-Lewis
(74) *Attorney, Agent, or Firm* — ArentFox Schiff LLP; Daniel W. Clarke; Shawn P. Foley

(57) ABSTRACT

Disclosed are macrocyclic compounds that possess inhibitory activity against DYRK, TRK, TLK, and/or RET. Also disclosed are pharmaceutical compositions containing the compounds, methods of making the compounds, and methods of using the compounds to treat diseases and disorders that are characterized or mediated by aberrant DYRK, TRK, TLK, and/or RET activity such as cancer, neurodegenerative disorders and genetic disorders.

33 Claims, No Drawings

MACROCYCLIC INHIBITORS OF DYRK1A

RELATED APPLICATIONS

This application claims the benefit of priority under 35 U.S.C. § 119(e) to U.S. Provisional Application No. 62/769,179, filed Nov. 19, 2018 and U.S. Provisional Application No. 62/902,021, filed Sep. 18, 2019, each of which are incorporated herein by reference in their entireties.

BACKGROUND OF THE INVENTION

Kinases catalyze the transfer of a phosphate group to a protein substrate, which alters the function of the protein. These enzymes play a critical and complex role in regulating cellular signal transduction for cell growth, proliferation, and survival (Zhou et al., Methods in Enzymology 504:317-340 (2012)). Inhibition of these signaling pathways presents promising opportunities for targeting cancer therapies and neurodegenerative diseases (Giamas et al., Pharmacogenomics 8(8):1005-1016 (2007) and Wagey et al., Prog. Drug Res. 51:133-183 (1998)).

Dual-specificity tyrosine phosphorylation-regulated kinases (DYRKs) are a family of eukaryotic kinases that are related to cyclin-dependent kinases (CDKs), mitogen-activated protein kinases (MAPKs), glycogen synthase kinases (GSKs), and CDK-like kinases (CLKs), collectively known as the CMGC group. The DYRK family consists of subtypes 1A, 1B, 2, 3, and 4, of which only DYRKIA is located in the Down Syndrome Critical Region (DSCR) encoded by chromosome 21 (Dierssen, Nature Reviews Neuroscience 13(12):844-858 (2012)). DYRKIA is responsible for catalyzing the phosphorylation of serine and threonine residues in its substrates as well as the autophosphorylation on tyrosine residues in the positive feedback loop (Ryoo et al., Journal of Neurochemistry 104(5):1333-1344 (2008)). Both of these functions play a significant role in the mechanism of neuronal pathology (Ferrer, et al., Neurobiology of Disease 20(2):392-400 (2005)).

Increased levels of DYRK1A are present in the brain of patients with Alzheimer's disease ((AD) which is characterized by neuronal death and loss of gray matter in the frontal cortex and hippocampus) and in other neurodegenerative diseases, including Parkinson's disease, Huntington's disease, and Pick's syndrome (Ferrer, et al., Neurobiology of Disease 20(2):392-400 (2005)). Due to its location in the DSCR, overexpression of DYRKIA likely contributes to the neurological abnormalities associated with Down syndrome (Dierssen, Nature Reviews Neuroscience 13(12): 844-858 (2012)). With the central role that DYRKIA plays in the development and progression of AD and other neurodegenerative disorders, targeting its inhibition offers a novel approach as a method of treatment.

Both DYRK1A and DYRK1B have been reported to play significant roles in cancer. Recent studies show that DYRK1A can induce clonogenic and pro-survival properties in particular types of cells or in particular developmental conditions. For instance, harmine can block cell growth and tumorigenesis in myeloid leukemias and gliomas (Fernandez-Martinez, et al., Molecular & Cellular Oncology 2(1): 1-11 (2015)). In addition, DYRK1B is a potential oncogenic driver because it has been found to be over-expressed in certain cancers such as breast cancer (Chen et al., Human Pathology 66:48-58 (2017)).

SUMMARY OF THE INVENTION

A first aspect of the present invention is directed to a compound having a structure represented by formula (I):

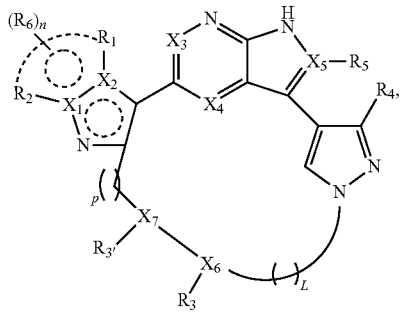

wherein $X_1$, $X_2$, $X_3$, $X_4$, $X_5$, $X_6$, $X_7$, $R_1$, $R_2$, $R_3$, $R_{3'}$, $R_4$, $R_5$, $R_6$, n, p, and L are as defined herein, or a pharmaceutically acceptable salt or stereoisomer thereof.

Another aspect of the present invention is directed to a pharmaceutical composition that includes a therapeutically effective amount of a compound of formula (I) or a pharmaceutically acceptable salt or stereoisomer thereof, and a pharmaceutically acceptable carrier.

A further aspect of the present invention is directed to a method of treating a disease or disorder involving aberrant DYRK (e.g., DYRK1A and 1), tyrosine receptor kinase (TRK), tousled-like kinase (TLK), or receptor tyrosine kinase (RET) activity, that entails administration of a therapeutically effective amount of a compound of formula (I) or a pharmaceutically acceptable salt or stereoisomer thereof, to a subject in need thereof.

As demonstrated in the working examples, compounds of the present invention are potent inhibitors of DYRK1A and DYRK1B. Compounds of the present invention may also inhibit TRK, TLK, and/or RET.

DETAILED DESCRIPTION OF THE INVENTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a" "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2%, or 1%) of the particular value modified by the term "about."

The transitional term "comprising," which is synonymous with "including," "containing," or "characterized by," is inclusive or open-ended and does not exclude additional, unrecited elements, or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of a molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group, "aralkoxy" wherein the oxygen atom is the point of attachment, or "aroxyalkyl" wherein the point of attachment is on the alkyl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—R$^c$-heterocyclyl where R$^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —R$^c$-heteroaryl, wherein R$^c$ is an alkylene chain as defined above. The term heteroaryl also embraces heteroaralkoxy (or heteroarylalkoxy) groups which as used herein refer to a group bonded through an oxygen atom of the formula —O—R$^c$-heteroaryl, where R$^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), haloalkyl (e.g., CF$_3$), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, sulfonyl, substituted sulfonyl, urea, substituted urea, carbamate, substituted carbamate, amino acid, and peptide groups.

Broadly, the compounds of the invention have a structure represented by formula (I):

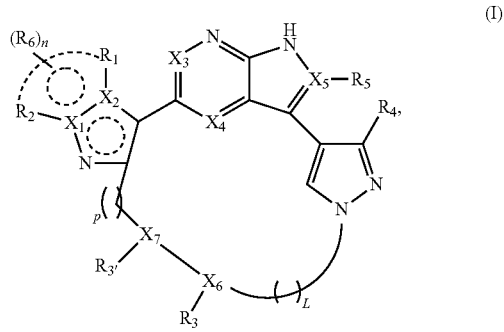

(I)

wherein:
X$_1$ represents C or N;
X$_2$ represents C or N;
provided that only one of X$_1$ and X$_2$ represents N;
X$_3$ represents C or N;
X$_4$ represents C or N;
provided that only one of X$_3$ and X$_4$ represents N;
X$_5$ represents C or N, provided that if X$_5$ represent N, R$_5$ is absent, X$_3$ represents C and X$_4$ represents C or N;
R$_1$ represents CH, C1-C3 alkyl, haloalkyl, optionally substituted alkoxy, halo, or cyano;
R$_2$ represents N, CH, optionally substituted C1-C3 alkyl, haloalkyl, or optionally substituted heterocyclyl;
or when X$_1$ represents C, X$_2$ represents N, and R$_2$ represents CH or N, R$_1$ and R$_2$ together with the atoms to which they are bound form a pyridine or pyrimidine ring that is optionally substituted with R$_6$ which represents C1-C3 alkyl, optionally substituted C1-C3 alkoxy, halo, or cyano, and wherein n is 0 or 1;
R$_3$ represents H, =O, optionally substituted C1-C3 alkyl, or alkylamine;

$R_{3'}$ represents H, =O, optionally substituted C1-C3 alkyl, or alkylamine;

$R_4$ represents H, is optionally substituted C1-C3 alkyl, optionally substituted C1-C3 alkoxy, halo, haloalkyl, or cyano;

$R_5$ is absent or represents H, optionally substituted C1-C3 alkyl, halo, or cyano;

L represents C2-C5 alkylene, optionally interrupted by —O—, and which is optionally substituted with hydroxyl, alkoxy, or optionally substituted amino;

$X_6$ represents C or N, provided that if $R_3$ represents =O, $X_6$ is C, and if $R_3$ represents H, optionally substituted C1-C3 alkyl, or alkylamine, $X_6$ is N;

$X_7$ represents C or N, provided that if $R_{3'}$ represents =O, $X_7$ is C, and if $R_{3'}$ represents H, optionally substituted C1-C3 alkyl, or alkylamine, $X_7$ is N;

provided that only one of $X_6$ and $X_7$ represents N; and p is 0 or 1; or a pharmaceutically acceptable salt or stereoisomer thereof.

In some embodiments, p is 1, $X_6$ is C, $R_3$ is =O, and $X_7$ is N, and the compounds of the invention have a structure represented by formula Ia:

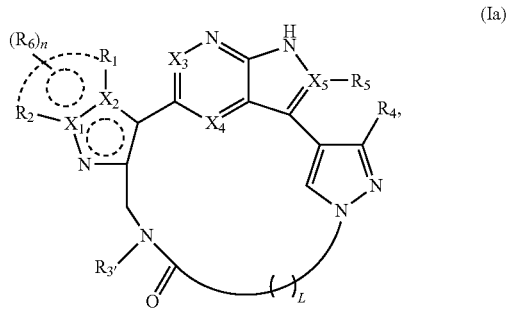

(Ia)

or a pharmaceutically acceptable salt or stereoisomer thereof.

In some embodiments, p is 0, $X_6$ is C, $R_3$ is =O, and $X_7$ is N and the compounds of the invention have a structure represented by formula Ib:

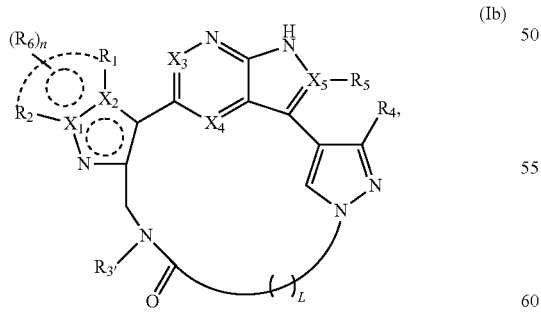

(Ib)

or a pharmaceutically acceptable salt or stereoisomer thereof.

In some embodiments, p is 0 and $X_6$ is N, $X_7$ is C, and $R_3$ is =O and the compounds of the invention have a structure represented by formula Ic:

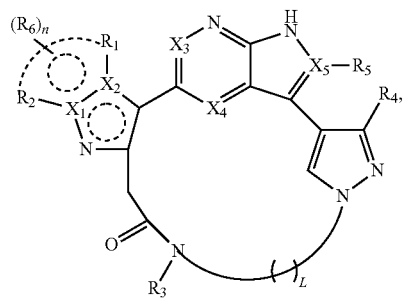

(Ic)

or a pharmaceutically acceptable salt or stereoisomer thereof.

In some embodiments, $X_3$, $X_4$, and $X_5$ each represent C and the compounds of the invention have a structure represented by formula Ia1:

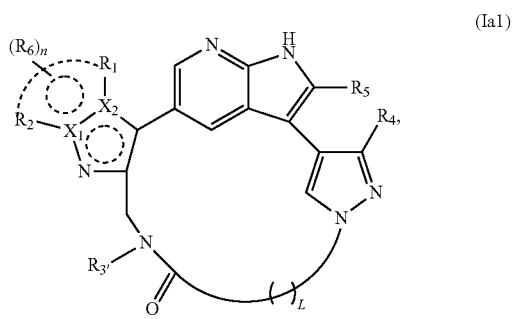

(Ia1)

or a pharmaceutically acceptable salt or stereoisomer thereof.

In certain embodiments, $X_1$ is N and $X_2$ is C, and the compounds of the invention have a structure represented by formula Ia1a:

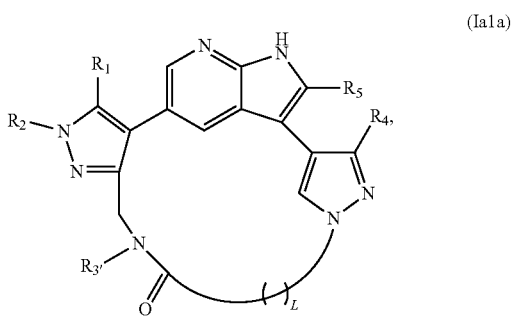

(Ia1a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ia1b:

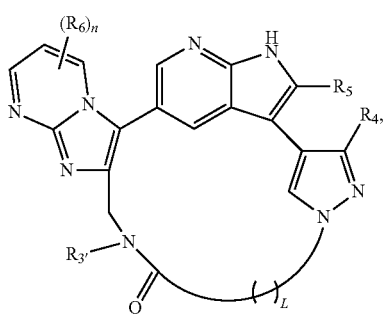

(Ia1b)

or a pharmaceutically acceptable salt or stereoisomer thereof.

In certain embodiments, $X_1$ is C, $X_2$ is N and $R_1$ and $R_2$ together with the atoms to which they are bound form a pyridine ring that is optionally substituted with $R_6$, and the compounds of the invention may be represented by the structure of formula Ia1c:

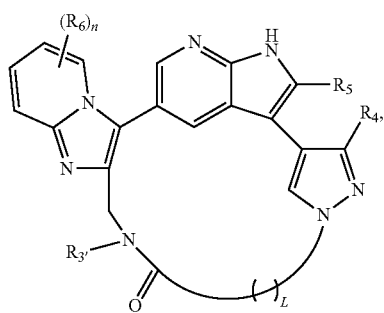

(Ia1c)

or a pharmaceutically acceptable salt or stereoisomer thereof.

In some embodiments, $X_4$ and $X_5$ represent C, $X_3$ represents N, and the compounds of the invention have a structure represented by formula Ia2:

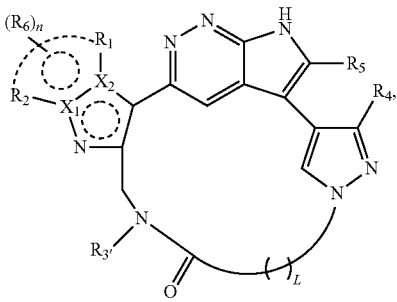

(Ia2)

or a pharmaceutically acceptable salt or stereoisomer thereof.

In certain embodiments, $X_1$ is N and $X_2$ is C, and the compounds of the invention have a structure represented by formula Ia2a:

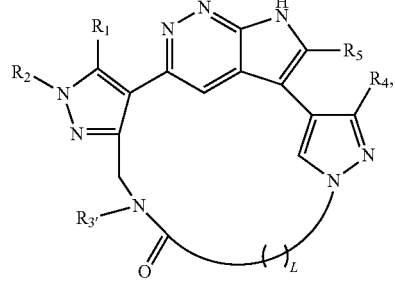

(Ia2a)

or a pharmaceutically acceptable salt or stereoisomer thereof.

In certain embodiments, $X_1$ is C, $X_2$ is N and $R_1$ and $R_2$ together with the atoms to which they are bound form a pyrimidine ring that is optionally substituted with $R_6$, and the compounds of the invention may be represented by the structure of formula Ia2b:

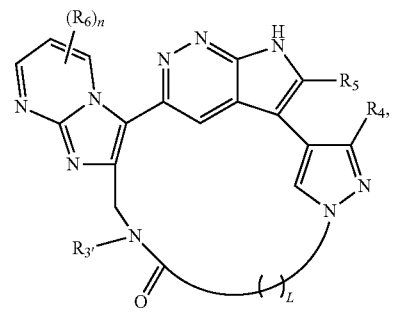

(Ia2b)

or a pharmaceutically acceptable salt or stereoisomer thereof. Same here

In certain embodiments, $X_1$ is C, $X_2$ is N and $R_1$ and $R_2$ together with the atoms to which they are bound form a pyridine ring that is optionally substituted with $R_6$, and the compounds of the invention may be represented by the structure of formula Ia2c:

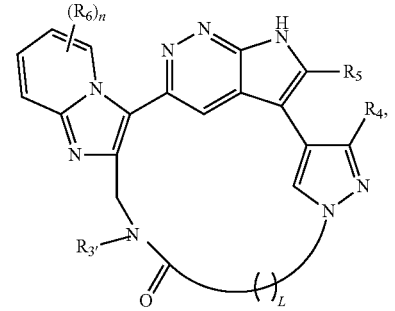

(Ia2c)

or a pharmaceutically acceptable salt or stereoisomer thereof.

In some embodiments, $X_3$ and $X_5$ represent C, $X_4$ represents N, and the compounds of the invention have a structure represented by formula Ia3:

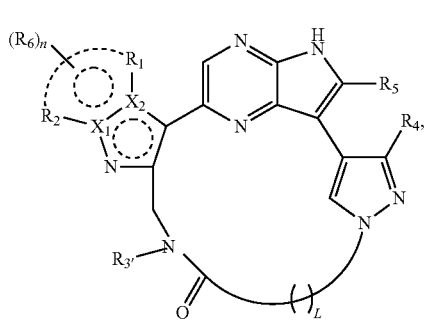

(Ia3)

or a pharmaceutically acceptable salt or stereoisomer thereof.

In certain embodiments, $X_1$ is N and $X_2$ is C, and the compounds of the invention have a structure represented by formula Ia3a:

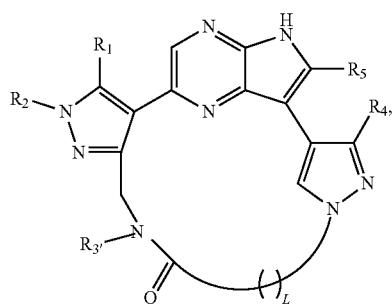

(Ia3a)

or a pharmaceutically acceptable salt or stereoisomer thereof.

In certain embodiments, $X_1$ is C, $X_2$ is N and $R_1$ and $R_2$ together with the atoms to which they are bound form a pyrimidine ring that is optionally substituted with $R_6$, and the compounds of the invention may be represented by the structure of formula Ia3b:

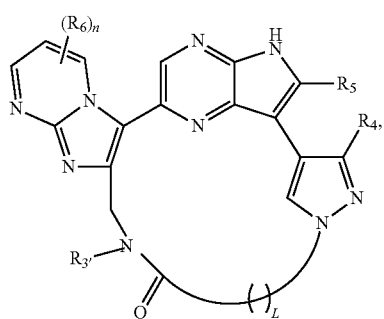

(Ia3b)

or a pharmaceutically acceptable salt or stereoisomer thereof.

In certain embodiments, $X_1$ is C, $X_2$ is N and $R_1$ and $R_2$ together with the atoms to which they are bound form a pyridine ring that is optionally substituted with $R_6$, and the compounds of the invention may be represented by the structure of formula Ia3c:

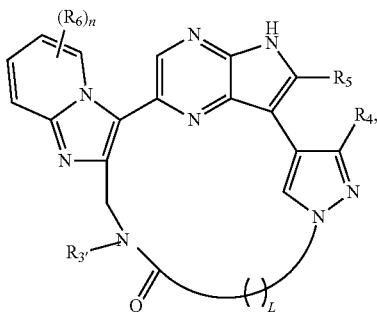

(Ia3c)

or a pharmaceutically acceptable salt or stereoisomer thereof.

In some embodiments, $X_3$ and $X_4$ represent C, $X_5$ represents N, and the compounds of the invention have a structure represented by formula Ia4:

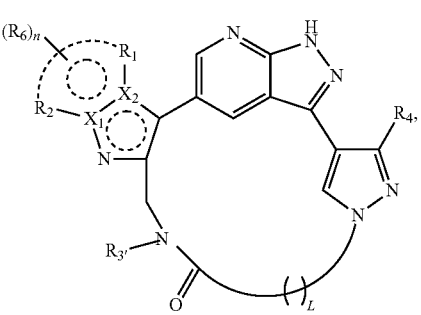

(Ia4)

or a pharmaceutically acceptable salt or stereoisomer thereof.

In certain embodiments, $X_1$ is N and $X_2$ is C, and the compounds of the invention have a structure represented by formula Ia4a:

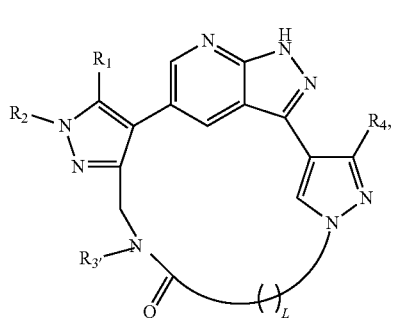

(Ia4a)

or a pharmaceutically acceptable salt or stereoisomer thereof.

In certain embodiments, $X_1$ is C, $X_2$ is N and $R_1$ and $R_2$ together with the atoms to which they are bound form a pyrimidine ring that is optionally substituted with $R_6$, and the compounds of the invention may be represented by the structure of formula Ia4b:

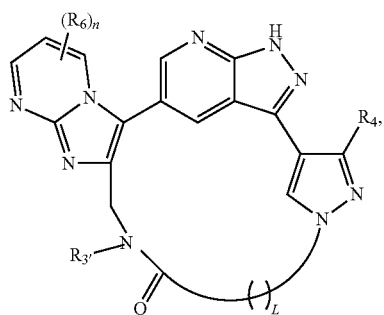

(Ia4b)

or a pharmaceutically acceptable salt or stereoisomer thereof.

In certain embodiments, $X_1$ is C, $X_2$ is N and $R_1$ and $R_2$ together with the atoms to which they are bound form a pyridine ring that is optionally substituted with $R_6$, and the compounds of the invention may be represented by the structure of formula Ia4c:

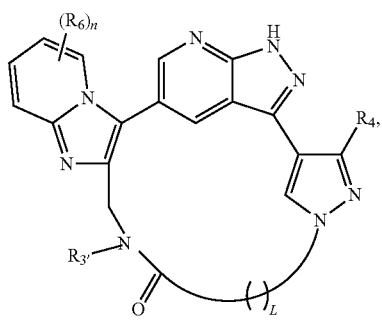

(Ia4c)

or a pharmaceutically acceptable salt or stereoisomer thereof.

In some embodiments, $X_3$ represents C, $X_4$ and $X_5$ represent N, and the compounds of the invention have a structure represented by formula Ia5:

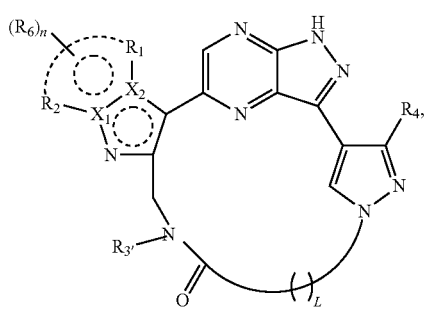

(Ia5)

or a pharmaceutically acceptable salt or stereoisomer thereof.

In certain embodiments, $X_1$ is N and $X_2$ is C, and the compounds of the invention have a structure represented by formula Ia5a:

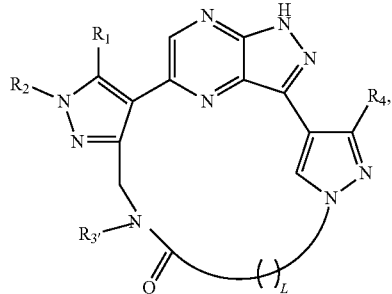

(Ia5a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ia5b:

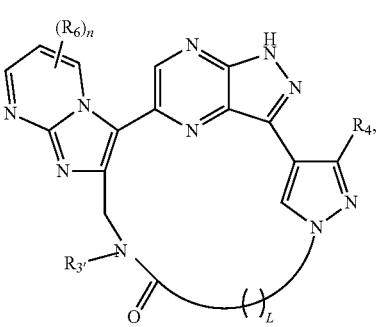

(Ia5b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ia5c:

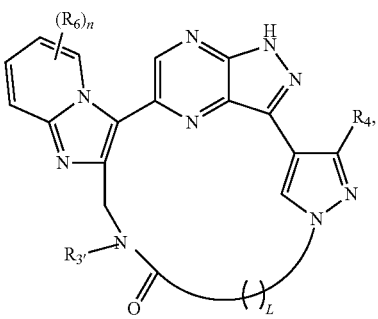

(Ia5c)

or a pharmaceutically acceptable salt or stereoisomer thereof.

In some embodiments, $X_3$, $X_4$, and $X_5$ each represent C and the compounds of the invention have a structure represented by formula Ib1:

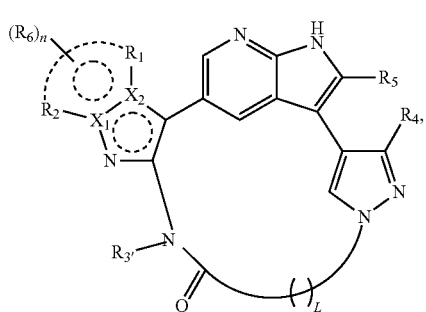

(Ib1)

or a pharmaceutically acceptable salt or stereoisomer thereof.

In certain embodiments, $X_1$ is N and $X_2$ is C, and the compounds of the invention have a structure represented by formula Ib1a:

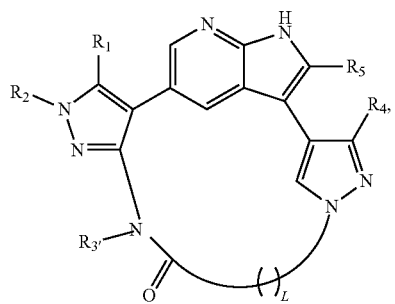

(Ib1a)

or a pharmaceutically acceptable salt or stereoisomer thereof.

In certain embodiments, $X_1$ is C, $X_2$ is N and $R_1$ and $R_2$ together with the atoms to which they are bound form a pyrimidine ring that is optionally substituted with $R_6$, and the compounds of the invention may be represented by the structure of formula Ib1b:

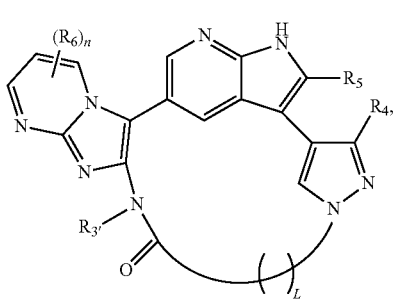

(Ib1b)

or a pharmaceutically acceptable salt or stereoisomer thereof.

In certain embodiments, $X_1$ is C, $X_2$ is N and $R_1$ and $R_2$ together with the atoms to which they are bound form a pyridine ring that is optionally substituted with $R_6$, and the compounds of the invention may be represented by the structure of formula Ib1c:

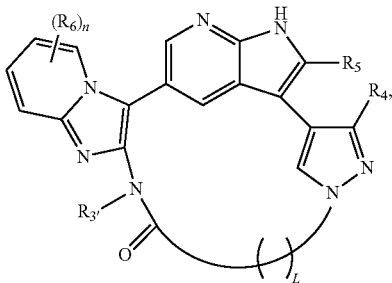

(Ib1c)

or a pharmaceutically acceptable salt or stereoisomer thereof.

In some embodiments, $X_4$ and $X_5$ each represent C, $X_3$ represents N, and the compounds of the invention have a structure represented by formula Ib2:

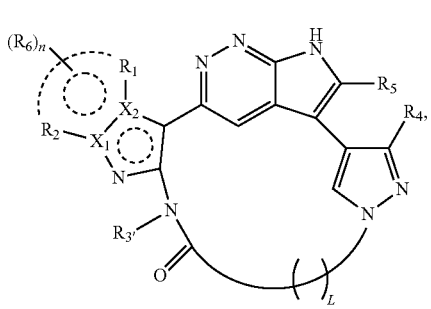

(Ib2)

or a pharmaceutically acceptable salt or stereoisomer thereof.

In certain embodiments, $X_1$ is N and $X_2$ is C, and the compounds of the invention have a structure represented by formula Ib2a:

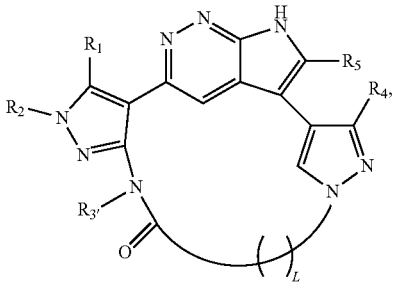

(Ib2a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ib2b:

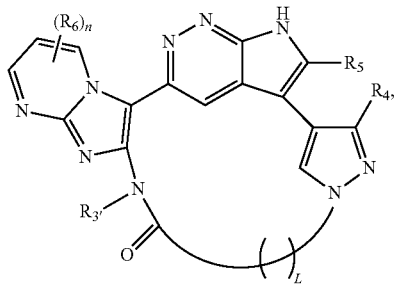

(Ib2b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ib2c:

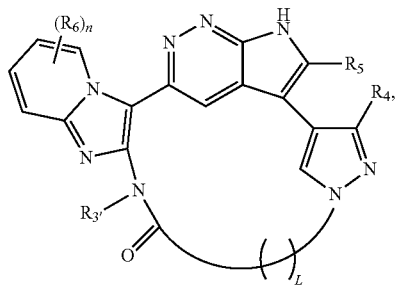

(Ib2c)

or a pharmaceutically acceptable salt or stereoisomer thereof.

In some embodiments, $X_3$ and $X_5$ represent C, $X_4$ represents N, and the compounds of the invention have a structure represented by formula Ib3:

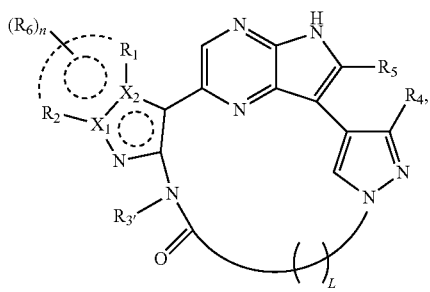

(Ib3)

or a pharmaceutically acceptable salt or stereoisomer thereof.

In certain embodiments, $X_1$ is N and $X_2$ is C, and the compounds of the invention have a structure represented by formula Ib3a:

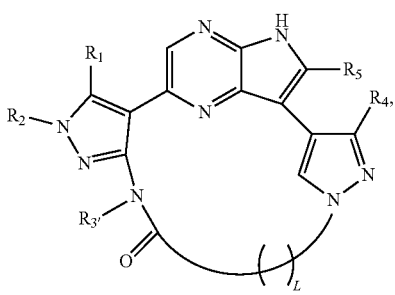

(Ib3a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ib3b:

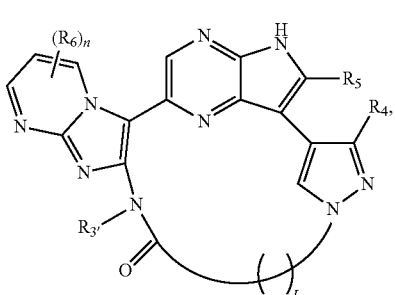

(Ib3b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ib3c:

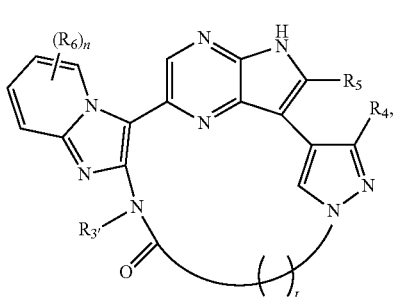

(Ib3c)

or a pharmaceutically acceptable salt or stereoisomer thereof.

In some embodiments, $X_3$ and $X_4$ represent C, $X_5$ represents N, and the compounds of the invention have a structure represented by formula Ib4:

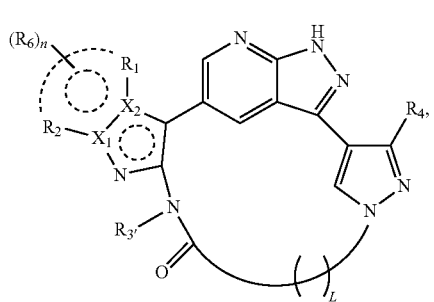

(Ib4)

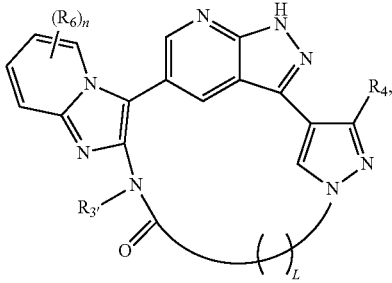

(Ib4c)

or a pharmaceutically acceptable salt or stereoisomer thereof.

In certain embodiments, $X_1$ is N and $X_2$ is C, and the compounds of the invention have a structure represented by formula Ib4a:

In some embodiments, $X_3$ represents C, $X_4$ and $X_5$ represent N, and the compounds of the invention have a structure represented by formula Ib5:

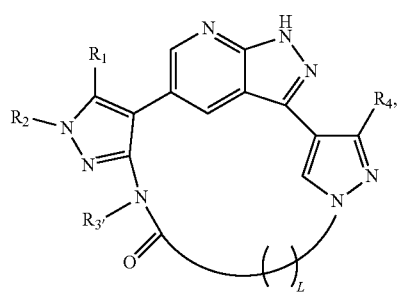

(Ib4a)


(Ib5)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ib4b:

or a pharmaceutically acceptable salt or stereoisomer thereof.

In certain embodiments, $X_1$ is N and $X_2$ is C, and the compounds of the invention have a structure represented by formula Ib5a:

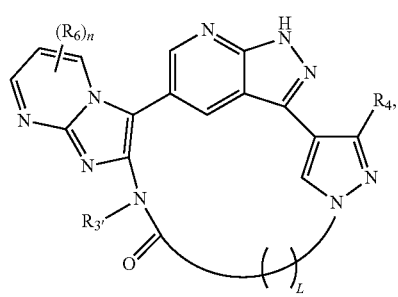

(Ib4b)

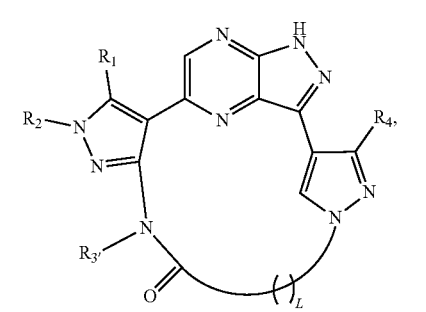

(Ib5a)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ib4c:

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ib5b:

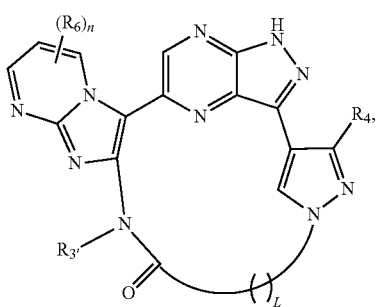

(Ib5b)

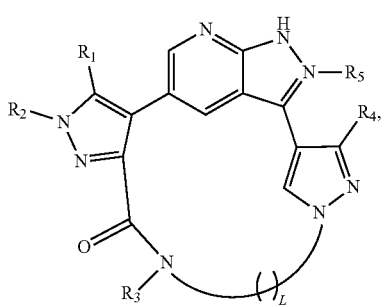

(Ic1a)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ib5c:

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ic1b:

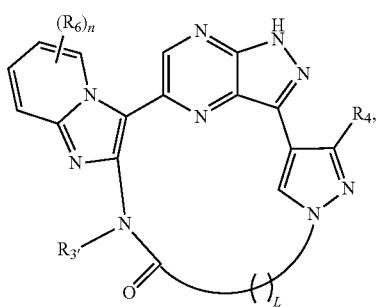

(Ib5c)

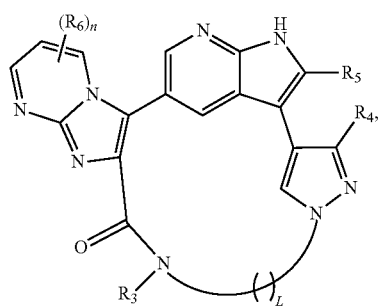

(Ic1b)

or a pharmaceutically acceptable salt or stereoisomer thereof.

In some embodiments, $X_3$, $X_4$, and $X_5$ each represent C and the compounds of the invention have a structure represented by formula Ic1:

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ic1c:

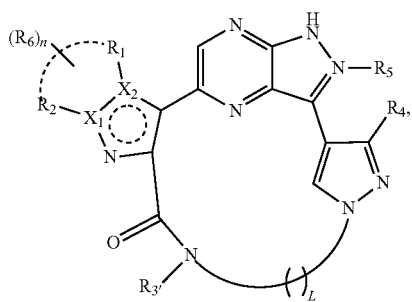

(Ic1)

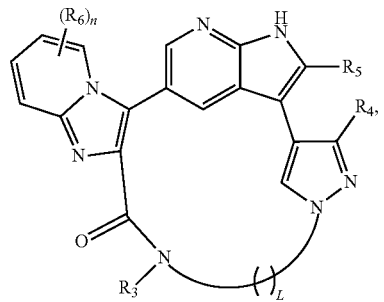

(Ic1c)

or a pharmaceutically acceptable salt or stereoisomer thereof.

In certain embodiments, $X_1$ is N and $X_2$ is C, and the compounds of the invention have a structure represented by formula Ic1a:

or a pharmaceutically acceptable salt or stereoisomer thereof.

In some embodiments, $X_4$ and $X_5$ represent C, $X_3$ represents N, and the compounds of the invention have a structure represented by formula Ic2:

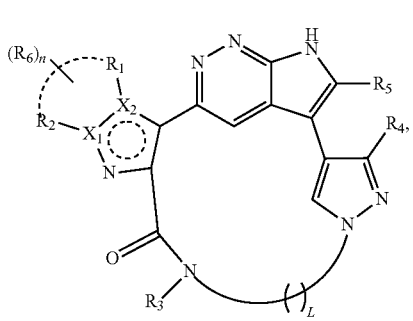
(Ic1)

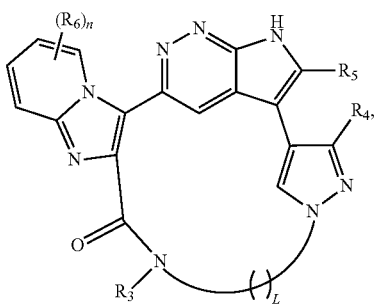
(Ic2c)

or a pharmaceutically acceptable salt or stereoisomer thereof.

In certain embodiments, $X_1$ is N and $X_2$ is C, and the compounds of the invention have a structure represented by formula Ic2a:

or a pharmaceutically acceptable salt or stereoisomer thereof.

In some embodiments, $X_3$ and $X_5$ each represent C, $X_4$ represents N, and the compounds of the invention have a structure represented by formula Ic3:

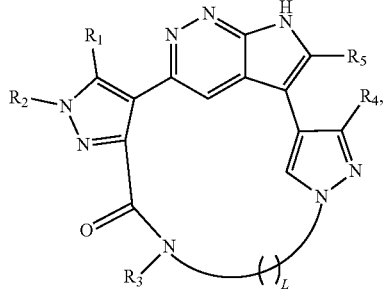
(Ic2a)

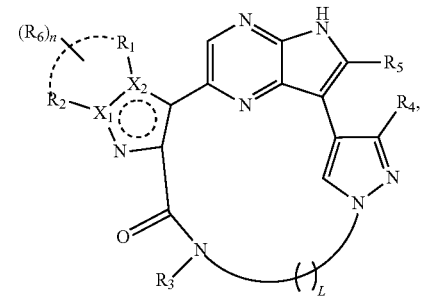

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ic2b:

or a pharmaceutically acceptable salt or stereoisomer thereof.

In certain embodiments, $X_1$ is N and $X_2$ is C, and the compounds of the invention have a structure represented by formula Ic3a:

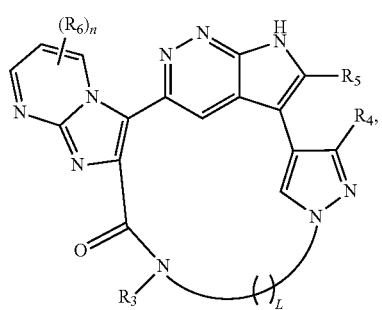
(Ic2b)

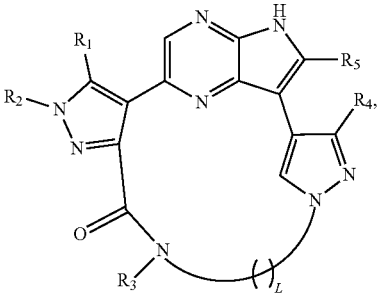
(Ic3a)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ic2c:

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ic3b:

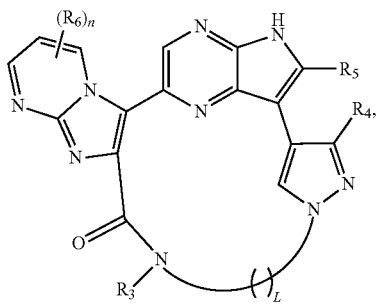
(Ic3b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and compounds of the invention may be represented by the structure of formula Ic3c:

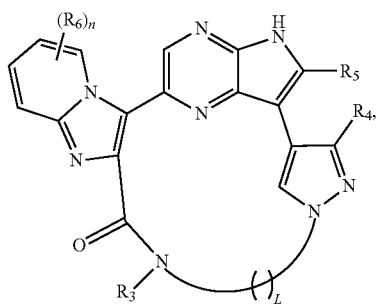
(Ic3c)

or a pharmaceutically acceptable salt or stereoisomer thereof.

In some embodiments, $X_3$ and $X_4$ represent C, $X_5$ represents N, and the compounds of the invention have a structure represented by formula Ic4:

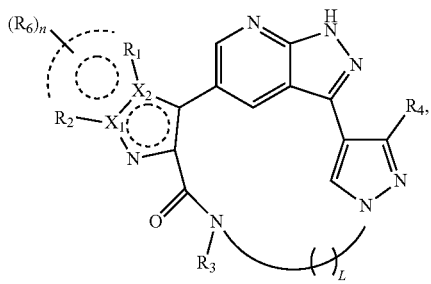
(Ic4)

or a pharmaceutically acceptable salt or stereoisomer thereof.

In certain embodiments, $X_1$ is N and $X_2$ is C, and the compounds of the invention have a structure represented by formula Ic4a:

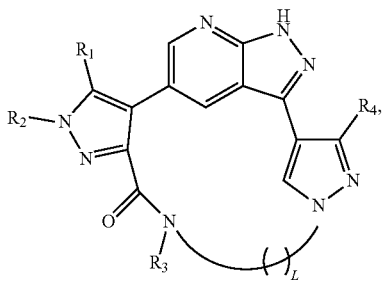
(Ic4a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ic4b:

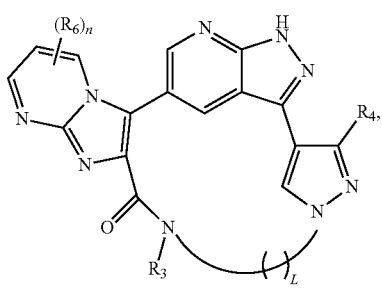
(Ic4b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ic4c:

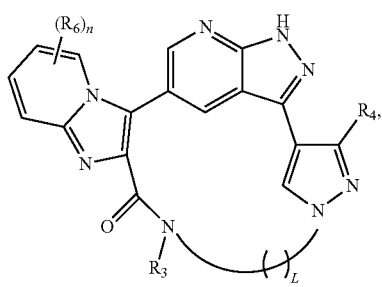
(Ic4c)

or a pharmaceutically acceptable salt or stereoisomer thereof.

In some embodiments, $X_3$ represents C, $X_4$ and $X_5$ represent N, and the compounds of the invention have a structure represented by formula Ic5:

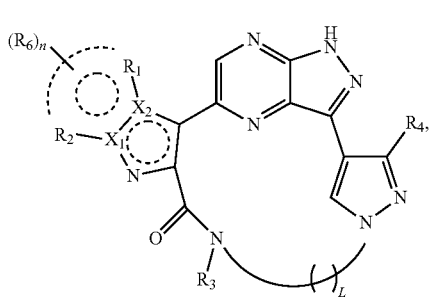

(Ic5)

or a pharmaceutically acceptable salt or stereoisomer thereof.

In certain embodiments, $X_1$ is N and $X_2$ is C, and the compounds of the invention have a structure represented by formula Ic5a:

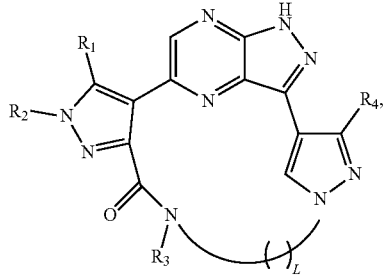

(Ic5a)

or a pharmaceutically acceptable salt or stereoisomer thereof.

In certain embodiments, $X_1$ is C, $X_2$ is N, $R_1$ and $R_2$ together with the atoms to which they are bound form a pyrimidine ring that is optionally substituted with $R_6$, and the compounds of the invention may be represented by the structure of formula Ic5b:

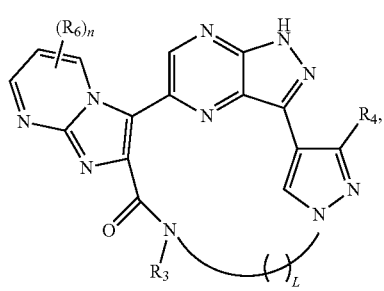

(Ic5b)

or a pharmaceutically acceptable salt or stereoisomer thereof.

In certain embodiments, $X_1$ is C, $X_2$ is N, $R_1$ and $R_2$ together with the atoms to which they are bound form a pyridine ring that is optionally substituted with $R_6$, and the compounds of the invention may be represented by the structure of formula Ic5c:

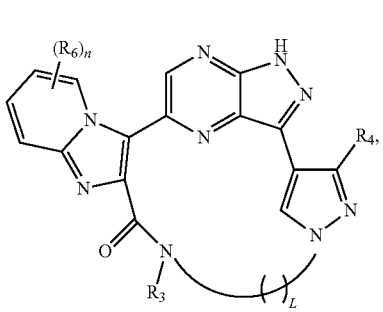

(Ic5c)

or a pharmaceutically acceptable salt or stereoisomer thereof.

In some embodiments with respect to compounds of formula I, $R_1$ is H, Me, Et, iPr, cyclopropyl, OMe, $OCF_3$, $OCHF_2$, Cl, or CN.

In some embodiments with respect to compounds of formula I, $R_2$ is Me, Et, iPr, cyclopropyl, $CHF_2$, $CH_2CF_3$, $CH_2CHF_2$, $CF_3$, $CH_2OH$, $CH_2OMe$, $CH_2CH_2OMe$, or

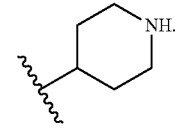

In some embodiments with respect to compounds of formula I, $R_3$ is H, Me, Et, iPr, cyclopropyl

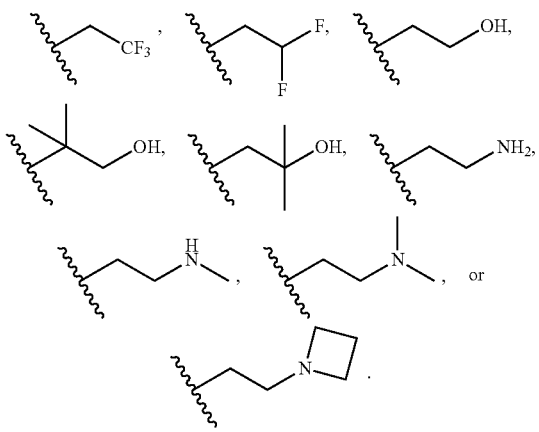

In some embodiments with respect to compounds of formula I, $R_3$ is H, Me, Et, iPr, cyclopropyl,

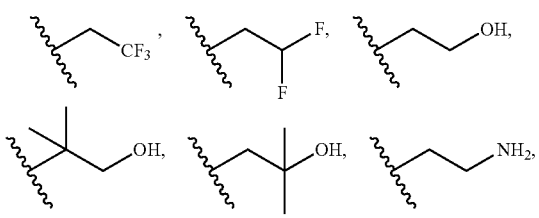

-continued

In some embodiments with respect to compounds of formula I, $R_4$ is H, Cl, $CF_3$, $CHF_2$, CN, Me, Et, cyclopropyl, OMe, OEt, OiPr, or O-cyclopropyl.

In some embodiments with respect to compounds of formula I, $R_5$ is H, Me, Et, iPr, cyclopropyl, Cl, CN, $CF_3$, or $CHF_2$.

In some embodiments with respect to compounds of formula I, $R_6$ is Me, Et, iPr, cyclopropyl, OMe, $OCF_3$, $OCHF_2$, Cl, or CN.

In some embodiments with respect to compounds of formula I, L is C2 alkylene, optionally interrupted by —O— and wherein the linker is optionally substituted with hydroxyl, alkoxy, or optionally substituted amino.

In some embodiments with respect to compounds of formula I, L is C3 alkylene, optionally interrupted by —O— and wherein the linker is optionally substituted with hydroxyl, alkoxy, or optionally substituted amino.

In some embodiments with respect to compounds of formula I, L is C4 alkylene, optionally interrupted by —O— and wherein the linker is optionally substituted with hydroxyl, alkoxy, or optionally substituted amino.

In some embodiments with respect to compounds of formula I, L is C5 alkylene, optionally interrupted by —O— and wherein the linker is optionally substituted with hydroxyl, alkoxy, or optionally substituted amino.

In certain embodiments with respect to compounds of formula I, L is

In certain embodiments, the compound is of formula Ia1a, wherein $R_1$ is H.

In certain embodiments, the compound is of formula Ia1a, wherein $R_1$ is CN.

In certain embodiments, the compound is of formula Ia1a, wherein $R_1$ is OMe.

In certain embodiments, the compound is of formula Ia1a, wherein $R_1$ is Me.

In certain embodiments, the compound is of formula Ia1a, where $R_2$ is Me.

In certain embodiments, the compound is of formula Ia1a, where $R_2$ is $CH_2CH_2OMe$.

In certain embodiments, the compound is of formula Ia1a, where $R_2$ is

In certain embodiments, the compound is of formula Ia1a, where $R_{3'}$ is H.

In certain embodiments, the compound is of formula Ia1a, where $R_{3'}$ is Me.

In certain embodiments, the compound is of formula Ia1a, where $R_{3'}$ is Et.

In certain embodiments, the compound is of formula Ia1a, where $R_{3'}$ is isopropyl.

In certain embodiments, the compound is of formula Ia1a, where $R_{3'}$ is cyclopropyl.

In certain embodiments, the compound is of formula Ia1a, wherein $R_4$ is H.

In certain embodiments, the compound is of formula Ia1a, wherein $R_4$ is $CF_3$.

In certain embodiments, the compound is of formula Ia1a, wherein $R_4$ is cyclopropyl.

In certain embodiments, the compound is of formula Ia1a, wherein $R_5$ is H.

In certain embodiments, the compound is of formula Ia1a, wherein $R_5$ is Me.

In certain embodiments, the compound is of formula Ia1a, wherein $R_5$ is $CF_3$.

In certain embodiments, the compound is of formula Ia3a, wherein $R_1$ is H.

In certain embodiments, the compound is of formula Ia3a, wherein $R_1$ is CN.

In certain embodiments, the compound is of formula Ia3a, where $R_2$ is Me.

In certain embodiments, the compound is of formula Ia3a, where $R_2$ is $CH_2CH_2OMe$.

In certain embodiments, the compound is of formula Ia3a, where $R_2$ is

In certain embodiments, the compound is of formula Ia3a, where $R_{3'}$ is Me.

In certain embodiments, the compound is of formula Ia3a, wherein $R_5$ is H.

In certain embodiments, the compound is of formula Ia3a, wherein $R_5$ is $CF_3$.

In certain embodiments, the compound is of formula Ib1a, wherein $R_1$ is H.

In certain embodiments, the compound is of formula Ib1a, wherein $R_1$ is CN.

In certain embodiments, the compound is of formula Ib1a, where $R_2$ is Me.

In certain embodiments, the compound is of formula Ib1a, where $R_2$ is $CH_2CH_2OMe$.

In certain embodiments, the compound is of formula Ib1a, where $R_2$ is

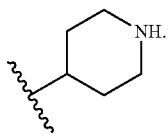 [SMILES: *C1CCNCC1]

In certain embodiments, the compound is of 2 formula Ib1a, where $R_{3'}$ is Me.

In certain embodiments, the compound is of formula Ib1a, wherein $R_5$ is H.

In certain embodiments, the compound is of formula Ib1a, wherein $R_5$ is $CF_3$.

In certain embodiments, the compound is of formula Ib1a, wherein $R_1$ is H.

In certain embodiments, the compound is of formula Ic1a, wherein $R_1$ is CN.

In certain embodiments, the compound is of formula Ic1a, where $R_2$ is Me.

In certain embodiments, the compound is of formula Ic1a, where $R_2$ is $CH_2CH_2OMe$.

In certain embodiments, the compound is of formula Ic1a, where $R_2$ is

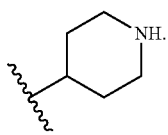 [SMILES: *C1CCNCC1]

In certain embodiments, the compound is of formula Ic1a, where $R_{3'}$ is Me.

In certain embodiments, the compound is of formula Ic1a, wherein $R_5$ is H.

In certain embodiments, the compound is of formula Ic1a, wherein $R_5$ is $CF_3$.

In some embodiments, the compound is selected from the group consisting of:

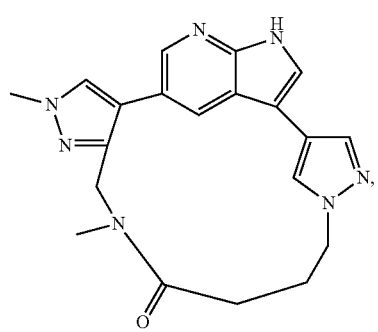

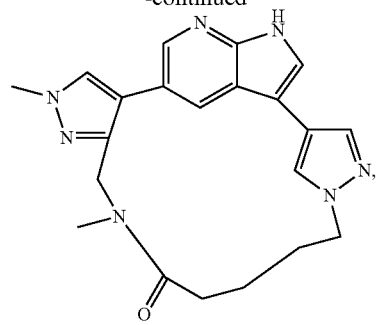

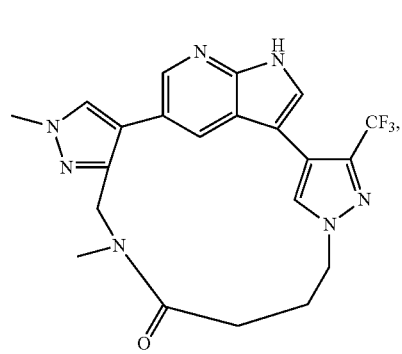

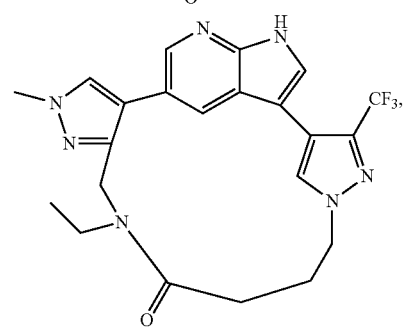

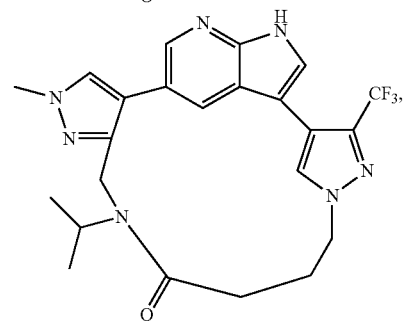

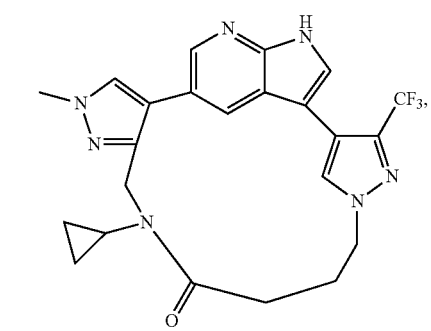

35
-continued
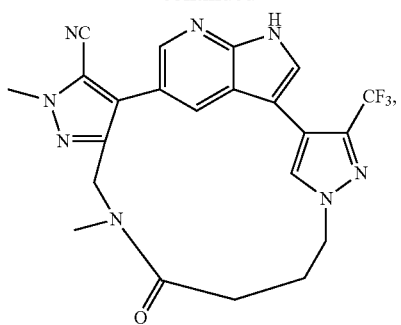
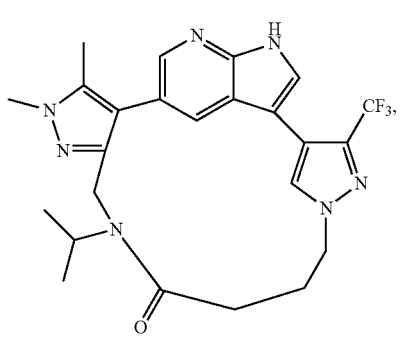
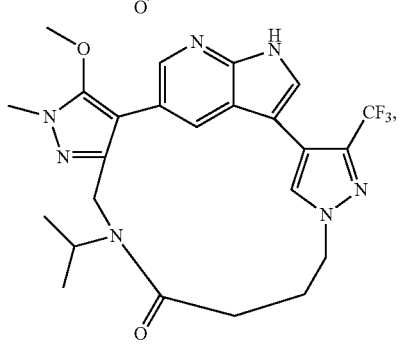
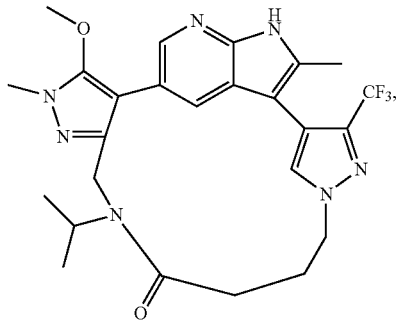
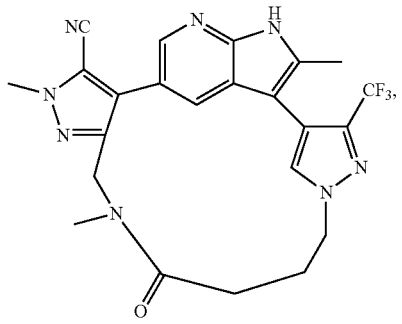
36
-continued
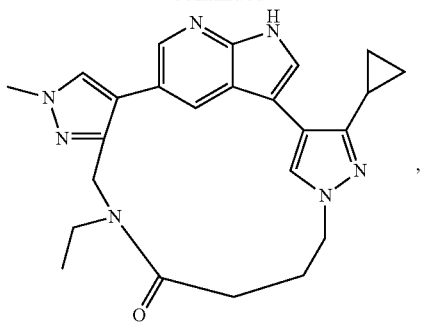
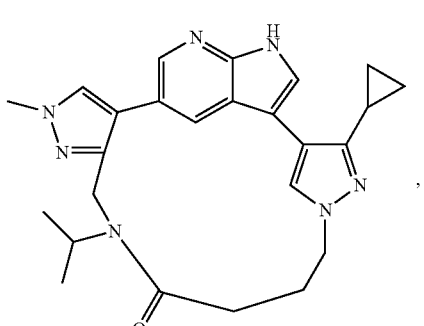
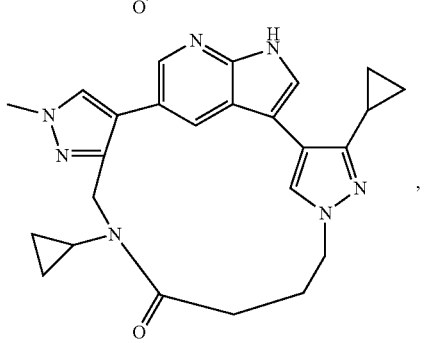
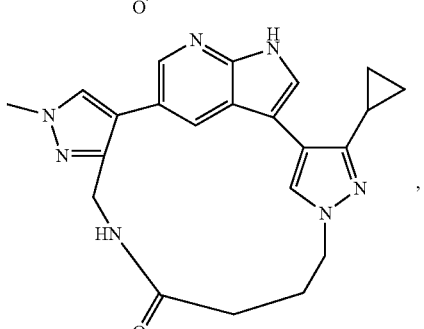
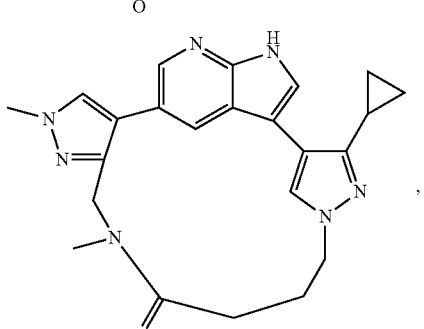

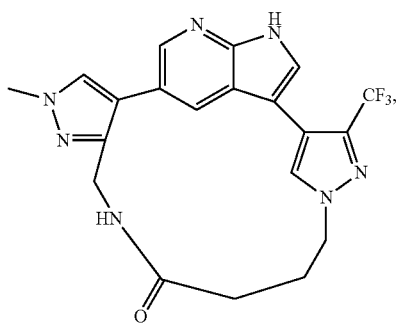
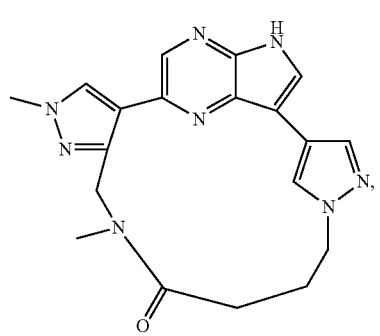
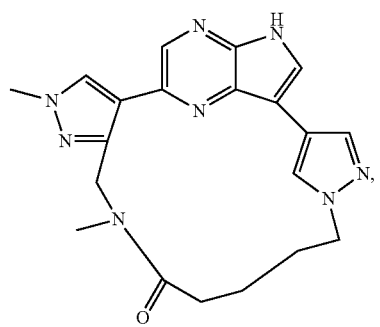
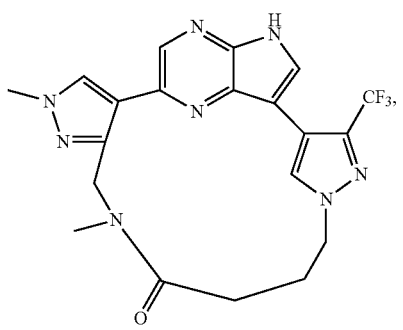
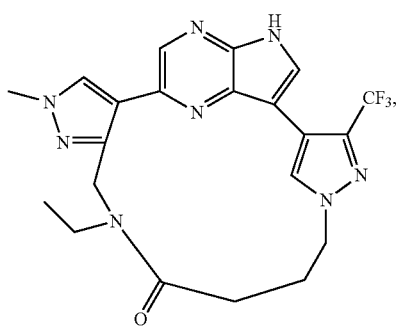
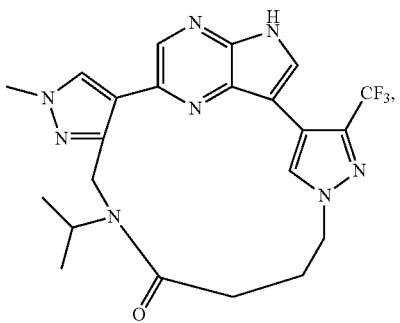
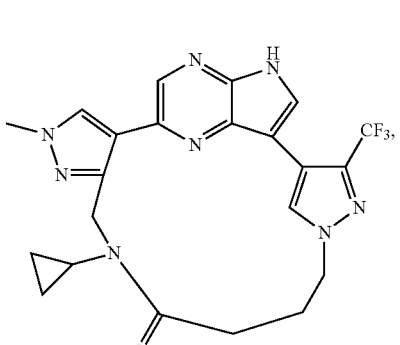
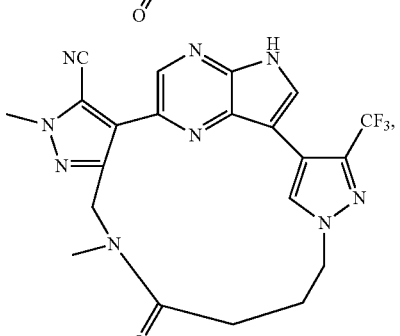
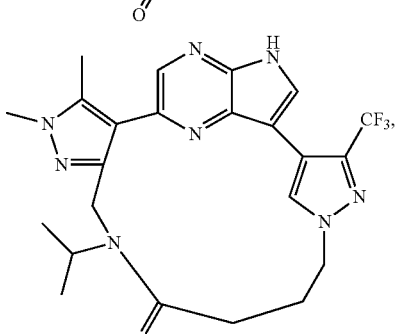
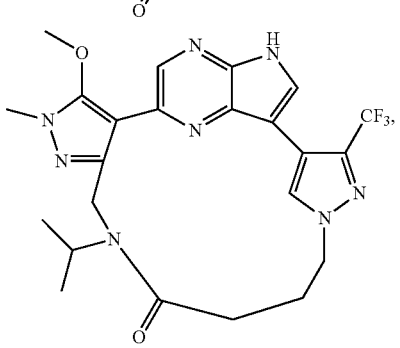

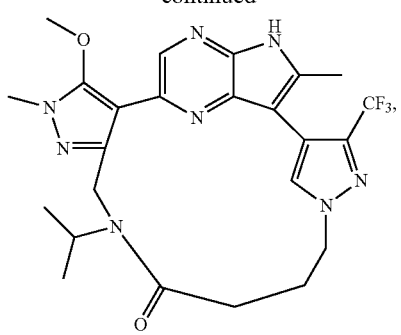
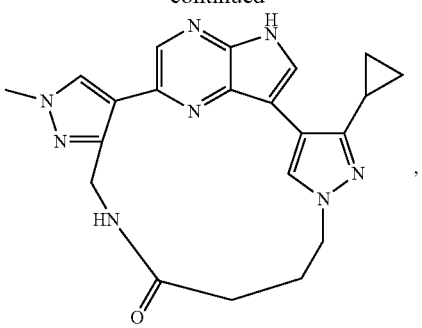
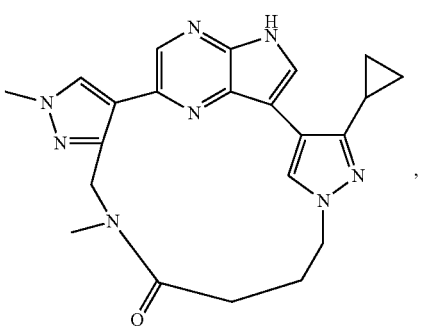
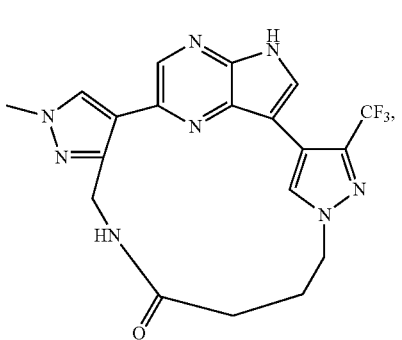
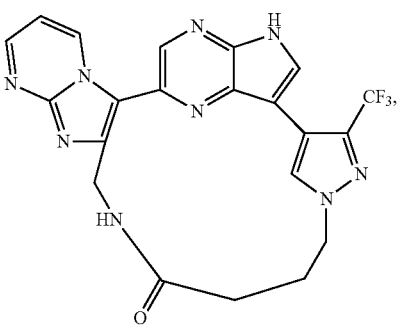
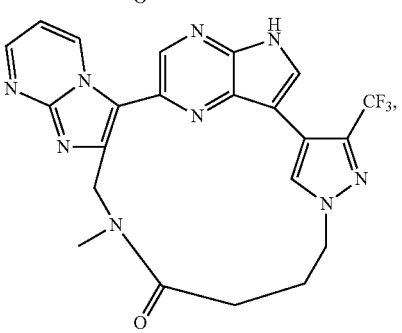

41
-continued
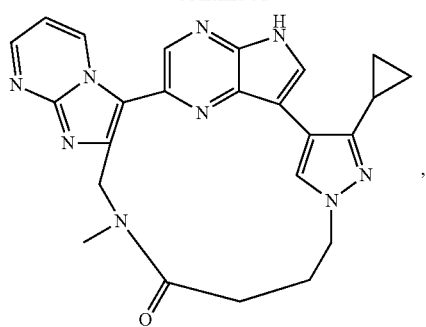
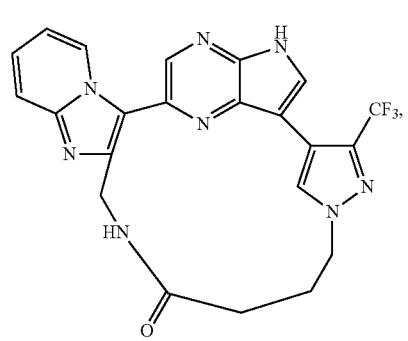
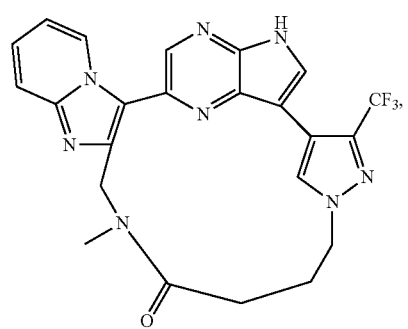
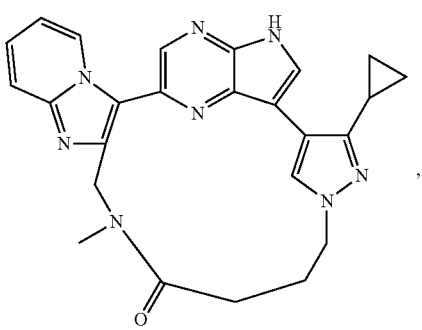
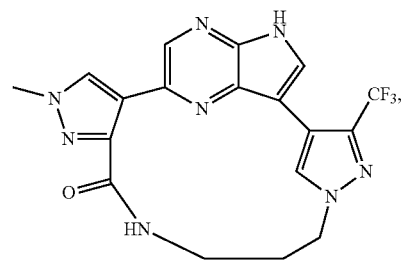
42
-continued
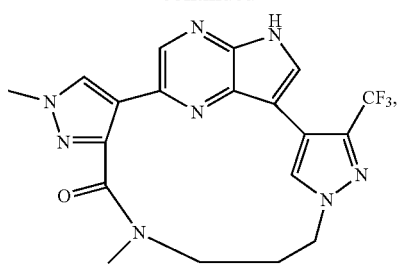
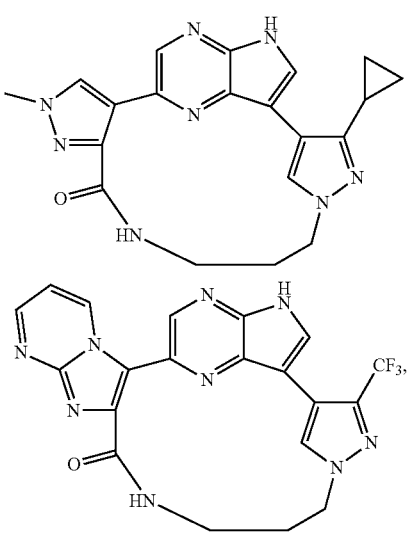
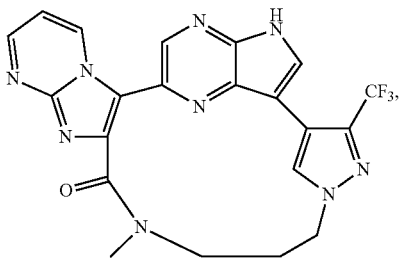
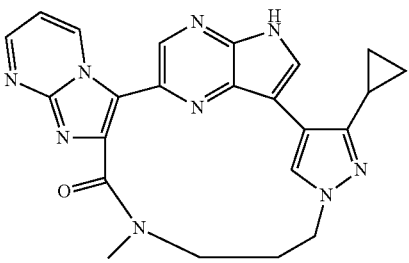
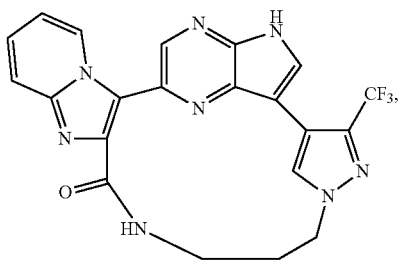

43
-continued
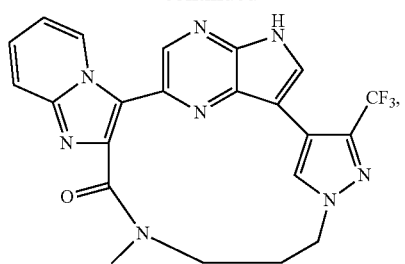
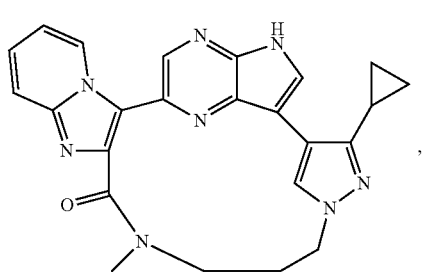
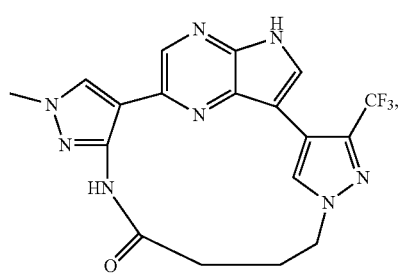,
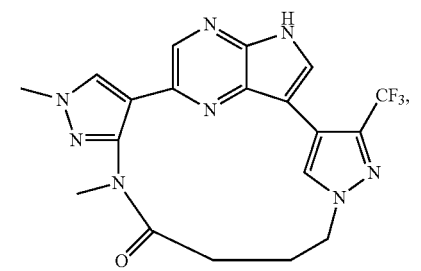
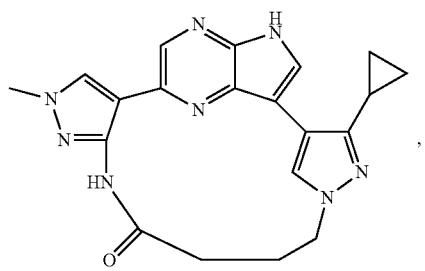,
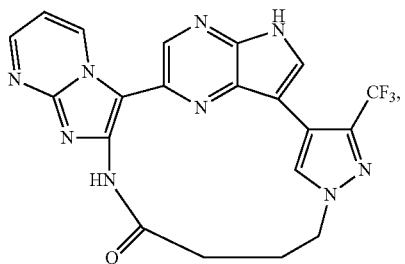
44
-continued
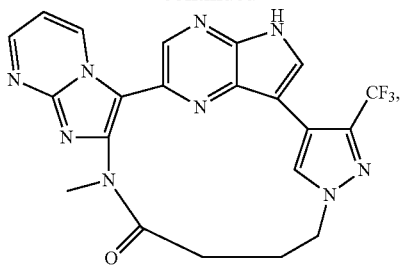
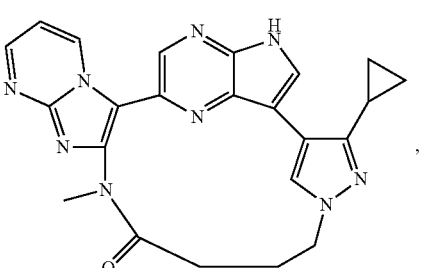,
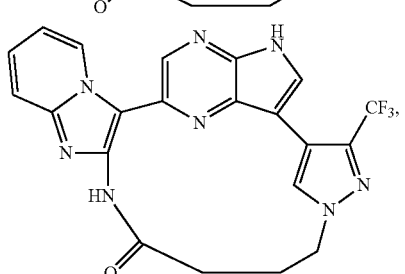
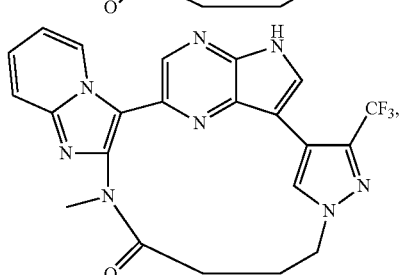
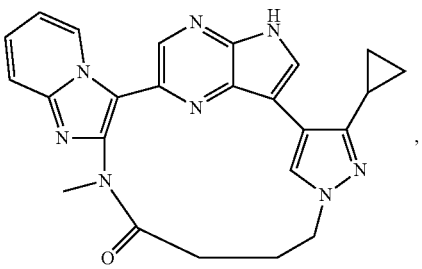,
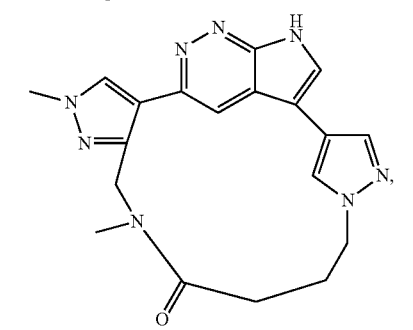

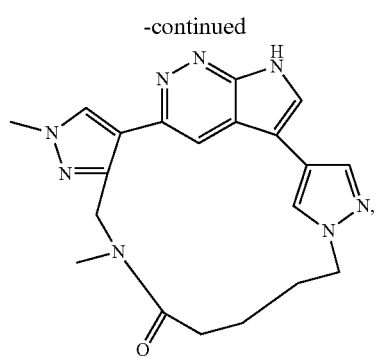
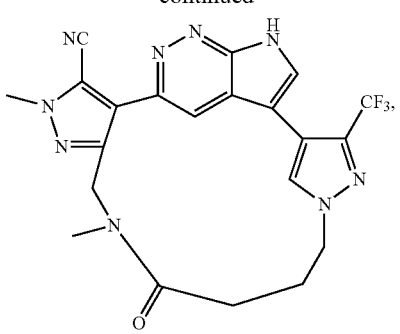

47
-continued
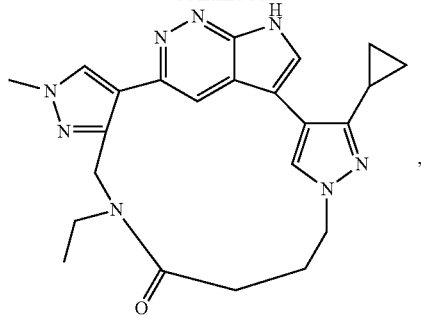
,
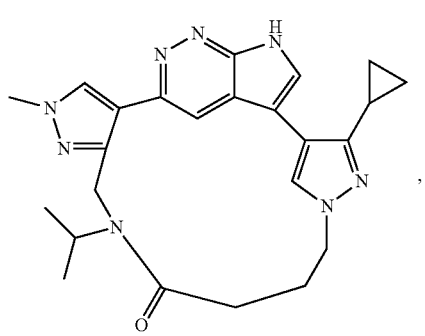
,
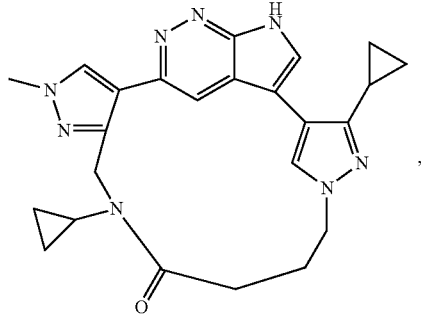
,
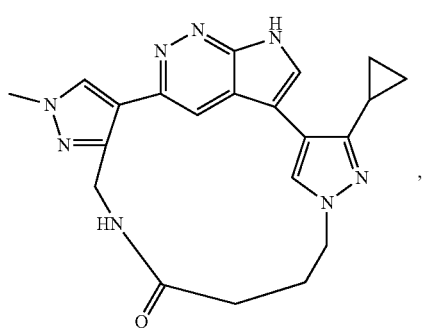
,
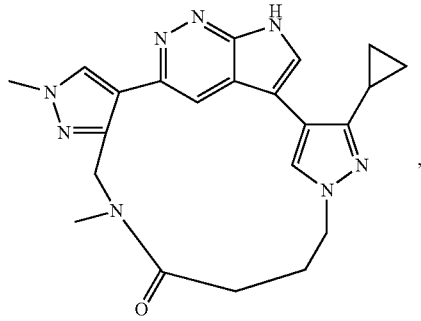
,
48
-continued
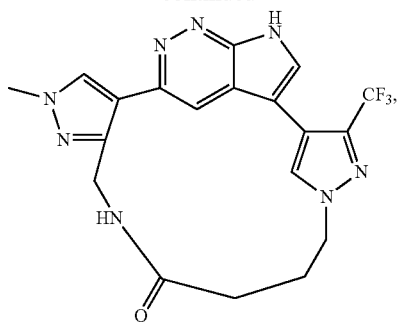
,
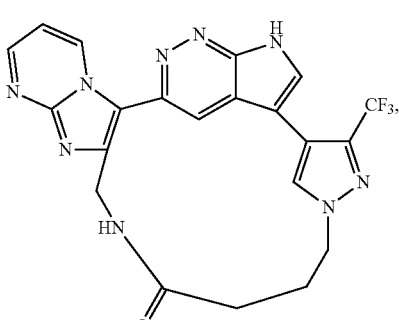
,
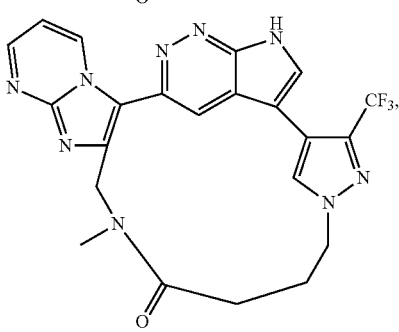
,
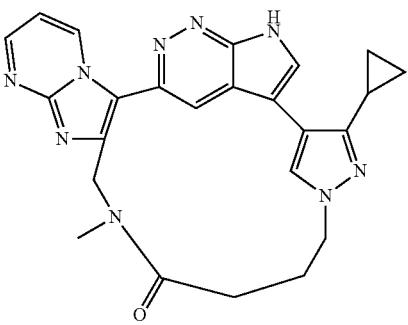
,
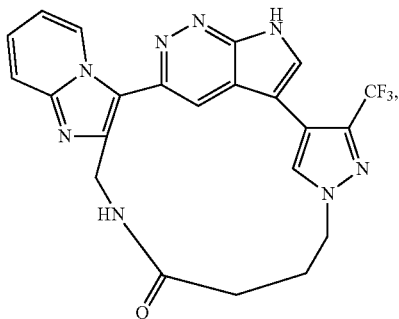
,

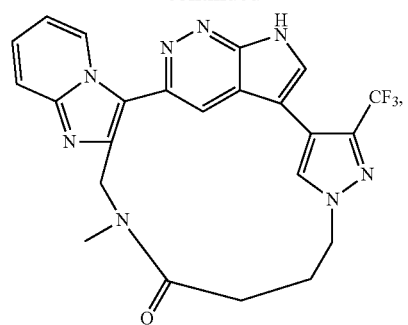
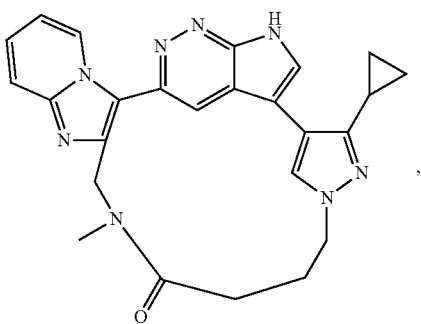
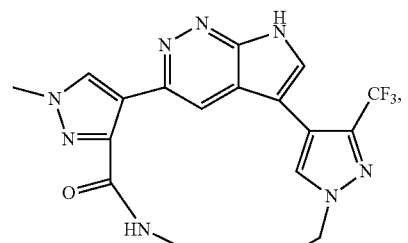
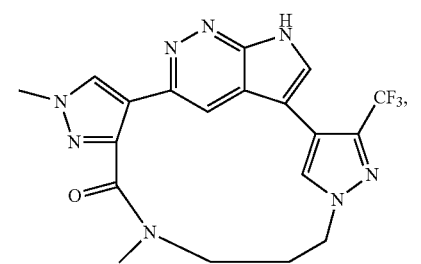
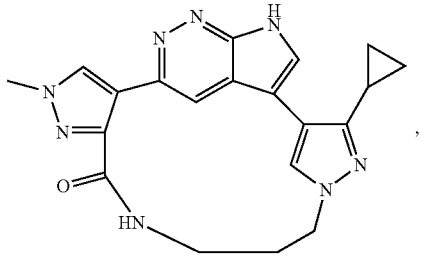
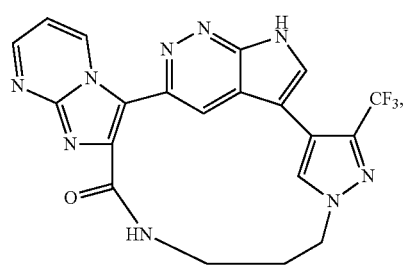
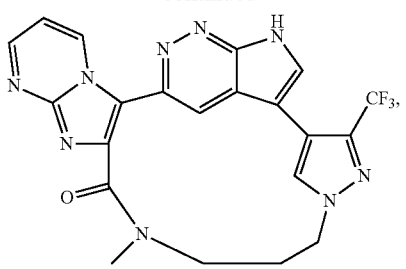
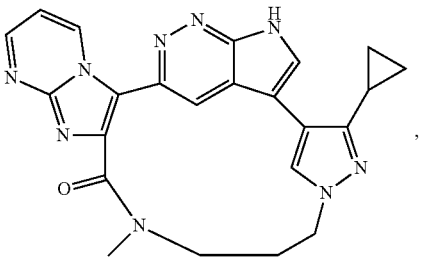
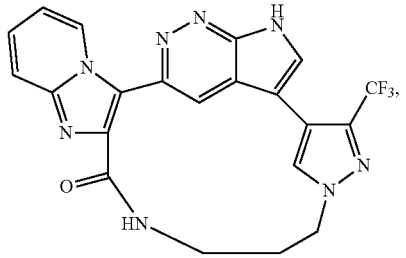
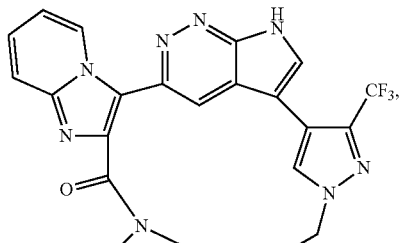
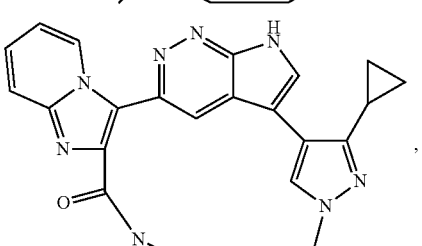
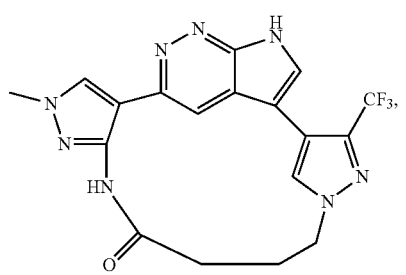

-continued
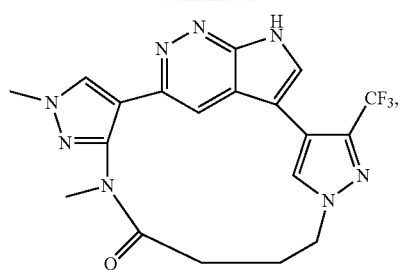
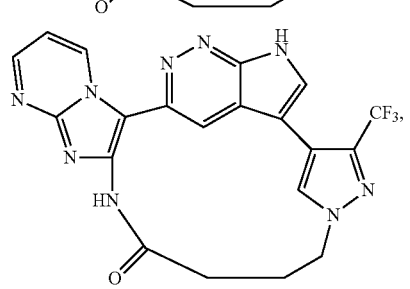
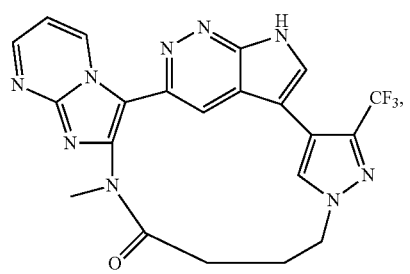
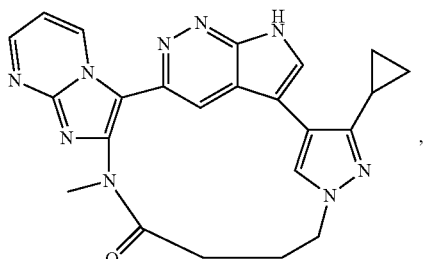
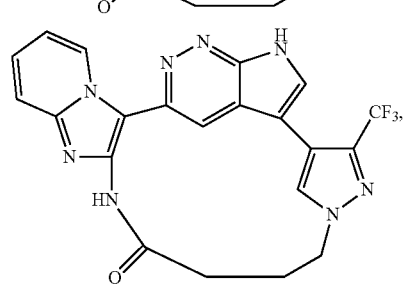
-continued
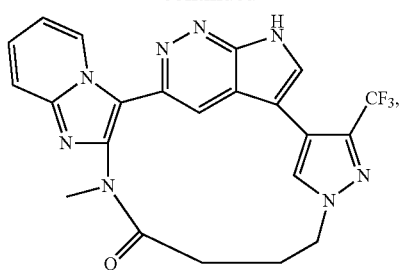
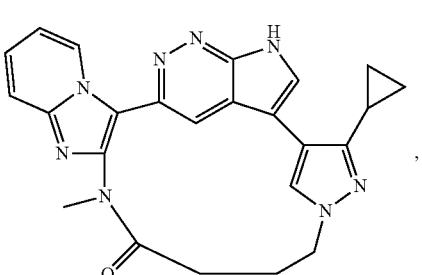
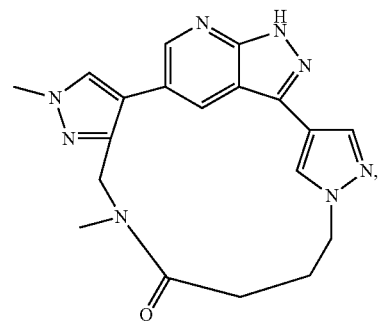
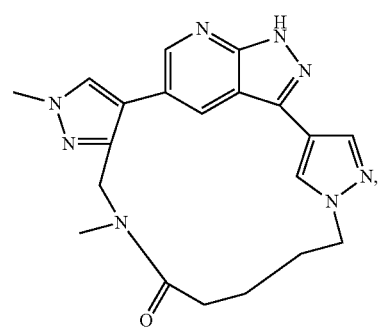
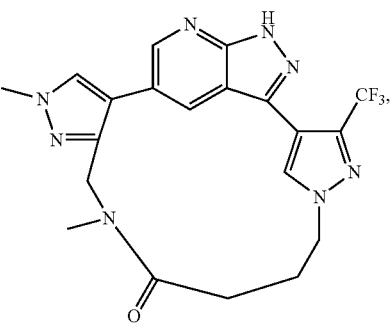

53
-continued
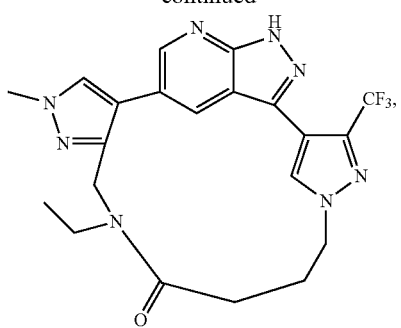
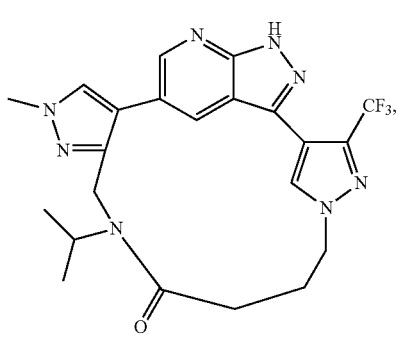
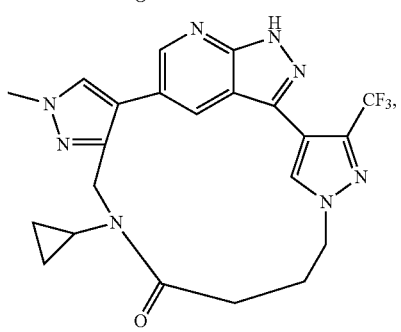
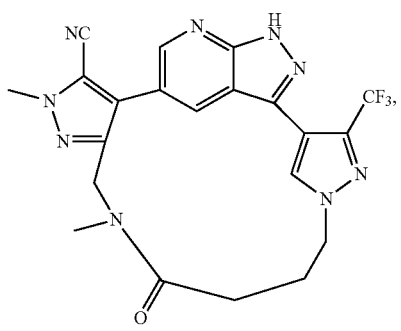
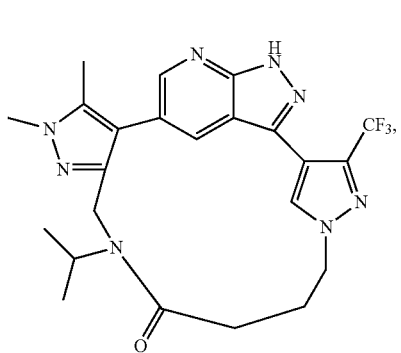
54
-continued
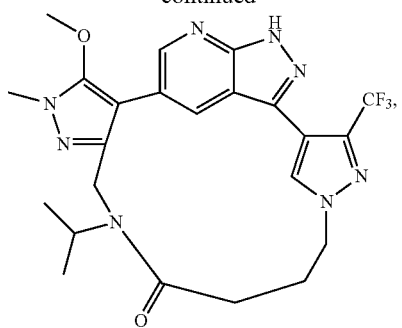
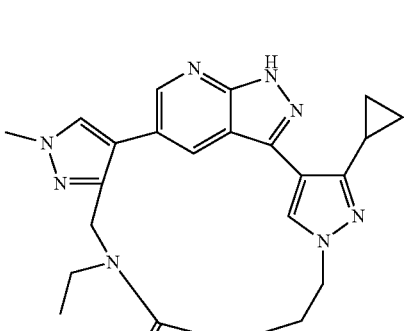
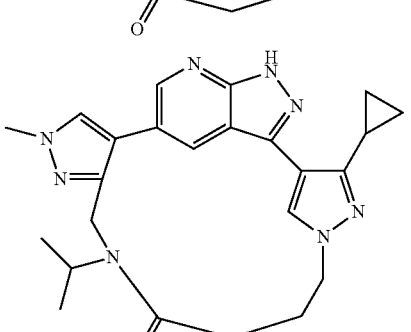
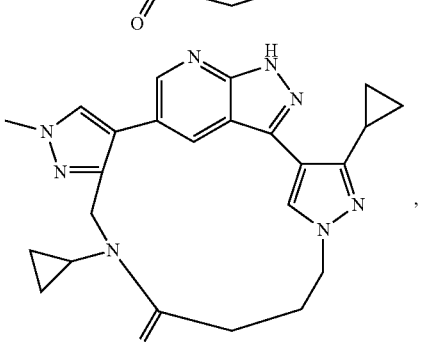
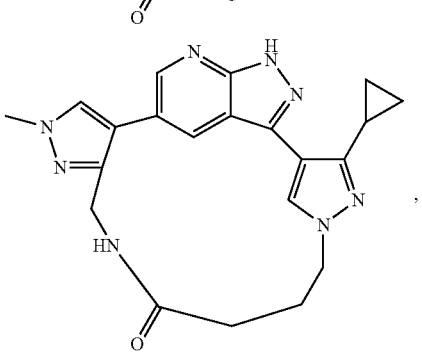

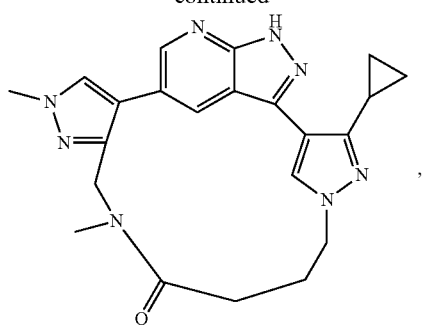
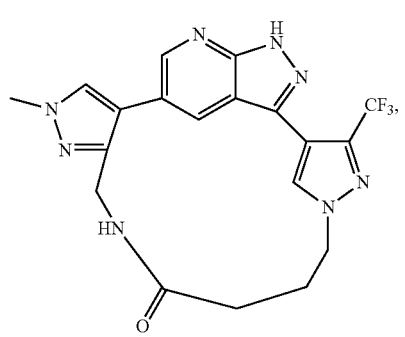
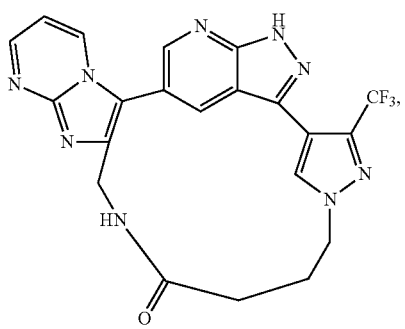
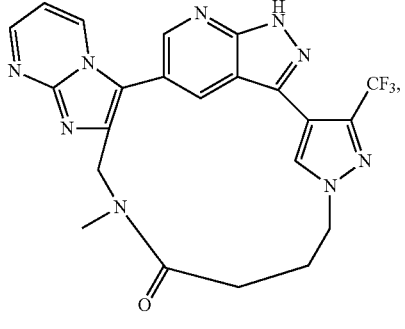
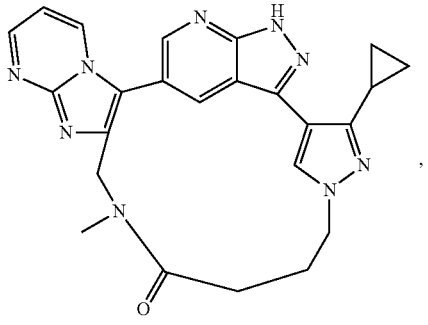
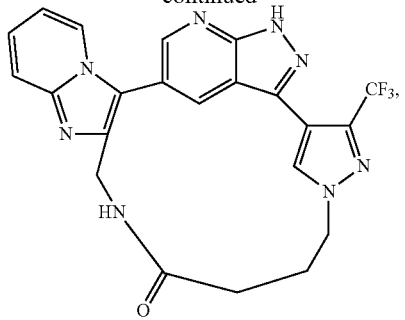
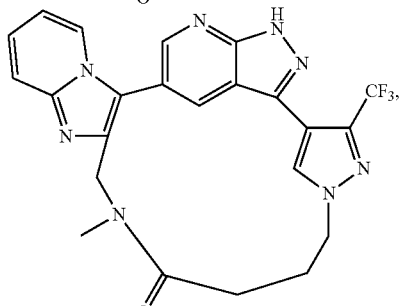
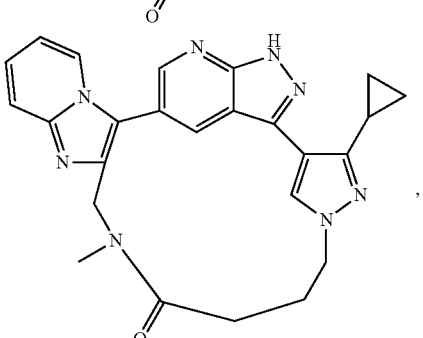
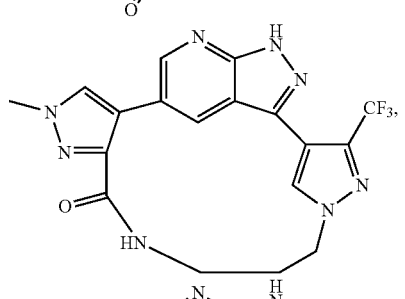
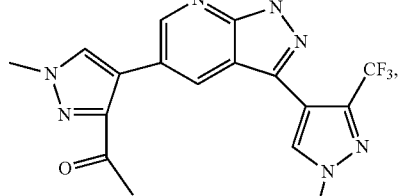
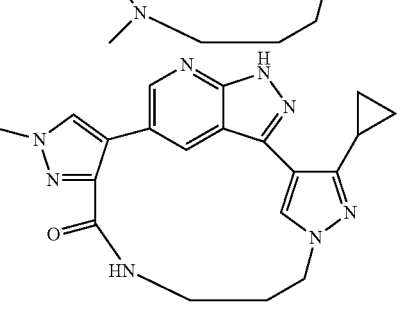

57
-continued
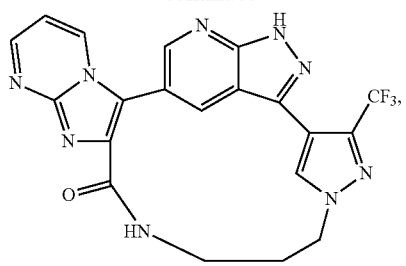
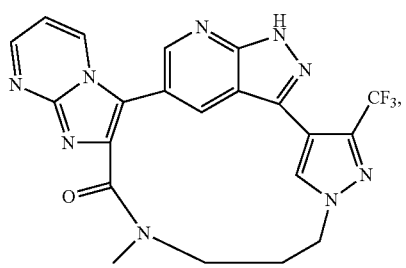
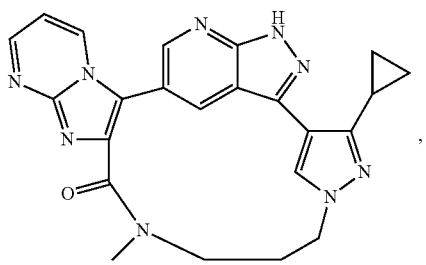,
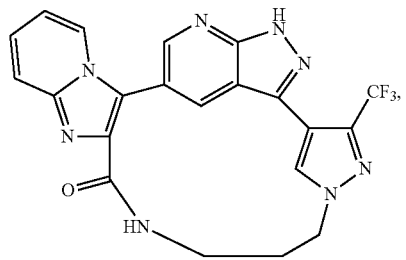
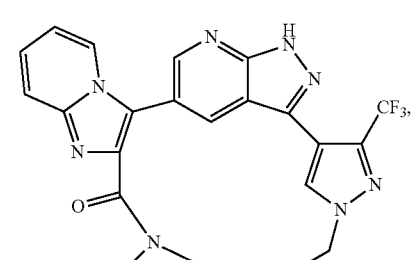
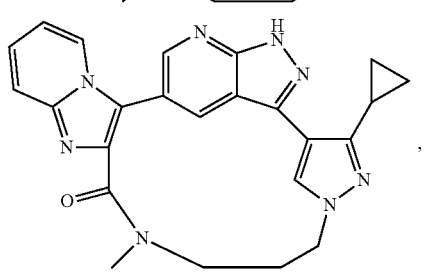,
58
-continued
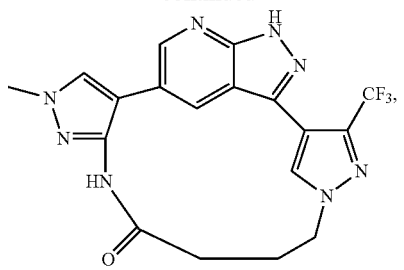
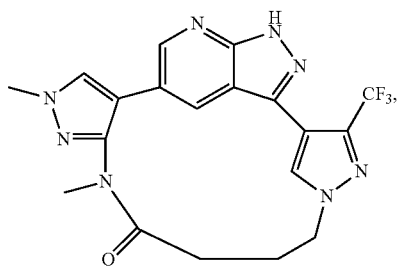
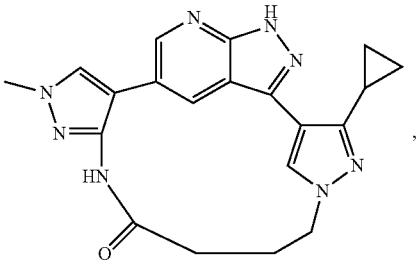,
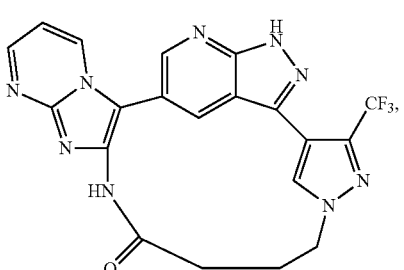
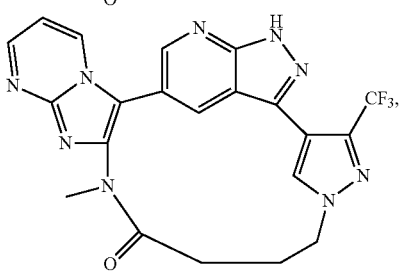
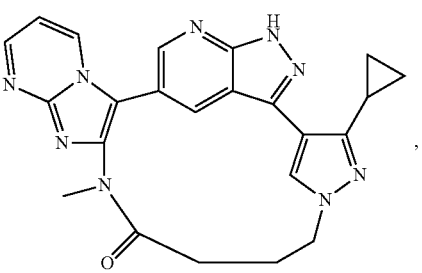, 59
-continued
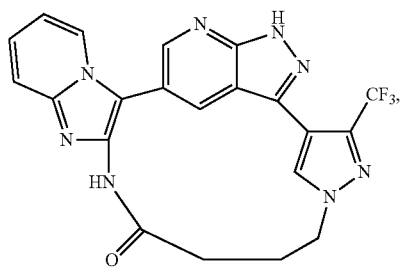
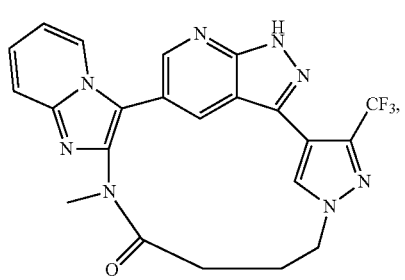
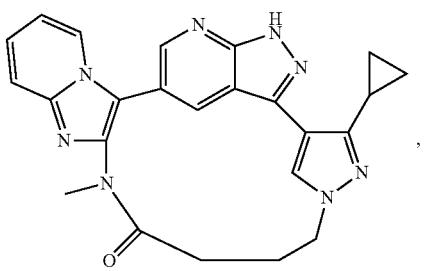
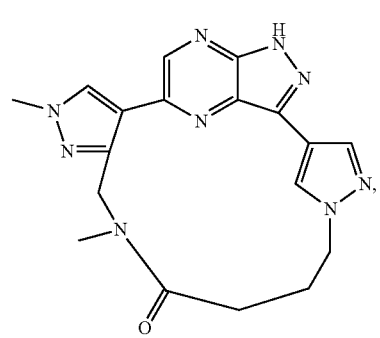
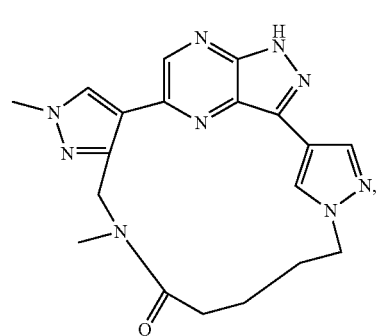
60
-continued
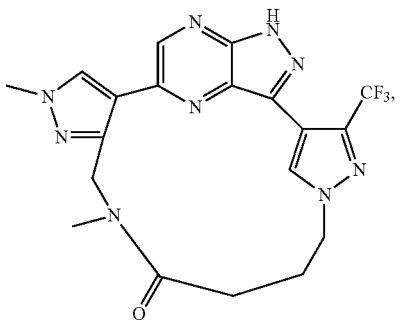
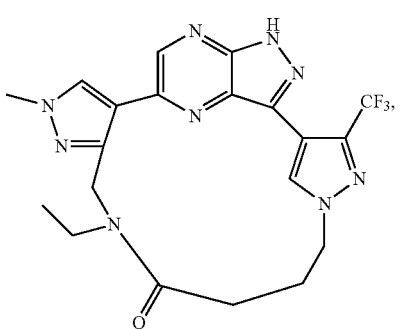
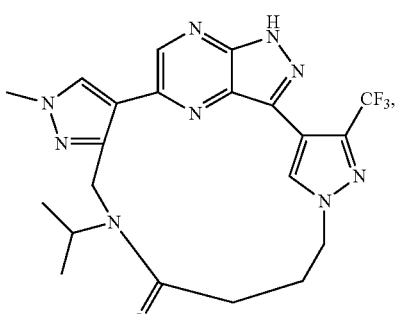
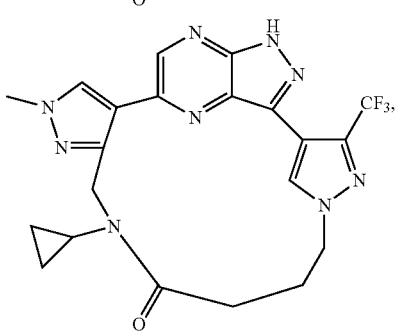
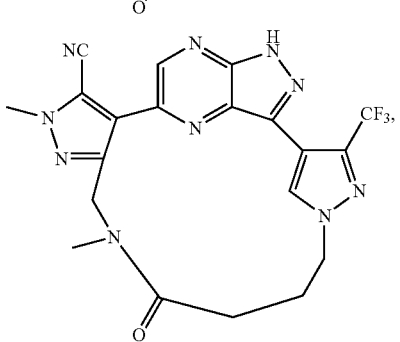

61
-continued
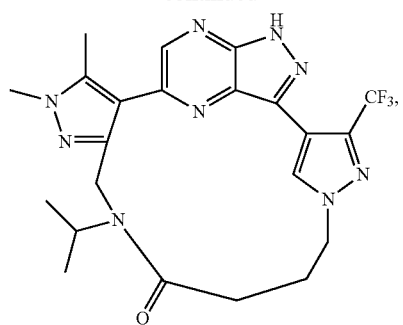
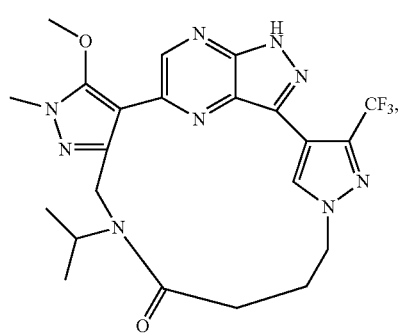
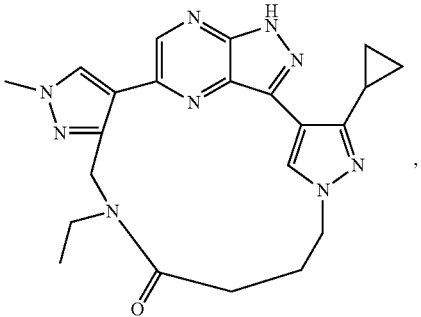
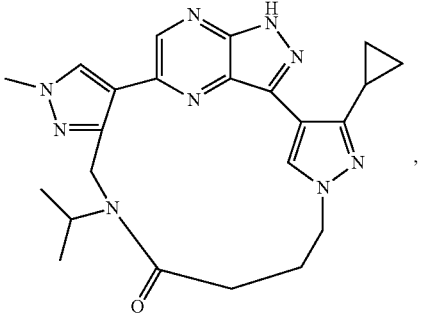
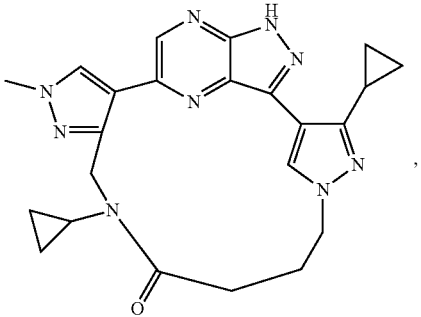
62
-continued
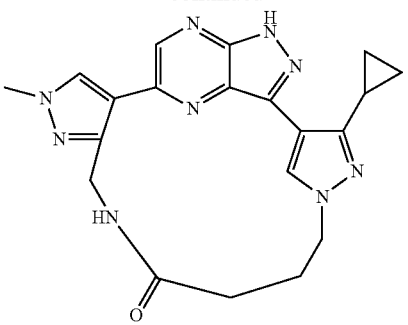
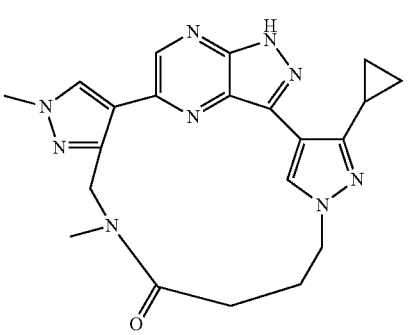
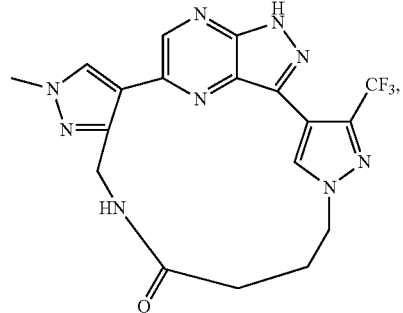
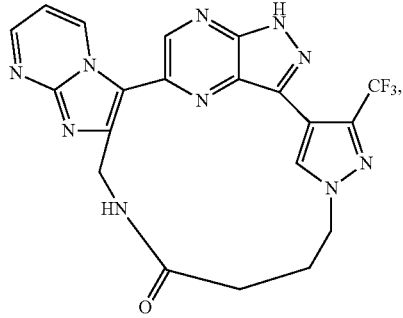
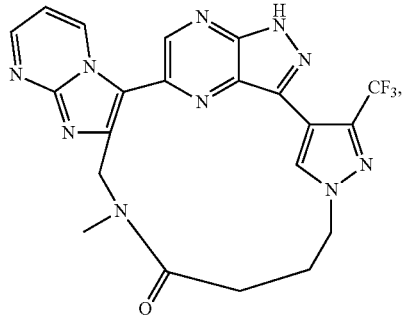

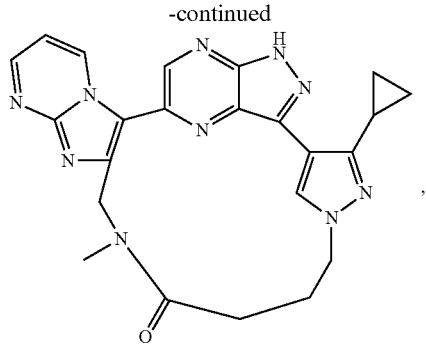
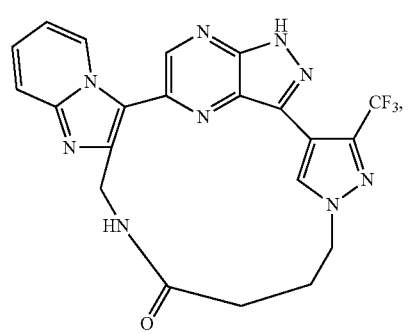
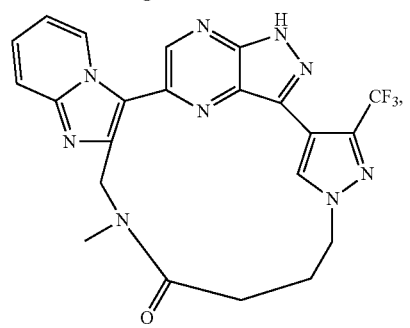
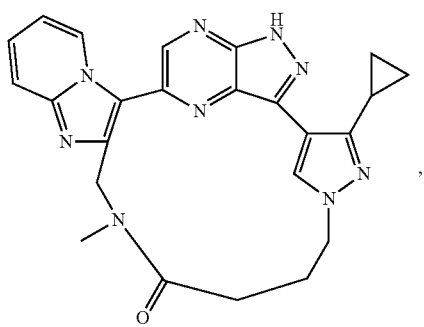
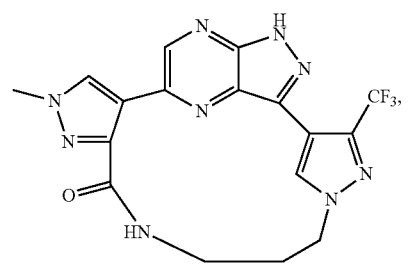
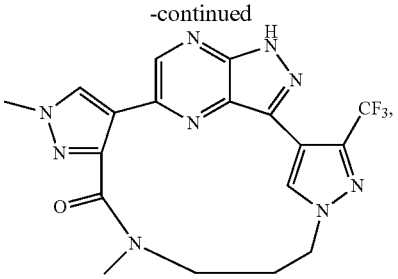
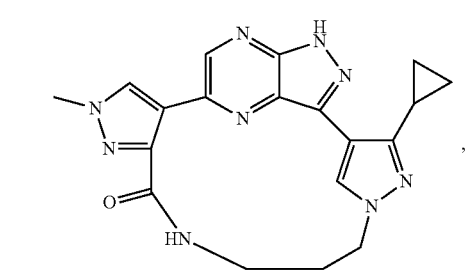
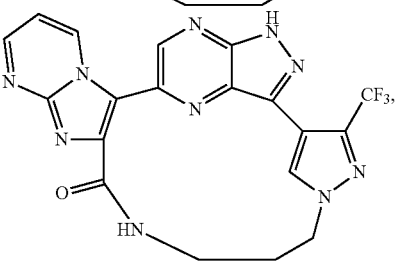
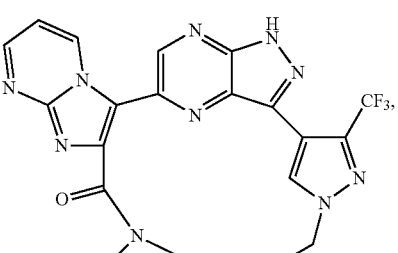
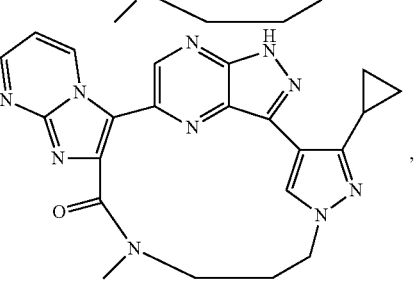
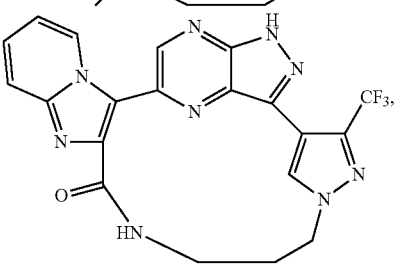

-continued
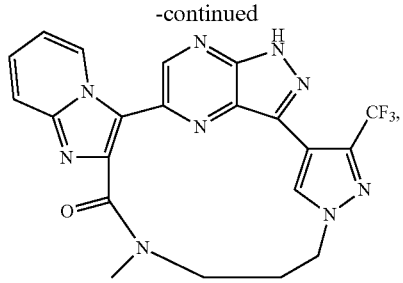
,
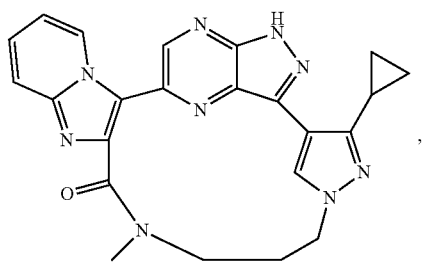
,
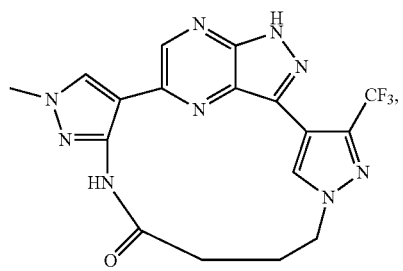
,
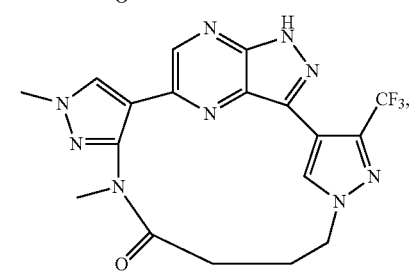
,
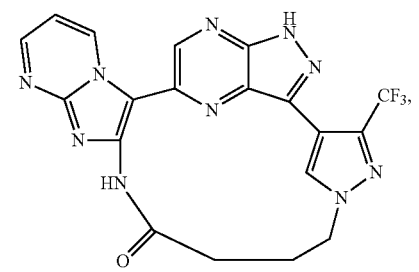
,
-continued
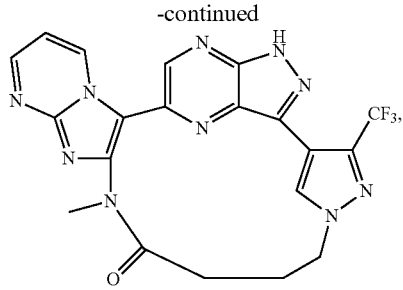
,
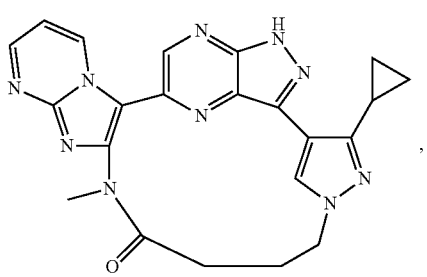
,
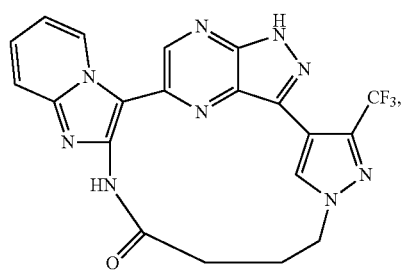
,
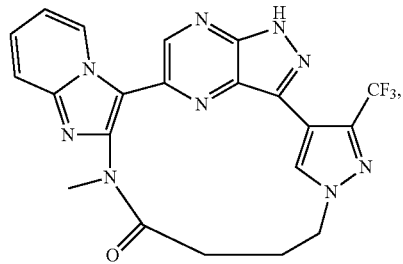
,
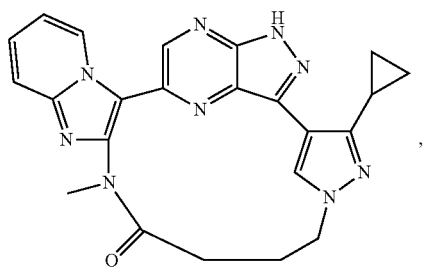
,

67
-continued
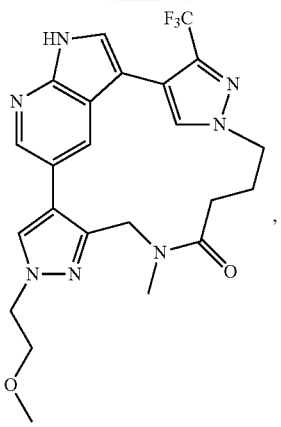
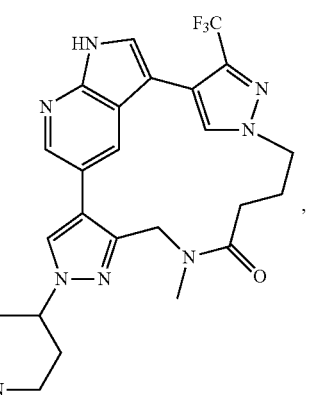
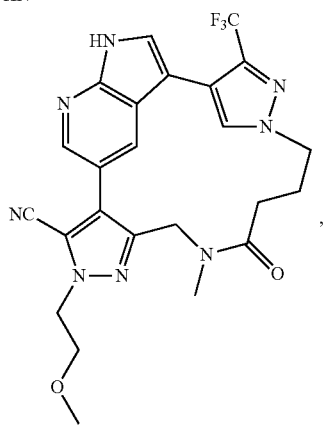
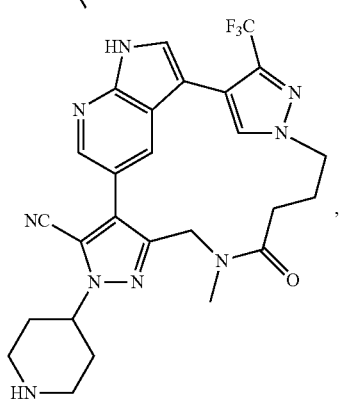
68
-continued
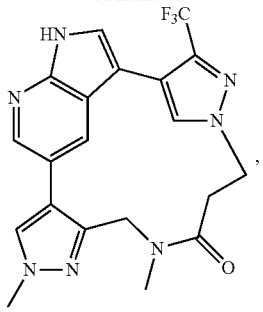
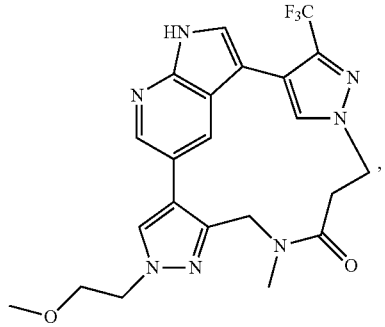
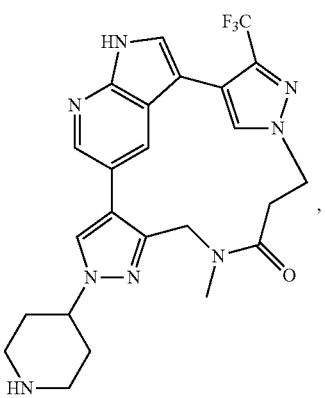
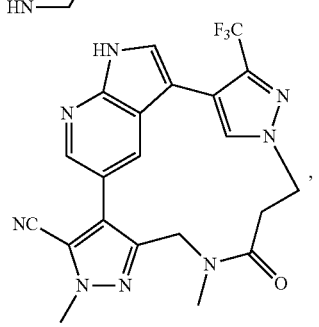
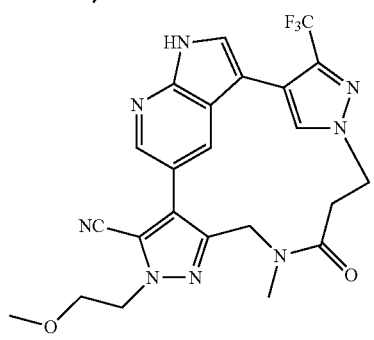

69
-continued
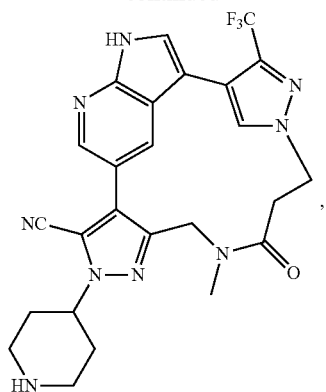
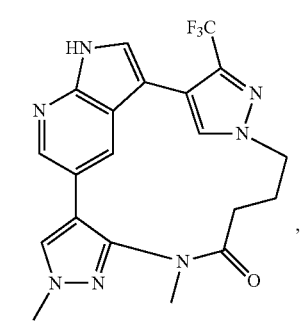
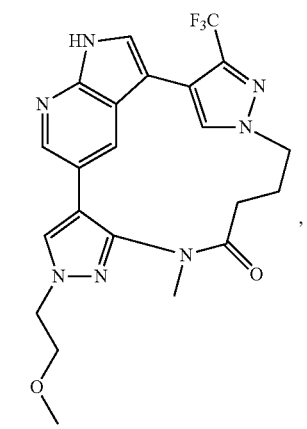
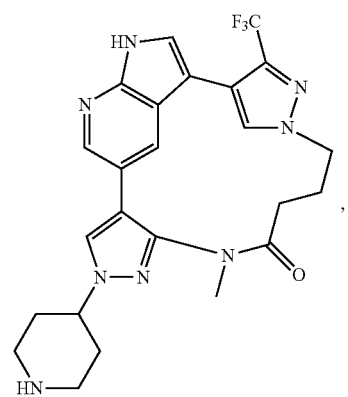
70
-continued
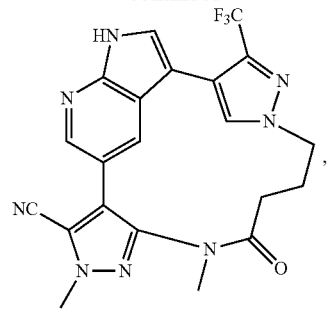
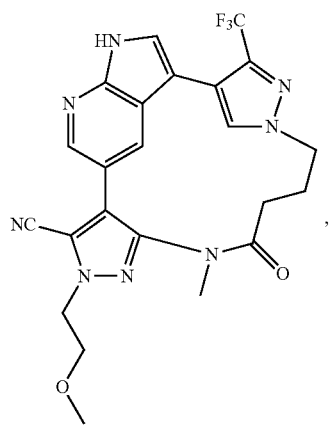
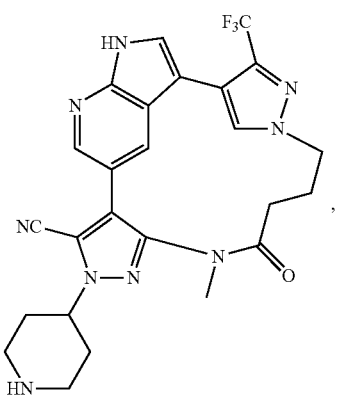
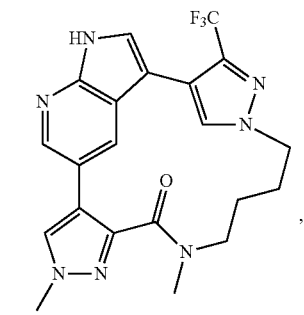

71
-continued
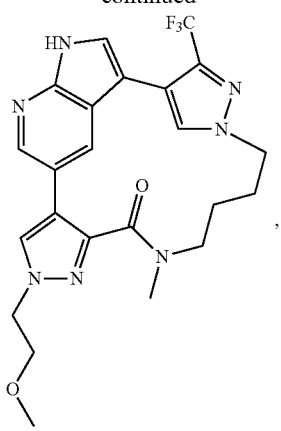
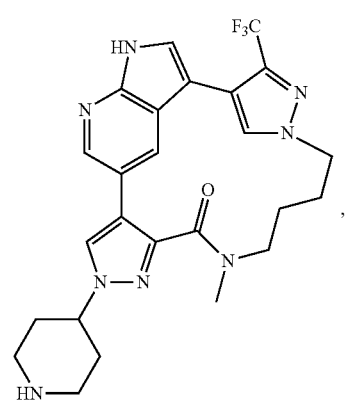
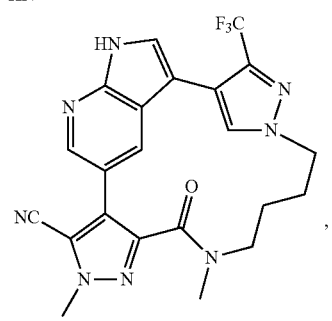
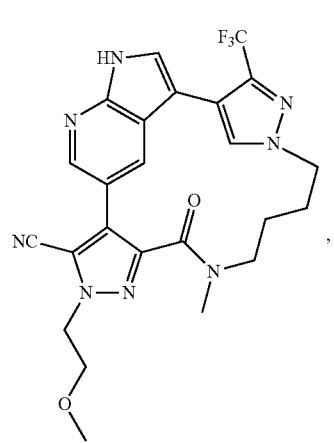
72
-continued
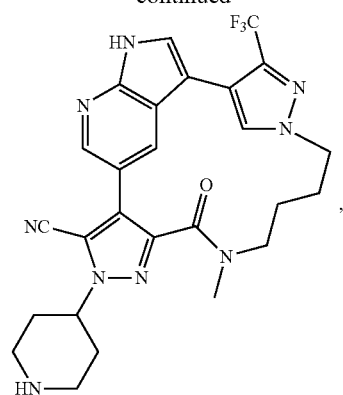
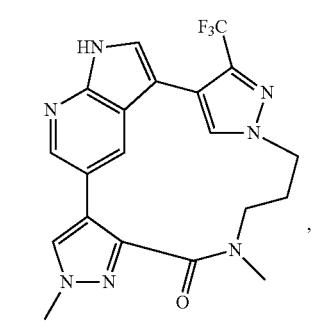
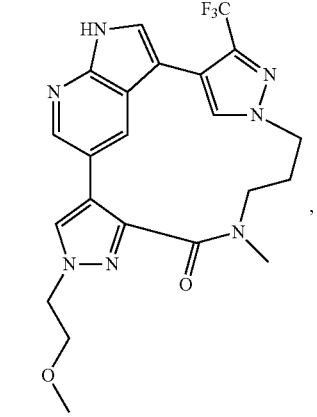
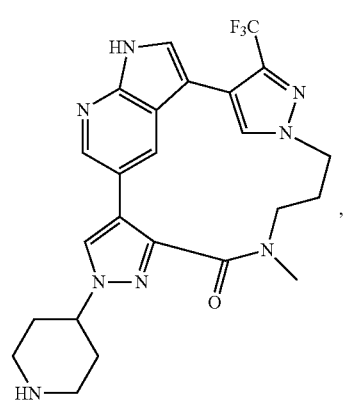

-continued
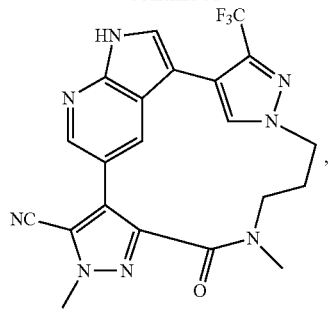
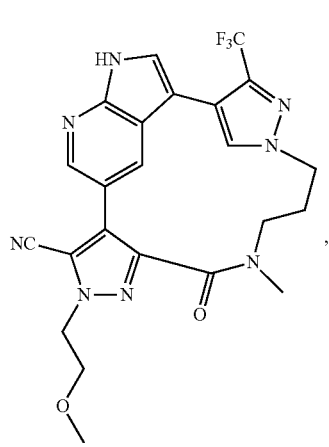
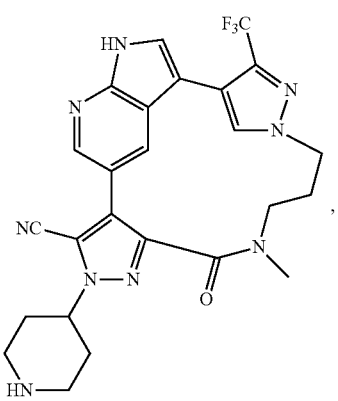
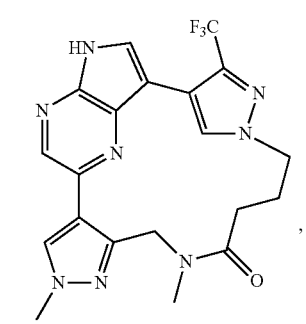
-continued
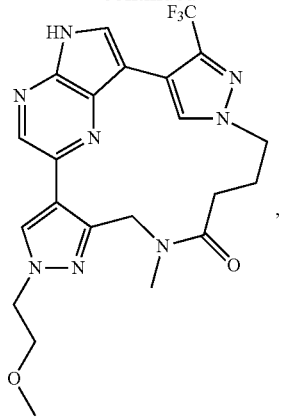
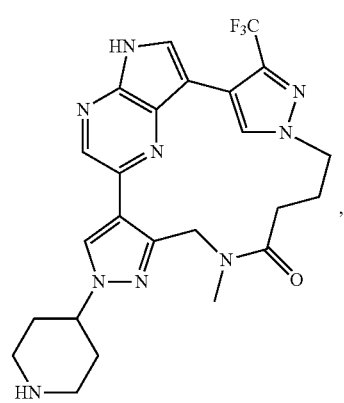
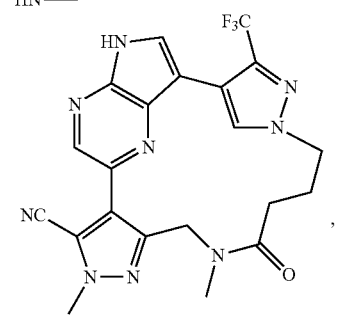
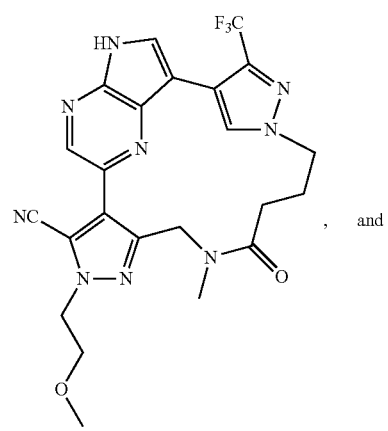, and

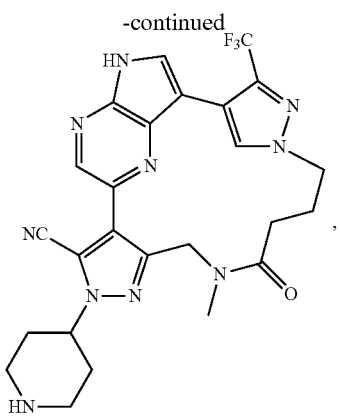

or a pharmaceutically acceptable salt or stereoisomer thereof.

Compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

Methods of Synthesis

In another aspect, the present invention is directed to a method for making an inventive compound, or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may further include one or more pharmaceutically acceptable excipients.

Broadly, compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, compounds of the present invention are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla., 1995, which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill., 1997. Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound or a pharmaceutically acceptable salt or a stereoisomer thereof, effective in producing the desired therapeutic response in a particular patient suffering from a disease or disorder. The term "therapeutically effective amount" includes the amount of the compound of the invention or a pharmaceutically acceptable salt or a stereoisomer thereof, when administered, may induce a positive modification in the disease or disorder to be treated (e.g., to inhibit and/or reduce expression of DYRK, TRK, TLK, and/or RET), or is sufficient to prevent development or progression of the disease or disorder, or alleviate to some extent, one or more of the symptoms of the disease or disorder being treated in a subject, or which simply kills or inhibits the growth of diseased cells, or reduces the amount of DYRK, TRK, TLK, and/or RET in diseased cells. In respect of the therapeutic amount of the compound, the amount of the compound used for the treatment of a subject is low enough to avoid undue or severe side effects, within the scope of sound medical judgment can also be considered.

The total daily dosage of the compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's, "The Pharmacological Basis of Therapeutics,"* 10th Edition, A. Gilman, J. Hardman and L. Limbird, eds., McGraw-Hill Press, 155-173 (2001)).

Compounds of the present invention and their pharmaceutically acceptable salts and stereoisomers may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to treating diseases and disorders, cancerous and non-cancerous alike, characterized or mediated by aberrant (e.g., elevated levels of protein or otherwise functionally abnormal relative to a non-pathological state) DYRK, TRK, TLK, and/or RET activity relative to a non-pathological state, which entails administering a therapeutically effective amount of a compound of formula (I) or a pharmaceutically acceptable salt or stereoisomer thereof, to a subject in need thereof. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors, or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the inventive compounds may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

Exemplary types of non-cancerous (e.g., cell proliferative) diseases or disorders that may be amenable to treatment with compounds of formula (I) include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In some embodiments, the compounds may be useful in the treatment of non-cancerous neurodegenerative diseases and disorders. As used herein, the term "neurodegenerative diseases and disorders" refers to the conditions characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), Pick's syndrome, spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD). In some embodiments, the neurodegenerative disease is AD.

In some embodiments, the compounds may be useful in the treatment of genetic disorders. As used herein, the term "genetic disorders" refers to a disease or disorder caused by one or more abnormalities formed in the genome (e.g., a change in the DNA sequence away from the normal sequence). Representative examples of such disorders include 2211.2 deletion syndrome, Angelman syndrome, Canavan disease, cystic fibrosis, Duchenne muscular dystrophy, familial hypercholesterolemia, Klinefelter syndrome, neurofibromatosis, phenylketonuria, polycystic kidney disease, Down syndrome, Prader-Willi syndrome, sickle cell disease, spinal muscular atrophy, Tay-Sachs disease, and Turner syndrome. In some embodiments, the genetic disorder is Down syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), polycythemia vera, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hepatocellular carcinoma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, essential thrombocythemia, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, skin, ovary, breast, skin, and endometrium.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, compounds of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The compounds of the present invention may be administered may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but became intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of an inventive compound or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day off period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

Compounds of formula (I) and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula (I) or a pharmaceutically acceptable salt or stereoisomer in combination with one or more additional therapeutics known for use in treating the disease or disorder (e.g., cancer). The dosage of the additional anticancer therapeutic may be the same or even lower than known or recommended doses. See, Hardman et al., eds., *Goodman & Gilman's The Pharmacological Basis Of Basis Of Therapeutics*, 10th ed., McGraw-Hill, New York, 2001; *Physician's Desk Reference* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the compound of formula (I) and the additional agent or therapeutic (e.g., an anti-cancer therapeutic) are cyclically administered. By way of example in the context of cancer treatment, cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the compound of the present invention may be used in combination with at least one other anti-cancer agent, examples of which include Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and nonlymphocytic leukemia), Vincristine (e.g., leukemia), Leucovorin (e.g., colon cancer), Altretamine (e.g., ovarian cancer), Daunorubicin (e.g., acute myeloid leukemia (AMIL), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymnphonia), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastro-intestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer), Temsirolimus (e.g., kidney cancer), Bortezomib (e.g., multiple myeloma and mantle cell lymphoma), Pegaspargase (e.g., acute lymphoblastic leukemia), Cabometyx (e.g., hepatocellular carcinoma, medullary thyroid cancer, and renal cell carcinoma), Keytruda (e.g., cervical cancer, gastric cancer, hepatocellular carcinoma, Hodgkin lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), and Regorafenib (e.g., colorectal cancer, gastrointestinal stromal tumor, and hepatocellular carcinoma).

In some embodiments where the inventive compounds and methods are used for treatment of neurodegenerative disease, a compound of the present invention may be used alone or in combination with one or more of Levodopa, Sinemet, Safinamide, Ropinirole, Pramipexole, Rotigotine Amantadine, Artane, Cogentin, Eldepryl, Zelapar, and Azilect (e.g., for Parkinson's disease. In some embodiments, a compound of the present invention may be used alone or in combination with one or more of Aricept, Exelon, Razadyne, Namenda, and Namzaric (e.g., for Alzheimer's disease) In some embodiments, a compound of the present invention may be used alone or in combination with one or more of Xenazine, Haldol, chlorpromazine, Risperdal, Seroquel, Keppra, Klonopin, Celexa, Prozac, Epitol, and Depacon (e.g., for Huntington's disease).

In some embodiments, a compound of the present invention may be used alone or in combination with one or more of trazodone, Zoloft, Luvox, Zyprexa, and Seroquel (e.g., for Pick's syndrome). Representative examples of other active agents known to treat neurodegenerative diseases and disorders include dopaminergic treatments (e.g., Carbidopa-levodopa, pramipexole (Mirapex), ropinirole (Requip) and rotigotine (Neupro, given as a patch)). Apomorphine and monoamine oxidase B (MAO-B) inhibitors (e.g., selegiline (Eldepryl, Zelapar), rasagiline (Azilect) and safinamide (Xadago)) for PD and movement disorders, cholinesterase inhibitors for cognitive disorders (e.g., benztropine (Cogentin) or trihexyphenidyl), antipsychotic drugs for behavioral and psychological symptoms of dementia, as well as agents aimed to slow the development of diseases, such as Riluzole for ALS, cerebellar ataxia and Huntington's disease, non-steroidal anti-inflammatory drugs for Alzheimer's disease, and caffeine A2A receptor antagonists and CERE-120 (adeno-associated virus serotype 2-neurturin) for the neuroprotection of Parkinson's disease. The term "concurrently" is not limited to the administration of the anti-neurodegenerative therapeutics at exactly the same time. Rather, it is meant that they are administered to a subject as part of the same course of treatment such as in a sequence and within a time interval such that they can act together (e.g., synergistically) to provide an increased benefit than if they were administered otherwise.

In some embodiments where the inventive compounds and methods are used for treatment of genetic disorders, a compound of the present invention may be used alone or in combination with one or more of Spinraza and Zolgensma (e.g., for spinal muscular atrophy). In some embodiments, a compound of the present invention may be used alone or in combination with one or more of Kynamro, Tobi, and Juxtapid (e.g., for familial hypercholesterolemia). In some embodiments, a compound of the present invention may be used alone or in combination with one or more of Zenpep and Pulmozyme (e.g., for cystic fibrosis). In some embodiments, a compound of the present invention may be used alone or in combination with Saizen (e.g., for Turner syndrome). In some embodiments, a compound of the present invention may be used alone or in combination with one or more of Galantamine, Rivastigmine, and Donepezil (e.g., for Down syndrome).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of the present invention, or a pharmaceutical composition which contains the compound and a pharmaceutically acceptable carrier wherein the compound and the carrier may be disposed in the same or separate containers. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: Representative Synthesis of Pyrazole Intermediates

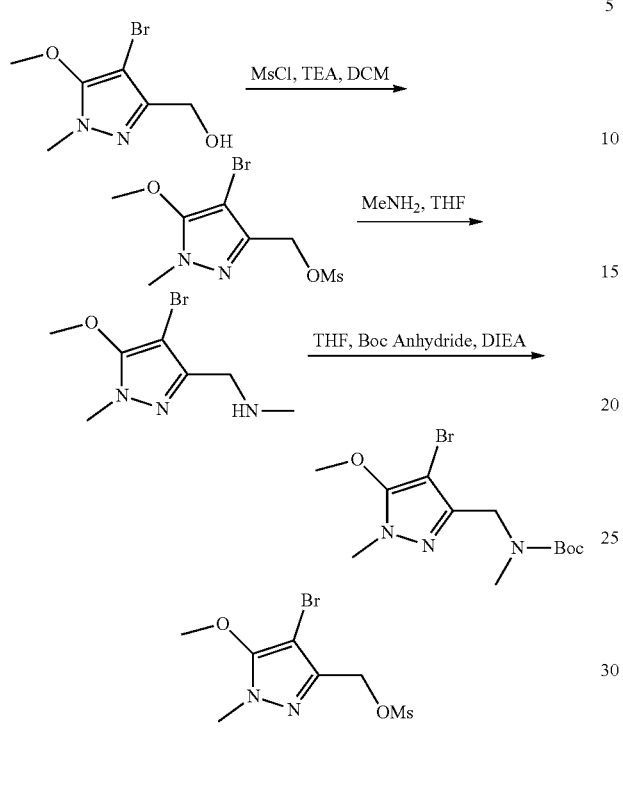

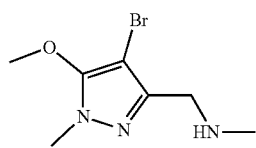

(4-bromo-5-methoxy-1-methyl-1H-pyrazol-3-yl) methyl methanesulfonate (5)

TEA (0.95 mL, 6.79 mmol) was added to a solution of (4-bromo-5-methoxy-1-methyl-1H-pyrazol-3-yl)methanol (1 g, 4.52 mmol) in DCM, followed by the addition of methanesulfonyl chloride (0.53 mL, 6.79 mmol) at 0° C. The mixture was stirred for 2 hours at room temperature, then quenched with saturated aqueous NaHCO$_3$, and extracted with DCM. The combined organic layers were dried over MgSO$_4$ and concentrated in vacuo to give a yellow solid (1.2 g, 89% yield) that was used without further purification.

1-(4-bromo-5-methoxy-1-methyl-1H-pyrazol-3-yl)-N-methylmethanamine (6)

A solution of methylamine 2M in THF (4.01 mL, 8.02 mmol) and N,N-diisopropylethylamine (DIEA) (1.4 mL, 8.02 mmol) were added to a solution of (4-bromo-5-methoxy-1-methyl-1H-pyrazol-3-yl)methyl methanesulfonate (1.2 g, 4.01 mmol) in THF (10 mL). The reaction mixture was heated to 60° C. for 1 h. The reaction was quenched with H$_2$O and extracted with EtOAc. The combined organic layers were dried over MgSO$_4$ and concentrated in vacuo to give a brown oil that was used without further purification. MS (ESI) m/z 235.62 (M+H)$^+$.

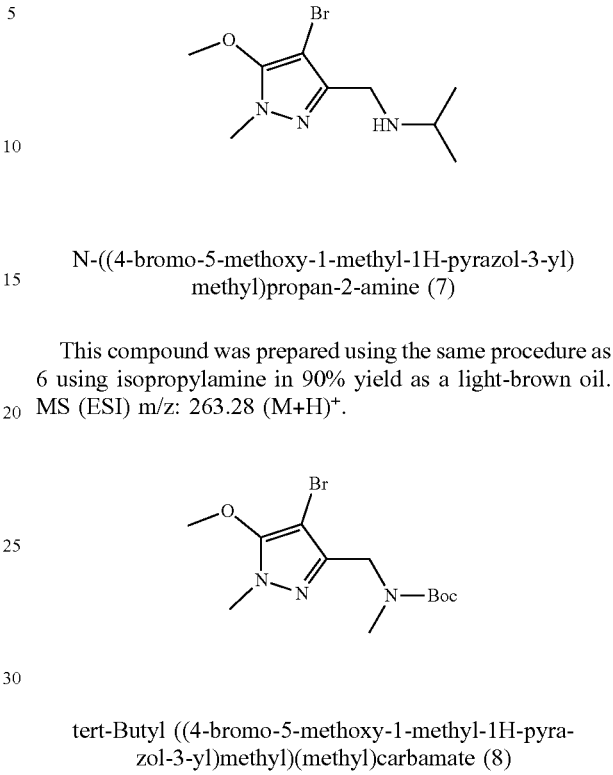

N-((4-bromo-5-methoxy-1-methyl-1H-pyrazol-3-yl) methyl)propan-2-amine (7)

This compound was prepared using the same procedure as 6 using isopropylamine in 90% yield as a light-brown oil. MS (ESI) m/z: 263.28 (M+H)$^+$.

tert-Butyl ((4-bromo-5-methoxy-1-methyl-1H-pyrazol-3-yl)methyl)(methyl)carbamate (8)

Boc anhydride (344 µL, 1.5 mmol), TEA (208 µL, 1.5 mmol) along with a catalytic amount of 4-(dimethylamino) pyridine (DMAP) were added to a solution of 1-(4-bromo-5-methoxy-1-methyl-1H-pyrazol-3-yl)-N-methylmethanamine (250 mg, 1.07 mmol) in THF (5 mL). The reaction mixture stirred for 1 h, quenched with H$_2$O, and extracted with EtOAc. The combined organic layers were dried over MgSO$_4$ and concentrated in vacuo to give a brown oil that was purified by flash chromatography using (20%-70% EtOAc:hexanes) to give the title compound as a clear oil (324 mg, 91% yield). $^1$H NMR (500 MHz, DMSO) δ 4.25 (s, 2H), 3.98 (s, 3H), 3.62 (s, 3H), 2.71 (s, 3H) 1.40 (s, 9H). MS (ESI) m/z 335.27 (M+H)$^+$.

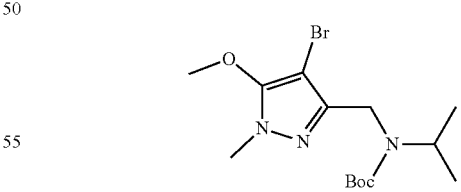

tert-Butyl ((4-bromo-5-methoxy-1-methyl-1H-pyrazol-3-yl)methyl)(isopropyl)carbamate (9)

This compound was prepared using the same procedure as 8 using N-((4-bromo-5-methoxy-1-methyl-1H-pyrazol-3-yl) methyl)propan-2-amine to give the title compound in 91% yield as a clear oil. MS (ESI) m/z: 363.78 (M+H)$^+$.

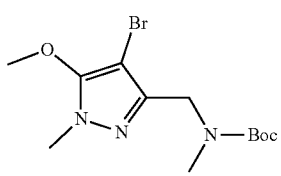 [SMILES: COc1c(Br)c(CN(C)C(=O)OC(C)(C)C)nn1C]

tert-butyl ((4-bromo-1,5-dimethyl-1H-pyrazol-3-yl)methyl)(methyl)carbamate (10)

This compound was prepared using the same procedure as 8 using 1-(4-bromo-1,5-dimethyl-1H-pyrazol-3-yl)methyl)(methylamine) to give the title compound in 94% yield as a clear oil. $^1$H NMR (500 MHz, DMSO) δ 4.25 (s, 2H), 3.73 (s, 3H), 2.70 (s, 3H), 2.21 (s, 3H) 1.40 (s, 9H). MS (ESI) m/z 319.56 (M+H)$^+$.

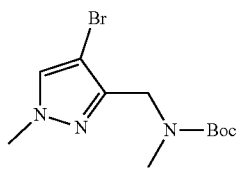 [SMILES: CN(Cc1nn(C)cc1Br)C(=O)OC(C)(C)C]

tert-butyl ((4-bromo-1-methyl-1H-pyrazol-3-yl)methyl)(methyl)carbamate (11)

This compound was prepared using the same procedure as 8 using 1-(4-bromo-1-methyl-1H-pyrazol-3-yl)methyl)(methylamine) to give the title compound in 90% yield as a clear oil. $^1$H NMR (500 MHz, DMSO) δ 7.97 (s, 1H), 4.26 (s, 2H), 3.86 (s, 3H), 2.72 (s, 3H), 1.40 (s, 9H). MS (ESI) m/z 305.63 (M+H)$^+$.

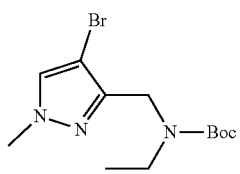 [SMILES: CCN(Cc1nn(C)cc1Br)C(=O)OC(C)(C)C]

tert-butyl ((4-bromo-1-methyl-1H-pyrazol-3-yl)methyl)(ethyl)carbamate (12)

This compound was prepared using the same procedure as 8 using 11-(4-bromo-1-methyl-1H-pyrazol-3-yl)methyl)(ethylamine) to give the title compound in 88% yield as a yellow solid. MS (ESI) m/z 319.26 (M+H)$^+$.

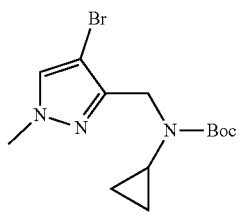 [SMILES: Cn1cc(Br)c(CN(C(=O)OC(C)(C)C)C2CC2)n1]

tert-butyl ((4-bromo-1-methyl-1H-pyrazol-3-yl)methyl)(cyclopropyl)carbamate (13)

This compound was prepared using the same procedure as 8 using 1-(4-bromo-1-methyl-1H-pyrazol-3-yl)methyl)(cyclopropylamine) to give the title compound in 92% yield as a yellow oil. MS (ESI) m/z 331.19 (M+H)$^+$.

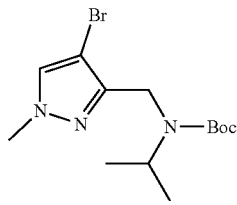 [SMILES: CC(C)N(Cc1nn(C)cc1Br)C(=O)OC(C)(C)C]

tert-butyl ((4-bromo-1-methyl-1H-pyrazol-3-yl)methyl)(isopropyl)carbamate (14)

This compound was prepared using the same procedure as 8 using 1-(4-bromo-1-methyl-1H-pyrazol-3-yl)methyl)(isopropylamine) to give the title compound in 90% yield as a clear oil. MS (ESI) m/z 333.41 (M+H)$^+$.

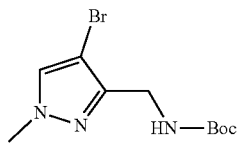 [SMILES: Cn1cc(Br)c(CNC(=O)OC(C)(C)C)n1]

tert-butyl ((4-bromo-1-methyl-1H-pyrazol-3-yl)methyl)carbamate (15)

This compound was prepared using the same procedure as 8 using 1-(4-bromo-1-methyl-1H-pyrazol-3-yl)methyl)(isopropylamine) to give the title compound in 88% yield as a clear oil. MS (ESI) m/z 291.36 (M+H)$^+$.

Example 2: Synthesis of (Z)-31,5-dimethyl-11H, 21H,31H-5-aza-2(3,5)-pyrrolo[2,3-b]pyridina-1(4,1), 3(4,3)-dipyrazolacyclononaphan-6-one (41)

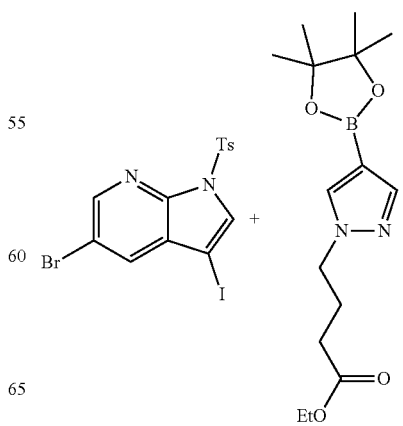

-continued

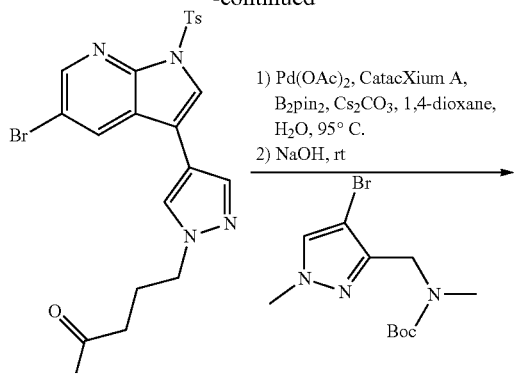

1) Pd(OAc)$_2$, CatacXium A, B$_2$pin$_2$, Cs$_2$CO$_3$, 1,4-dioxane, H$_2$O, 95° C.
2) NaOH, rt

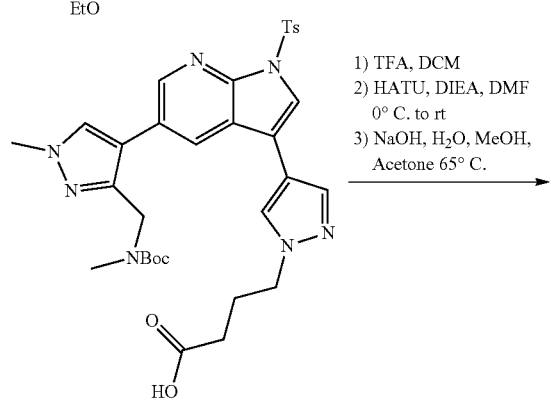

1) TFA, DCM
2) HATU, DIEA, DMF 0° C. to rt
3) NaOH, H$_2$O, MeOH, Acetone 65° C.

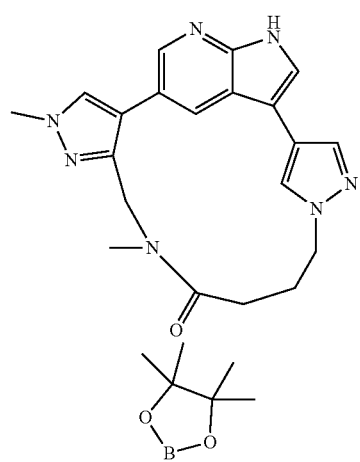

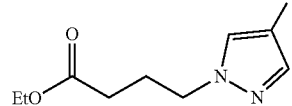

ethyl 4-(4-(4,4,5,5-tetramethyl-1,3,2-dioxaborolan-2-yl)-1H-pyrazol-1-yl)butanoate (1)

Ethyl 4-bromobutanoate (0.98 mL, 6.18 mmol) was added to a solution of 4-(4,4,5,5-tetramethyl-1,3,2-dioxaborolan-2-yl)-1H-pyrazole (1 g, 5.15 mmol) in DMF (30 mL), followed by the addition of K$_2$CO$_3$ (1.8 g, 12.9 mmol). The reaction mixture was heated to 80° C. for 16 h. The reaction was quenched with H$_2$O and extracted with EtOAc. The combined organic extracts were washed with brine, dried over MgSO$_4$ and condensed to give a light-brown oil that was used without further purification (1.42 g, 90% yield). MS (ESI) m/z: 309.42 (M+H)$^+$.

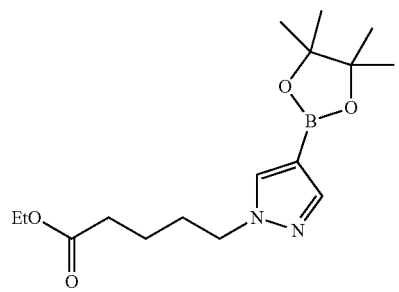 [SMILES: CCOC(=O)CCCCn1cc(B2OC(C)(C)C(C)(C)O2)cn1]

ethyl 5-(4-(4,4,5,5-tetramethyl-1,3,2-dioxaborolan-2-yl)-1H-pyrazol-1-yl)pentanoate (2)

This compound was prepared using the same procedure as 1 using ethyl 5-bromopentanoate to give the title compound in 95% yield as a light-brown oil. MS (ESI) m/z: 323.61 (M+H)$^+$.

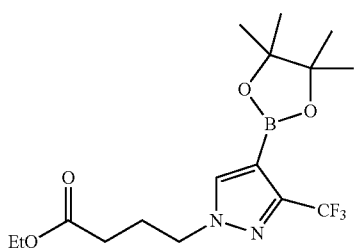 [SMILES: CCOC(=O)CCCn1cc(B2OC(C)(C)C(C)(C)O2)c(C(F)(F)F)n1]

ethyl 4-(4-(4,4,5,5-tetramethyl-1,3,2-dioxaborolan-2-yl)-3-(trifluoromethyl)-1H-pyrazol-1-yl)butanoate (3)

This compound was prepared using the same procedure as 1 using 4-(4,4,5,5-tetramethyl-1,3,2-dioxaborolan-2-yl)-3-(trifluoromethyl)-1H-pyrazole to give the title compound in 84% yield as a light-brown oil. MS (ESI) m/z: 377.34 (M+H)$^+$.

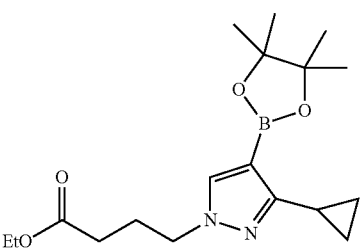 [SMILES: CCOC(=O)CCCn1cc(B2OC(C)(C)C(C)(C)O2)c(C2CC2)n1]

ethyl 4-(3-cyclopropyl-4-(4,4,5,5-tetramethyl-1,3,2-dioxaborolan-2-yl)-1H-pyrazol-1-yl)butanoate (4)

This compound was prepared using the same procedure as 1 using 3-cyclopropyl-4-(4,4,5,5-tetramethyl-1,3,2-dioxaborolan-2-yl)-1H-pyrazole to give the title compound in 78% yield as a light-brown oil. MS (ESI) m/z: 349.27 (M+H)$^+$.

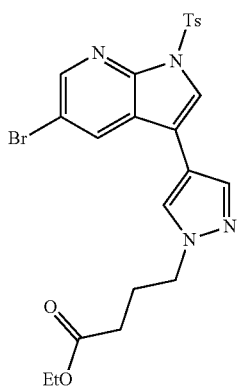 [SMILES: CCOC(=O)CCCn1cc(-c2cn(S(=O)(=O)c3ccc(C)cc3)c3ncc(Br)cc23)cn1]

Ethyl 4-(4-(5-bromo-1-tosyl-1H-pyrrolo[2,3-b]77yridine-3-yl)-1H-pyrazol-1-yl)butanoate (16)

2M Na$_2$CO$_3$ (3.15 mL, 6.3 mmol) was added to a solution of 5-bromo-3-iodo-1-tosyl-1H-pyrrolo[2,3-b]pyridine (1 g, 2.1 mmol) and ethyl 4-(4-(4,4,5,5-tetramethyl-1,3,2-dioxaborolan-2-yl)-1H-pyrazol-1-yl)butanoate (976 mg, 3.14 mmol) in CH$_3$CN (15 mL). This solution was degassed using a sonicator for 2 minutes and then Pd(PPh$_3$)$_2$Cl$_2$ (74 mg, 0.105 mmol) was added. The reaction mixture was stirred at 80° C. for 1 h, quenched with H$_2$O, and extracted with EtOAc. The combined extracts were washed with brine, dried over MgSO$_4$, and concentrated in vacuo. The residue was purified by flash chromatography (10%-40% EtOAc:Hexanes) to give the title compound as a yellow solid (780 mg, 70% yield). MS (ESI) m/z 532.71 (M+H)$^+$.

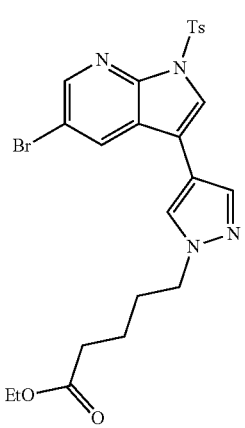 [SMILES: CCOC(=O)CCCCn1cc(-c2cn(S(=O)(=O)c3ccc(C)cc3)c3ncc(Br)cc23)cn1]

ethyl 5-(4-(5-bromo-1-tosyl-1H-pyrrolo[2,3-b]pyridin-3-yl)-1H-pyrazol-1-yl)pentanoate (17)

This compound was prepared using the same procedure as 14 using 2 to give the title compound in 71% yield as a clear oil. MS (ESI) m/z: 545.52 (M+H)$^+$.

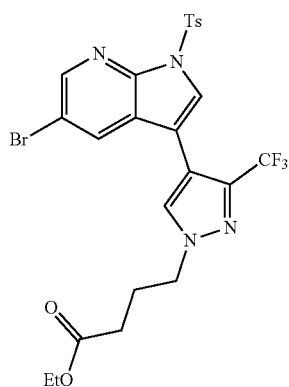 [SMILES: CCOC(=O)CCCn1cc(-c2cn(S(=O)(=O)c3ccc(C)cc3)c3ncc(Br)cc23)c(C(F)(F)F)n1]

ethyl 4-(4-(5-bromo-1-tosyl-1H-pyrrolo[2,3-b]pyridin-3-yl)-3-(trifluoromethyl)-1H-pyrazol-1-yl)butanoate (18)

This compound was prepared using the same procedure as 14 using 3 to give the title compound in 78% yield as a clear oil. MS (ESI) m/z: 600.82 (M+H)$^+$.

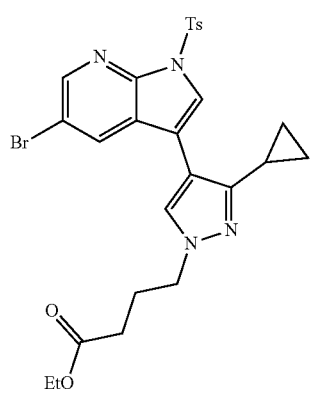 [SMILES: CCOC(=O)CCCn1cc(-c2cn(S(=O)(=O)c3ccc(C)cc3)c3ncc(Br)cc23)c(C2CC2)n1]

ethyl 4-(4-(5-bromo-1-tosyl-1H-pyrrolo[2,3-b]pyridin-3-yl)-3-cyclopropyl-1H-pyrazol-1-yl)butanoate (19)

This compound was prepared using the same procedure as 14 using 4 to give the title compound in 72% yield as a yellow solid. MS (ESI) m/z: 572.65 (M+H)$^+$.

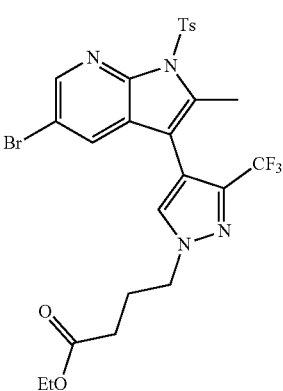 [SMILES: CCOC(=O)CCCn1cc(-c2c(C)n(S(=O)(=O)c3ccc(C)cc3)c3ncc(Br)cc23)c(C(F)(F)F)n1]

ethyl 4-(4-(5-bromo-2-methyl-1-tosyl-1H-pyrrolo[2,3-b]pyridin-3-yl)-3-(trifluoromethyl)-1H-pyrazol-1-yl)butanoate (20)

This compound was prepared using the same procedure as 14 using 3 and 5-bromo-3-iodo-2-methyl-1-tosyl-1H-pyrrolo[2,3-b]pyridine to give the title compound in 70% yield as a clear oil. MS (ESI) m/z: 614.47 (M+H)+.

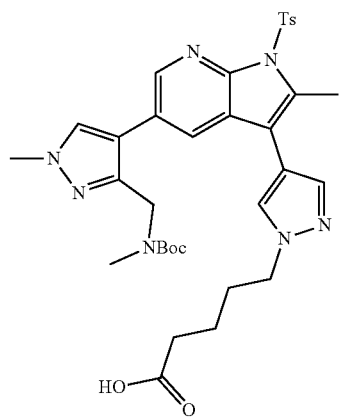

5-(4-(5-(3-(((tert-butoxycarbonyl)(methyl)amino)methyl)-1-methyl-1H-pyrazol-4-yl)-1-tosyl-1H-pyrrolo[2,3-b]pyridin-3-yl)-1H-pyrazol-1-yl)pentanoic acid (21)

CatacXium A [(60 mg, 0.16 mmol) and Pd(OAc)$_2$ (19 mg, 0.08 mmol) were added to a degassed solution of ethyl 4-(4-(5-bromo-1-tosyl-1H-pyrrolo[2,3-b]pyridin-3-yl)-1H-pyrazol-1-yl)butanoate (300 mg, 0.55 mmol), tert-butyl ((4-bromo-1-methyl-1H-pyrazol-3-yl)methyl)(methyl)carbamate (220 mg, 0.71 mmol), bis(pinacolato)diboron (210 mg, 0.82 mmol) and Cs$_2$CO$_3$ (896 mg, 2.75 mmol) in 1,4-dioxane (9 mL) and H$_2$O (1 mL). The reaction stirred at 95° C. for 1 h. The reaction mixture was cooled to rt (room temperature) and NaOH (44 mg, 1.1 mmol) in H$_2$O (1 mL) was added and the resulting mixture stirred for 2 hours. The mixture was filtered and the filtrate purified by HPLC (0%-70% MeCN:H$_2$O) to give the title compound as a beige solid (124 mg, 35% yield). MS (ESI) m/z: 648.46 (M+H)+.

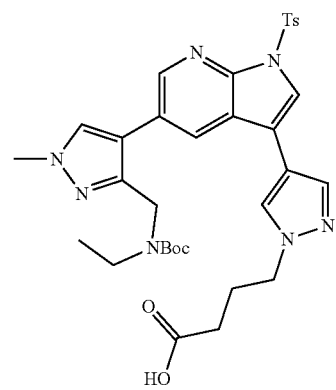 [SMILES: CCN(Cc1nn(C)cc1-c1cnc2c(c1)c(-c1cnn(CCCC(=O)O)c1)cn2S(=O)(=O)c1ccc(C)cc1)C(=O)OC(C)(C)C]

4-(4-(5-(3-(((tert-butoxycarbonyl)(ethyl)amino)methyl)-1-methyl-1H-pyrazol-4-yl)-1-tosyl-1H-pyrrolo[2,3-b]pyridin-3-yl)-1H-pyrazol-1-yl)butanoic acid (22)

This compound was prepared using the same procedure as 21 using 12 and 16 to give the title compound in 36% yield as a beige solid. MS (ESI) m/z: 662.74 (M+H)+.

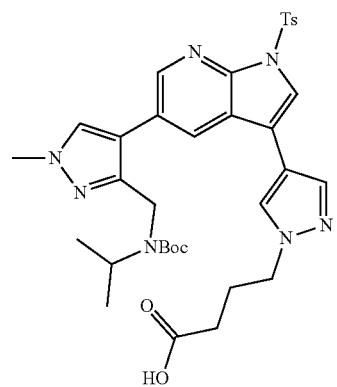 [SMILES: Cc1ccc(S(=O)(=O)n2cc(-c3cnn(CCCC(=O)O)c3)c3cc(-c4cn(C)nc4CN(C(=O)OC(C)(C)C)C(C)C)cnc32)cc1]

4-(4-(5-(3-(((tert-butoxycarbonyl)(isopropyl)amino)methyl)-1-methyl-1H-pyrazol-4-yl)-1-tosyl-1H-pyrrolo[2,3-b]pyridin-3-yl)-1H-pyrazol-1-yl)butanoic acid (23)

This compound was prepared using the same procedure as 21 using 14 and 16 to give the title compound in 32% yield as a beige solid. MS (ESI) m/z: 676.36 (M+H)+.

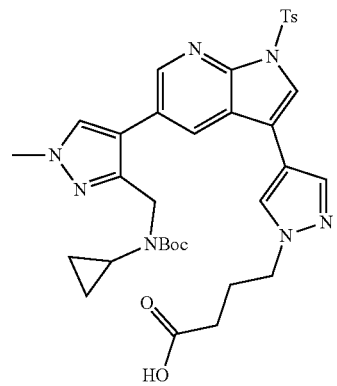 [SMILES: Cc1ccc(S(=O)(=O)n2cc(-c3cnn(CCCC(=O)O)c3)c3cc(-c4cn(C)nc4CN(C(=O)OC(C)(C)C)C4CC4)cnc32)cc1]

4-(4-(5-(3-(((tert-butoxycarbonyl)(cyclopropyl)amino)methyl)-1-methyl-1H-pyrazol-4-yl)-1-tosyl-1H-pyrrolo[2,3-b]pyridin-3-yl)-1H-pyrazol-1-yl)butanoic acid (24)

This compound was prepared using the same procedure as 21 using 13 and 16 to give the title compound in 35% yield as a yellow solid. MS (ESI) m/z: 674.29 (M+H)+.

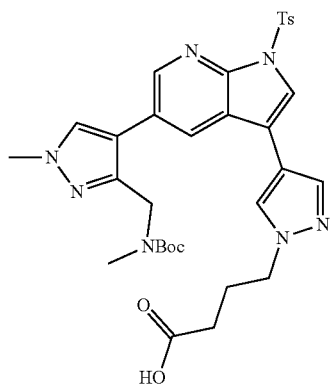 [SMILES: Cc1ccc(S(=O)(=O)n2cc(-c3cnn(CCCC(=O)O)c3)c3cc(-c4cn(C)nc4CN(C)C(=O)OC(C)(C)C)cnc32)cc1]

4-(4-(5-(3-(((tert-butoxycarbonyl)(methyl)amino)
methyl)-1-methyl-1H-pyrazol-4-yl)-1-tosyl-1H-pyr-
rolo[2,3-b]pyridin-3-yl)-1H-pyrazol-1-yl)butanoic
acid (25)

This compound was prepared using the same procedure as 21 using 11 and 16 to give the title compound in 36% yield as a brown solid. MS (ESI) m/z: 648.62 (M+H)+.

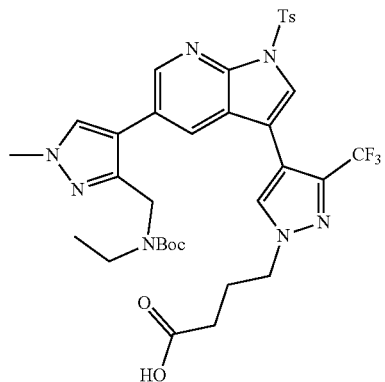

4-(4-(5-(3-(((tert-butoxycarbonyl)(ethyl)amino)
methyl)-1-methyl-1H-pyrazol-4-yl)-1-tosyl-1H-pyr-
rolo[2,3-b]pyridin-3-yl)-3-(trifluoromethyl)-1H-
pyrazol-1-yl)butanoic acid (27)

This compound was prepared using the same procedure as 21 using 12 and 18 to give the title compound in 35% yield as a white solid. MS (ESI) m/z: 730.73 (M+H)+.

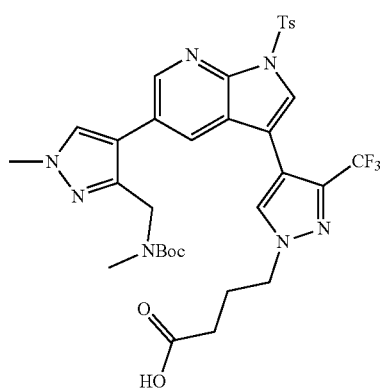 [SMILES: Cc1ccc(S(=O)(=O)n2cc(-c3cn(CCCC(=O)O)nc3C(F)(F)F)c3cc(-c4cn(C)nc4CN(C)C(=O)OC(C)(C)C)cnc32)cc1]

4-(4-(5-(3-(((tert-butoxycarbonyl)(methyl)amino)
methyl)-1-methyl-1H-pyrazol-4-yl)-1-tosyl-1H-pyr-
rolo[2,3-b]pyridin-3-yl)-3-(trifluoromethyl)-1H-
pyrazol-1-yl)butanoic acid (26)

This compound was prepared using the same procedure as 21 using 11 and 18 to give the title compound in 34% yield as a white solid. MS (ESI) m/z: 716.32 (M+H)+.

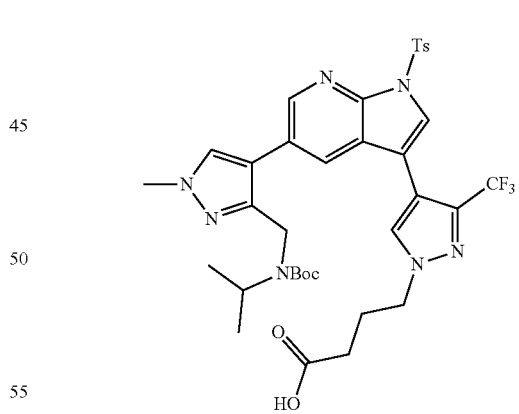

4-(4-(5-(3-(((tert-butoxycarbonyl)(isopropyl)amino)
methyl)-1-methyl-1H-pyrazol-4-yl)-1-tosyl-1H-pyr-
rolo[2,3-b]pyridin-3-yl)-3-(trifluoromethyl)-1H-
pyrazol-1-yl)butanoic acid (28)

This compound was prepared using the same procedure as 21 using 14 and 18 to give the title compound in 37% yield as a white solid. MS (ESI) m/z: 744.65 (M+H)+.

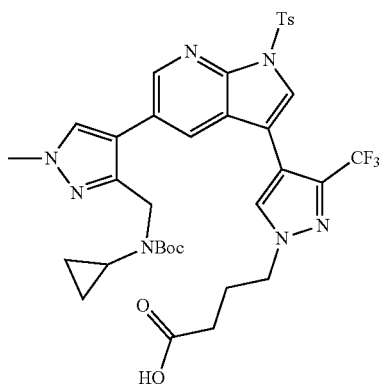 [SMILES: Cc1ccc(S(=O)(=O)n2cc(-c3cn(CCCC(=O)O)nc3C(F)(F)F)c3cc(-c4cn(C)nc4CN(C(=O)OC(C)(C)C)C4CC4)cnc32)cc1]

4-(4-(5-(3-(((tert-butoxycarbonyl)(cyclopropyl)amino)methyl)-1-methyl-1H-pyrazol-4-yl)-1-tosyl-1H-pyrrolo[2,3-b]pyridin-3-yl)-3-(trifluoromethyl)-1H-pyrazol-1-yl)butanoic acid (29)

This compound was prepared using the same procedure as 21 using 13 and 18 to give the title compound in 38% yield as a yellow solid. MS (ESI) m/z: 742.21 (M+H)$^+$.

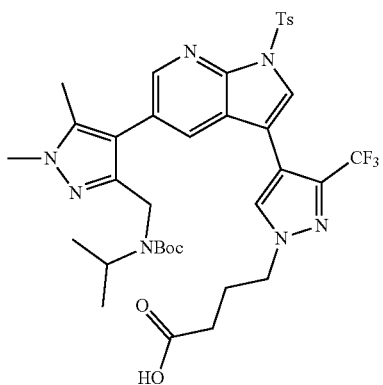

4-(4-(5-(3-(((tert-butoxycarbonyl)(isopropyl)amino)methyl)-1,5-dimethyl-1H-pyrazol-4-yl)-1-tosyl-11H-pyrrolo[2,3-b]pyridin-3-yl)-3-(trifluoromethyl)-11H-pyrazol-1-yl)butanoic acid (31)

This compound was prepared using the same procedure as 21 using 18 and tert-butyl ((4-bromo-1,5-dimethyl-1H-pyrazol-3-yl)methyl)(isopropyl)carbamate to give the title compound in 28% yield as a white solid. MS (ESI) m/z: 758.32 (M+H)$^+$.

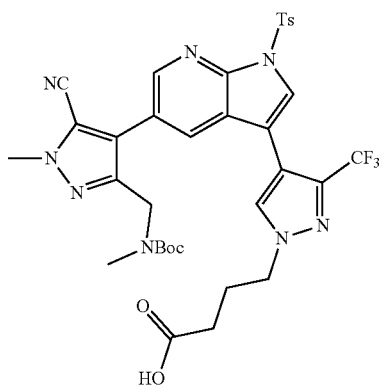 [SMILES: Cc1ccc(S(=O)(=O)n2cc(-c3cn(CCCC(=O)O)nc3C(F)(F)F)c3cc(-c4c(CN(C)C(=O)OC(C)(C)C)nn(C)c4C#N)cnc32)cc1]

4-(4-(5-(3-(((tert-butoxycarbonyl)(methyl)amino)methyl)-5-cyano-1-methyl-1H-pyrazol-4-yl)-1-tosyl-1H-pyrrolo [2,3-b]pyridin-3-yl)-3-(trifluoromethyl)-1H-pyrazol-1-yl)butanoic acid (30)

This compound was prepared using the same procedure as 21 using 18 and tert-Butyl ((4-bromo-5-cyano-1-methyl-1H-pyrazol-3-yl)methyl)(methyl)carbamate to give the title compound in 29% yield as a white solid. MS (ESI) m/z: 741.84 (M+H)$^+$.

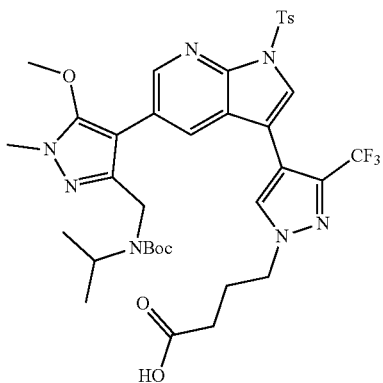 [SMILES: COc1c(-c2cnc3c(c2)c(-c2cn(CCCC(=O)O)nc2C(F)(F)F)cn3S(=O)(=O)c2ccc(C)cc2)c(CN(C(=O)OC(C)(C)C)C(C)C)nn1C]

4-(4-(5-(3-(((tert-butoxycarbonyl)(isopropyl)amino)methyl)-5-methoxy-1-methyl-11H-pyrazol-4-yl)-1-tosyl-1H-pyrrolo [2,3-b]pyridin-3-yl)-3-(trifluoromethyl)-1H-pyrazol-1-yl)butanoic acid (32)

This compound was prepared using the same procedure as 21 using 9 and 18 to give the title compound in 31% yield as a white solid. MS (ESI) m/z: 774.41 (M+H)$^+$.

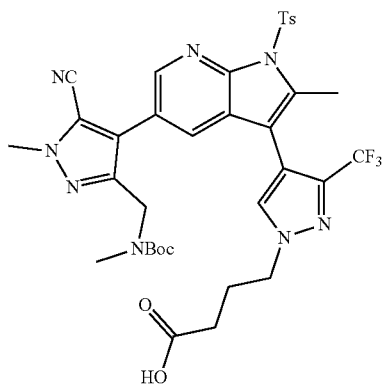 [SMILES: Cc1ccc(S(=O)(=O)n2c(C)c(-c3cn(CCCC(=O)O)nc3C(F)(F)F)c3cc(-c4c(CN(C)C(=O)OC(C)(C)C)nn(C)c4C#N)cnc32)cc1]

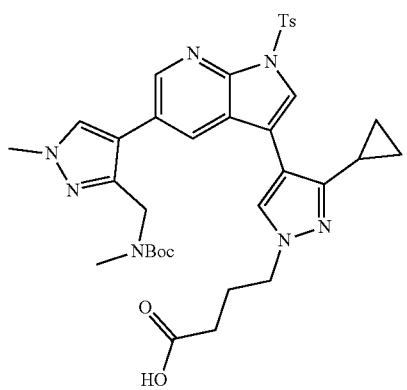

4-(4-(5-(3-(((tert-butoxycarbonyl)(methyl)amino)methyl)-5-cyano-1-methyl-1H-pyrazol-4-yl)-2-methyl-1-tosyl-11H-pyrrolo[2,3-b]pyridin-3-yl)-3-(trifluoromethyl)-1H-pyrazol-1-yl)butanoic acid (33)

This compound was prepared using the same procedure as 21 using 20 and tert-Butyl ((4-bromo-5-cyano-1-methyl-1H-pyrazol-3-yl)methyl)(methyl)carbamate to give the title compound in 29% yield as a white solid. MS (ESI) m/z: 755.61 (M+H)$^+$.

4-(4-(5-(3-(((tert-butoxycarbonyl)(methyl)amino)methyl)-1-methyl-1H-pyrazol-4-yl)-1-tosyl-1H-pyrrolo[2,3-b]pyridin-3-yl)-3-cyclopropyl-1H-pyrazol-1-yl)butanoic acid (35)

This compound was prepared using the same procedure as 21 using 11 and 19 to give the title compound in 26% yield as a yellow solid. MS (ESI) m/z: 688.23 (M+H)$^+$.

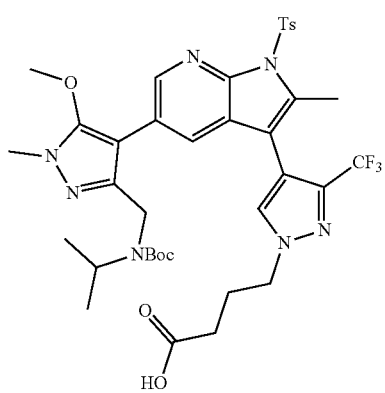 [SMILES: COc1c(-c2cnc3c(c2)c(-c2cn(CCCC(=O)O)nc2C(F)(F)F)c(C)n3S(=O)(=O)c2ccc(C)cc2)c(CN(C(=O)OC(C)(C)C)C(C)C)nn1C]

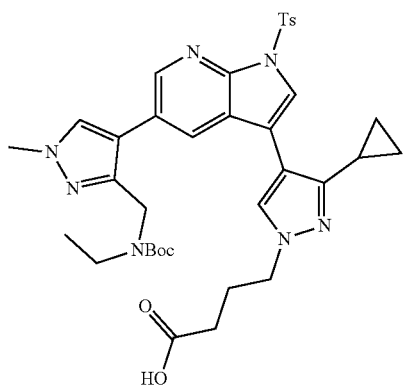 [SMILES: CCN(Cc1nn(C)cc1-c1cnc2c(c1)c(-c1cn(CCCC(=O)O)nc1C1CC1)cn2S(=O)(=O)c1ccc(C)cc1)C(=O)OC(C)(C)C]

4-(4-(5-(3-(((tert-butoxycarbonyl)(isopropyl)amino)methyl)-5-methoxy-1-methyl-1H-pyrazol-4-yl)-2-methyl-1-tosyl-1H-pyrrolo[2,3-b]pyridin-3-yl)-3-(trifluoromethyl)-1H-pyrazol-1-yl)butanoic acid (34)

This compound was prepared using the same procedure as 21 using 9 and 20 to give the title compound in 28% yield as a white solid. MS (ESI) m/z: 788.43 (M+H)$^+$.

4-(4-(5-(3-(((tert-butoxycarbonyl)(ethyl)amino)methyl)-1-methyl-1H-pyrazol-4-yl)-1-tosyl-1H-pyrrolo[2,3-b]pyridin-3-yl)-3-cyclopropyl-1H-pyrazol-1-yl)butanoic acid (36)

This compound was prepared using the same procedure as 21 using 12 and 19 to give the title compound in 24% yield as a yellow solid. MS (ESI) m/z: 702.49 (M+H)$^+$.

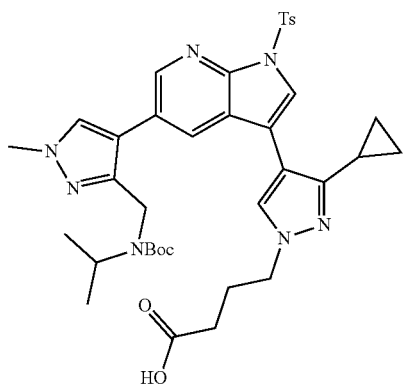 [SMILES: Cc1ccc(S(=O)(=O)n2cc(-c3cn(CCCC(=O)O)nc3C3CC3)c3cc(-c4cn(C)nc4CN(C(=O)OC(C)(C)C)C(C)C)cnc32)cc1]

4-(4-(5-(3-(((tert-butoxycarbonyl)(isopropyl)amino)methyl)-1-methyl-1H-pyrazol-4-yl)-1-tosyl-1H-pyrrolo[2,3-b]pyridin-3-yl)-3-cyclopropyl-1H-pyrazol-1-yl)butanoic acid (37)

This compound was prepared using the same procedure as 21 using 14 and 19 to give the title compound in 27% yield as a yellow solid. MS (ESI) m/z: 716.36 (M+H)$^+$.

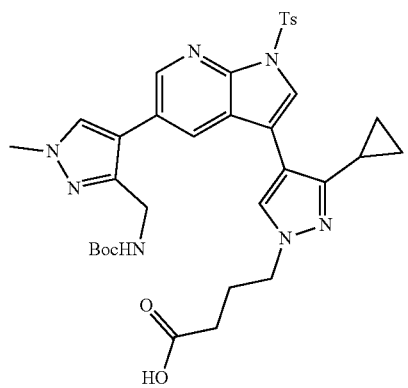

4-(4-(5-(3-(((tert-butoxycarbonyl)amino)methyl)-1-methyl-1H-pyrazol-4-yl)-1-tosyl-1H-pyrrolo[2,3-b]pyridin-3-yl)-3-cyclopropyl-1H-pyrazol-1-yl)butanoic acid (39)

This compound was prepared using the same procedure as 21 using 15 and 19 to give the title compound in 22% yield as a yellow solid. MS (ESI) m/z: 674.71 (M+H)$^+$.

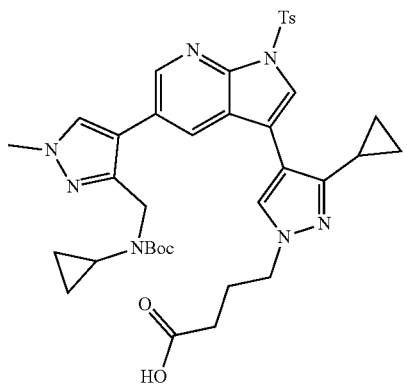 [SMILES: Cc1ccc(S(=O)(=O)n2cc(-c3cn(CCCC(=O)O)nc3C3CC3)c3cc(-c4cn(C)nc4CN(C(=O)OC(C)(C)C)C4CC4)cnc32)cc1]

4-(4-(5-(3-(((tert-butoxycarbonyl)(cyclopropyl)amino)methyl)-1-methyl-1H-pyrazol-4-yl)-1-tosyl-1H-pyrrolo[2,3-b]pyridin-3-yl)-3-cyclopropyl-1H-pyrazol-1-yl)butanoic acid (38)

This compound was prepared using the same procedure as 21 using 13 and 19 to give the title compound in 28% yield as a yellow solid. MS (ESI) m/z: 714.24 (M+H)$^+$.

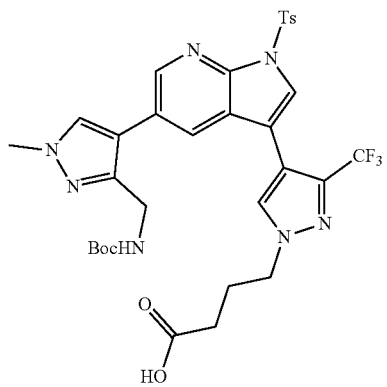 [SMILES: Cc1ccc(S(=O)(=O)n2cc(-c3cn(CCCC(=O)O)nc3C(F)(F)F)c3cc(-c4cn(C)nc4CNC(=O)OC(C)(C)C)cnc32)cc1]

4-(4-(5-(3-(((tert-butoxycarbonyl)amino)methyl)-1-methyl-1H-pyrazol-4-yl)-1-tosyl-1H-pyrrolo [2,3-b]pyridin-3-yl)-3-(trifluoromethyl)-1H-pyrazol-1-yl)butanoic acid (40)

This compound was prepared using the same procedure as 21 using 15 and 18 to give the title compound in 21% yield as a white solid. MS (ESI) m/z: 702.27 (M+H)$^+$.

Example 3: Synthesis of (Z)-31,5-dimethyl-11H, 21H,31H-5-aza-2(3,5)-pyrrolo[2,3-b]pyridina-1(4,1), 3(4,3)-dipyrazolacyclononaphan-6-one (41)

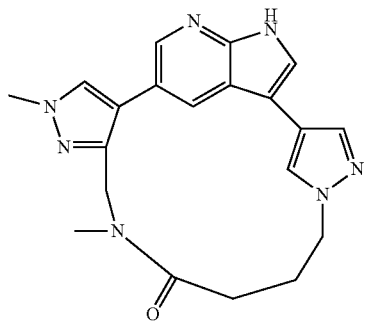 [SMILES: CN1Cc2nn(C)cc2-c2cnc3[nH]cc(c3c2)-c2cnn(c2)CCCC1=O]

4-(4-(5-(3-(((tert-butoxycarbonyl)(methyl)amino)methyl)-1-methyl-1H-pyrazol-4-yl)-1-tosyl-1H-pyrrolo[2,3-b]pyridin-3-yl)-1H-pyrazol-1-yl)butanoic acid (100 mg, 0.154 mmol) was dissolved in DCM (10 mL). Trifluoroacetic acid (TFA) (1 mL) was added and the reaction was stirred for 1 h. The reaction mixture was concentrated in vacuo to a brown residue which was dissolved in DMF (4 mL) and DIEA (135 μL, 0.772 mmol). This solution was added dropwise over 30 min to a solution of 1-[Bis(dimethylamino)methylene]-1H-1,2,3-triazolo[4,5-b]pyridinium 3-oxid hexafluorophosphate (HATU) (117 mg, 0.308 mmol) in DMF (20 mL) at 0° C. The reaction mixture was stirred for an additional 15 min at rt, then quenched with H₂O, and extracted with EtOAc. The combined organic extracts were washed with water, brine, dried over MgSO₄, and concentrated in vacuo to give a brown oil that was dissolved in MeOH (3 mL), acetone (3 mL), and NaOH 3M (3 mL). The reaction mixture was heated to 65° C. for 30 min, then cooled to rt, and extracted with EtOAc. The combined organic layers were washed with H₂O, brine, dried over MgSO₄, and concentrated in vacuo to give a brown oil that was purified by reverse phase HPLC (0%-60% MeCN:H₂O) to give the title compound as a white solid (28 mg, 48% yield over 3 steps). ¹H NMR (500 MHz, DMSO) δ 11.67 (s, 1H), 8.49 (s, 1H), 7.79 (s, 1H), 7.75 (s, 1H), 7.51 (m, 2H), 4.49 (t, J=6 Hz, 2H), 4.34 (m, 2H), 3.89 (s, 3H), 2.74, (s, 3H), 2.61 (m, 2H), 2.16 (m, 2H). MS (ESI) m/z 376.47 (M+H)⁺.

Example 4: Synthesis of (Z)-31,5-dimethyl-11H, 21H,31H-5-aza-2(3,5)-pyrrolo[2,3-b]pyridina-1(4,1), 3(4,3)-dipyrazolacyclodecaphan-6-one (42)

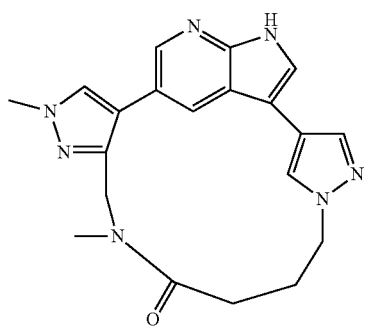 [SMILES: CN1Cc2nn(C)cc2-c2cnc3[nH]cc(c3c2)-c2cnn(c2)CCCC1=O]

This compound was prepared using the same procedure as 41 using 21 to give the title compound in 46% yield as a white solid. ¹H NMR (500 MHz, DMSO) δ 11.71 (s, 1H), 8.25 (s, 1H), 8.09 (s, 1H), 7.98 (s, 1H), 7.72 (s, 1H), 7.68 (s, 1H), 4.38 (m, 2H), 4.28 (t, J=6 Hz, 2H), 3.91 (s, 3H), 2.98 (s, 3H), 2.52, (m, 2H), 1.81 (m, 2H), 1.0 (m, 2H). MS (ESI) m/z 390.71 (M+H)⁺.

Example 5: Synthesis of (Z)-31,5-dimethyl-13-(trifluoromethyl)-11H,21H,31H-5-aza-2(3,5)-pyrrolo[2,3-b]pyridina-1(4,1),3(4,3)-dipyrazolacyclononaphan-6-one (43)

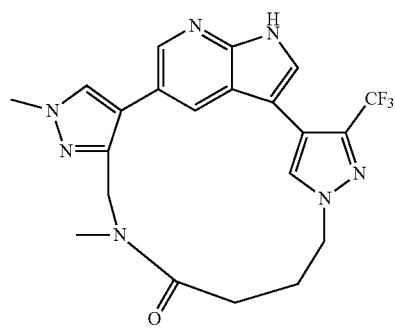 [SMILES: CN1Cc2nn(C)cc2-c2cnc3[nH]cc(c3c2)-c2cn(nc2C(F)(F)F)CCCC1=O]

This compound was prepared using the same procedure as 41 using 26 to give the title compound in 39% yield as a white solid. ¹H NMR (500 MHz, DMSO) δ 11.87 (s, 1H), 8.51 (s, 1H), 8.27 (s, 1H), 8.04 (s, 1H), 7.67 (s, 1H), 7.41 (s, 1H), 4.56 (t, J=6 Hz, 2H), 4.41 (m, 2H), 3.89 (s, 3H), 2.80 (s, 3H), 2.60, (m, 2H), 2.15 (m, 2H). MS (ESI) m/z 444.27 (M+H)⁺.

Example 6: Synthesis of (Z)-5-ethyl-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (44)

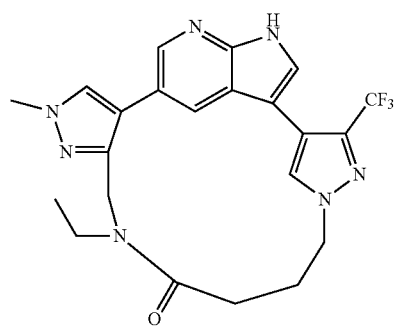 [SMILES: CCN1Cc2nn(C)cc2-c2cnc3[nH]cc(c3c2)-c2cn(nc2C(F)(F)F)CCCC1=O]

This compound was prepared using the same procedure as 41 using 27 to give the title compound in 52% yield as a white solid. ¹H NMR (500 MHz, DMSO) δ 11.88 (s, 1H), 8.52 (s, 1H), 8.28 (s, 1H), 7.97 (s, 1H), 7.67 (s, 1H), 7.41 (s, 1H), 4.59 (t, J=6 Hz, 2H), 4.42 (m, 2H), 4.03 (q, J=8 Hz, 2H), 3.89 (s, 3H), 2.63 (m, 2H), 2.18, (m, 2H), 0.98 (t, J=7 Hz, 3H). MS (ESI) m/z 458.53 (M+H)⁺.

Example 7: Synthesis of (Z)-5-isopropyl-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (45)

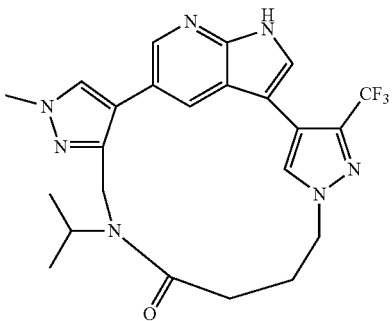 [SMILES: CC(C)N1Cc2nn(C)cc2-c2cnc3[nH]cc(c3c2)-c2cn(nc2C(F)(F)F)CCCC1=O]

This compound was prepared using the same procedure as 41 using 28 to give the title compound in 54% yield as a white solid. $^1$H NMR (500 MHz, DMSO) δ 11.86 (s, 1H), 8.53 (s, 1H), 8.27 (s, 1H) 8.01 (s, 1H), 7.69 (s, 1H), 7.41 (s, 1H), 4.41 (t, J=6 Hz, 2H), 4.23 (m, 2H), 3.89 (s, 3H), 2.68 (m, 2H), 2.26, (m, 2H), 1.99 (m, 1H), 1.06 (s, 6H). MS (ESI) m/z 472.42 (M+H)$^+$.

Example 8: Synthesis of (Z)-5-cyclopropyl-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (46)

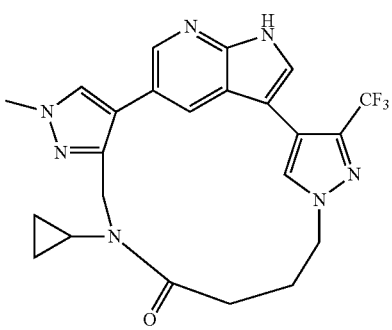 [SMILES: Cn1cc2c(n1)CN(C1CC1)C(=O)CCCn1cc(c(C(F)(F)F)n1)-c1c[nH]c3ncc-2cc13]

This compound was prepared using the same procedure as 41 using 29 to give the title compound in 52% yield as a yellow solid. $^1$H NMR (500 MHz, DMSO) δ 11.88 (s, 1H), 8.56 (s, 1H), 8.30 (s, 1H) 8.00 (s, 1H), 7.67 (s, 1H), 7.42 (s, 1H), 4.62 (m, 2H), 4.46 (t, J=6 Hz, 2H), 3.89 (s, 3H), 2.62 (m, 2H), 2.29, (m, 2H), 2.17 (m, 1H), 0.71 (m, 2H), 0.58 (m, 2H). MS (ESI) m/z 470.57 (M+H)$^+$.

Example 9: (Z)-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (47)

[Structure]

This compound was prepared using the same procedure as 41 using 39 to give the title compound in 57% yield as a white solid. MS (ESI) m/z 440.47 (M+H)$^+$.

Example 10: Synthesis of (Z)-31,5-dimethyl-6-oxo-13-(trifluoromethyl)-11H,21H,31H-5-aza-2(3,5)-pyrrolo[2,3-b]pyridina-1(4,1),3(4,3)-dipyrazolacyclononaphane-35-carbonitrile (48)

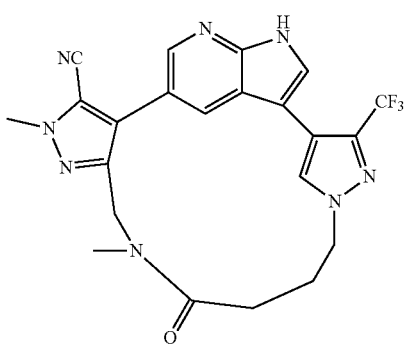 [SMILES: CN1Cc2nn(C)c(C#N)c2-c2cnc3[nH]cc(c3c2)-c2cn(nc2C(F)(F)F)CCCC1=O]

This compound was prepared using the same procedure as 41 using 30 to give the title compound in 57% yield as a white solid. $^1$H NMR (500 MHz, DMSO) δ 12.01 (s, 1H), 8.61 (s, 1H), 8.14 (s, 1H) 7.71 (s, 1H), 7.53 (s, 1H), 4.55 (m, 2H), 4.34 (t, J=6 Hz, 2H), 4.13 (s, 3H), 2.83 (s, 3H), 2.71, (m, 2H), 2.22 (m, 2H). MS (ESI) m/z 469.26 (M+H)$^+$.

Example 11: Synthesis of (Z)-5-isopropyl-31,35-dimethyl-13-(trifluoromethyl)-11H,21H,31H-5-aza-2(3,5)-pyrrolo[2,3-b]pyridina-1(4,1),3(4,3)-dipyrazolacyclononaphan-6-one (49')

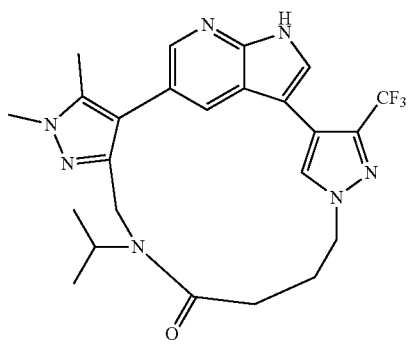 [SMILES: Cc1c2c(nn1C)CN(C(C)C)C(=O)CCCn1cc(c(C(F)(F)F)n1)-c1c[nH]c3ncc-2cc13]

This compound was prepared using the same procedure as 41 using 31 to give the title compound in 50% yield as a white solid. $^1$H NMR (500 MHz, DMSO) δ 11.93 (s, 1H), 8.23 (s, 1H), 8.16 (s, 1H) 7.52 (s, 1H), 7.45 (s, 1H), 4.66 (m, 2H), 4.35 (t, J=6 Hz, 2H), 3.83 (s, 3H), 2.70 (m, 2H), 2.43, (m, 2H), 2.39 (s, 3H), 1.92 (m, 1H), 1.09 (s, 6H). MS (ESI) m/z 486.29 (M+H)$^+$.

Example 12: Synthesis of (Z)-5-isopropyl-35-methoxy-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (50)

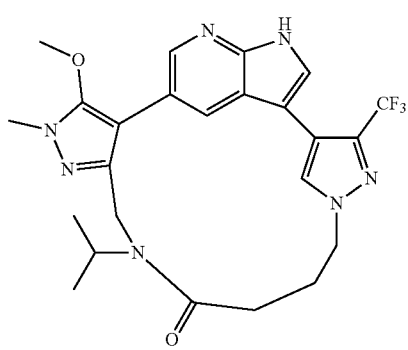 [SMILES: COc1c2c(nn1C)CN(C(C)C)C(=O)CCCn1cc(c(C(F)(F)F)n1)-c1c[nH]c3ncc-2cc13]

This compound was prepared using the same procedure as 41 using 32 to give the title compound in 46% yield as a white solid. $^1$H NMR (500 MHz, DMSO) δ 11.90 (s, 1H), 8.58 (s, 1H), 8.05 (s, 1H) 7.61 (s, 1H), 7.42 (s, 1H), 4.64 (m, 2H), 4.38 (t, J=6 Hz, 2H), 3.75 (s, 3H), 3.73 (s, 3H), 2.70 (m, 2H), 2.31, (m, 2H), 2.0 (m, 1H), 1.10 (s, 6H). MS (ESI) m/z 502.37 (M+H)$^+$.

Example 13: Synthesis of (Z)-5-isopropyl-35-methoxy-22,31-dimethyl-13-(trifluoromethyl)-11H,21H,31H-5-aza-2(3,5)-pyrrolo[2,3-b]pyridina-1(4,1),3(4,3)-dipyrazolacyclononaphan-6-one (51)

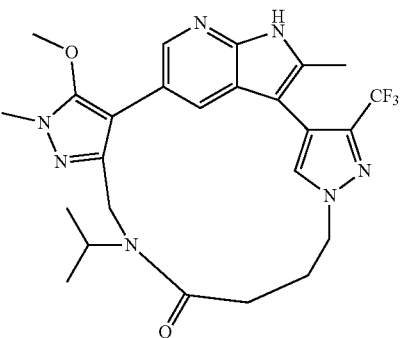 [SMILES: COc1c2c(nn1C)CN(C(C)C)C(=O)CCCn1cc(c(C(F)(F)F)n1)-c1c(C)[nH]c3ncc-2cc13]

This compound was prepared using the same procedure as 41 using 34 to give the title compound in 52% yield as a white solid. $^1$H NMR (500 MHz, DMSO) δ 11.71 (s, 1H), 8.43 (s, 1H), 7.90 (s, 1H) 7.31 (s, 1H), 4.58 (m, 2H), 4.38 (t, J=6 Hz, 2H), 3.74 (s, 3H), 3.72 (s, 3H), 2.70 (m, 2H), 2.33 (s, 3H), 2.30, (m, 2H), 1.81 (m, 1H), 1.05 (s, 6H). MS (ESI) m/z 516.74 (M+H)$^+$.

Example 14: Synthesis of (Z)-22,31,5-trimethyl-6-oxo-13-(trifluoromethyl)-11H,21H,31H-5-aza-2(3,5)-pyrrolo[2,3-b]pyridina-1(4,1),3(4,3)-dipyrazolacyclononaphane-35-carbonitrile (52)

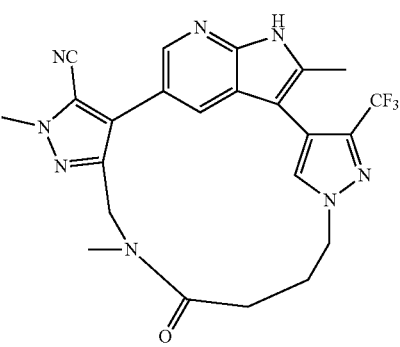 [SMILES: Cc1[nH]c2ncc3cc2c1-c1cn(nc1C(F)(F)F)CCCC(=O)N(C)Cc1nn(C)c(C#N)c1-3]

This compound was prepared using the same procedure as 41 using 33 to give the title compound in 48% yield as a white solid. $^1$H NMR (500 MHz, DMSO) δ 11.94 (s, 1H), 8.47 (s, 1H), 7.93 (s, 1H) 7.32 (s, 1H), 4.52 (m, 2H), 4.37 (t, J=6 Hz, 2H), 4.08 (s, 3H), 2.75 (s, 3H), 2.60 (m, 2H), 2.36 (s, 3H), 2.26, (m, 2H). MS (ESI) m/z 483.28 (M+H)$^+$.

Example 15: Synthesis of (Z)-13-cyclopropyl-31-methyl-11H,21H,31H-5-aza-2(3,5)-pyrrolo[2,3-b]pyridina-1(4,1),3(4,3)-dipyrazolacyclononaphan-6-one (53)

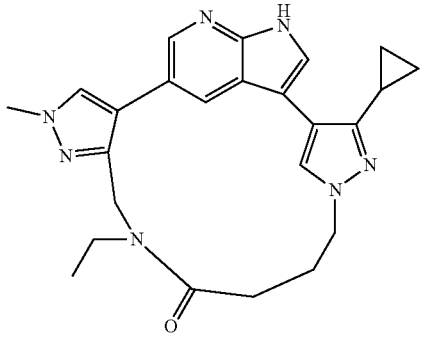 [SMILES: CCN1Cc2nn(C)cc2-c2cnc3[nH]cc(c3c2)-c2cn(nc2C2CC2)CCCC1=O]

This compound was prepared using the same procedure as 41 using 36. MS (ESI) m/z 402.83 (M+H)$^+$.

Example 16: Synthesis of (Z)-13-cyclopropyl-31,5-dimethyl-11H,21H,31H-5-aza-2(3,5)-pyrrolo[2,3-b]pyridina-1(4,1),3(4,3)-dipyrazolacyclononaphan-6-one (54)

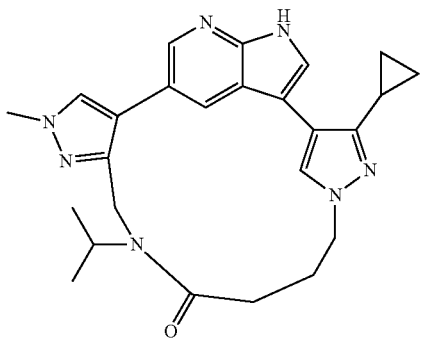 [SMILES: CC(C)N1Cc2nn(C)cc2-c2cnc3[nH]cc(c3c2)-c2cn(nc2C2CC2)CCCC1=O]

This compound was prepared using the same procedure as 41 using 37. MS (ESI) m/z 416.41 (M+H)$^+$.

Example 17: Synthesis of (Z)-13,5-dicyclopropyl-31-methyl-11H,21H,31H-5-aza-2(3,5)-pyrrolo[2,3-b]pyridina-1(4,1),3(4,3)-dipyrazolacyclononaphan-6-one (55)

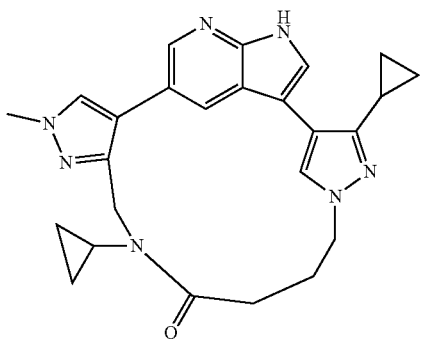 [SMILES: Cn1cc2c(n1)CN(C1CC1)C(=O)CCCn1cc(c(C3CC3)n1)-c1c[nH]c3ncc-2cc13]

This compound was prepared using the same procedure as 41 using 38. MS (ESI) m/z 442.52 (M+H)$^+$.

Example 18: Synthesis of (Z)-13-cyclopropyl-31-methyl-11H,21H,31H-5-aza-2(3,5)-pyrrolo[2,3-b]pyridina-1(4,1),3(4,3)-dipyrazolacyclononaphan-6-one (56)

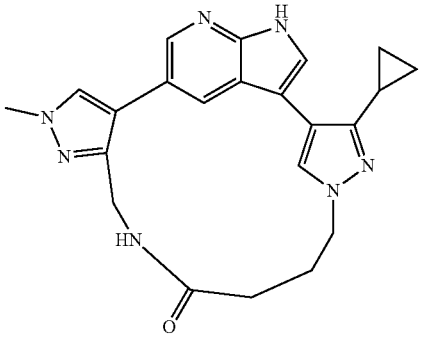 [SMILES: Cn1cc2c(n1)CNC(=O)CCCn1cc(c(C3CC3)n1)-c1c[nH]c3ncc-2cc13]

This compound was prepared using the same procedure as 41 using 39. MS (ESI) m/z 402.83 (M+H)$^+$.

Example 19: Synthesis of (Z)-13-cyclopropyl-31,5-dimethyl-11H,21H,31H-5-aza-2(3,5)-pyrrolo[2,3-b]pyridina-1(4,1),3(4,3)-dipyrazolacyclononaphan-6-one (57)

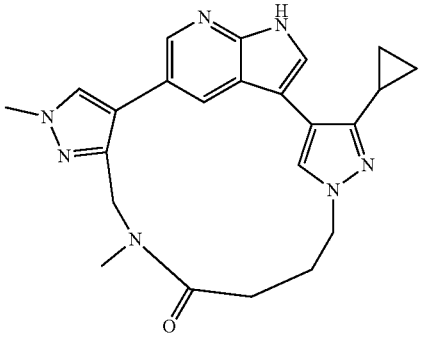 [SMILES: CN1Cc2nn(C)cc2-c2cnc3[nH]cc(c3c2)-c2cn(nc2C2CC2)CCCC1=O]

This compound was prepared using the same procedure as 41 using 35. MS (ESI) m/z 416.41 (M+H)$^+$.

Example 20: Synthesis of (Z)-31-methyl-13-(trifluoromethyl)-11H,21H,31H-5-aza-2(3,5)-pyrrolo[2,3-b]pyridina-1(4,1),3(4,3)-dipyrazolacyclononaphan-6-one (58)

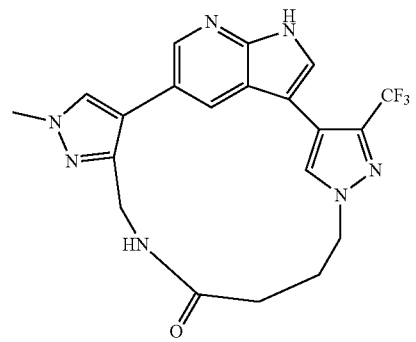 [SMILES: Cn1cc2c(n1)CNC(=O)CCCn1cc(c(C(F)(F)F)n1)-c1c[nH]c3ncc-2cc13]

This compound was prepared using the same procedure as 41 using 39. MS (ESI) m/z 430.47 (M+H)$^+$.

Example 21: Synthesis of (Z)-3¹-(2-methoxyethyl)-5-methyl-1³-(trifluoromethyl)-1¹H,2¹H,3¹H-5-aza-2(3,5)-pyrrolo[2,3-b]pyridina-1(4,1),3(4,3)-dipyrazolacyclononaphan-6-one

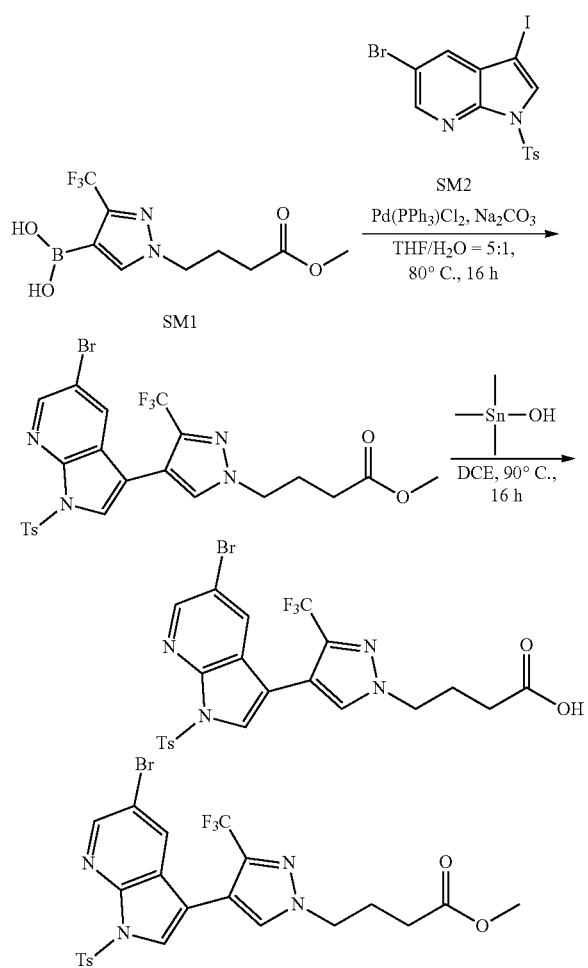

Methyl 4-(4-(5-bromo-1-tosyl-1H-pyrrolo[2,3-b]pyridin-3-yl)-3-(trifluoromethyl)-1H-pyrazol-1-yl)butanoate Bis(triphenylphosphine)palladium(II) chloride (0.25 g, 0.36 mmol) was added to a mixture of SM1 (1 g, 3.57 mmol), SM2 (1.71 g, 3.57 mmol) and sodium carbonate (1.90 g, 17.86 mmol) in THF (30 mL) and H₂O (6 mL). The yellow mixture was degassed with nitrogen×3 and stirred at 80° C. for 16 h. The reaction mixture was poured into water (100 mL), and extracted with EtOAc (100 mL×3). The combined organic layers were washed with water, brine (200 mL), dried over Na₂SO₄ and concentrated under vacuum. The crude compound was purified by silica gel column (PE/EtOAc=2:1, V/V) to give 1.3 g of the title compound as a yellow solid.

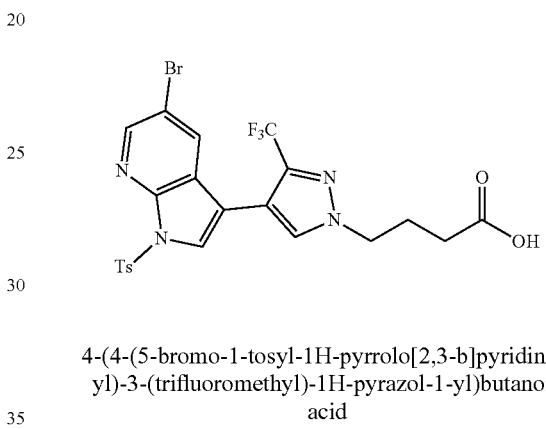

4-(4-(5-bromo-1-tosyl-1H-pyrrolo[2,3-b]pyridin-3-yl)-3-(trifluoromethyl)-1H-pyrazol-1-yl)butanoic acid Trimethyltin hydroxide (167.1 mg, 0.924 mmol) was added to a solution of methyl 4-(4-(5-bromo-1-tosyl-1H-pyrrolo[2,3-b]pyridin-3-yl)-3-(trifluoromethyl)-1H-pyrazol-1-yl)butanoate (132 mg, 0.231 mmol) in DCE (5 mL). The mixture stirred at 80° C. overnight under a nitrogen atmosphere. The mixture was concentrated under vacuum and the crude compound was purified by silica gel column (DCM/MeOH=10:1, V/V) to give 120 mg of the title compound as a yellow solid.

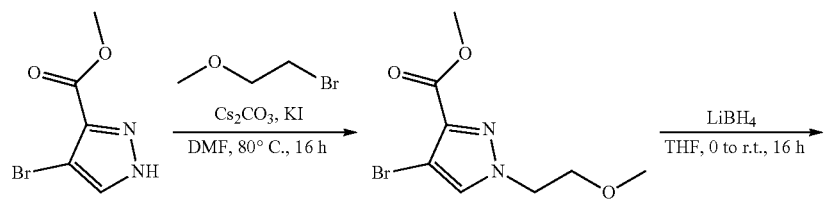

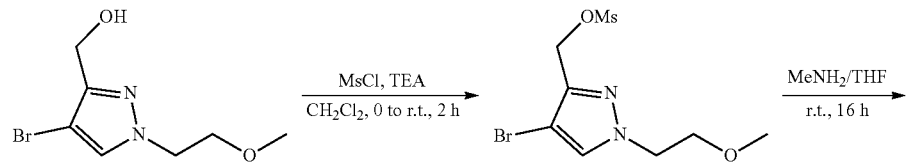

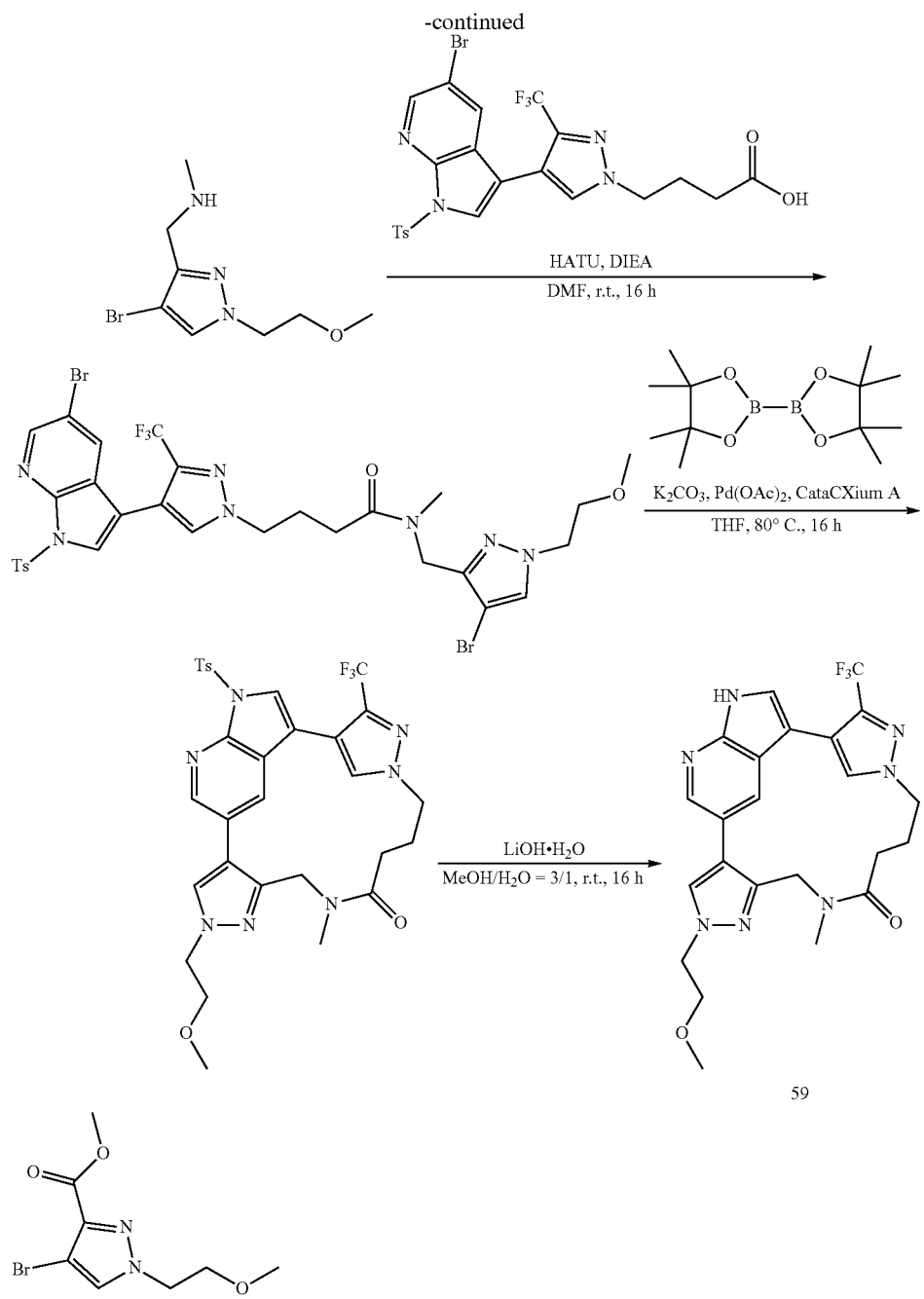

59

Methyl 4-bromo-1-(2-methoxyethyl)-1H-pyrazole-3-caroxylate

Cs₂CO₃ (2.2 g, 6.89 mmol) and KI (572 mg, 3.445 mmol) was added to a solution of methyl 4-bromo-1H-pyrazole-3-caroxylate (658 mg, 3.445 mmol) and 1-bromo-2-methyoxyethane (718 mg, 5.167 mmol) in DMF (4 mL) at rt and then heated to 130° C. The reaction mixture stirred for 16 h. After cooling to rt, the reaction mixture was diluted with water (20 mL) and extracted with EtOAc (15 mL×3). The combined organic layer was washed with water (50 mL), brine (50 mL), dried over Na₂SO₄ and then concentrated under vacuum. The crude was purified by silica gel column (Pet.ether:EtOAc=5:1, V/V) to give 174 mg of the title compound as oil.

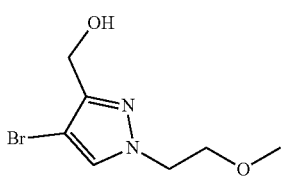

(4-bromo-1-(2-methoxyethyl)-1H-pyrazol-3-yl) methanol

LiBH₄ (1.6 mL, 3.26 mmol, 2 M in THF) was added slowly at 0° C. to a solution of methyl 4-bromo-1-(2- methoxyethyl)-1H-pyrazole-3-carboxylate (167 mg, 0.544 mmol) in THF (2 mL). The reaction mixture stirred at rt for 16 h. The reaction mixture was diluted with NH₄Cl aq. (10 mL), water (20 mL) and extracted with EtOAc (15 mL×3). The combined organic layers were washed with brine (50 mL), dried over Na₂SO₄ and concentrated under vacuum. The crude compound was purified by silica gel column (DCM/MeOH=40:1, V/V) to give 100 mg of the title compound as colorless oil.

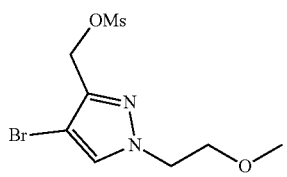 [SMILES: COCCn1cc(Br)c(COS(C)(=O)=O)n1]

(4-bromo-1-(2-methoxyethyl)-1H-pyrazol-3-yl) methyl methanesulfonate

TEA (63 mg, 0.63 mmol) and MsCl (72 mg, 0.63 mmol) were slowly added at 0° C. to a solution of (4-bromo-1-(2-methoxyethyl)-1H-pyrazol-3-yl)methanol (98 mg, 0.42 mmol) in DCM (2 mL) and then the reaction mixture stirred at rt for 1 h. The reaction mixture was diluted with water (20 mL) and extracted with DCM (15 mL×3). The combined organic layers were washed with water (50 mL), brine (50 mL), dried over Na₂SO₄ and then concentrated under vacuum to give 123 mg yellow oil. The crude material was used in the next step without further purification.

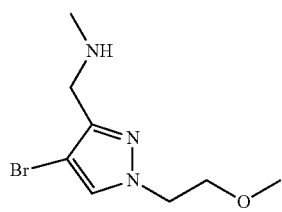

1-(4-bromo-1-(2-methoxyethyl)-1H-pyrazol-3-yl)-N-methylmethanamine

A solution of crude (4-bromo-1-(2-methoxyethyl)-1H-pyrazol-3-yl)methyl methanesulfonate (123 mg, 0.39 mmol) in MeNH₂/THF (10 mL) was stirred in a sealed tube at rt for 16 h. The mixture was concentrated under vacuum and then purified by silica gel column (DCM/MeOH=40:1, V/V) to give 58 mg of the title compound as yellow oil.

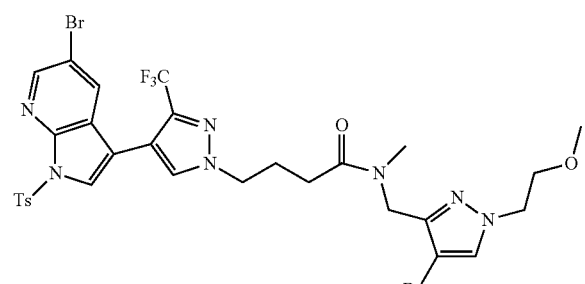

N-((4-bromo-1-(2-methoxyethyl)-1H-pyrazol-3-yl) methyl)-4-(4-(5-bromo-1-tosyl-1H-pyrrolo[2,3-b] pyridin-3-yl)-3-(trifluoromethyl)-1H-pyrazol-1-yl)-N-methylbutanamide HATU (200 mg, 0.525 mmol) and DIEA (113 mg, 0.875 mmol) was added to a solution of 4-(4-(5-bromo-1-tosyl-1H-pyrrolo[2,3-b]pyridin-3-yl)-3-(trifluoromethyl)-1H-pyrazol-1-yl)butanoic acid (100 mg, 0.175 mmol) in DMF (2 mL) at rt and stirred for 30 min. 1-(4-Bromo-1-(2-methoxyethyl)-1H-pyrazol-3-yl)-N-methylmethanamine (43 mg, 0.175 mmol, 1.0 eq) was added to the reaction mixture at rt and then stirred for 16 h. The reaction mixture was diluted with water (20 mL) and extracted with EtOAc (15 mL×3). The combined organic layers were washed with water (50 mL), brine (50 mL), dried over Na₂SO₄ and then concentrated under vacuum. The crude was purified by silica gel column (DCM/MeOH=50:1, V/V) to give 100 mg of the title compound as a yellowish solid.

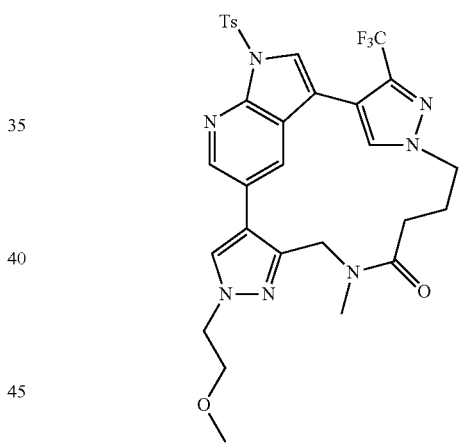

(Z)-31-(2-methoxyethyl)-5-methyl-21-tosyl-13-(trifluoromethyl)-11H,21H,31H-5-aza-2(3,5)-pyrrolo[2,3-b]pyridina-1(4,1),3(4,3)-dipyrazolacyclononaphan-6-one Pd(OAc)₂ (2.8 mg, 0.013 mmol) and CataCXium A (9 mg, 0.025 mmol) were added to a solution of N-((4-bromo-1-(2-methoxyethyl)-1H-pyrazol-3-yl)methyl)-4-(4-(5-bromo-1-tosyl-1H-pyrrolo[2,3-b]pyridin-3-yl)-3-(trifluoromethyl)-1H-pyrazol-1-yl)-N-methylbutanamide (100 mg, 0.125 mmol), bis(pinacolate)diboron (34.8 mg, 0.137 mmol) and K₂CO₃ (86 mg, 0.624 mmol) in THF (15 mL) at rt and then stirred under a nitrogen atmosphere at 80° C. for 16 h. The reaction mixture was concentrated under vacuum. The crude compound was purified by silica gel column (DCM/MeOH=50:1, V/V) to give 46 mg of the title compound as a yellow solid.

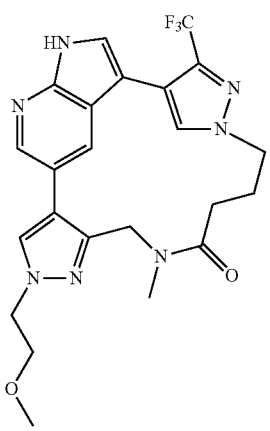 [SMILES: COCCn1cc2c(n1)CN(C)C(=O)CCCn1cc(c(C(F)(F)F)n1)-c1c[nH]c3ncc-2cc13]

(Z)-31-(2-methoxyethyl)-5-methyl-13-(trifluoromethyl)-11H,21H,31H-5-aza-2(3,5)-pyrrolo[2,3-b]pyridina-1(4,1),3(4,3)-dipyrazolacyclononaphan-6-one (59)

LiOH·H₂O (9 mg, 0.215 mmol) was added to a solution of (Z)-31-(2-methoxyethyl)-5-methyl-21-tosyl-13-(trifluoromethyl)-11H,21H,31H-5-aza-2(3,5)-pyrrolo[2,3-b]pyridina-1(4,1),3(4,3)-dipyrazolacyclononaphan-6-one (46 mg, 0.072 mmol) in MeOH/H₂O (4.5 mL/1.5 mL) at rt and stirred for 16 h. The reaction mixture was diluted with water (10 mL) and extracted with EtOAc (5 mL×3). The combined organic layers were washed with brine (20 mL), dried over Na₂SO₄ and concentrated under vacuum. The crude was purified by prep-TLC (DCM/MeOH=20:1, V/V) to give 13 mg of the title compound as a white solid. ¹H NMR (400 MHz, DMSO) δ 11.83 (s, 1H), 8.50 (s, 1H), 8.27 (s, 1H), 8.04 (s, 1H), 7.65 (s, 1H), 7.39 (s, 1H), 4.35 (br, 2H), 4.3 (t, J=5.2 Hz, 2H), 3.75 (t, J=5.2 Hz, 2H), 3.34 (br, 2H), 3.25 (s, 3H), 2.78 (s, 3H), 2.62 (br, 2H), 2.13 (br, 2H). MS (ESI) m/z 488.2 (M+H)⁺.

Example 22: Synthesis of (Z)-5-methyl-31-(piperidin-4-yl)-13-(trifluoromethyl)-11H,21H,31H-5-aza-2(3,5)-pyrrolo[2,3-b]pyridina-1(4,1),3(4,3)-dipyrazolacyclononaphan-6-one (60)

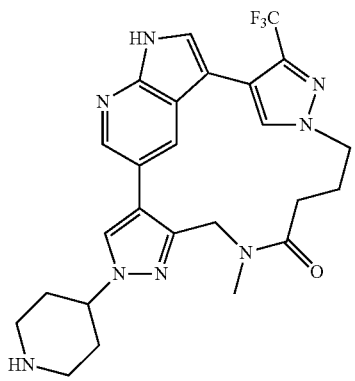 [SMILES: CN1Cc2nn(C3CCNCC3)cc2-c2cnc3[nH]cc(c3c2)-c2cn(nc2C(F)(F)F)CCCC1=O]

This compound was prepared in an analogous manner to 59 to give the title compound as a yellow solid. ¹H NMR (400 MHz, DMSO) δ 12.06 (s, 1H), 9.59 (s, 1H), 9.25 (s, 1H), 8.60 (s, 1H), 8.40 (s, 1H), 8.08 (s, 1H), 7.72 (s, 1H), 7.42 (s, 1H), 4.56 (br, 2H), 4.36 (br, 3H), 3.38 (br, 2H), 3.09 (br, 2H), 2.79 (s, 3H), 2.66 (s, 2H), 2.27 (s, 4H), 2.14 (brs, 2H). MS (ESI) m/z 513.3

Example 23: Synthesis of (Z)-31-(2-methoxyethyl)-5-methyl-6-oxo-13-(trifluoromethyl)-11H,21H,31H-5-aza-2(3,5)-pyrrolo[2,3-b]pyridina-1(4,1),3(4,3)-dipyrazolacyclononaphane-35-carbonitrile (61)

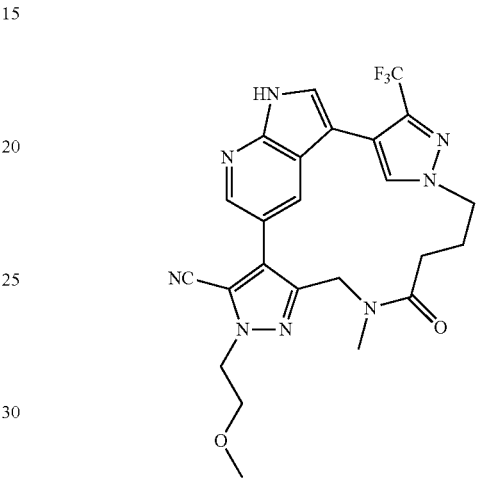

This compound was prepared in an analogous manner to 59 to give the title compound as a white solid. ¹H NMR (400 MHz, DMSO) δ 9.67 (s, 1H), 8.80 (s, 1H), 7.85 (s, 1H), 7.69 (s, 1H), 4.80 (br, 2H), 4.66 (br, 2H), 4.53 (5, J=4.0 Hz, 2H), 3.85 (t, J=4.0 Hz, 2H), 3.38 (s, 3H), 2.78 (s, 3H), 2.44 (br, 2H), 2.36 (br, 2H). MS (ESI) m/z 513.5 (M+H)⁺.

Example 24: Synthesis of (Z)-5-methyl-6-oxo-31-(piperidin-4-yl)-13-(trifluoromethyl)-11H,21H,31H-5-aza-2(3,5)-pyrrolo[2,3-b]pyridina-1(4,1),3(4,3)-dipyrazolacyclononaphane-35-carbonitrile (62)

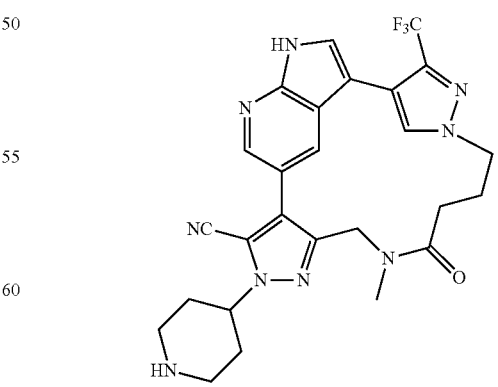

This compound was prepared in an analogous manner to 59. MS (ESI) m/z 538.2

Example 25: Synthesis of (Z)-31,5-dimethyl-13-(trifluoromethyl)-11H,21H,31H-5-aza-2(3,5)-pyrrolo[2,3-b]pyridina-1(4,1),3(4,3)-dipyrazolacyclooctaphan-6-one (63)

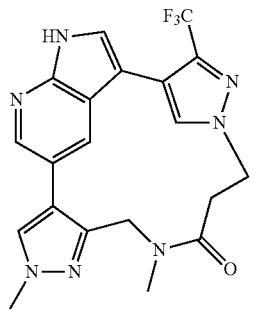 [SMILES: CN1Cc2nn(C)cc2-c2cnc3[nH]cc(c3c2)-c2cn(nc2C(F)(F)F)CCC1=O]

This compound was prepared in an analogous manner to 59 to give the title compound as a white solid. $^1$H NMR (400 MHz, DMSO) δ 11.83 (s, 1H), 8.50 (d, J=2.0 Hz, 1H), 8.25 (s, 1H), 8.10 (s, 1H), 7.51 (d, J=2.0 Hz, 1H), 7.45 (d, J=1.6 Hz, 1H), 5.15 (d, J=14.4 Hz, 1H), 4.78 (t, J=24.4 Hz, 1H), 4.44 (d, J=13.6 Hz, 1H), 3.96 (d, J=14.4 Hz, 1H), 3.89 (s, 3H), 3.25 (d, J=14.8 Hz, 1H), 2.84 (d, J=14.8 Hz, 1H), 2.82 (s, 3H). MS (ESI) m/z 430.0 (M+H)$^+$.

Example 26: Synthesis of (Z)-31-(2-methoxyethyl)-5-methyl-13-(trifluoromethyl)-11H,21H,31H-5-aza-2(3,5)-pyrrolo[2,3-b]pyridina-1(4,1),3(4,3)-dipyrazolacyclooctaphan-6-one (64)

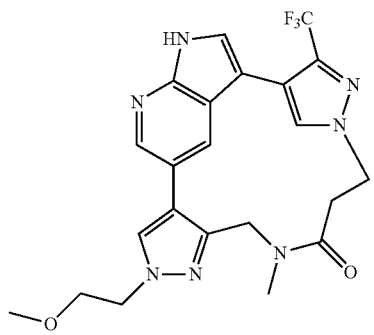 [SMILES: COCCn1cc2c(n1)CN(C)C(=O)CCn1cc(c(C(F)(F)F)n1)-c1c[nH]c3ncc-2cc13]

This compound was prepared in an analogous manner to 59 to give the title compound as a white solid. $^1$H NMR (400 MHz, DMSO) δ 11.84 (s, 1H), 8.51 (d, J=2.0 Hz, 1H), 8.28 (s, 1H), 8.12 (s, 1H), 7.52 (d, J=2.0 Hz, 1H), 7.47 (d, J=2.4 Hz, 1H), 5.15 (d, J=14.4 Hz, 1H), 4.78 (t, J=24.4 Hz, 1H), 4.48 (m, 1H), 4.30 (t, J=5.6, 2H), 3.96 (d, J=14.4 Hz, 1H), 3.74 (m, 2H), 3.25 (m, 4H), 2.82 (m, 4H). MS (ESI) m/z 474.1 (M+H)$^+$.

Example 27: Synthesis of (Z)-5-methyl-31-(piperidin-4-yl)-13-(trifluoromethyl)-11H,21H,31H-5-aza-2(3,5)-pyrrolo[2,3-b]pyridina-1(4,1),3(4,3)-dipyrazolacyclooctaphan-6-one (65)

This compound was prepared in an analogous manner to 59 to give the title compound as a white solid. $^1$H NMR (400 MHz, DMSO) δ 11.85 (s, 1H), 8.78 (br, 1H), 8.57 (s, 1H), 8.47 (br, 1H), 8.36 (s, 1H), 8.10 (s, 1H), 7.51 (s, 1H), 7.47 (s, 1H), 5.21 (d, J=14.4, 1H), 4.77 (t, J=13.2 1H), 4.43-4.56 (m, 2H), 3.97 (d, J=14.4, 1H), 3.46 (br, 2H), 3.28 (m, 1H), 3.10 (q, J=11.2 Hz, 2H), 2.81 (s, 3H), 2.28-2.13 (m, 4H). MS (ESI) m/z 499.0 (M+H)$^+$.

Example 28: Synthesis of (Z)-31,5-dimethyl-6-oxo-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (66)

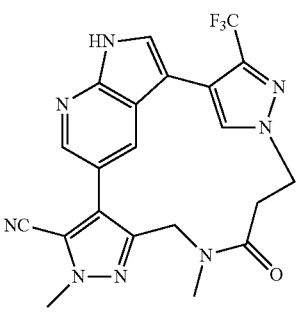 [SMILES: CN1Cc2nn(C)c(C#N)c2-c2cnc3[nH]cc(c3c2)-c2cn(nc2C(F)(F)F)CCC1=O]

This compound was prepared in an analogous manner to 59 to give the title compound as a white solid. $^1$H NMR (400 MHz, DMSO) δ 12.11 (s, 1H), 8.64 (s, 1H), 8.07 (s, 1H), 7.58 (s, 1H), 7.52 (s, 1H), 5.18 (d, J=14.4 Hz, 1H), 4.83 (br, 1H), 4.47 (d, J=13.6 Hz, 1H), 4.10 (s, 3H), 4.03 (br, 1H), 3.22-3.11 (m, 2H), 2.81 (br, 3H). MS (ESI) m/z 455.0 (M+H)$^+$.

Example 29: Synthesis of (Z)-31-(2-methoxyethyl)-5-methyl-6-oxo-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (67)

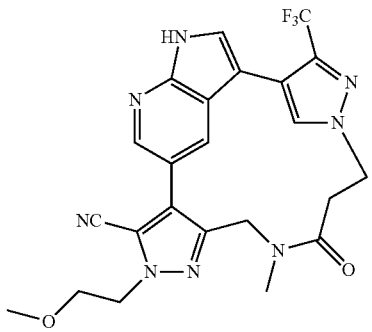 [SMILES: COCCn1nc2c(c1C#N)-c1cnc3[nH]cc(c3c1)-c1cn(nc1C(F)(F)F)CCC(=O)N(C)C2]

This compound was prepared in an analogous manner to 59. MS (ESI) m/z 499.2 (M+H)+.

Example 30: Synthesis of (Z)-5-methyl-6-oxo-31-(piperidin-4-yl)-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (68)

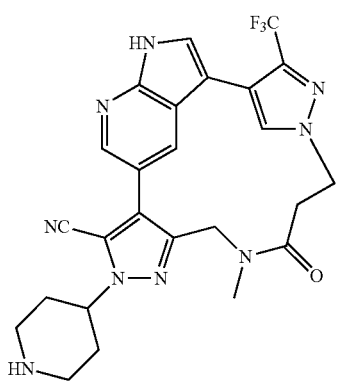 [SMILES: CN1Cc2nn(C3CCNCC3)c(C#N)c2-c2cnc3[nH]cc(c3c2)-c2cn(nc2C(F)(F)F)CCC1=O]

This compound was prepared in an analogous manner to 59. MS (ESI) m/z 524.2

Example 31: Synthesis of (Z)-31,4-dimethyl-13-(trifluoromethyl)-11H,21H,31H-4-aza-2(3,5)-pyrrolo[2,3-b]pyridina-1(4,1),3(4,3)-dipyrazolacyclooctaphan-5-one (69)

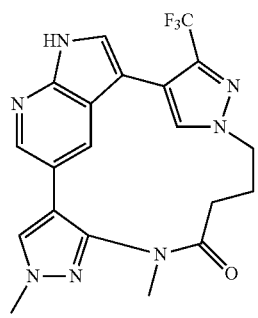 [SMILES: CN1C(=O)CCCn2cc(c(C(F)(F)F)n2)-c2c[nH]c3ncc(cc23)-c2cn(C)nc21]

This compound was prepared in an analogous manner to 59. MS (ESI) m/z 430.2 (M+H)+.

Example 32: Synthesis of (Z)-31-(2-methoxyethyl)-4-methyl-13-(trifluoromethyl)-11H,21H,31H-4-aza-2(3,5)-pyrrolo[2,3-b]pyridina-1(4,1),3(4,3)-dipyrazolacyclooctaphan-5-one (70)

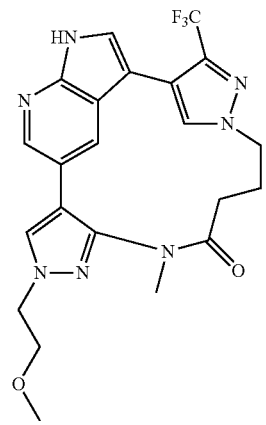 [SMILES: COCCn1cc2c(n1)N(C)C(=O)CCCn1cc(c(C(F)(F)F)n1)-c1c[nH]c3ncc-2cc13]

This compound was prepared in an analogous manner to 59. MS (ESI) m/z 474.2

Example 33: Synthesis of (Z)-4-methyl-31-(piperidin-4-yl)-13-(trifluoromethyl)-11H,21H,31H-4-aza-2(3,5)-pyrrolo[2,3-b]pyridina-1(4,1),3(4,3)-dipyrazolacyclooctaphan-5-one (71)

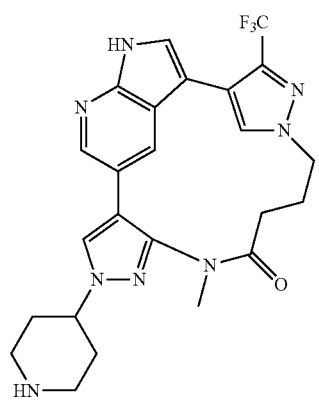 [SMILES: CN1C(=O)CCCn2cc(c(C(F)(F)F)n2)-c2c[nH]c3ncc(cc23)-c2cn(C3CCNCC3)nc21]

This compound was prepared in an analogous manner to 59. MS (ESI) m/z 499.2 (M+H)+.

Example 34: Synthesis of (Z)-31,4-dimethyl-5-oxo-13-(trifluoromethyl)-11H,21H,31H-4-aza-2(3,5)-pyrrolo[2,3-b]pyridina-1(4,1),3(4,3)-dipyrazolacyclooctaphane-35-carbonitrile (72)

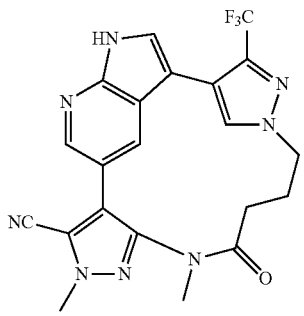 [SMILES: CN1C(=O)CCCn2cc(c(C(F)(F)F)n2)-c2c[nH]c3ncc(cc23)-c2c1nn(C)c2C#N]

This compound was prepared in an analogous manner to 59. MS (ESI) m/z 455.2

Example 35: Synthesis of (Z)-31-(2-methoxyethyl)-4-methyl-5-oxo-13-(trifluoromethyl)-11H,21H,31H-4-aza-2(3,5)-pyrrolo[2,3-b]pyridina-1(4,1),3(4,3)-dipyrazolacyclooctaphane-35-carbonitrile (73)

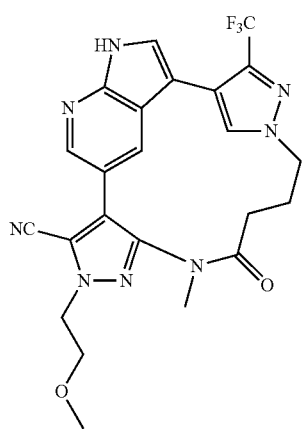 [SMILES: COCCn1nc2c(c1C#N)-c1cnc3[nH]cc(c3c1)-c1cn(nc1C(F)(F)F)CCCC(=O)N2C]

This compound was prepared in an analogous manner to 59. MS (ESI) m/z 499.2 (M+H)⁺.

Example 36: Synthesis of (Z)-4-methyl-5-oxo-31-(piperidin-4-yl)-13-(trifluoromethyl)-11H,21H,31H-4-aza-2(3,5)-pyrrolo[2,3-b]pyridina-1(4,1),3(4,3)-dipyrazolacyclooctaphane-35-carbonitrile (74)

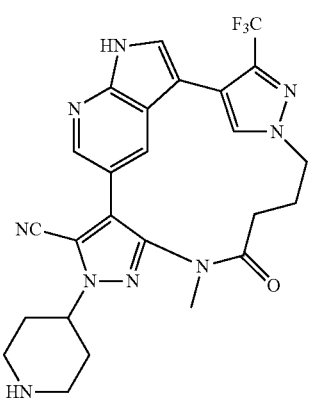 [SMILES: CN1C(=O)CCCn2cc(c(C(F)(F)F)n2)-c2c[nH]c3ncc(cc23)-c2c1nn(C1CCNCC1)c2C#N]

This compound was prepared in an analogous manner to 59. MS (ESI) m/z 524.2

Example 37: Synthesis of (Z)-31,5-dimethyl-13-(trifluoromethyl)-11H,21H,31H-5-aza-2(3,5)-pyrrolo[2,3-b]pyridina-1(4,1),3(4,3)-dipyrazolacyclononaphan-4-one (75)

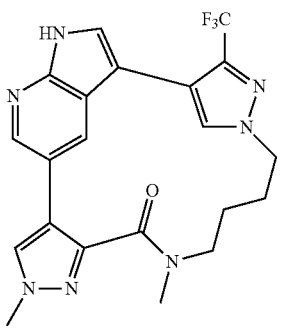 [SMILES: CN1CCCCn2cc(c(C(F)(F)F)n2)-c2c[nH]c3ncc(cc23)-c2cn(C)nc2C1=O]

This compound was prepared in an analogous manner to 59 to give the title compound as a white solid. ¹H NMR (400 MHz, DMSO) δ 12.29 (s, 1H), 8.45 (s, 1H), 8.14 (s, 1H), 7.76 (s, 1H), 7.46 (s, 1H), 6.77 (s, 1H), 4.39 (br, 2H), 3.89 (s, 3H), 2.77 (s, 3H), 2.60 (br, 2H), 2.15 (br, 2H), 1.23 (br, 2H). MS (ESI) m/z 444.1 (M+H)⁺.

Example 38: Synthesis of (Z)-31-(2-methoxyethyl)-5-methyl-13-(trifluoromethyl)-11H,21H,31H-5-aza-2(3,5)-pyrrolo[2,3-b]pyridina-1(4,1),3(4,3)-dipyrazolacyclononaphan-4-one (76)

This compound was prepared in an analogous manner to 59 to give the title compound as a white solid. ¹H NMR (400 MHz, DMSO) δ 12.30 (s, 1H), 8.48 (s, 1H), 8.19 (s, 1H), 7.77 (d, J=2.4 Hz, 1H), 7.48 (s, 1H), 6.79 (s, 1H), 4.31 (t, J=5.6 Hz, 2H), 4.23 (t, J=10.4 Hz, 1H), 4.09-3.97 (m, 1H), 3.89 (m, 1H), 3.75 (t, J=5.2 Hz, 2H), 3.26 (m, 4H), 2.69 (br, 1H), 1.84-1.70 (br, 2H), 1.56 (br, 1H), 1.29 (br, 1H). MS (ESI) m/z 488.1 (M+H)⁺.

Example 39: Synthesis of (Z)-5-methyl-31-(piperidin-4-yl)-13-(trifluoromethyl)-11H,21H,31H-5-aza-2(3,5)-pyrrolo[2,3-b]pyridina-1(4,1),3(4,3)-dipyrazolacyclononaphan-4-one (77)

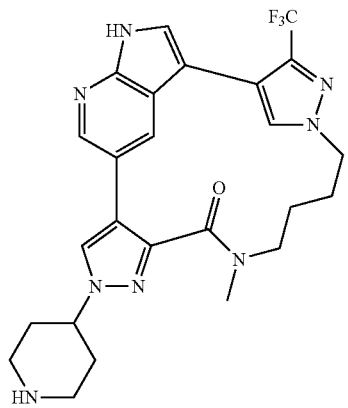 [SMILES: CN1CCCCn2cc(c(C(F)(F)F)n2)-c2c[nH]c3ncc(cc23)-c2cn(C3CCNCC3)nc2C1=O]

This compound was prepared in an analogous manner to 59 to give the title compound as a white solid. $^1$H NMR (400 MHz, DMSO) δ 12.36 (s, 1H), 9.16 (s, 1H), 8.91 (s, 1H), 8.52 (s, 1H), 8.30 (s, 1H), 7.78 (s, 1H), 7.48 (s, 1H), 6.78 (s, 1H), 4.55 (br, 1H), 4.22 (br, 1H), 4.00 (m, 1H), 3.71 (m, 1H), 3.37 (br, 2H), 3.10 (q, J=2.0 Hz, 2H), 2.69 (br, 1H), 2.26-2.19 (m, 5H) 1.98 (br, 1H), 1.76 (br, 2H), 1.52 (br, 2H). MS (ESI) m/z 513.1 (M+H)$^+$.

Example 40: Synthesis of (Z)-31,5-dimethyl-4-oxo-13-(trifluoromethyl)-11H,21H,31H-5-aza-2(3,5)-pyrrolo[2,3-b]pyridina-1(4,1),3(4,3)-dipyrazolacyclononaphane-35-carbonitrile (78)

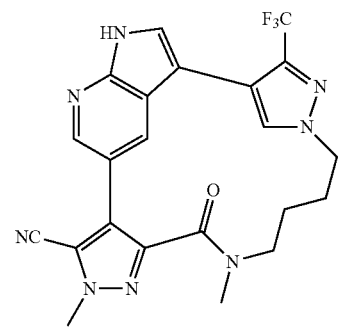 [SMILES: CN1CCCCn2cc(c(C(F)(F)F)n2)-c2c[nH]c3ncc(cc23)-c2c(nn(C)c2C#N)C1=O]

This compound was prepared in an analogous manner to 59 to give the title compound as a white solid. $^1$H NMR (400 MHz, DMSO) δ 12.54 (s, 1H), 8.56 (s, 1H), 7.87 (s, 1H), 7.53 (s, 1H), 6.81 (s, 1H), 4.22-4.17 (m, 1H), 4.10 (s, 3H), 4.04-3.96 (m, 1H), 3.86-3.79 (m, 1H), 2.73-2.69 (m, 1H), 2.54 (s, 3H), 2.03-1.95 (m, 1H), 1.71 (t, J=15.2 Hz, 2H), 1.55-1.44 (m, 1H). MS (ESI) m/z 469.1 (M+H)$^+$.

Example 41: Synthesis of (Z)-31-(2-methoxyethyl)-5-methyl-4-oxo-13-(trifluoromethyl)-11H,21H,31H-5-aza-2(3,5)-pyrrolo[2,3-b]pyridina-1(4,1),3(4,3)-dipyrazolacyclononaphane-35-carbonitrile (79)

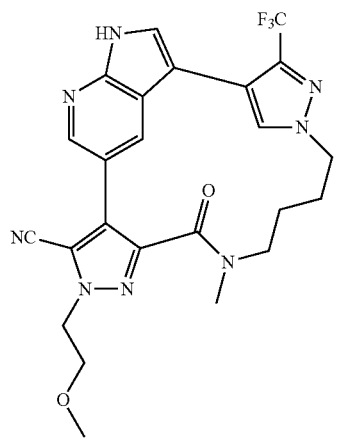 [SMILES: COCCn1nc2c(c1C#N)-c1cnc3[nH]cc(c3c1)-c1cn(nc1C(F)(F)F)CCCCN(C)C2=O]

This compound was prepared in an analogous manner to 59 to give the title compound as a white solid. $^1$H NMR (400 MHz, DMSO) δ 12.54 (s, 1H), 8.55 (d, J=2.0 Hz, 1H), 7.87 (d, J=2.4 Hz, 1H), 7.53 (d, J=1.6 Hz, 1H), 6.80 (s, 1H), 4.52 (m, 2H), 4.18 (t, J=4.0 Hz, 1H), 3.99 (m, 1H), 3.83 (m, 1H), 3.77 (t, J=10.4 Hz, 2H), 3.26 (s, 3H), 2.72 (m, 1H), 2.55 (s, 3H), 1.71 (m, 2H), 1.51 (m, 1H), 1.33 (m, 1H). MS (ESI) m/z 513.1 (M+H)$^+$.

Example 42: Synthesis of (Z)-5-methyl-4-oxo-31-(piperidin-4-yl)-13-(trifluoromethyl)-11H,21H,31H-5-aza-2(3,5)-pyrrolo[2,3-b]pyridina-1(4,1),3(4,3)-dipyrazolacyclononaphane-35-carbonitrile (80)

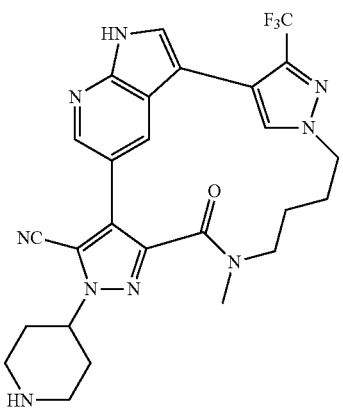 [SMILES: CN1CCCCn2cc(c(C(F)(F)F)n2)-c2c[nH]c3ncc(cc23)-c2c(nn(C3CCNCC3)c2C#N)C1=O]

This compound was prepared in an analogous manner to 59. MS (ESI) m/z 538.2

Example 43: Synthesis of (Z)-31,5-dimethyl-13-(trifluoromethyl)-11H,21H,31H-5-aza-2(3,5)-pyrrolo[2,3-b]pyridina-1(4,1),3(4,3)-dipyrazolacyclooctaphan-4-one (81)

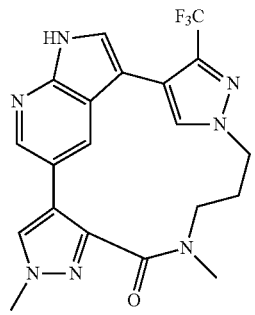 [SMILES: CN1CCCn2cc(c(C(F)(F)F)n2)-c2c[nH]c3ncc(cc23)-c2cn(C)nc2C1=O]

This compound was prepared in an analogous manner to 59. MS (ESI) m/z 430.2 (M+H)+.

Example 44: Synthesis of (Z)-31-(2-methoxyethyl)-5-methyl-13-(trifluoromethyl)-11H,21H,31H-5-aza-2(3,5)-pyrrolo[2,3-b]pyridina-1(4,1),3(4,3)-dipyrazolacyclooctaphan-4-one (82)

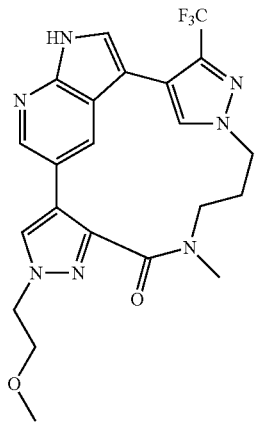 [SMILES: COCCn1cc2c(n1)C(=O)N(C)CCCn1cc(c(C(F)(F)F)n1)-c1c[nH]c3ncc-2cc13]

This compound was prepared in an analogous manner to 59. MS (ESI) m/z 474.2

Example 45: Synthesis of (Z)-5-methyl-31-(piperidin-4-yl)-13-(trifluoromethyl)-11H,21H,31H-5-aza-2(3,5)-pyrrolo[2,3-b]pyridina-1(4,1),3(4,3)-dipyrazolacyclooctaphan-4-one (83)

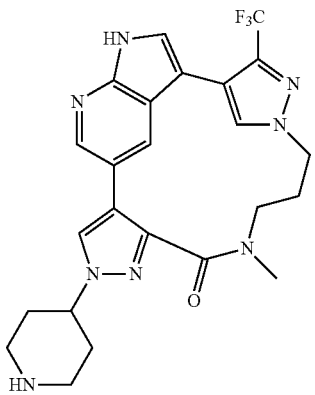 [SMILES: CN1CCCn2cc(c(C(F)(F)F)n2)-c2c[nH]c3ncc(cc23)-c2cn(C3CCNCC3)nc2C1=O]

This compound was prepared in an analogous manner to 59. MS (ESI) m/z 499.2 (M+H)+.

Example 46: Synthesis of (Z)-31,5-dimethyl-4-oxo-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (84)

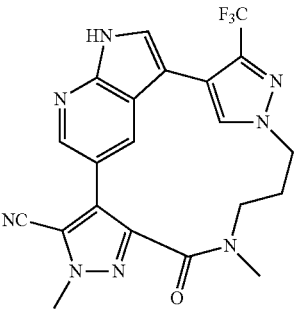 [SMILES: CN1CCCn2cc(c(C(F)(F)F)n2)-c2c[nH]c3ncc(cc23)-c2c(nn(C)c2C#N)C1=O]

This compound was prepared in an analogous manner to 59. MS (ESI) m/z 455.2

Example 47: Synthesis of (Z)-31-(2-methoxyethyl)-5-methyl-4-oxo-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (85)

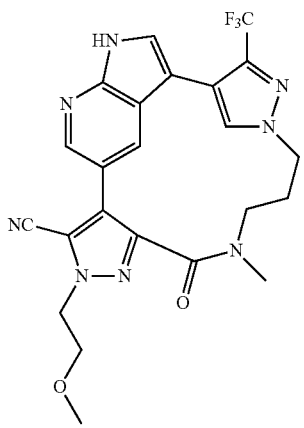 [SMILES: COCCn1nc2c(c1C#N)-c1cnc3[nH]cc(c3c1)-c1cn(nc1C(F)(F)F)CCCN(C)C2=O]

This compound was prepared in an analogous manner to 59. MS (ESI) m/z 499.2 (M+H)+.

Example 48: Synthesis of (Z)-5-methyl-4-oxo-31-(piperidin-4-yl)-13-(trifluoromethyl)-11H,21H,31H-5-aza-2(3,5)-pyrrolo[2,3-b]pyridina-1(4,1),3(4,3)-dipyrazolacyclooctaphane-35-carbonitrile (86)

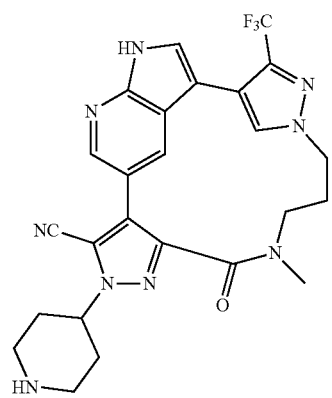 [SMILES: CN1CCCn2cc(c(C(F)(F)F)n2)-c2c[nH]c3ncc(cc23)-c2c(nn(C3CCNCC3)c2C#N)C1=O]

This compound was prepared in an analogous manner to 59. MS (ESI) m/z 524.2

Example 49: Synthesis of (Z)-31,5-dimethyl-13-(trifluoromethyl)-11H,25H,31H-5-aza-2(7,2)-pyrrolo[2,3-b]pyrazina-1(4,1),3(4,3)-dipyrazolacyclononaphan-6-one (87)

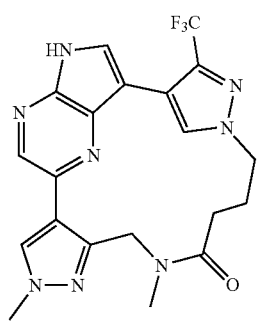 [SMILES: CN1Cc2nn(C)cc2-c2cnc3[nH]cc(c3n2)-c2cn(nc2C(F)(F)F)CCCC1=O]

This compound was prepared in an analogous manner to 59. MS (ESI) m/z 445.2 (M+H)+.

Example 50: Synthesis of (Z)-31-(2-methoxyethyl)-5-methyl-13-(trifluoromethyl)-11H,25H,31H-5-aza-2(7,2)-pyrrolo[2,3-b]pyrazina-1(4,1),3(4,3)-dipyrazolacyclononaphan-6-one (88)

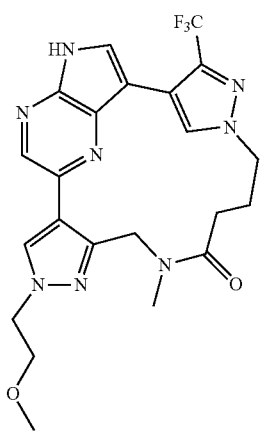 [SMILES: COCCn1cc2c(n1)CN(C)C(=O)CCCn1cc(c(C(F)(F)F)n1)-c1c[nH]c3ncc-2nc13]

This compound was prepared in an analogous manner to 59. MS (ESI) m/z 489.2

Example 51: Synthesis of (Z)-5-methyl-31-(piperidin-4-yl)-13-(trifluoromethyl)-11H,25H,31H-5-aza-2(7,2)-pyrrolo[2,3-b]pyrazina-1(4,1),3(4,3)-dipyrazolacyclononaphan-6-one (89)

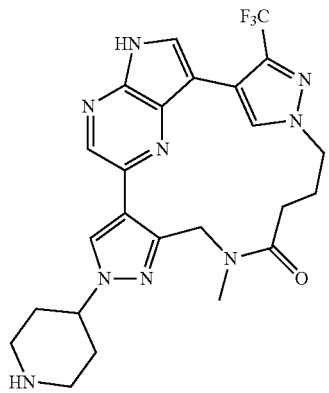 [SMILES: CN1Cc2nn(C3CCNCC3)cc2-c2cnc3[nH]cc(c3n2)-c2cn(nc2C(F)(F)F)CCCC1=O]

This compound was prepared in an analogous manner to 59. MS (ESI) m/z 514.2 (M+H)+.

Example 52: Synthesis of (Z)-31,5-dimethyl-6-oxo-13-(trifluoromethyl)-11H,25H,31H-5-aza-2(7,2)-pyrrolo[2,3-b]pyrazina-1(4,1),3(4,3)-dipyrazolacyclononaphane-35-carbonitrile (90)

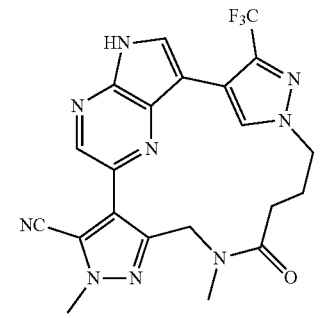 [SMILES: CN1Cc2nn(C)c(C#N)c2-c2cnc3[nH]cc(c3n2)-c2cn(nc2C(F)(F)F)CCCC1=O]

This compound was prepared in an analogous manner to 59. MS (ESI) m/z 470.2

Example 53: Synthesis of (Z)-31-(2-methoxyethyl)-5-methyl-6-oxo-13-(trifluoromethyl)-11H,25H,31H-5-aza-2(7,2)-pyrrolo[2,3-b]pyrazina-1(4,1),3(4,3)-dipyrazolacyclononaphane-35-carbonitrile (91)

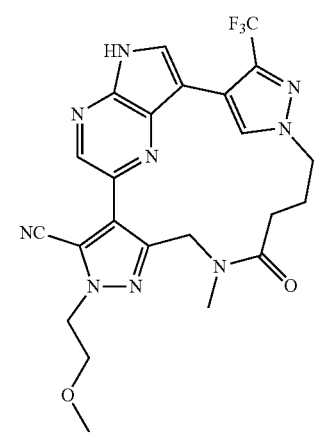 [SMILES: COCCn1nc2c(c1C#N)-c1cnc3[nH]cc(c3n1)-c1cn(nc1C(F)(F)F)CCCC(=O)N(C)C2]

This compound was prepared in an analogous manner to 59. MS (ESI) m/z 514.2 (M+H)⁺.

Example 54: Synthesis of (Z)-5-methyl-6-oxo-31-(piperidin-4-yl)-13-(trifluoromethyl)-11H,25H,31H-5-aza-2(7,2)-pyrrolo[2,3-b]pyrazina-1(4,1),3(4,3)-dipyrazolacyclononaphane-35-carbonitrile (92)

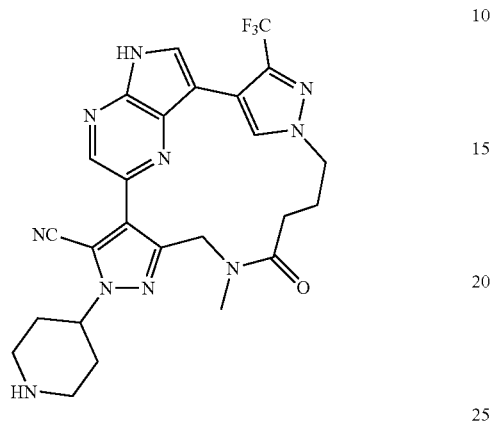

This compound was prepared in an analogous manner to 59. MS (ESI) m/z 539.2 (M+H)⁺.

Example 55: Determination of IC$_{50}$ Values Relative to Various Other Kinases

The IC$_{50}$ values were generated by Invitrogen™ using a Zlyte™ assay format for RET, RET V804M, RET V804L, TRKA, TRKB, and TRKC. TLK1 and TLK2 use a LanthaScreen™ assay format. The results, shown in Table 1, indicate that the inventive compounds tested are quite potent against TRKA, TRKB, and TRKC.

TABLE 1

IC$_{50}$ of compound 44 and analogues

| Inventive Compound | RET wt | RET V804M (RET V804L) | TRKA | TRKB | TRKC | TLK1 | TLK2 |
|---|---|---|---|---|---|---|---|
| 44 | 13 | 66 | 5 | 4 | 2 | 108 | 796 |
| 45 | 10 | 33 | 4 | 4 | 2 | 32 | 976 |
| 46 | 6 | 12 | 2 | 1 | 1 | 109 | 743 |
| 53 | 9 | 109 | — | — | — | — | — |
| 54 | 4 | 58 | — | — | — | — | — |
| 55 | 5 | 69 | 10 | 16 | 4 | — | — |
| 41 | 46 | 35 (15) | 14 | 14 | 5 | 105 | 310 |
| 56 | 157 | 2160 | — | — | — | — | — |
| 57 | 12 | 97 | — | — | — | — | — |
| 43 | 11 | 38 | 2 | 1 | 1 | 37 | 296 |
| 58 | 110 | 739 | 9 | 9 | 2 | — | — |

Example 56: Determination of IC$_{50}$ Values Relative to DYRK1A and DYRK1B

The IC$_{50}$ values were generated by Invitrogen™ using a Zlyte™ assay format. The data, shown in Table 2, indicates that the inventive compounds tested are quite potent against DYRK1A and DYRK1B.

TABLE 2

| IC$_{50}$ of compound 48 and analogues | | |
|---|---|---|
| Inventive | IC$_{50}$ (nM) | |
| Compound | DYRK1A | DYRK1B |
| 48 | 14 | 15 |
| 50 | 86 | 146 |
| 51 | 327 | 533 |
| 52 | 44 | 55 |

Example 57: Determination of IC$_{50}$ Values Relative to Various Enzymes

Ambit profiling from Eurofins (formerly Discoverx) was conducted in accordance with the manufacturer's instructions. The data set forth below in Table 3 shows that compound 48 is extremely selective for DYRK1A.

TABLE 3

IC$_{50}$ values relative to various enzymes

| Structure | Enzyme IC50 (nM) | Structure | |
|---|---|---|---|
| Compound Number | 48 | Compound Number | 41 |
| Compound Concentration (uM) | 1 | (uM) | 1 |
| DYRK1A | 0 | ABL1(T315I)-nonphosphorylated | 0 |
| MYLK | 0.25 | CLK4 | 0 |
| FLT3(D835V) | 0.35 | FLT3(D835Y) | 0 |
| SGK | 1.7 | GSK3A | 0 |
| FLT3(ITD, D835V) | 2.2 | GSK3B | 0 |
| DYRK1B | 2.6 | JNK1 | 0.1 |
| CAMK1B | 2.9 | TAOK1 | 0.1 |
| TNIK | 3.2 | AXL | 0.15 |
| MEK3 | 3.4 | FLT3(ITD) | 0.15 |
| HIPK4 | 3.6 | FLT3(N841) | 0.25 |
| MEK4 | 3.7 | MEK4 | 0.25 |
| TRKA | 4 | TRKB | 0.4 |
| CAMK2A | 5.8 | YSK4 | 0.45 |
| CAMK2D | 6.2 | JAK2(JH1domain-catalytic) | 0.5 |
| HUNK | 7.1 | IRAK1 | 0.55 |
| RSK2(Kin.Dom.1-N-terminal) | 7.1 | MERTK | 0.55 |
| FAK | 7.3 | RET(V804M) | 0.55 |
| RSK4(Kin.Dom.1-N-terminal) | 7.5 | TRKA | 0.55 |
| CAMK2B | 7.7 | TRKC | 0.55 |
| HASPIN | 8 | BIKE | 0.7 |
| GAK | 8.1 | MAP3K2 | 0.7 |
| JNK2 | 8.1 | HIPK2 | 0.75 |
| SGK3 | 8.5 | JNK3 | 0.75 |
| CAMK2G | 8.6 | HIPK3 | 0.8 |
| PIK4CB | 8.6 | PLK4 | 0.8 |
| CLK4 | 8.9 | DYRK1A | 1.1 |
| MINK | 8.9 | FLT3 | 1.1 |
| CLK2 | 10 | FLT3(D835H) | 1.1 |
| TTK | 10 | JNK2 | 1.1 |
| DYRK2 | 11 | PKNB(*M. tuberculosis*) | 1.2 |
| MYO3A | 12 | AURKA | 1.3 |
| TNK1 | 12 | RET(V804L) | 1.3 |
| TNK2 | 12 | MST2 | 1.4 |
| CSNK1D | 13 | FLT3(K663Q) | 1.5 |
| FLT3(D835Y) | 14 | MAP4K2 | 1.5 |
| FLT4 | 14 | JAK3(JH1domain-catalytic) | 1.6 |
| JNK3 | 14 | MEK2 | 1.6 |
| CLK1 | 15 | CLK1 | 1.8 |
| FLT3(N841) | 16 | MAP4K5 | 1.9 |
| ROS1 | 16 | CAMKK1 | 2 |
| CAMK1D | 18 | HIPK1 | 2 |

<sub></sub>

Additional values present in middle (Enzyme IC50 column):
14, 212, 354, 19, 830, 87, 173, 477, 488, 141, 258, 225, 250, 104, 2860, 91, 593, 4190, 46, 80, 193

TABLE 3-continued

IC₅₀ values relative to various enzymes

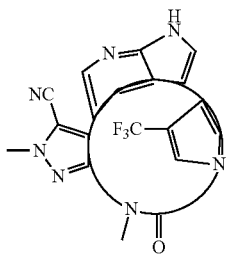
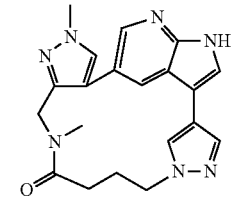 [SMILES: CN1Cc2nn(C)cc2-c2cnc3[nH]cc(c3c2)-c2cnn(c2)CCCC1=O]

| Structure | Enzyme IC50 (nM) | Structure | Enzyme IC50 (nM) |
|---|---|---|---|
| MYO3B | 18 | IRAK3 | 2 |
| CAMKK1 | 19 | MEK3 | 2 |
| CSNK1E | 19 | RPS6KA5(Kin.Dom.2-C-terminal) | 2.1 |
| CAMK1 | 20 | TAK1 | 2.1 |
| CSNK2A2 | 20 | TNIK | 2.1 |
| JNK1 | 20 | KIT(A828P) | 2.2 |
| SLK | 20 | RET | 2.2 |
| FLT3(ITD) | 21 | NEK10 | 2.3 |
| MEK2 | 21 | TYK2(JH1domain-catalytic) | 2.3 |
| ALK(C1156Y) | 22 | MAP3K3 | 2.4 |
| FRK | 22 | TAOK3 | 2.5 |
| S6K1 | 22 | MEK1 | 2.6 |
| TRKC | 22 | PRKD1 | 2.6 |
| BUB1 | 23 | HPK1 | 2.8 |
| FLT3 | 23 | KIT(D816V) | 3 |
| FLT3(D835H) | 23 | DYRKIB | 3.1 |
| STK33 | 25 | DRAK1 | 3.2 |
| MEK5 | 26 | CAMKK2 | 3.3 |
| PFCDPK1(*P.falciparum*) | 26 | SGK | 3.3 |
| ALK | 27 | ABL1(T315I)-phosphorylated | 3.4 |
| PDGFRB | 27 | ERK8 | 3.5 |
| FER | 28 | PRKD2 | 3.5 |
| PLK4 | 28 | TAOK2 | 3.7 |
| TRKB | 29 | MEK6 | 3.8 |
| TSSK1B | 29 | PDGFRB | 3.9 |
| SGK2 | 30 | BMPR2 | 4.1 |
| VEGFR2 | 30 | RET(M918T) | 4.1 |
| ALK(L1196M) | 32 | CDKL5 | 4.3 |
| TBK1 | 32 | SNARK | 4.3 |
| YSK4 | 32 | ICK | 4.4 |
| MAP4K4 | 34 | MST1 | 4.7 |
| AURKA | 35 | MELK | 4.8 |
| EGFR(E746-A750del) | 35 | MINK | 5.1 |
| PHKG1 | 35 | AAK1 | 5.5 |
| RSK3(Kin.Dom.1-N-terminal) | 35 | CDKL3 | 5.5 |
| FLT3(K663Q) | 36 | HIPK4 | 5.5 |
| YANK1 | 36 | RSK4(Kin.Dom.1-N-terminal) | 5.6 |
| VRK2 | 37 | ULK3 | 5.6 |
| PIP5K1C | 38 | ACVR1 | 6.1 |
| CAMKK2 | 39 | NEK6 | 6.1 |
| ERBB3 | 39 | S6K1 | 6.2 |
| CDK7 | 40 | TTK | 6.3 |
| EGFR(L747-E749del, A750) | 40 | ABL1(H396P)-nonphosphorylated | 6.5 |
| MELK | 40 | RIOK1 | 6.9 |
| TNNI3K | 40 | GRK7 | 7.1 |
| TYRO3 | 40 | EMPR1B | 7.2 |
| IRAK1 | 41 | TBK1 | 7.2 |
| MEK6 | 41 | CLK2 | 7.3 |
| PYK2 | 41 | EPHA7 | 7.3 |
| MEK1 | 42 | STK16 | 7.7 |
| NDR2 | 42 | TLK2 | 7.7 |
| ABL1(F317L)-phosphorylate | 43 | MAP4K3 | 7.8 |
| AXL | 44 | MAP4K4 | 7.8 |
| CSNK2A1 | 44 | RIPK5 | 7.8 |
| HIPK1 | 45 | LRRK2(G2019S) | 8.4 |
| FLT3(ITD, F691L) | 46 | FLT4 | 8.7 |
| PHKG2 | 46 | GRK1 | 8.7 |
| ADCK4 | 47 | INSR | 8.8 |
| HIPK3 | 47 | ARK5 | 8.9 |
| LTK | 47 | JAK1(JH2domain-pseudokinase) | 9.1 |
| PRKCQ | 47 | PRKR | 9.2 |
| FGFR3(G697C) | 48 | ALK(C1156Y) | 10 |
| INSR | 48 | ABL1(Q252H)-nonphosphoryl | 11 |
| MET | 48 | GAK | 11 |
| YANK2 | 48 | LZK | 11 |

TABLE 3-continued

IC₅₀ values relative to various enzymes

| Structure | Enzyme IC50 (nM) | Structure | |
|---|---|---|---|
| GRK7 | 49 | SRPK1 | 11 |
| PAK3 | 49 | TGFBR2 | 11 |
| EGFR(L747-T751del, Sins) | 50 | AURKC | 12 |
| EGFR(L858R, T790M) | 50 | CSF1R-autoinhibited | 12 |
| GRK1 | 50 | DMPK | 12 |
| HIPK2 | 51 | HASPIN | 12 |
| MET(Y1235D) | 51 | IRAK4 | 12 |
| PRKD3 | 51 | KIT(D816H) | 12 |
| TAK1 | 51 | PIP5K2C | 12 |
| LOK | 52 | FLT3-autoinhibited | 13 |
| WNK4 | 52 | LCK | 13 |
| KIT(D816V) | 53 | NEK7 | 13 |
| FGFR2 | 55 | RIOK3 | 13 |
| ERK5 | 56 | ROS1 | 13 |
| IRAK3 | 56 | SLK | 13 |
| CAMK4 | 58 | YSK1 | 13 |
| LKB1 | 58 | ALK | 14 |
| MAP4K5 | 58 | EGFR(L858R, T790M) | 14 |
| EGFR(L861Q) | 59 | EPHB6 | 14 |
| FGFR3 | 59 | MARK2 | 14 |
| PRKD2 | 59 | RSK2(Kin.Dom.1-N-terminal) | 14 |
| CLK3 | 61 | LRRK2 | 15 |
| FGFR1 | 61 | RPS6KA4(Kin.Dom.2-C-terminal | 15 |
| INSRR | 62 | TLK1 | 15 |
| MAP3K15 | 62 | CDK7 | 16 |
| RIPK5 | 62 | FGFR3(G697C) | 16 |
| EGFR(L858R) | 63 | LTK | 16 |
| FGFR4 | 63 | PIK3CA(I800L) | 16 |
| TIE1 | 63 | VEGFR2 | 16 |
| AURKB | 64 | ABL1(E255K)-phosphorylated | 17 |
| RET | 66 | AURKB | 17 |
| MERTK | 67 | EPHA1 | 17 |
| NLK | 67 | FLT3(R834Q) | 17 |
| PRKCI | 67 | EPHA3 | 18 |
| ABL1-nonphosphorylated | 68 | JAK1(JH1domain-catalytic) | 18 |
| FES | 68 | PAK7 | 19 |
| SYK | 68 | MET(M1250T) | 20 |
| PRKD1 | 69 | PAK4 | 20 |
| RSK4(Kin.Dom.2-C-terminal) | 69 | PIP5K1C | 20 |
| STK39 | 69 | PYK2 | 21 |
| CHEK2 | 70 | ABL1(Q252H)-phosphorylated | 22 |
| ERBB2 | 70 | AMPK-alpha2 | 22 |
| ICK | 70 | PHKG1 | 22 |
| PIK3CB | 70 | PIM1 | 22 |
| STK16 | 70 | SGK3 | 22 |
| DAPK1 | 71 | ULK1 | 22 |
| EGFR(G719S) | 71 | DLK | 23 |
| MAST1 | 71 | MAP3K15 | 23 |
| AURKC | 72 | MEK5 | 23 |
| ERBB4 | 72 | PHKG2 | 23 |
| MAP3K1 | 72 | ASK1 | 24 |
| PIP5K2C | 72 | CSF1R | 24 |
| RPS6KA5(Kin.Dom.1-N-terminal) | 72 | PIP5K1A | 24 |
| YANK3 | 72 | ACVRL1 | 25 |
| DCAMKL2 | 73 | ALK(L1196M) | 25 |
| LRRK2(G2019S) | 73 | KIT(L576P) | 25 |
| MKNK2 | 73 | ABL1-phosphorylated | 26 |
| PRKCD | 73 | CDKL2 | 26 |
| RSK1(Kin.Dom.1-N-terminal) | 73 | MST4 | 26 |
| VPS34 | 73 | NEK3 | 26 |
| CDKL2 | 74 | DRAK2 | 27 |
| CIT | 74 | MARK4 | 27 |
| EGFR(L747-S752del, P753S) | 74 | PIP5K2B | 27 |
| MST2 | 74 | ULK2 | 27 |
| PIP5K2B | 74 | MKK7 | 28 |

TABLE 3-continued

IC₅₀ values relative to various enzymes

| Structure | Enzyme IC50 (nM) | Structure | |
|---|---|---|---|
| RIOK2 | 74 | EPHA6 | 29 |
| FLT1 | 75 | KIT(V559D) | 29 |
| MAP3K3 | 75 | ANKK1 | 30 |
| MET(M1250T) | 75 | FGFR1 | 30 |
| PKNB(*M. tuberculosis*) | 75 | KIT(V559D, T670I) | 30 |
| SRPK1 | 75 | MET | 30 |
| EGFR | 76 | PIK3CG | 30 |
| PCTK3 | 76 | LYN | 31 |
| RIPK2 | 76 | NEK9 | 31 |
| EGFR(S752-I759del) | 77 | MLCK | 32 |
| HCK | 77 | FAK | 33 |
| MAP4K3 | 77 | FLT1 | 33 |
| PKMYT1 | 77 | PRP4 | 33 |
| PKN1 | 77 | PAK6 | 34 |
| MLK2 | 78 | RIPK1 | 34 |
| PRKCE | 78 | RIPK4 | 34 |
| RSK1(Kin.Dom.2-C-terminal) | 78 | CSNK2A2 | 35 |
| FGR | 79 | PCTK1 | 35 |
| NEK5 | 79 | ROCK1 | 35 |
| p38-gamma | 79 | ASK2 | 36 |
| PDGFRA | 79 | MYO3A | 36 |
| RET(M918T) | 79 | FER | 37 |
| ZAP70 | 79 | KIT | 37 |
| ABL1(F317I)-phosphorylated | 80 | RSK1(Kin.Dom.1-N-terminal) | 37 |
| EGFR(T790M) | 80 | ABL1(H396P)-phosphorylated | 38 |
| MLK1 | 80 | CAMK1G | 38 |
| MLK3 | 80 | FGFR2 | 39 |
| NEK3 | 80 | MST3 | 39 |
| PRP4 | 80 | MYLK | 39 |
| JAK2(JH1domain-catalytic) | 81 | DCAMKL3 | 40 |
| KIT | 81 | MYLK4 | 40 |
| RSK3(Kin.Dom.2-C-terminal) | 81 | PIK3CA(H1047L) | 40 |
| EPHB6 | 82 | PIM3 | 40 |
| GSK3B | 82 | PRKCE | 40 |
| LIMK1 | 82 | ZAK | 40 |
| RIOK1 | 82 | CDK4-cyclinD1 | 41 |
| RIPK4 | 82 | EGFR(T790M) | 41 |
| CDK4-cyclinD1 | 83 | FGFR3 | 41 |
| FYN | 83 | PAK3 | 41 |
| NEK7 | 83 | PRKD3 | 41 |
| RPS6KA5(Kin.Dom.2-C-terminal) | 83 | RIOK2 | 41 |
| GSK3A | 84 | RPS6KA5(Kin.Dom.1-N-terminal) | 41 |
| KIT(L576P) | 84 | CHEK2 | 42 |
| TYK2(JH1domain-catalytic) | 84 | MARK1 | 43 |
| BMPR2 | 85 | ABL1(Y253F)-phosphorylated | 44 |
| CDC2L2 | 85 | MET(Y12350) | 44 |
| IGF1R | 85 | NIK | 44 |
| MARK1 | 85 | PAK2 | 45 |
| NEK10 | 85 | PDGFRA | 45 |
| NIK | 85 | ABL1-nonphosphorylated | 46 |
| RET(V804M) | 85 | CAMK2G | 46 |
| RPS6KA4(Kin.Dom.1-N-terminal) | 85 | EPHB1 | 46 |
| SRPK3 | 85 | PFCDPK1(*P. falciparum*) | 46 |
| BRSK2 | 86 | ROCK2 | 46 |
| EGFR(G719C) | 86 | SRC | 46 |
| ERN1 | 86 | SRPK3 | 46 |
| JAK3(JH1domain-catalytic) | 86 | TIE1 | 46 |
| MST3 | 86 | ABL1(M351T)-phosphorylated | 47 |
| TIE2 | 86 | Sgk110 | 47 |
| CDC2L5 | 87 | TIE2 | 47 |
| DAPK2 | 87 | FGR | 48 |
| DDR1 | 87 | GRK4 | 48 |
| STK35 | 87 | HUNK | 48 |
| KIT(V559D) | 88 | NDR1 | 48 |
| MRCKB | 88 | TESK1 | 48 |

TABLE 3-continued

IC50 values relative to various enzymes

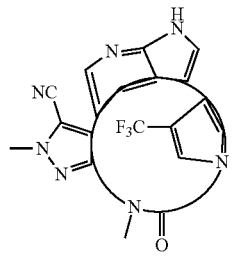 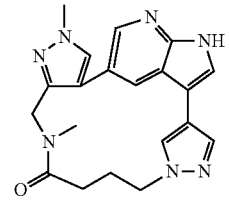

| Structure | Enzyme IC50 (nM) | Structure | IC50 (nM) |
|---|---|---|---|
| PIK3C2B | 88 | CAMK2D | 49 |
| PIK3CA(M1043I) | 88 | MARK3 | 49 |
| ULK2 | 88 | CDK3 | 50 |
| CAMK1G | 89 | STK33 | 50 |
| CSF1R | 89 | STK35 | 50 |
| CSNK1A1 | 89 | CAMK1 | 51 |
| FLT3(R834Q) | 89 | EPHA2 | 51 |
| PKAC-alpha | 89 | PRKCI | 51 |
| RIPK1 | 89 | CDK9 | 52 |
| SIK | 59 | PCTK2 | 52 |
| SIK2 | 89 | CASK | 53 |
| SRPK2 | 89 | PIK4CB | 53 |
| ABL1(M351T)-phosphorylated | 90 | FYN | 54 |
| BMX | 90 | LKB1 | 54 |
| CSF1R-autoinhibited | 90 | MLK2 | 54 |
| DAPK3 | 90 | PIK3CA(E545K) | 54 |
| EPHA6 | 90 | RSK3(Kin.Dom.1-N-terminal) | 54 |
| GRK4 | 90 | SGK2 | 54 |
| NEK4 | 90 | CDK2 | 55 |
| PAK4 | 90 | CDKL1 | 55 |
| BIKE | 91 | DYRK2 | 55 |
| CDK2 | 91 | DAPK1 | 56 |
| EPHB3 | 91 | PIK3CA(Q546K) | 56 |
| PAK1 | 91 | TXK | 56 |
| PAK2 | 91 | CAMK2A | 57 |
| PFTK1 | 91 | CDK4-cyclinD3 | 58 |
| BRSK1 | 92 | EPHA5 | 58 |
| CDK5 | 92 | HCK | 59 |
| CSNK1A1L | 92 | PAK1 | 59 |
| DCAMKL1 | 92 | PIK3CA(H1047Y) | 59 |
| DCAMKL3 | 92 | STK39 | 59 |
| ERK2 | 92 | AMPK-alpha1 | 60 |
| ERK8 | 92 | BLK | 60 |
| MAP3K2 | 92 | DAPK3 | 60 |
| MARK4 | 92 | FRK | 60 |
| MTOR | 92 | PIK3CA(3542K) | 60 |
| NEK6 | 92 | PRKG1 | 60 |
| PIK3CA(I800L) | 92 | BTK | 61 |
| TGFBR1 | 92 | BUB1 | 61 |
| TXK | 92 | DDR1 | 61 |
| ACVR1 | 93 | MLK1 | 61 |
| CHEK1 | 93 | p38-gamma | 61 |
| KIT(A829P) | 93 | TSSK1B | 61 |
| LATS1 | 93 | ADCK4 | 62 |
| MARK3 | 93 | DAPK2 | 62 |
| MLCK | 93 | CSK | 63 |
| PIK3CA(H1047L) | 93 | LATS2 | 63 |
| PLK1 | 93 | RSK4(Kin.Dom.2-C-terminal) | 63 |
| RET(V804L) | 93 | PKMYT1 | 64 |
| RIOK3 | 93 | PKN2 | 64 |
| TESK1 | 93 | ACVR2B | 65 |
| YSK1 | 93 | CLK3 | 65 |
| AKT2 | 94 | CSNK1D | 65 |
| EPHA4 | 94 | DCAMKL1 | 65 |
| EPHB4 | 94 | EPHB4 | 65 |
| GRK3 | 94 | ITK | 65 |
| IKK-epsilon | 94 | MAP3K4 | 66 |
| PIKFYVE | 94 | KIT-autoinhibited | 67 |
| PIM2 | 94 | MTOR | 67 |
| SRMS | 94 | MYO38 | 68 |
| TLK1 | 94 | CSNK2A1 | 69 |
| WEE2 | 94 | MLK3 | 69 |
| CDKL1 | 95 | PFTK1 | 69 |
| CSK | 95 | RSK3(Kin.Dom.2-C-terminal) | 69 |
| CTK | 95 | PCTK3 | 70 |

TABLE 3-continued

IC₅₀ values relative to various enzymes

| Structure | Enzyme IC50 (nM) | Structure | |
|---|---|---|---|
| DMPK | 95 | SYK | 70 |
| DMPK2 | 95 | ABL1(F317L)-nonphosphorylated | 71 |
| IKK-alpha | 95 | CSNK1A1 | 71 |
| MAP3K4 | 95 | BMPR1A | 72 |
| MUSK | 95 | INSRR | 72 |
| NEK9 | 95 | NDR2 | 72 |
| p38-alpha | 95 | TNK2 | 72 |
| PDPK1 | 95 | ABL1(F317I)-phosphorylated | 73 |
| ABL1(Q252H)-phosphorylated | 96 | MAST1 | 73 |
| ADCK3 | 96 | ABL1(F317L)-phosphorylated | 74 |
| AKT3 | 96 | EPHA8 | 74 |
| BMPR1B | 96 | LOK | 74 |
| EPHB1 | 96 | PLK3 | 74 |
| LIMK2 | 96 | SRMS | 74 |
| SBK1 | 96 | CSNK1E | 75 |
| SRC | 96 | NIM1 | 75 |
| TLK2 | 96 | PIK3CB | 75 |
| ZAK | 96 | CTK | 76 |
| ABL1(H396P)-nonphosphorylated | 97 | S6K1 | 76 |
| ACVR2A | 97 | IGF1R | 77 |
| AKT1 | 97 | PIK3CA(E545A) | 77 |
| BTK | 97 | YES | 77 |
| EPHA5 | 97 | IKK-beta | 78 |
| EPHA8 | 97 | WEE1 | 78 |
| KIT(V559D, V654A) | 97 | CDK5 | 79 |
| LRRK2 | 97 | EGFR(L747-E749del, A750P) | 79 |
| MYLK2 | 97 | ERBB4 | 79 |
| PAK7 | 97 | PDPK1 | 79 |
| PFTAIRE2 | 97 | EPHB2 | 80 |
| PIK3CA(E645K) | 97 | KIT(V559D, V654A) | 80 |
| PIM3 | 97 | PRKCH | 80 |
| PKAC-beta | 97 | SIK2 | 80 |
| ROCK2 | 97 | ACVR1B | 81 |
| STK36 | 97 | CAMK1D | 81 |
| ULK3 | 97 | MYLK2 | 81 |
| ABL1(Q252H)-nonphosphorylated | 98 | CDK11 | 84 |
| ABL1-phosphorylated | 98 | CSNK1G1 | 84 |
| ACVR2B | 98 | FES | 84 |
| ANKK1 | 98 | GCN2(Kin.Dom.2, S808G) | 84 |
| CSNK1G3 | 98 | PIK3CA | 84 |
| DRAK2 | 98 | PIK3CA(C420R) | 84 |
| FLT3-autoinhibited | 98 | SIK | 84 |
| GRK2 | 98 | LATS1 | 85 |
| LYN | 98 | NEK2 | 85 |
| MAK | 98 | PFTAIRE2 | 85 |
| PCTK2 | 98 | RPS6KA4(Kin.Dom.1-N-terminal) | 85 |
| WEE1 | 98 | EGFR | 86 |
| YES | 98 | ERK2 | 86 |
| ABL1(H396P)-phosphorylated | 99 | EGFR(L856R) | 87 |
| EPHA2 | 99 | ERK5 | 87 |
| EPHB2 | 99 | PIK3C2B | 87 |
| KIT(D816H) | 99 | TGFBR1 | 87 |
| LCK | 99 | p38-beta | 88 |
| MKK7 | 99 | PLK1 | 88 |
| MRCKA | 99 | PRKX | 88 |
| PIK3C2G | 99 | FGFR4 | 89 |
| PIK3CA(H1047Y) | 99 | MAPBK1 | 89 |
| PIP5K1A | 99 | NEK1 | 89 |
| TRPM6 | 99 | NEK4 | 89 |
| TSSK3 | 99 | PIK3C2G | 89 |
| AAK1 | 100 | QSK | 89 |
| ABL1(E255K)-phosphorylated | 100 | ACVR2A | 90 |
| ABL1(F317I)-nonphosphorylated | 100 | PLK2 | 90 |
| ABL1(F317L)-nonphosphorylated | 100 | DCAMKL2 | 91 |
| ABL1(T315I)-nonphosphorylated | 100 | ERN1 | 91 |

TABLE 3-continued

IC$_{50}$ values relative to various enzymes

| Structure | Enzyme IC50 (nM) | Structure | |
|---|---|---|---|
| ABL1(T315I)-phosphorylated | 100 | RSK1(Kin.Dom.2-C-terminal) | 91 |
| ABL1(Y253F)-phosphorylated | 100 | CAMK2B | 92 |
| ABL2 | 100 | EPHA4 | 92 |
| ACVR1B | 100 | PIK3CA(M1043I) | 92 |
| ACVRL1 | 100 | TYRO3 | 92 |
| AMPK-alpha1 | 100 | NEK5 | 93 |
| AMPK-alpha2 | 100 | RSK2(Kin.Dom.2-C-terminal) | 93 |
| ARK5 | 100 | ZAP70 | 94 |
| ASK1 | 100 | NLK | 95 |
| ASK2 | 100 | PRKCD | 95 |
| BLK | 100 | WNK1 | 95 |
| BMPR1A | 100 | RAF1 | 96 |
| BRAF | 100 | WNK3 | 96 |
| BRAF(V600E) | 100 | BRSK2 | 97 |
| BRK | 100 | MRCKA | 97 |
| CASK | 100 | STK36 | 97 |
| CDC2L1 | 100 | TNNI3K | 97 |
| CDK11 | 100 | TRPM6 | 97 |
| CDK3 | 100 | AKT2 | 98 |
| CDK4 | 100 | DMPK2 | 98 |
| CDK4-cyclinD3 | 100 | ERBB2 | 98 |
| CDK8 | 100 | ERBB3 | 98 |
| CDK9 | 100 | MRCKB | 98 |
| CDKL3 | 100 | VRK2 | 98 |
| CDKL5 | 100 | BRAF | 99 |
| CSNK1G1 | 100 | CIT | 99 |
| CSNK1G2 | 100 | p38-alpha | 99 |
| DDR2 | 100 | ABL1(F317I)-nonphosphorylated | 100 |
| DLK | 100 | ABL2 | 100 |
| DRAK1 | 100 | ADCK5 | 100 |
| EIF2AK1 | 100 | AKT1 | 100 |
| EPHA1 | 100 | AKT3 | 100 |
| EPHA3 | 100 | BMX | 100 |
| EPHA7 | 100 | BRAF(V600E) | 100 |
| ERK1 | 100 | BRK | 100 |
| ERK3 | 100 | BRSK1 | 100 |
| ERK4 | 100 | CAMK4 | 100 |
| GCN2(Kin.Dom.2, S808G) | 100 | CDC2L1 | 100 |
| HPK1 | 100 | CDC2L2 | 100 |
| IKK-beta | 100 | CDC2L5 | 100 |
| IRAK4 | 100 | CDK8 | 100 |
| ITK | 100 | CHEK1 | 100 |
| JAK1(JH1domain-catalytic) | 100 | CSNK1A1L | 100 |
| JAK1(JH2domain-pseudokinase) | 100 | CSNK1G2 | 100 |
| KIT(V559D, 7670I) | 100 | CSNK1G3 | 100 |
| KIT-autoinhibited | 100 | DDR2 | 100 |
| LATS2 | 100 | EGFR(E746-A750del) | 100 |
| LZK | 100 | EGFR(G719C) | 100 |
| MAP4K2 | 100 | EGFR(G719S) | 100 |
| MAPKAPK2 | 100 | EGFR(L747-S752del, P753S) | 100 |
| MAPKAPK5 | 100 | EGFR(L747-T751del, Sins) | 100 |
| MARK2 | 100 | EGFR(L861Q) | 100 |
| MKNK1 | 100 | EGFR(S752-I759del) | 100 |
| MST1 | 100 | E1FZAK1 | 100 |
| MST1R | 100 | EPHB3 | 100 |
| MST4 | 100 | ERK1 | 100 |
| MYLK4 | 100 | ERK3 | 100 |
| NDR1 | 100 | ERK4 | 100 |
| NEK1 | 100 | IKK-alpha | 100 |

TABLE 3-continued

IC$_{50}$ values relative to various enzymes

| Structure | 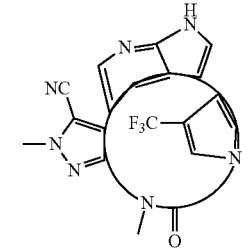 Enzyme IC50 (nM) | Structure | 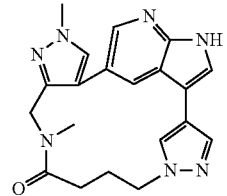 |
|---|---|---|---|
| NEK11 | 100 | IKK-epsilon | 100 |
| NEK2 | 100 | LIMK1 | 100 |
| NIM1 | 100 | LIMK2 | 100 |
| OSR1 | 100 | MAK | 100 |
| p38-beta | 100 | MAPKAPK2 | 100 |
| P38-delta | 100 | MAPKAPK5 | 100 |
| PAK6 | 100 | MKNK1 | 100 |
| PCTK1 | 100 | MKNK2 | 100 |
| PFPK5(*P. falciparum*) | 100 | MST1R | 100 |
| PIK3CA | 100 | MUSK | 100 |
| PIK3CA(C420R) | 100 | NEK11 | 100 |
| PIK3CA(E542K) | 100 | OSR1 | 100 |
| PIK3CA(E545A) | 100 | p38-delta | 100 |
| PIK3CA(Q546K) | 100 | PFPK5(*P. falciparum*) | 100 |
| PIK3CD | 100 | PIK3CD | 100 |
| PIK3CG | 100 | PIM2 | 100 |
| PIM1 | 100 | PKAC-alpha | 100 |
| PKN2 | 100 | PKAC-beta | 100 |
| PLK2 | 100 | PKN1 | 100 |
| PLK3 | 100 | PRKCQ | 100 |
| PRKCH | 100 | PRKG2 | 100 |
| PRKG1 | 100 | RIPK2 | 100 |
| PRKG2 | 100 | SNRK | 100 |
| PRKR | 100 | SRPK2 | 100 |
| PRKX | 100 | TEC | 100 |
| QSK | 100 | TNK1 | 100 |
| RAF1 | 100 | TYK2(JH2domain-pseudokinase) | 100 |
| ROCK1 | 100 | WEE2 | 100 |
| RPS6KA4(Kin.Dom.2-C-terminal) | 100 | YANK1 | 100 |
| RSK2(Kin.Dom.2-C-terminal) | 100 | YANK2 | 100 |
| Sck110 | 100 | YANK3 | 100 |
| SNARK | 100 | | |
| SNRK | 100 | | |
| TAOK1 | 100 | | |
| TAOK2 | 100 | | |
| TAOK3 | 100 | | |
| TEC | 100 | | |
| TGFBR2 | 100 | | |
| TYK2(JH2domain-pseudokinase) | 100 | | |
| ULK1 | 100 | | |
| WNK1 | 100 | | |
| WNK2 | 100 | | |
| WNK3 | 100 | | |

Example 58: Determination of $IC_{50}$ Values Relative to Various Enzymes

Ambit profiling was conducted in accordance with the manufacturer's instructions. The data shown in Table 4 below demonstrates that compounds 45 and 50 are not as selective for DYRK1A as compound 48.

TABLE 4

$IC_{50}$ values relative to various enzymes

| Structure | | Structure | |
|---|---|---|---|
| Compound Number | 45 | Compound Number | 50 |
| Compound Concentration (uM) | 1 | Compound Concentration (uM) | 1 |
| AXL | 0 | FLT3(D835V) | 0 |
| FLT3 | 0 | FLT3(ITD, F691L) | 0 |
| FLT3(D835V) | 0 | FLT3(N841) | 0 |
| FLT3(ITD, D835V) | 0 | FLT3(R834Q) | 0 |
| FLT3(ITD, F691L) | 0 | HPK1 | 0 |
| FLT3(N841I) | 0 | JAK3(JH1domain-catalytic) | 0 |
| JAK3(JH1domain-catalytic) | 0 | MEK5 | 0 |
| MEK3 | 0 | MINK | 0 |
| MST2 | 0 | PDGFRB | 0 |
| TBK1 | 0 | TBKA | 0 |
| TRKA | 0 | TRKB | 0 |
| FLT4 | 0.1 | TRKC | 0 |
| PDGFRB | 0.1 | FLT4 | 0.1 |
| TRKC | 0.1 | RET | 0.1 |
| DDR1 | 0.15 | YSK4 | 0.1 |
| RET | 0.15 | DYRK1A | 0.15 |
| RET(M918T) | 0.2 | ABL1(H396P)-nonphosphorylated | 0.2 |
| MELK | 0.25 | RET(M918T) | 0.25 |
| TRKB | 0.25 | MAP3K3 | 0.3 |
| DYRK1A | 0.3 | DDR1 | 0.35 |
| FLT3(ITD) | 0.3 | FLT3(ITD) | 0.35 |
| MAP3K3 | 0.35 | KIT(D816V) | 0.35 |
| MAP3K2 | 0.45 | LOK | 0.4 |
| MEK4 | 0.5 | SLK | 0.4 |
| DYRK18 | 0.55 | MAP3K2 | 0.5 |
| AURKA | 0.6 | FLT3(ITD, D835V) | 0.55 |
| MERTK | 0.6 | EPH86 | 0.7 |
| LCK | 0.65 | FLT3(D835Y) | 0.7 |
| RSK2(Kin.Dom.1-N-terminal) | 0.9 | VEGFR2 | 0.8 |
| ICK | 0.95 | FLT3(K663Q) | 0.9 |
| BIKE | 1.2 | KIT(V559D) | 0.95 |
| MAP4KS | 1.2 | FLT3 | 1.1 |
| FLT3(D835Y) | 1.3 | RSK2(Kin.Dom.1-N-terminal) | 1.2 |
| SGK | 1.3 | MET(Y1235D) | 1.4 |
| IRAK1 | 1.4 | HIPK4 | 1.5 |
| RICK1 | 1.4 | ABL1(Q252H)-phosphorylated | 1.6 |
| FLT3(D835H) | 1.6 | AKL | 1.6 |
| CSNK2A2 | 1.8 | BLK | 1.6 |
| MINK | 1.8 | LCK | 1.9 |
| ABL1(H396P)-nonphosphorylated | 1.9 | TNK2 | 1.9 |
| STK16 | 1.9 | ABL1(E255K)-phosphorylated | 2 |
| FLT3(K663Q) | 2 | IRAK1 | 2.1 |
| VEGFR2 | 2 | MST1 | 2.2 |
| HIPK4 | 2.1 | RSK4(Kin.Dom.1-N-terminal) | 2.3 |
| HASPIN | 2.3 | ABL1(Q252H)-nonphosphorylated | 2.4 |
| FGFR1 | 2.5 | ABL1(F317L)-phosphorylated | 2.5 |
| S6K1 | 2.5 | TIE2 | 2.7 |
| IRAK3 | 2.6 | FLT3(D835H) | 2.8 |
| RSK4(Kin.Dom.1-N-terminal) | 2.6 | KIT | 2.9 |
| MST1 | 2.8 | MAP4K4 | 3 |
| PFCDPK1(*P. falciparum*) | 2.8 | EGFR(L747-E749del, A750P) | 3.1 |
| SLK | 2.8 | MST2 | 3.1 |

TABLE 4-continued

IC$_{50}$ values relative to various enzymes

| Structure | | Structure | |
|---|---|---|---|
| ABL1(Q252H)-nonphosphorylated | 3.2 | TXK | 3.2 |
| KIT(V559D) | 3.2 | CSF1R | 3.3 |
| MAP4K4 | 3.5 | MERTK | 3.5 |
| CAMKK1 | 3.6 | ABL1-phosphorylated | 3.8 |
| BLK | 3.7 | MET | 3.8 |
| ADCK4 | 3.9 | RSK1(Kin.Dom.1-N-terminal) | 3.8 |
| CSK | 3.9 | TBK1 | 3.8 |
| MAP4K2 | 3.9 | ABL1(H396P)-phosphorylated | 3.9 |
| TAK1 | 4.1 | GAK | 4 |
| KIT(D816V) | 4.2 | KIT(L576P) | 4 |
| CLK2 | 4.3 | RSK3(Kin.Dom.1-N-terminal) | 4 |
| MET(M1250T) | 4.3 | ABL1(M351T)-phosphorylated | 4.1 |
| FGFR3(G697C) | 4.5 | JNK1 | 4.1 |
| KIT(L576P) | 4.5 | MAP4K5 | 4.1 |
| SRPK1 | 4.5 | MET(M1250T) | 4.2 |
| LOK | 4.7 | KIT(D816H) | 4.5 |
| RSK3(Kin.Dom.1-N-terminal) | 4.7 | CSK | 4.7 |
| EPHB6 | 4.8 | ABLT(T315I)-phosphorylated | 4.9 |
| MET(Y1235D) | 4.8 | BMPR1B | 5.1 |
| JAK2(JH1domain-catalytic) | 4.9 | ROS1 | 5.1 |
| FGFR3 | 5.4 | DYRK1B | 5.2 |
| FLT1 | 5.4 | FGR | 5.2 |
| TNIK | 5.6 | FAK | 5.3 |
| AURKB | 5.7 | PDGFRA | 5.6 |
| GAK | 5.7 | CAMKK2 | 5.8 |
| CAMKK2 | 5.8 | FGFR1 | 5.8 |
| PIP5K1C | 5.8 | EGFR(E746-A750del) | 5.9 |
| HPK1 | 5.9 | FLT1 | 5.9 |
| HIPK2 | 6 | CDK7 | 6 |
| RIOK3 | 6 | RET(V804M) | 6 |
| ERK8 | 6.1 | SGK | 6 |
| EGFR(E746-A750del) | 6.4 | FGFR3(G697C) | 6.4 |
| HIPK1 | 6.5 | FLT3-autoinhibited | 6.4 |
| KIT | 6.5 | MEK3 | 7.1 |
| MYO3B | 6.7 | JNK2 | 7.5 |
| TIE2 | 6.7 | FGFR3 | 7.6 |
| BMPR1B | 6.8 | ADCK4 | 7.7 |
| PKNB(*M. tuberculosis*) | 7 | CAMKK1 | 8 |
| TIE1 | 7.2 | HUNK | 8 |
| CASK | 7.4 | HCK | 8.1 |
| ABL1(E255K)-phosphorylated | 7.7 | S6K1 | 8.6 |
| CAMK2A | 7.7 | CSNK2A2 | 8.7 |
| KIT(V559D, T670I) | 8.2 | LTK | 8.7 |
| RET(V804M) | 8.2 | ABLT(T315I)-nonphosphorylated | 8.8 |
| CSF1R | 8.4 | JNK3 | 8.8 |
| EPHA8 | 8.7 | MYO3B | 9 |
| FLT3(R834Q) | 8.7 | TAK1 | 9.1 |
| TAOK1 | 8.8 | TIE1 | 9.2 |
| ABL1-phosphorylated | 9 | GRK7 | 9.7 |
| PRKCI | 9.1 | ABL1(Y253F)-phosphorylated | 10 |
| ABL1(T315I)-nonphosphorylated | 9.4 | BIKE | 10 |
| FGFR2 | 9.5 | FER | 10 |
| CLK1 | 9.9 | FRK | 10 |
| EGFR(L747-E749del, A750P) | 10 | KIT(V559D, T670I) | 10 |
| RET(V804L) | 10 | PLK4 | 10 |
| ABL1(T315I)-phosphorylated | 11 | ABL1-nonphosphorylated | 11 |
| FRK | 11 | CLK2 | 11 |
| MEK5 | 11 | CSNK10 | 11 |
| MET | 11 | FGFR2 | 11 |
| PDGFRA | 11 | MEK2 | 11 |
| PRKD3 | 11 | MELK | 11 |
| ROS1 | 11 | MLK3 | 11 |
| TNK2 | 11 | MYO3A | 11 |

TABLE 4-continued

IC$_{50}$ values relative to various enzymes

| Structure | | Structure | |
|---|---|---|---|
| MEK2 | 12 | PIKFYVE | 11 |
| PAK3 | 12 | RIOK3 | 11 |
| RIPK2 | 12 | RIPK2 | 11 |
| TNK1 | 12 | ALK(L119M) | 12 |
| CDK7 | 13 | CAMK2A | 12 |
| DDR2 | 13 | ICK | 12 |
| PIKFYVE | 13 | MEK1 | 12 |
| SRPK3 | 13 | STK16 | 12 |
| CDKL2 | 14 | CSNK1E | 13 |
| GRK4 | 14 | HIPK1 | 13 |
| KIT(A829P) | 14 | HIPK2 | 13 |
| PFTK1 | 14 | PRKCQ | 13 |
| SNARK | 14 | SRC | 13 |
| CAMK2D | 15 | TNIK | 13 |
| EGFR(L747-S752del, P753S) | 15 | ACVR1 | 14 |
| HIPK3 | 15 | EGFR(L747-S752del, P753S) | 14 |
| MEK6 | 15 | EPHA6 | 14 |
| TXK | 15 | MYLK | 14 |
| ALK(C1156Y) | 16 | AURKA | 15 |
| HUNK | 16 | IRAK3 | 15 |
| CIT | 17 | LYN | 15 |
| GRK1 | 17 | PRKD3 | 15 |
| GSK3A | 17 | CAMK1B | 16 |
| MEK1 | 17 | MAP4K3 | 16 |
| RSK1(Kin.Dom.1-N-terminal) | 17 | MEK4 | 16 |
| YSK4 | 17 | RIOK1 | 16 |
| ACVR1 | 18 | CLK4 | 17 |
| ALK | 18 | EGFR(L861Q) | 17 |
| ALK(L1196M) | 18 | AURKB | 18 |
| EPHA6 | 18 | CLK1 | 18 |
| JNK1 | 18 | EGFR(L858R) | 18 |
| LTK | 18 | ERK8 | 18 |
| MAP4K3 | 18 | RET(V804L) | 18 |
| ABL1(M351T)-phosphorylated | 19 | RPS6KA5(Kin.Dom.1-N-terminal) | 18 |
| CLK4 | 19 | ABL1(F317I)-phosphorylated | 19 |
| CSNK2A1 | 19 | EGFR(L858R, T790M) | 19 |
| DCAMKL3 | 19 | IKK-epsilon | 19 |
| PCTK2 | 19 | KIT(A829P) | 19 |
| TYK2(JH1domain-catalytic) | 19 | PIP5K1A | 19 |
| ABL1(Q252H)-phosphorylated | 20 | PYK2 | 19 |
| ABL1-nonphosphorylated | 20 | TYK2(JH1domain-catalytic) | 19 |
| AURKC | 20 | CAMK2D | 20 |
| DMPK | 20 | CDKL2 | 20 |
| FAK | 20 | IRAK4 | 20 |
| PCTK1 | 20 | PIP5K2C | 20 |
| TTK | 20 | TGFBR2 | 20 |
| FLT3-autoinhibited | 21 | VRK2 | 20 |
| JNK2 | 21 | ALK | 21 |
| LYN | 22 | YES | 21 |
| MAST1 | 22 | ABL2 | 22 |
| TAOK3 | 22 | EGFR(L747-T751del, Sins) | 22 |
| CSNK1E | 23 | INSR | 22 |
| FGR | 223 | STK33 | 23 |
| MYO3A | 23 | TTK | 23 |
| PIP5K2B | 23 | BMX | 24 |
| SGK2 | 23 | PAK3 | 24 |
| ABL1(H396P)-phosphorylated | 24 | PFCDPK1(*P. falciparum*) | 24 |
| CAMK2G | 24 | YANK1 | 24 |
| GSK3B | 24 | DLK | 25 |
| HCK | 24 | YSK1 | 25 |
| MST4 | 24 | ALK(C1156Y) | 26 |
| ABL1(F317L)-phosphorylated | 25 | CLK3 | 26 |
| CAMK1B | 25 | EPHA8 | 26 |

TABLE 4-continued

IC50 values relative to various enzymes

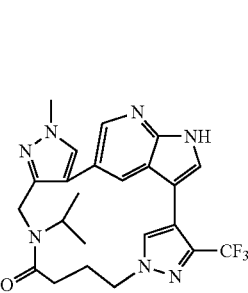 [SMILES: CC(C)N1Cc2nn(C)cc2-c2cnc3[nH]cc(c3c2)-c2cn(nc2C(F)(F)F)CCCC1=O] 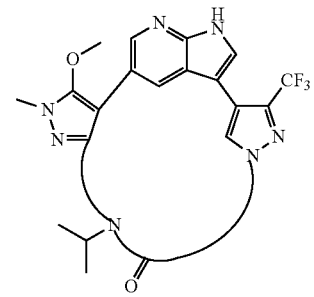

| Structure | | Structure | |
|---|---|---|---|
| DYRK2 | 25 | HIPK3 | 26 |
| EGFR(L858R) | 25 | SYK | 26 |
| SRC | 25 | CSF1R-autoinhibited | 27 |
| EPHA1 | 26 | EGFR | 27 |
| EGFR(L858R, T790M) | 27 | LRRK2(G2019S) | 27 |
| PIP5K1A | 27 | FYN | 28 |
| PRKCQ | 27 | MLK1 | 28 |
| RIPK5 | 27 | TNK1 | 28 |
| SIK2 | 27 | EPHA1 | 29 |
| CSNK1D | 28 | JAK2(JH1domain-catalytic) | 29 |
| EGFR(L861Q) | 28 | PRKCE | 30 |
| GRK7 | 28 | SRPK1 | 30 |
| MARK4 | 28 | CAMK2G | 31 |
| MLK3 | 28 | CIT | 31 |
| TAOK2 | 28 | FES | 31 |
| EGFR | 29 | PIK4CB | 31 |
| JNK3 | 29 | DDR2 | 32 |
| MYLK2 | 29 | EGFR(T790M) | 32 |
| PLK4 | 29 | ERBB4 | 32 |
| PCTK3 | 30 | PIP5K1C | 32 |
| PYK2 | 30 | SIK2 | 32 |
| SGK3 | 30 | TEC | 32 |
| ULK3 | 30 | LKB1 | 33 |
| EGFR(L747-T751del, Sins) | 31 | PRKD1 | 33 |
| DLK | 32 | PHKG1 | 34 |
| EPHA3 | 32 | PKN1 | 34 |
| MARK3 | 32 | ABL1(F317L)-nonphosphorylated | 35 |
| QSK | 32 | BUB1 | 35 |
| CDK3 | 33 | PIP5K2B | 35 |
| CLK3 | 33 | CASK | 36 |
| MARK1 | 33 | PKNB(M. tuberculosis) | 36 |
| MAK | 34 | TGFBR1 | 36 |
| PHKG1 | 34 | CAMK1D | 38 |
| BMX | 35 | GRK4 | 38 |
| CDK2 | 35 | SRPK3 | 38 |
| KIT(D816H) | 35 | WEE1 | 38 |
| SYK | 35 | AURKC | 39 |
| ACVRL1 | 36 | MARK1 | 39 |
| JAK1(JH1domain-catalytic) | 36 | MYLK2 | 39 |
| MLK2 | 36 | EPHB4 | 40 |
| PRKD1 | 36 | MAST1 | 40 |
| PRP4 | 36 | EGFR(G719S) | 41 |
| MYLK | 37 | HASPIN | 42 |
| VRK2 | 37 | MST1R | 42 |
| ITK | 38 | PRKCI | 42 |
| YSK1 | 38 | AAK1 | 43 |
| CDKL1 | 39 | MARK3 | 43 |
| CSF1R-autoinhibited | 39 | PRKCD | 43 |
| FYN | 39 | TSSK1B | 43 |
| IRAK4 | 39 | GRK1 | 44 |
| PFTAIRE2 | 39 | MAP4K2 | 44 |
| AAK1 | 40 | EPHA3 | 45 |
| IKK-epsilon | 40 | MEK6 | 45 |
| EGFR(G719S) | 41 | PKAC-beta | 45 |
| ABL2 | 42 | YANK2 | 45 |
| LZK | 42 | CAMK2B | 46 |
| INSR | 43 | ITK | 46 |
| PRKD2 | 43 | WNK2 | 46 |
| LRRK2 | 44 | CDK9 | 47 |
| PHKG2 | 44 | DMPK2 | 47 |
| ZAK | 45 | SNARK | 47 |
| MLK1 | 46 | EGFR(S752-I759del) | 48 |
| EPHA2 | 48 | EPHB1 | 48 |

TABLE 4-continued

IC$_{50}$ values relative to various enzymes

| Structure | | Structure | |
|---|---|---|---|
| MARK2 | 48 | CDK11 | 49 |
| FER | 49 | EPHA7 | 50 |
| NEK2 | 49 | LRRK2 | 50 |
| AMPK-alpha1 | 50 | SGK3 | 50 |
| NEK3 | 50 | CDKL1 | 51 |
| EPHB1 | 51 | EGFR(G719C) | 51 |
| INSRR | 51 | NEK3 | 51 |
| PAK7 | 51 | CAMK1 | 53 |
| PIK3CA(E545K) | 51 | CTK | 53 |
| PKAC-alpha | 51 | MKNK2 | 53 |
| CDK4-cyclinD1 | 53 | PHKG2 | 53 |
| DMPK2 | 53 | CAMK1G | 54 |
| LRRK2(G2019S) | 53 | DCAMKL1 | 54 |
| ASK2 | 54 | PIK3CG | 54 |
| PKAC-beta | 54 | EPHB2 | 55 |
| ABL1(F317L)-nonphosphorylated | 55 | MARK4 | 55 |
| BTK | 55 | PRKD2 | 55 |
| ERBB4 | 55 | ABL1(F317I)-nonphosphorylated | 56 |
| TLK1 | 55 | BTK | 56 |
| PIK3CA(E545A) | 56 | DCAMKL3 | 56 |
| ULK2 | 56 | DYRK2 | 56 |
| YES | 56 | EPHA2 | 56 |
| MST3 | 57 | INSRR | 56 |
| EGFR(G719C) | 59 | PCTK2 | 56 |
| EPHA7 | 59 | ACVR1B | 57 |
| NDR1 | 59 | AMPK-alpha2 | 57 |
| CAMK1D | 60 | SIK | 57 |
| CDK9 | 60 | PIK3C2G | 58 |
| BRSK2 | 64 | TLK1 | 58 |
| WNK2 | 64 | ZAK | 58 |
| CAMK2B | 65 | CSNK2A1 | 59 |
| EGFR(T790M) | 65 | RIPK1 | 59 |
| JAK1(JH2domain-pseudokinase) | 65 | SGK2 | 59 |
| EGFR(S752-I759del) | 66 | MAP3K4 | 60 |
| CDKL5 | 68 | MLK2 | 60 |
| KIT-autoinhibited | 69 | MST4 | 60 |
| MTOR | 69 | PFTAIRE2 | 60 |
| PAK1 | 69 | PFTK1 | 60 |
| SRMS | 69 | CDK2 | 62 |
| CTK | 70 | EPHB3 | 62 |
| MST1R | 70 | RPS6KA4(Kin.Dom.1-N-terminal) | 62 |
| PAK6 | 70 | EPHA4 | 63 |
| RPS6KA5(Kin.Dom.1-N-terminal) | 70 | MST3 | 63 |
| ABL1(F317I)-phosphorylated | 71 | TAOK3 | 63 |
| PRKCD | 71 | LIMK2 | 64 |
| PRKR | 71 | NDR1 | 64 |
| STK33 | 71 | NEK5 | 64 |
| PKN1 | 72 | RIOK2 | 64 |
| TNNI3K | 72 | DAPK1 | 65 |
| WEE1 | 73 | EIF2AK1 | 66 |
| FES | 74 | PCTK1 | 66 |
| p38-gamma | 74 | ACVRL1 | 67 |
| PAK2 | 74 | CDK8 | 67 |
| RIOK2 | 74 | CSNK1A1L | 67 |
| SIK | 74 | DAPK2 | 67 |
| PIM1 | 75 | EPHA5 | 67 |
| ULK1 | 75 | ROCK2 | 67 |
| ABL1(V253F)-phosphorylated | 76 | LZK | 68 |
| EPHB4 | 76 | NEK2 | 68 |
| MKK7 | 76 | NEK7 | 68 |
| PAK4 | 76 | ERK3 | 69 |
| EPHB2 | 77 | IGF1R | 69 |
| BMPR2 | 78 | PCTK3 | 69 |

TABLE 4-continued

IC$_{50}$ values relative to various enzymes

| Structure | | Structure | |
|---|---|---|---|
| CSNK1A1 | 78 | TAOK2 | 69 |
| ACVR2B | 79 | TESK1 | 69 |
| DCAMKL1 | 80 | ERK5 | 70 |
| BUB1 | 81 | KIT(V559D, V654A) | 70 |
| PIK3CA(M1043I) | 81 | DAPK3 | 71 |
| CHEK2 | 82 | ERN1 | 71 |
| PFPK5(*P. falciparum*) | 82 | NEK1 | 71 |
| TRPM6 | 83 | BRSK2 | 72 |
| TSSK1B | 83 | LATS1 | 72 |
| ZAP70 | 83 | MAP3K1 | 72 |
| MAP3K15 | 84 | PKAC-alpha | 72 |
| NLK | 84 | RPS6KA5(Kin.Dom.2-C-terminal) | 72 |
| PIK3CA(H1047Y) | 84 | TNNI3K | 72 |
| FGFR4 | 85 | ADCK3 | 73 |
| RIPK1 | 85 | CDC2L1 | 73 |
| RSK1(Kin.Dom.2-C-terminal) | 85 | QSK | 73 |
| CDK5 | 86 | ULK3 | 73 |
| IGF1R | 86 | WEE2 | 73 |
| MRCKB | 86 | CSNK1A1 | 74 |
| p38-alpha | 86 | PIK3CA(E545K) | 74 |
| TLK2 | 86 | RSK4(Kin.Dom.2-C-terminal) | 74 |
| ABL1(F317I)-nonphosphorylated | 87 | SRPK2 | 74 |
| AMPK-alpha2 | 87 | YANK3 | 74 |
| PIK3CA(I800L) | 87 | p38-gamma | 75 |
| TGFBR1 | 87 | CDK4-cyclinD1 | 76 |
| TYRO3 | 87 | KIT-autoinhibited | 76 |
| CAMK1G | 88 | MAP3K15 | 76 |
| EPHA4 | 88 | PAK1 | 76 |
| ACVR1B | 89 | MAK | 77 |
| MUSK | 89 | MYLK4 | 77 |
| ERN1 | 90 | PIM1 | 77 |
| PLK2 | 90 | PLK3 | 77 |
| PRKCE | 90 | CDK3 | 78 |
| TSSK3 | 90 | NDR2 | 78 |
| CAMK1 | 91 | CSNK1G3 | 79 |
| TGFBR2 | 91 | FGFR4 | 79 |
| DAPK1 | 92 | PFPK5(*P. falciparum*) | 79 |
| EPHA5 | 92 | ROCK1 | 79 |
| NDR2 | 92 | BRK | 80 |
| PIK3C2B | 92 | CDKL3 | 80 |
| PIK3CD | 92 | CHEK2 | 80 |
| PKMYT1 | 92 | MKK7 | 80 |
| LIMK1 | 93 | RSK3(Kin.Dom.2-C-terminal) | 80 |
| NEK4 | 93 | CDK4-cyclinD3 | 81 |
| PLK1 | 93 | CSNK1G1 | 81 |
| MAP3K4 | 94 | JAK1(JH2domain-pseudokinase) | 81 |
| NIK | 94 | p36-alpha | 81 |
| PIK3CG | 94 | RSK1(Kin.Dom.2-C-terminal) | 81 |
| PIM3 | 94 | SRMS | 81 |
| MAP3K1 | 95 | ERK4 | 82 |
| PLK3 | 95 | MLCK | 82 |
| ROCK1 | 95 | NEK9 | 82 |
| RSK4(Kin.Dom.2-C-terminal) | 95 | PIK3CA(E545A) | 82 |
| RSK3(Kin.Dom.2-C-terminal) | 96 | TAOK1 | 82 |
| BMPR1A | 97 | CSNK1G2 | 83 |
| EPHB3 | 97 | IKK-alpha | 83 |
| NEK10 | 97 | MKNK1 | 83 |
| NEK7 | 97 | p38-beta | 83 |
| PIK3C2G | 97 | PIK3CA | 83 |
| TEC | 97 | PIK3CA(H1047L) | 83 |
| WNK4 | 97 | VPS34 | 83 |
| NEK6 | 98 | NLK | 84 |
| PDPK1 | 98 | PRKR | 84 |

TABLE 4-continued

IC$_{50}$ values relative to various enzymes

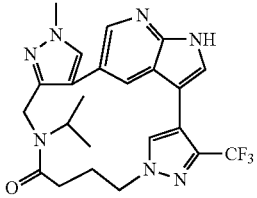
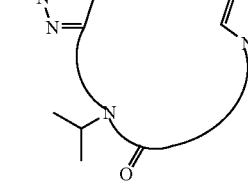

| Structure | | Structure | |
|---|---|---|---|
| PIK3CA(E542K) | 98 | TYK2(JH2domain-pseudokinase) | 84 |
| RPS6KA4(Kin.Dom.1-N-terminal) | 98 | GRK3 | 85 |
| SgK110 | 98 | PIK3CA(E542K) | 85 |
| STK39 | 98 | PRKCH | 85 |
| CDC2L5 | 99 | RIPK4 | 85 |
| DAPK3 | 99 | AKT2 | 86 |
| MLCK | 99 | ERBB2 | 86 |
| PIK4CB | 99 | NIK | 86 |
| TESK1 | 99 | PAK8 | 86 |
| ACVR2A | 100 | PIK3CA(I600L) | 86 |
| ADCK3 | 100 | PIK3CA(M1043I) | 86 |
| AKT1 | 100 | PIK3CA(Q546K) | 86 |
| AKT2 | 100 | PKMYT1 | 86 |
| AKT3 | 100 | SNRK | 86 |
| ANKK1 | 100 | BRAF | 87 |
| ARK5 | 100 | ERK2 | 87 |
| ASK1 | 100 | GRK2 | 87 |
| BRAF | 100 | IKK-beta | 87 |
| BRAF(V600E) | 100 | NEK10 | 87 |
| BRK | 100 | PRKG2 | 87 |
| BRSK1 | 100 | PRP4 | 87 |
| CAMK4 | 100 | BMPR1A | 88 |
| CDC2L1 | 100 | CDK4 | 88 |
| CDC2L2 | 100 | BMPR2 | 89 |
| CDK11 | 100 | BRSK1 | 89 |
| CDK4 | 100 | CDC2L2 | 89 |
| CDK4-cyclinD3 | 100 | CDC2L5 | 89 |
| CDK8 | 100 | CDK5 | 89 |
| CDKL3 | 100 | AMPK-alpha1 | 90 |
| CHEK1 | 100 | DCAMKL2 | 90 |
| CSNK1A1L | 100 | GSK3B | 90 |
| CSNK1G1 | 100 | MUSK | 90 |
| CSNK1G2 | 100 | LIMK1 | 91 |
| CSNK1G3 | 100 | PAK4 | 91 |
| DAPK2 | 100 | PIK3CA(C420R) | 91 |
| DCAMKL2 | 100 | PIM3 | 91 |
| DRAK1 | 100 | TLK2 | 91 |
| DRAK2 | 100 | ACVR2B | 92 |
| EIF2AK1 | 100 | BRAF(V600E) | 93 |
| ERBB2 | 100 | GSK3A | 93 |
| ERBB3 | 100 | RAF1 | 93 |
| ERK1 | 100 | ULK1 | 93 |
| ERK2 | 100 | ANKK1 | 94 |
| ERK3 | 100 | NEK11 | 94 |
| ERK4 | 100 | PIK3CD | 94 |
| ERK5 | 100 | STK35 | 94 |
| GCN2(Kin.Dom.2, S808G) | 100 | ERK1 | 95 |
| GRK2 | 100 | PLK2 | 95 |
| GRK3 | 100 | RIPK5 | 95 |
| IKK-alpha | 100 | ACVR2A | 96 |
| IKK-beta | 100 | ULK2 | 96 |
| KIT(V559D, V654A) | 100 | LATS2 | 97 |
| LATS1 | 100 | ASK2 | 98 |
| LATS2 | 100 | DRAK2 | 98 |
| LIMK2 | 100 | MTOR | 98 |
| LKB1 | 100 | SBK1 | 98 |
| MAPKAPK2 | 100 | MRCKA | 99 |
| MAPKAPK5 | 100 | MRCKB | 99 |
| MKNK1 | 100 | p38-delta | 99 |
| MKNK2 | 100 | SgK110 | 99 |
| MRCKA | 100 | TYRO3 | 99 |
| MYLK4 | 100 | AKT1 | 100 |
| NEK1 | 100 | AKT3 | 100 |

TABLE 4-continued

IC$_{50}$ values relative to various enzymes

| Structure | | Structure | |
|---|---|---|---|
| NEK11 | 100 | ARK5 | 100 |
| NEK5 | 100 | ASK1 | 100 |
| NEK9 | 100 | CAMK4 | 100 |
| NIM1 | 100 | CDKL5 | 100 |
| OSR1 | 100 | CHEK1 | 100 |
| p38-beta | 100 | DMPK | 100 |
| p38-delta | 100 | DRAK1 | 100 |
| PIK3CA | 100 | ERBB3 | 100 |
| PIK3CA(C420R) | 100 | GCN2(Kin.Dom.2, S808G) | 100 |
| PIK3CA(H1047L) | 100 | JAK1(JH1domain-catalytic) | 100 |
| PIK3CA(Q546K) | 100 | MAPKAPK2 | 100 |
| PIK3CB | 100 | MAPKAPK5 | 100 |
| PIM2 | 100 | MARK2 | 100 |
| PIP5K2C | 100 | NEK4 | 100 |
| PKN2 | 100 | NEK6 | 100 |
| PRKCH | 100 | NIM1 | 100 |
| PRKG1 | 100 | OSR1 | 100 |
| PRKG2 | 100 | PAK2 | 100 |
| PRKX | 100 | PAK7 | 100 |
| RAF1 | 100 | PDPK1 | 100 |
| RIPK4 | 100 | PIK3C2B | 100 |
| ROCK2 | 100 | PIK3CA(H1047Y) | 100 |
| RPS6KA4(Kin.Dom.2-C-terminal) | 100 | PIK3CB | 100 |
| RPS6KA5(Kin.Dom.2-C-terminal) | 100 | PIM2 | 100 |
| RSK2(Kin.Dom.2-C-terminal) | 100 | PKN2 | 100 |
| SBK1 | 100 | PLK1 | 100 |
| SNRK | 100 | PRKG1 | 100 |
| SRPK2 | 100 | PRKX | 100 |
| STK35 | 100 | RPS6KA4(Kin.Dom.2-C-terminal) | 100 |
| STK36 | 100 | RSK2(Kin.Dom.2-C-terminal) | 100 |
| TYK2(JK2domain-pseudokinase) | 100 | STK36 | 100 |
| VPS34 | 100 | STK39 | 100 |
| WEE2 | 100 | TRPM6 | 100 |
| WNK1 | 100 | TSSK3 | 100 |
| WNK3 | 100 | WNK1 | 100 |
| YANK1 | 100 | WNK3 | 100 |
| YANK2 | 100 | WNK4 | 100 |
| YANK3 | 100 | ZAP70 | 100 |

Example 59: DYRK1A, CLK1, and LRRK2 (G2019S) Inhibition DYRK1A Enzyme Assay

All DYRK1A kinase inhibition assays were conducted by using Promega™ ADP-Glo™ Kinase assay systems (Cat No. V9102). Inhibitors were tested with 12 concentrations over a 3-fold serial dilution series (Final concentration: 10 µM, 3.3 µM, 1.1 µM, 370 nM, 123 nM, 41 nM, 13.7 nM, 4.6 nM, 1.5 nM, 500 pM, 170 pM and DMSO control).

For DYRK1A enzyme assay, each inhibitor mixed with 0.2 µg/µL of substrate (MVBP, SignalChem, M42-51N), 3 µM ATP (Promega™, Cat No. V9102), 3 ng of DYRK1A enzyme (Thermo Fisher Scientific, PR7189B) in 384-well plate. All samples were diluted with kinase reaction buffer (40 mM Tris HCl, 10 mM MgCL$_2$, and 0.1 µg/µL BSA (bovine serum albumin), 0.05 mM DTT). After 1 h reaction at 25° C., ADP-Glo™ (Proeg™, V9102) reagent was added and incubated at rt for 40 min. Finally, kinase detection reagent (Promega™, Cat No. V6930) was added and reacted at 25° C. for 10 min. The luminescence signals were detected by using Synergy™ Neo2 microplate reader (BioTek®). Compound inhibition curve was fitted using GraphPad Prism 8.0 software.

CLK1 Enzyme Assay

All CLK1 kinase inhibition assays were conducted by using Promega™ ADP-Glo™ Kinase assay systems (Cat No. V9102). Inhibitors were tested with 12 concentrations over a 3-fold serial dilution series (Final concentration: 10 µM, 3.3 µM, 1.1 µM, 370 nM, 123 nM, 41 nM, 13.7 nM, 4.6 nM, 1.5 nM, 500 pM, 170 pM and DMSO control).

For DYRKIA enzyme assay, each inhibitor mixed with 0.1 µg/µL of substrate (MBP, SignalChem, M42-51N), 10 µM ATP (Promega™, Cat No. V9102), 1.6 ng of CLK1 enzyme (Signalchem, C57-11G) in 384-well plate. All samples were diluted with kinase reaction buffer (40 mM Tris HCl, 10 mM MgCL$_2$, and 0.1 µg/µL BSA, 0.05 mM DTT). After 1 h reaction at 25° C., ADP-Glo™ (Promega™, Cat No. V9102) reagent was added and incubated at rt for 40 min. Finally, kinase detection reagent (Promega™, Cat No. V6930) was added and reacted at 25° C. for 10 min. The luminescence signals were detected by using Synergy™ Neo2 microplate reader (BioTek®). Compound inhibition curve was fitted using GraphPad Prism 8.0 software.

LRRK2(G2019S) Enzyme Assay

All LRRK2 kinase inhibition assays were conducted by using Promega™ ADP-Glo™ Kinase assay systems (Cat No. V4475). Inhibitors were tested with 12 concentrations over a 5-fold serial dilution series Final concentration: 10 µM, 3.3 µM, 1.1 µM, 370 nM, 123 nM, 41 nM, 13.7 nM, 4.6 nM, 1.5 nM, 500 pM, 170 pM, DMSO control) and PF06447475 as positive control.

For LRRK G2019S, each compound mixed with 0.2 µg/µL of substrate, 25 µM ATP, 16 ng of LRRK2 G2019S enzyme (SignalChem, L10-12GG). All samples were diluted with kinase reaction buffer (40 mmol/L TrisHCl, 10 mmol/L $MgCl_2$, and 0.1 µg/µL BSA, 0.05 mM DTT). After a 2 h reaction at 25° C., ADP-Glo™ (Promega™, V9102) reagent was added and incubated at rt for 40 min. Finally, kinase detection reagent (Promega™, Cat No. V6930) was added and reacted at 25° C. for 10 min. The luminescence signals were detected by using Synergy™ Neo2 microplate reader (BioTek®). Compound inhibition curve was fitted using GraphPad Prism 8.0 software. The results, set forth in Table 5 below, show that inventive compounds 43, 48, 59, 60, 61, and 67 are the most potent against DYRKIA.

TABLE 5

Enzyme activity against DYRK1A, CLK1, and LRRK2 (G2019S)

| Inventive Compound | DYRK1A | CLK1 | LRRK2 |
|---|---|---|---|
| 43 | A | A | C |
| 59 | A | A | C |
| 60 | A | A | C |
| 48 | A | C | C |
| 61 | A | C | C |
| 63 | B | A | B |
| 65 | C | C | C |
| 67 | A | C | C |
| 75 | C | C | C |
| 78 | C | C | C |

A: <0.05 µM;
B: 0.05-0.100 µM;
C: >0.100 µM

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound represented by a structure of formula I:

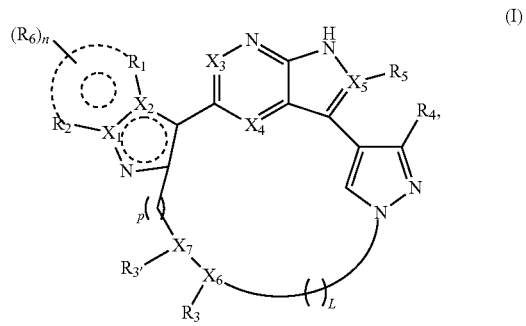

wherein:

$X_1$ represents C or N;

$X_2$ represents C or N;

provided that only one of $X_1$ and $X_2$ represents N;

$X_3$ represents C or N;

$X_4$ represents C or N;

provided that only one of $X_3$ and $X_4$ represents N;

$X_5$ represents C or N, provided that if $X_5$ represent N, $R_5$ is absent, $X_3$ represents C and $X_4$ represents C or N;

$R_1$ represents CH, C1-C3 alkyl, haloalkyl, optionally substituted alkoxy, halo, or cyano;

$R_2$ represents N, CH, optionally substituted C1-C3 alkyl, haloalkyl, or optionally substituted heterocyclyl;

or when $X_1$ represents C, $X_2$ represents N, and $R_2$ represents CH or N, $R_1$ and $R_2$ together with the atoms to which they are bound form a pyridine or pyrimidine ring that is optionally substituted with $R_6$, wherein each $R_6$ independently represents $C_1$-$C_3$ alkyl, optionally substituted C1-C3 alkoxy, halo, or cyano, and n is 0 or 1;

$R_3$ represents H, =O, optionally substituted C1-C3 alkyl, or alkylamine;

$R_3'$ represents H, =O, optionally substituted C1-C3 alkyl, or alkylamine;

$R_4$ represents H, is optionally substituted C1-C3 alkyl, optionally substituted C1-C3 alkoxy, halo, haloalkyl, or cyano;

$R_5$ is absent or represents H, optionally substituted C1-C3 alkyl, halo, or cyano;

L represents C2-C5 alkylene, optionally interrupted by —O—, and which is optionally substituted with hydroxyl, alkoxy, or optionally substituted amino;

$X_6$ represents C or N, provided that if $R_3$ represents =O, $X_6$ is C, and if $R_3$ represents H, optionally substituted C1-C3 alkyl, or alkylamine, $X_6$ is N;

$X_7$ represents C or N, provided that if $R_3'$ represents =O, $X_7$ is C, and if $R_3'$ represents H, optionally substituted C1-C3 alkyl, or alkylamine, $X_7$ is N;

provided that only one of $X_6$ and $X_7$ represents N; and p is 0 or 1; or a pharmaceutically acceptable salt or stereoisomer thereof.

2. The compound of claim 1, wherein p is 1 and $X_6$ is C, $R_3$ is =O, and $X_7$ is N and the compound is represented by a structure of formula Ia:

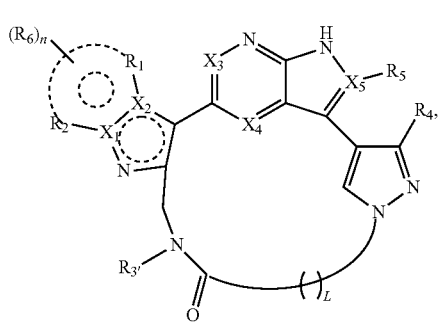

(Ia)

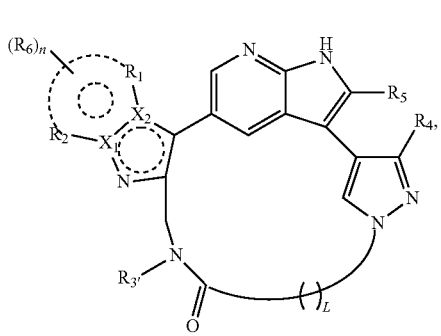

(Ia1)

or p is 0 and $X_6$ is C, $R_3$ is =O, and $X_7$ is N and the compound is represented by a structure of formula Ib:

or $X_4$ and $X_5$ represent C, $X_3$ represents N in the structure of formula Ia, and the compound is represented by a structure of formula Ia2:

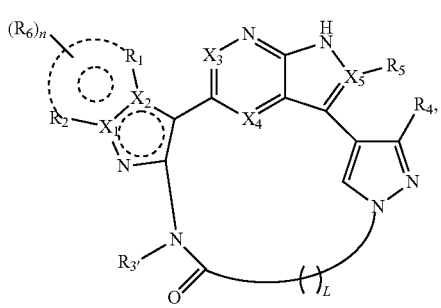

(Ib)

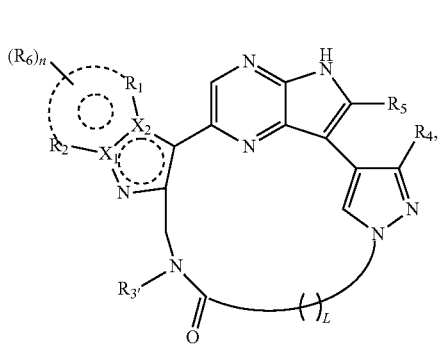

(Ia2)

or p is 0 and $X_6$ is N, $X_7$ is C, and $R_3'$ is =O and the compound is represented by a structure of formula Ic:

or $X_3$ and $X_5$ represent C, $X_4$ represents N in the structure of formula Ia, and the compound is represented by a structure of formula Ia3:

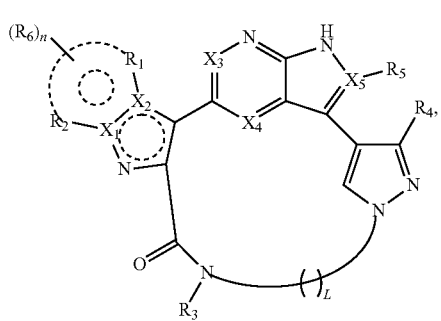

(Ic)

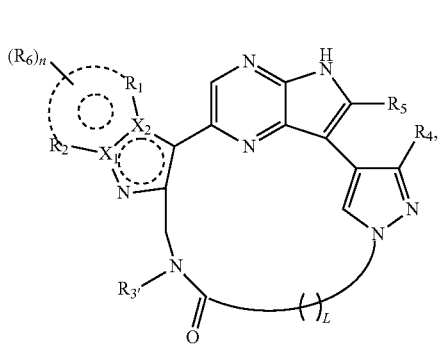

(Ia3)

or a pharmaceutically acceptable salt or stereoisomer thereof.

3. The compound of claim 2, wherein $X_3$, $X_4$, and $X_5$ each represent C in the structure of formula Ia and the compound is represented by a structure of formula Ia1:

or $X_3$ and $X_4$ represent C, $X_5$ represents N in the structure of formula Ia, and the compound is represented by a structure of formula Ia4:

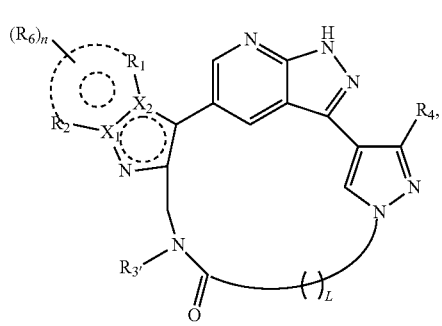

(Ia4)

or

X$_3$ represents C, X$_4$ and X$_5$ represent N in the structure of formula Ia, and the compound is represented by a structure of formula Ia5:

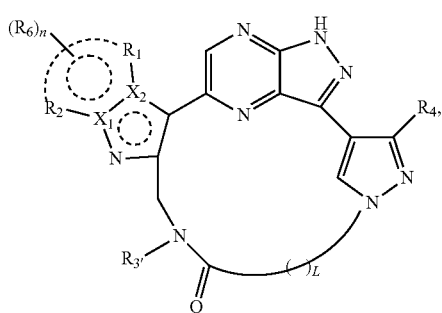

(Ia5)

or a pharmaceutically acceptable salt or stereoisomer thereof.

4. The compound of claim 3, wherein X$_1$ is N and X$_2$ is C in the structure of formula Ia1, and the compound is represented by the structure of formula Ia1a:

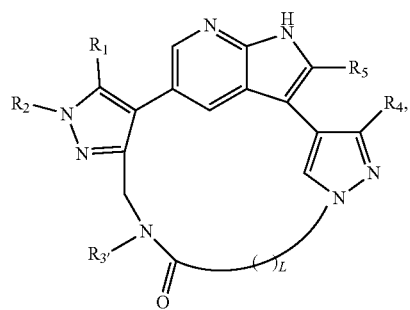

(Ia1a)

or

X$_1$ is C, X$_2$ is N and R$_1$ and R$_2$ together with the atoms to which they are bound form a pyrimidine ring that is optionally substituted with R$_6$ in the structure of formula Ia1, and the compound is represented by the structure of formula Ia1b:

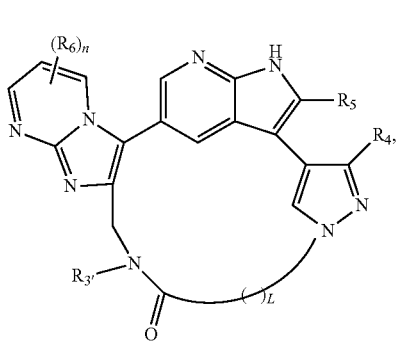

(Ia1b)

or

X$_1$ is C, X$_2$ is N and R$_1$ and R$_2$ together with the atoms to which they are bound form a pyridine ring that is optionally substituted with R$_6$ in the structure of formula Ia1, and the compound is represented by the structure of formula Ia1c:

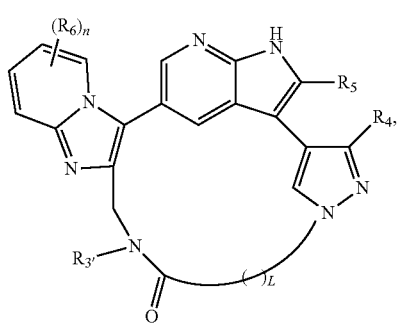

(Ia1c)

or a pharmaceutically acceptable salt or stereoisomer thereof.

5. The compound of claim 3, wherein X$_1$ is N and X$_2$ is C in the structure of formula Ia2, and the compound is represented by the structure of formula Ia2a:

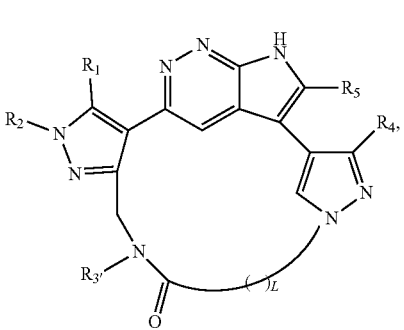

(Ia2a)

or

X$_1$ is C, X$_2$ is N and R$_1$ and R$_2$ together with the atoms to which they are bound form a pyrimidine ring that is optionally substituted with R$_6$ in the structure of formula Ia2, and the compound is represented by the structure of formula Ia2b:

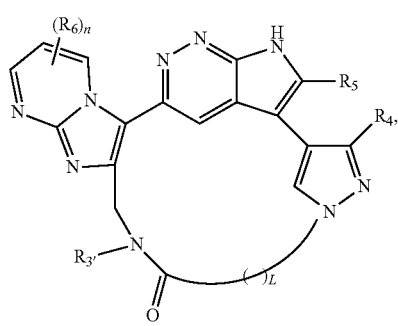

(Ia2b)

or

X$_1$ is C, X$_2$ is N and R$_1$ and R$_2$ together with the atoms to which they are bound form a pyridine ring that is optionally substituted with R$_6$ in the structure of formula Ia2, and the compound is represented by the structure of formula Ia2c:

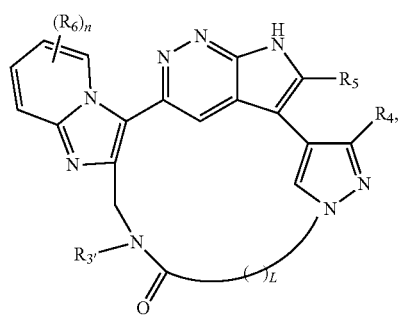

(Ia2c)

or a pharmaceutically acceptable salt or stereoisomer thereof.

6. The compound of claim 3, wherein X$_1$ is N and X$_2$ is C in the structure of formula Ia3, and the compound is represented by the structure of formula Ia3a:

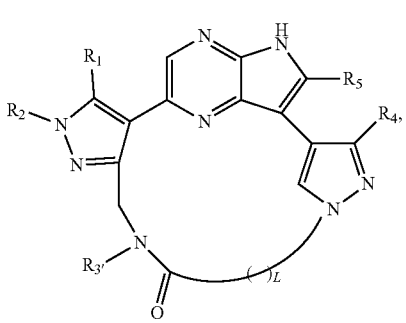

(Ia3a)

or

X$_1$ is C, X$_2$ is N and R$_1$ and R$_2$ together with the atoms to which they are bound form a pyrimidine ring that is optionally substituted with R$_6$ in the structure of formula Ia3, and the compound is represented by the structure of formula Ia3b:

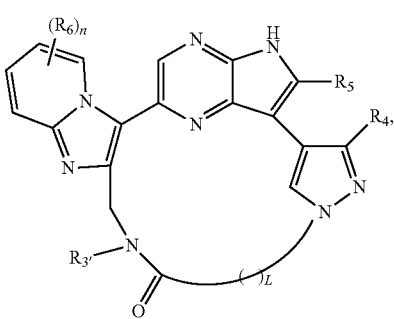

(Ia3b)

or

X$_1$ is C, X$_2$ is N and R$_1$ and R$_2$ together with the atoms to which they are bound form a pyridine ring that is optionally substituted with R$_6$ in the structure of formula Ia3, and the compound is represented by the structure of formula Ia3c:

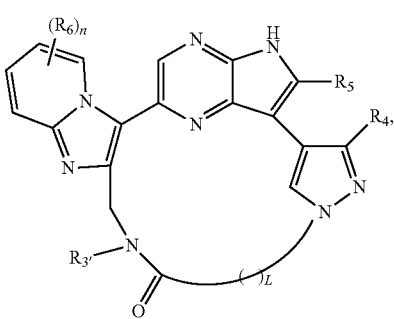

(Ia3c)

or a pharmaceutically acceptable salt or stereoisomer thereof.

7. The compound of claim 3, wherein X$_1$ is N and X$_2$ is C in the structure of formula Ia4, and the compound is represented by the structure of formula Ia4a:

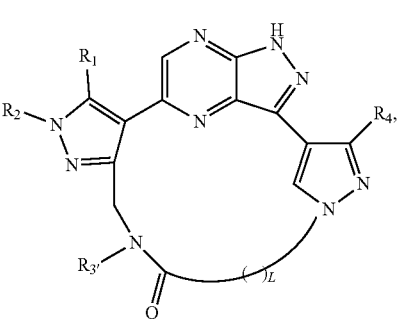

(Ia4a)

or

X$_1$ is C, X$_2$ is N and R$_1$ and R$_2$ together with the atoms to which they are bound form a pyrimidine ring that is optionally substituted with R$_6$ in the structure of formula Ia4, and the compound is represented by the structure of formula Ia4b:

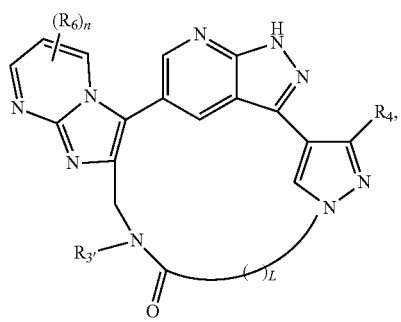

(Ia4b)

or

X$_1$ is C, X$_2$ is N and R$_1$ and R$_2$ together with the atoms to which they are bound form a pyridine ring that is optionally substituted with R$_6$ in the structure of formula Ia4, and the compound is represented by the structure of formula Ia4c:

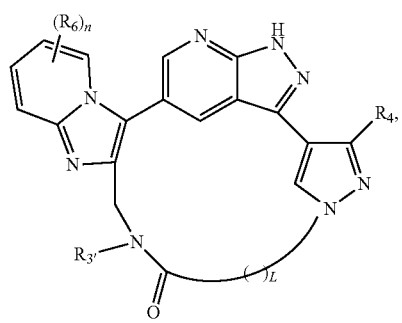

(Ia4c)

or a pharmaceutically acceptable salt or stereoisomer thereof.

8. The compound of claim 3, wherein X$_1$ is N and X$_2$ is C in the structure of formula Ia5, and the compound is represented by the structure of formula Ia5a:

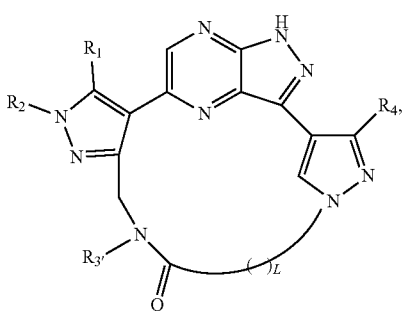

(Ia5a)

or

X$_1$ is C, X$_2$ is N and R$_1$ and R$_2$ together with the atoms to which they are bound form a pyrimidine ring that is optionally substituted with R$_6$ in the structure of formula Ia5, and the compound is represented by the structure of formula Ia5b:

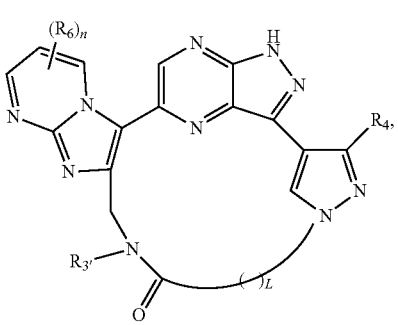

(Ia5b)

or

X$_1$ is C, X$_2$ is N and R$_1$ and R$_2$ together with the atoms to which they are bound form a pyridine ring that is optionally substituted with R$_6$ in the structure of formula Ia5, and the compound is represented by the structure of formula Ia5c:

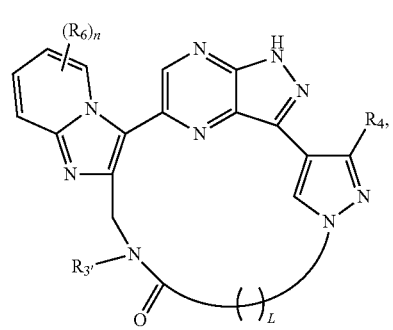

(Ia5c)

or a pharmaceutically acceptable salt or stereoisomer thereof.

9. The compound of claim 2, wherein X$_3$, X$_4$, and X$_5$ each represent C in the structure of formula Ib and the compound is represented by a structure of formula Ib1:

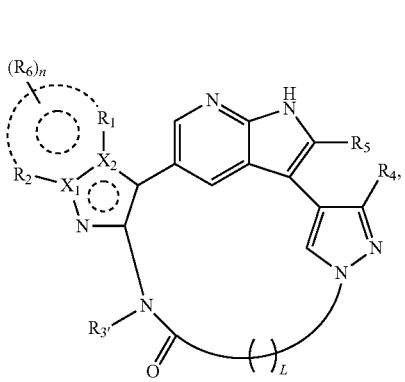

(Ib1)

or wherein X$_4$ and X$_5$ represent C, X$_3$ represents N in the structure of formula Ib, and the compound is represented by a structure of formula Ib2:

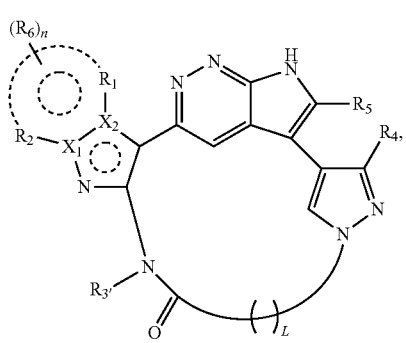

(Ib2)

or

X₃ and X₅ represent C, X₄ represents N in the structure of formula Ib, and the compound is represented by a structure of formula Ib3:

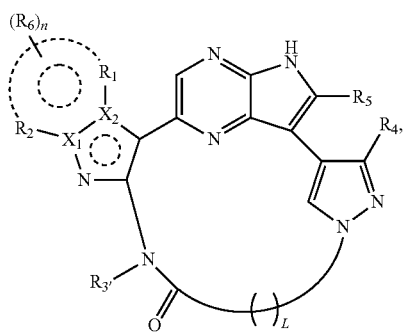

(Ib3)

or

X₃ and X₄ represent C, X₅ represents N in the structure of formula Ib, and the compound is represented by a structure of formula Ib4:

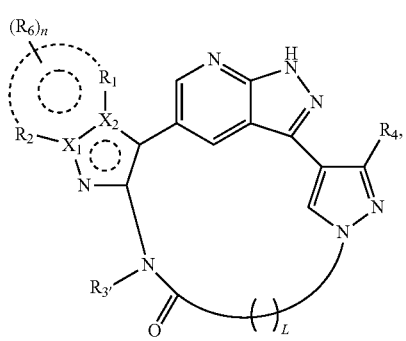

(Ib4)

or

X₃ represents C, X₄ and X₅ represent N in the structure of formula Ib, and the compound is represented by a structure of formula Ib5:

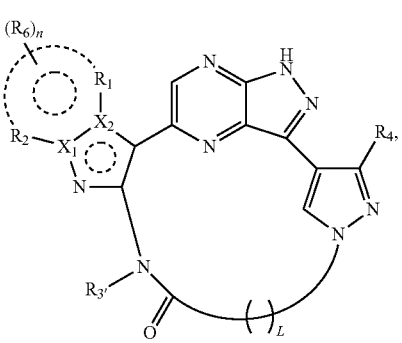

(Ib5)

or a pharmaceutically acceptable salt or stereoisomer thereof.

10. The compound of claim 9, wherein $X_1$ is N and $X_2$ is C in the structure of formula Ib1, and the compound is represented by the structure of formula Ib1a:

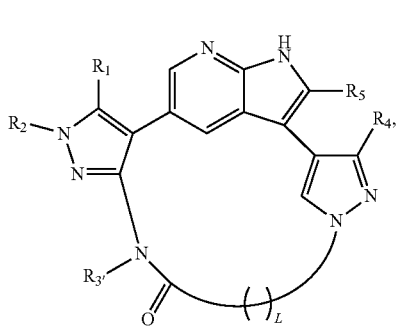

(Ib1a)

or $X_1$ is C, $X_2$ is N and $R_1$ and $R_2$ together with the atoms to which they are bound form a pyrimidine ring that is optionally substituted with $R_6$ in the structure of formula Ib1, and the compound is represented by the structure of formula Ib1b:

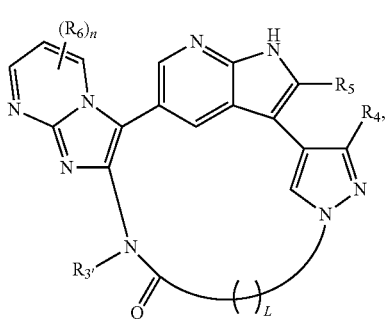

(Ib1b)

or $X_1$ is C, $X_2$ is N and $R_1$ and $R_2$ together with the atoms to which they are bound form a pyridine ring that is optionally substituted with $R_6$ in the structure of formula Ib1, and the compound is represented by the structure of formula Ib1c:

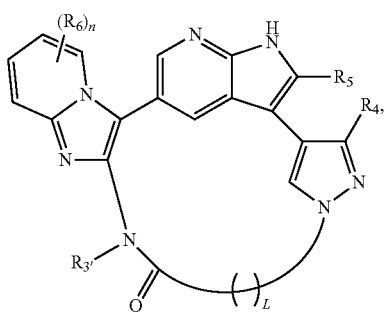

(Ib1c)

or a pharmaceutically acceptable salt or stereoisomer thereof.

11. The compound of claim 9, wherein $X_1$ is N and $X_2$ is C in the structure of formula Ib2, and the compound is represented by the structure of formula Ib2a:

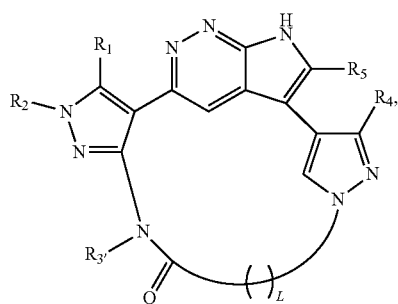

(Ib2a)

or $X_1$ is C, $X_2$ is N and $R_1$ and $R_2$ together with the atoms to which they are bound form a pyrimidine ring that is optionally substituted with $R_6$ in the structure of formula Ib2, and the compound is represented by the structure of formula Ib2b:

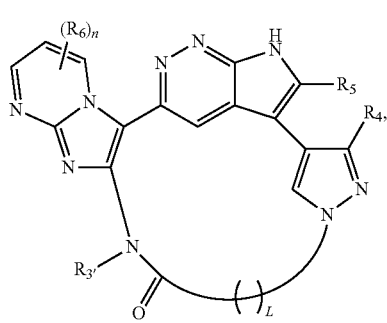

(Ib2b)

or $X_1$ is C, $X_2$ is N and $R_1$ and $R_2$ together with the atoms to which they are bound form a pyridine ring that is optionally substituted with $R_6$ in the structure of formula Ib2, and the compound is represented by the structure of formula Ib2c:

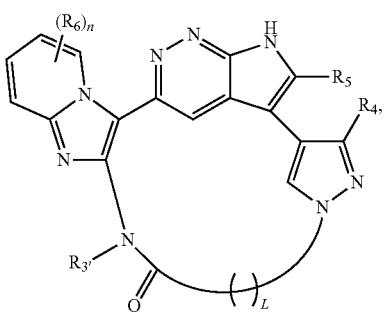

(Ib2c)

or a pharmaceutically acceptable salt or stereoisomer thereof.

12. The compound of claim 9, wherein $X_1$ is N and $X_2$ is C in the structure of formula Ib3, and the compound is represented by the structure of formula Ib3a:

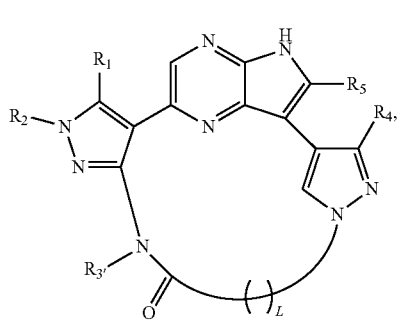

(Ib3a)

or $X_1$ is C, $X_2$ is N and $R_1$ and $R_2$ together with the atoms to which they are bound form a pyrimidine ring that is optionally substituted with $R_6$ in the structure of formula Ib3, and the compound is represented by the structure of formula Ib3b:

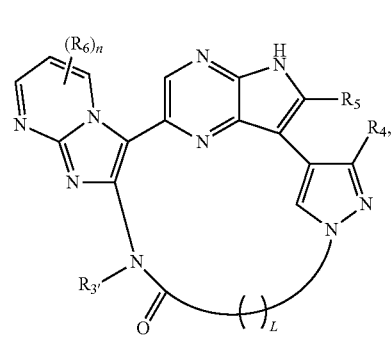

(Ib3b)

or $X_1$ is C, $X_2$ is N and $R_1$ and $R_2$ together with the atoms to which they are bound form a pyridine ring that is optionally substituted with $R_6$ in the structure of formula Ib3, and the compound is represented by the structure of formula Ib3c:

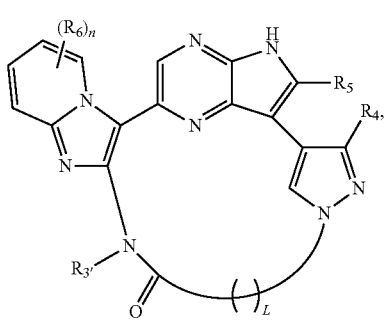

(Ib3c)

or a pharmaceutically acceptable salt or stereoisomer thereof.

13. The compound of claim 9, wherein $X_1$ is N and $X_2$ is C in the structure of formula Ib4, and the compound is represented by the structure of formula Ib4a:

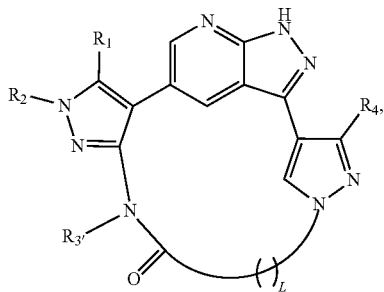

(Ib4a)

or $X_1$ is C, $X_2$ is N and $R_1$ and $R_2$ together with the atoms to which they are bound form a pyrimidine ring that is optionally substituted with $R_6$ in the structure of formula Ib4, and the compound is represented by the structure of formula Ib4b:

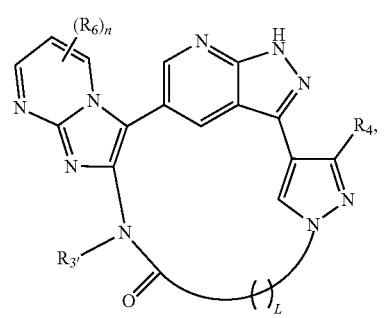

(Ib4b)

or $X_1$ is C, $X_2$ is N and $R_1$ and $R_2$ together with the atoms to which they are bound form a pyridine ring that is optionally substituted with $R_6$ in the structure of formula Ib4, and the compound is represented by the structure of formula Ib4c:

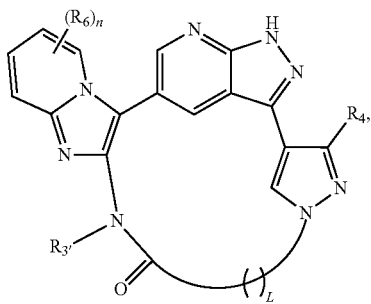

(Ib4c)

or a pharmaceutically acceptable salt or stereoisomer thereof.

14. The compound of claim 9, wherein $X_1$ is N and $X_2$ is C in the structure of formula Ib5, and the compound is represented by the structure of formula Ib5a:

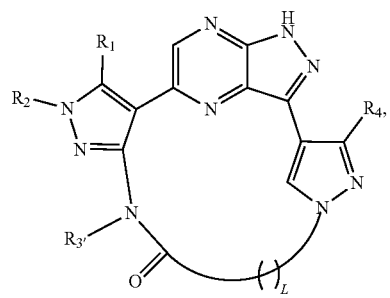

(Ib5a)

or $X_1$ is C, $X_2$ is N and $R_1$ and $R_2$ together with the atoms to which they are bound form a pyrimidine ring that is optionally substituted with $R_6$ in the structure of formula Ib5, and the compound is represented by the structure of formula Ib5b:

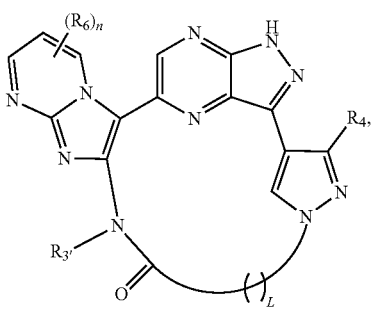

(Ib5b)

or $X_1$ is C, $X_2$ is N and $R_1$ and $R_2$ together with the atoms to which they are bound form a pyridine ring that is optionally substituted with $R_6$ in the structure of formula Ib5, and the compound is represented by the structure of formula Ib5c:

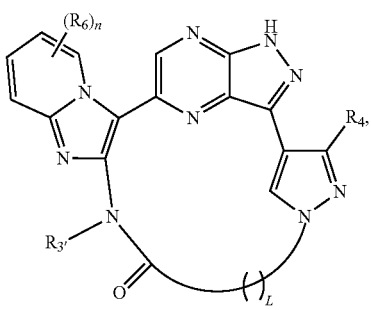

(Ib5c)

or a pharmaceutically acceptable salt or stereoisomer thereof.

15. The compound of claim 2, wherein $X_3$, $X_4$, and $X_5$ each represent C in the structure of formula Ic and the compound is represented by a structure of formula Ic1:

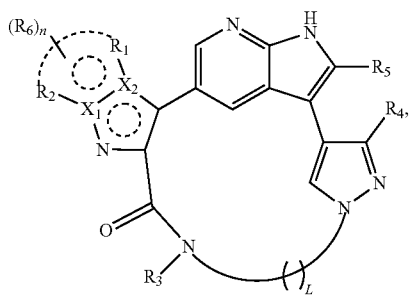

(Ic1)

or $X_4$ and $X_5$ represent C, $X_3$ represents N in the structure of formula Ic, and the compound is represented by a structure of formula Ic2:

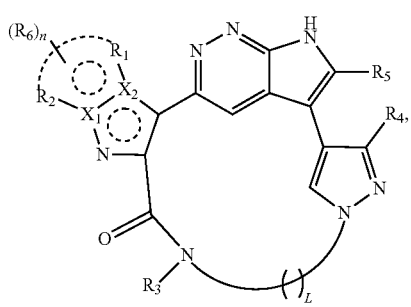

(Ic2)

or $X_3$ and $X_5$ represent C, $X_4$ represents N in the structure of formula Ic, and the compound is represented by a structure of formula Ic3:

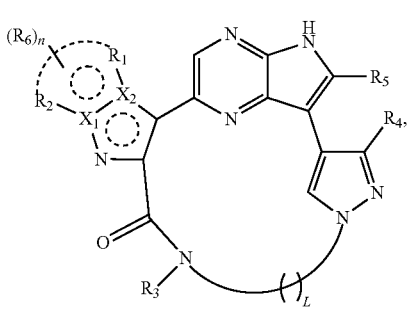

(Ic3)

or $X_3$ and $X_4$ represent C, $X_5$ represents N in the structure of formula Ic, and the compound is represented by a structure of formula Ic4:

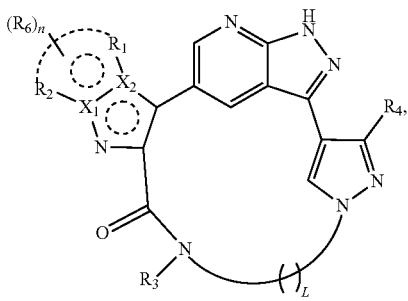

(Ic4)

or $X_3$ represents C, $X_4$ and $X_5$ represent N in the structure of formula Ic, and the compound is represented by a structure of formula Ic5:

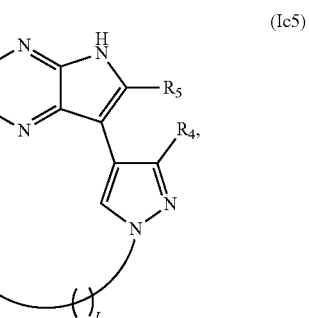

(Ic5)

or a pharmaceutically acceptable salt or stereoisomer thereof.

16. The compound of claim 15, wherein $X_1$ is N and $X_2$ is C in the structure of formula Ic1, and the compound is represented by the structure of formula Ic1a:

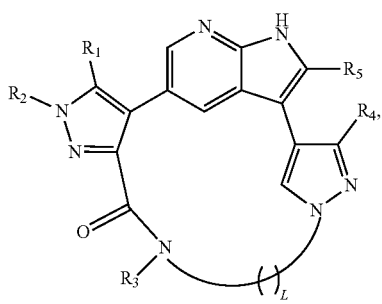

(Ic1a)

or $X_1$ is C, $X_2$ is N and $R_1$ and $R_2$ together with the atoms to which they are bound form a pyrimidine ring that is optionally substituted with $R_6$ in the structure of formula Ic1, and the compound is represented by the structure of formula Ic1b:

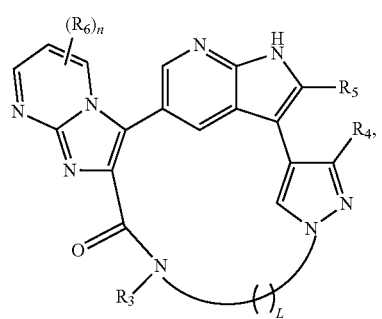

(Ic1b)

or $X_1$ is C, $X_2$ is N and $R_1$ and $R_2$ together with the atoms to which they are bound form a pyridine ring that is optionally substituted with $R_6$ in the structure of formula Ic1, and the compound is represented by the structure of formula Ic1c:

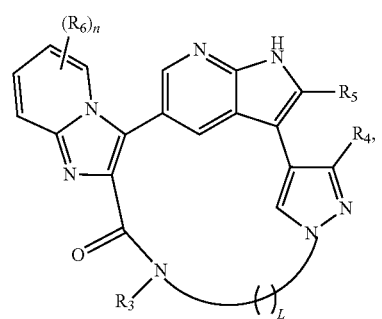

(Ic1c)

or a pharmaceutically acceptable salt or stereoisomer thereof.

17. The compound of claim 15, wherein $X_1$ is N and $X_2$ is C in the structure of formula Ic2, and the compound is represented by the structure of formula Ic2a:

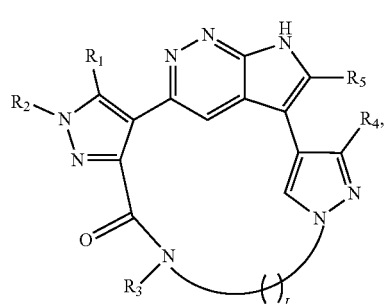

(Ic2a)

or $X_1$ is C, $X_2$ is N and $R_1$ and $R_2$ together with the atoms to which they are bound form a pyrimidine ring that is optionally substituted with $R_6$ in the structure of formula Ic2, and the compound is represented by the structure of formula Ic2b:

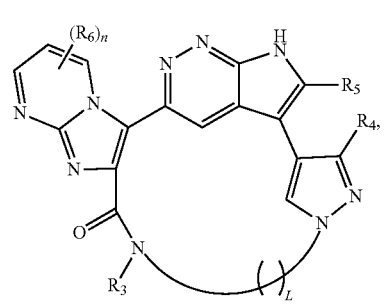

(Ic2b)

or $X_1$ is C, $X_2$ is N and $R_1$ and $R_2$ together with the atoms to which they are bound form a pyridine ring that is optionally substituted with $R_6$ in the structure of formula Ic2, and the compound is represented by the structure of formula Ic2c:

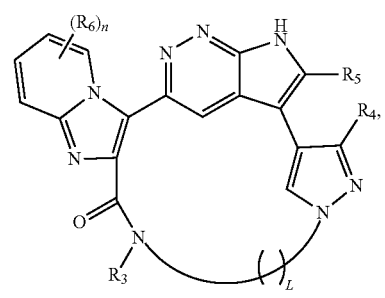

(Ic2c)

or a pharmaceutically acceptable salt or stereoisomer thereof.

18. The compound of claim 15, wherein $X_1$ is N and $X_2$ is C in the structure of formula Ic3, and the compound is represented by the structure of formula Ic3a:

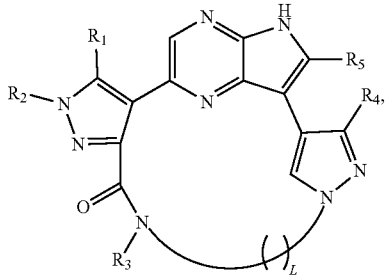

(Ic3a)

or

X₁ is C, X₂ is N and R₁ and R₂ together with the atoms to which they are bound form a pyrimidine ring that is optionally substituted with R₆ in the structure of formula Ic3, and the compound is represented by the structure of formula Ic3b:

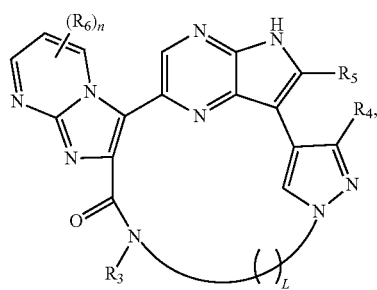

(Ic3b)

or

X₁ is C, X₂ is N and R₁ and R₂ together with the atoms to which they are bound form a pyridine ring that is optionally substituted with R₆ in the structure of formula Ic3, and the compound is represented by the structure of formula Ic3c:

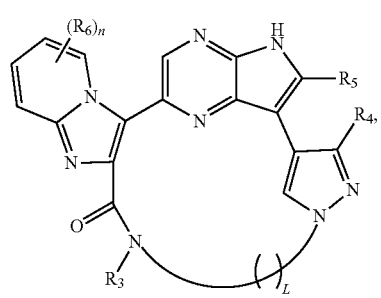

(Ic3c)

or a pharmaceutically acceptable salt or stereoisomer thereof.

19. The compound of claim 15, wherein X₁ is N and X₂ is C in the structure of formula Ic4, and the compound is represented by the structure of formula Ic4a:

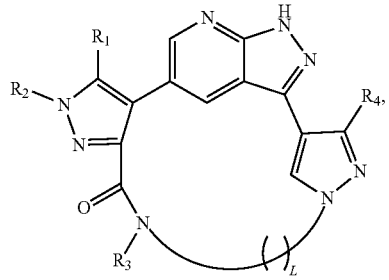

(Ic4a)

or

X₁ is C, X₂ is N and R₁ and R₂ together with the atoms to which they are bound form a pyrimidine ring that is optionally substituted with R₆ in the structure of formula Ic4, and the compound is represented by the structure of formula Ic4b:

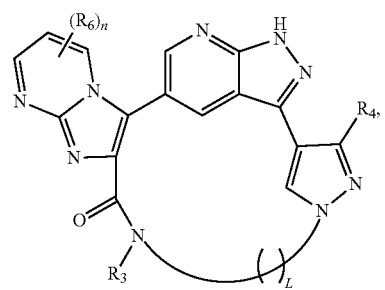

(Ic4b)

or

X₁ is C, X₂ is N and R₁ and R₂ together with the atoms to which they are bound form a pyridine ring that is optionally substituted with R₆ in the structure of formula Ic4, and the compound is represented by the structure of formula Ic4c:

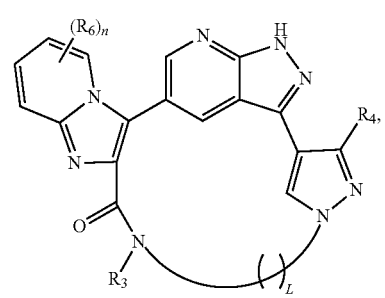

(Ic4c)

or a pharmaceutically acceptable salt or stereoisomer thereof.

20. The compound of claim 15, wherein X₁ is N and X₂ is C in the structure of formula Ic5, and the compound is represented by the structure of formula Ic5a:

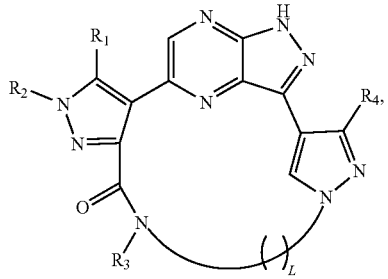

(Ic5a)

or

X₁ is C, X₂ is N and R₁ and R₂ together with the atoms to which they are bound form a pyrimidine ring that is optionally substituted with R₆ in the structure of formula Ic5, and the compound is represented by the structure of formula Ic5b:

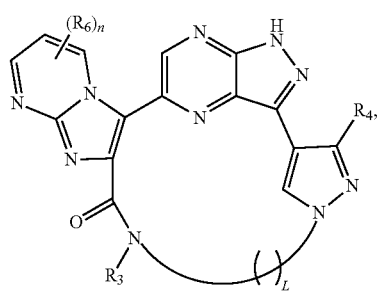

(Ic5b)

or

X₁ is C, X₂ is N and R₁ and R₂ together with the atoms to which they are bound form a pyridine ring that is optionally substituted with R₆ in the structure of formula Ic5, and the compound is represented by the structure of formula Ic5c:

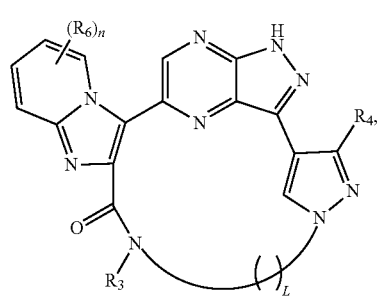

(Ic5c)

or a pharmaceutically acceptable salt or stereoisomer thereof.

21. The compound of claim 1, wherein $R_1$ is H, Me, Et, iPr, cyclopropyl, OMe, OCF₃, OCHF₂, Cl, or CN.

22. The compound of claim 1, wherein $R_3'$ is H, Me, Et, iPr cyclopropyl,

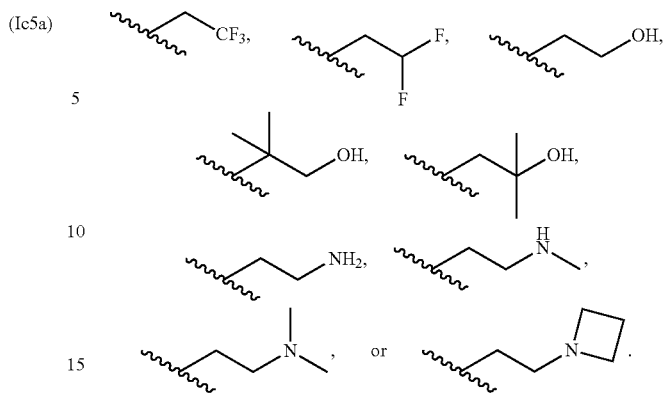

23. The compound of claim 1, wherein $R_3$ is H, Me, Et, iPr, cyclopropyl,

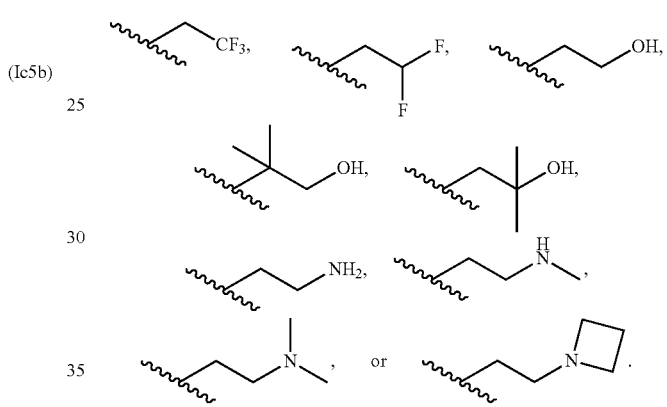

24. The compound of claim 1, wherein $R_4$ is H, Cl, CF₃, CHF₂, CN, Me, Et, cyclopropyl, OMe, OEt, OiPr, or O-cyclopropyl.

25. The compound of claim 1, wherein $R_5$ is H, Me, Et, iPr, cyclopropyl, Cl, CN, CF₃, or CHF₂.

26. The compound of claim 1, wherein $R_2$ is Me, Et, iPr, cyclopropyl, CHF₂, CH₂CF₃, CH₂CHF₂, CF₃, CH₂OH, CH₂OMe, CH₂CH₂OMe, or

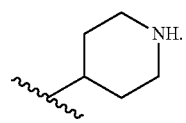 [SMILES: *C1CCNCC1]

27. The compound of claim 1, where in $R_6$ is Me, Et, iPr, cyclopropyl, OMe, OCF₃, OCHF₂, Cl, or CN.

28. The compound of claim 1, wherein L is

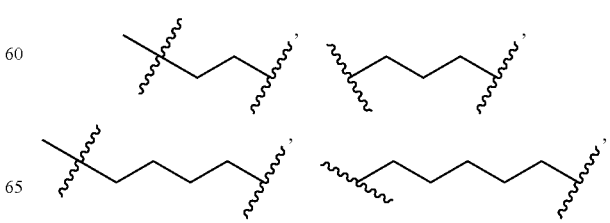

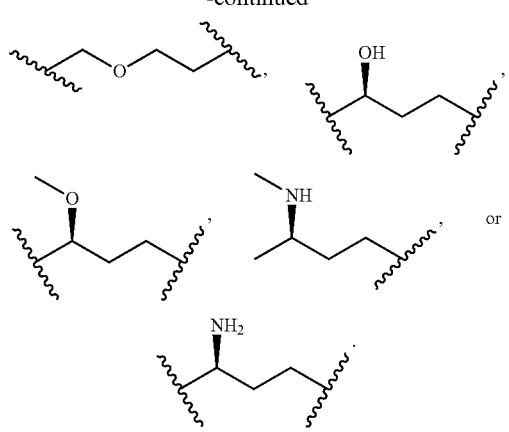
29. The compound of claim 1, which is selected from the group consisting of:
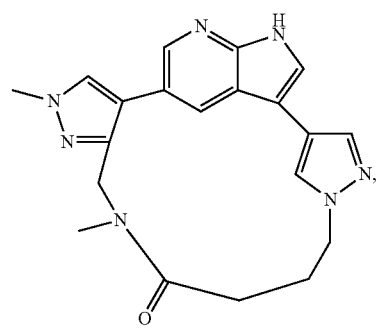
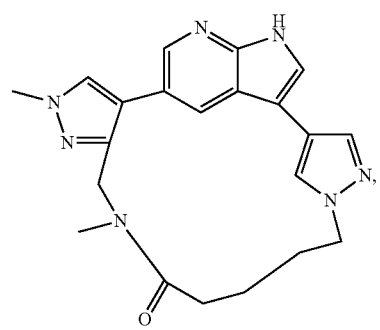
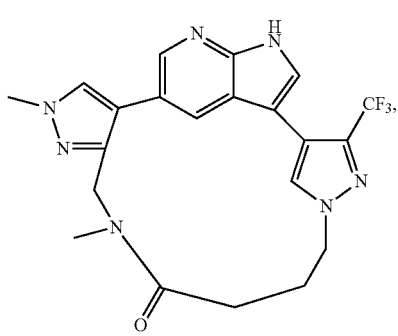
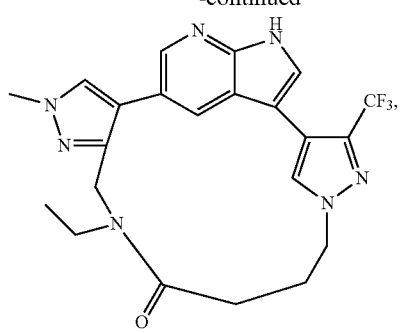
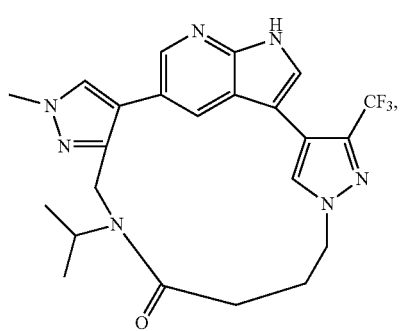
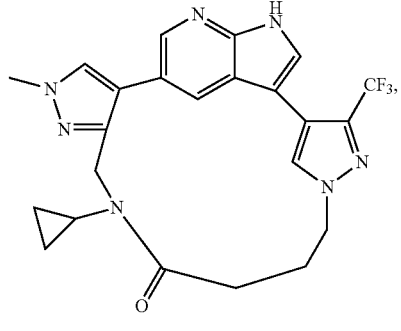
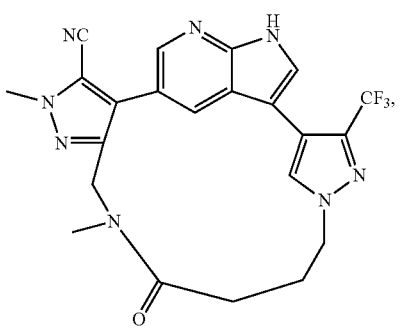
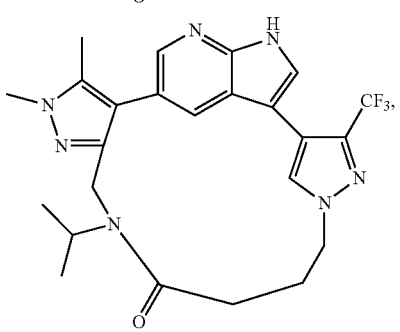

197
-continued
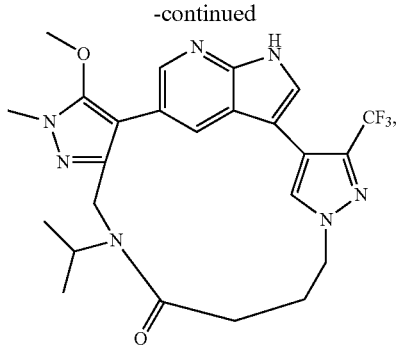
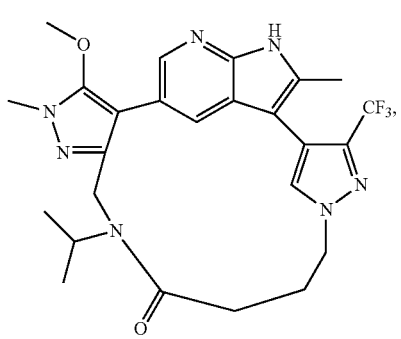
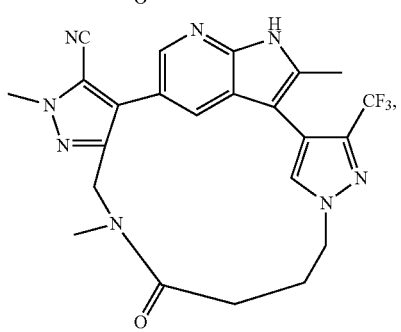
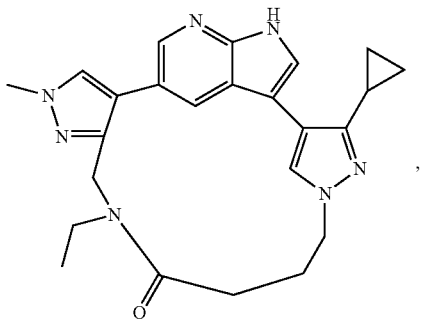
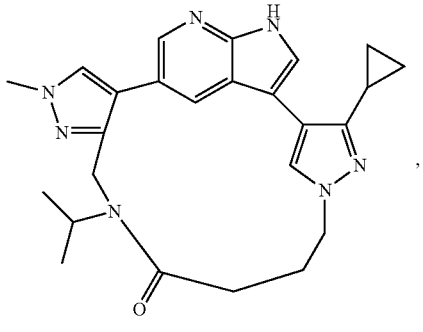
198
-continued
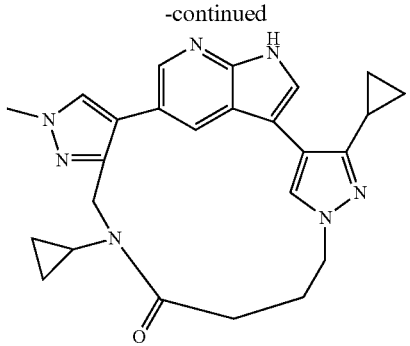
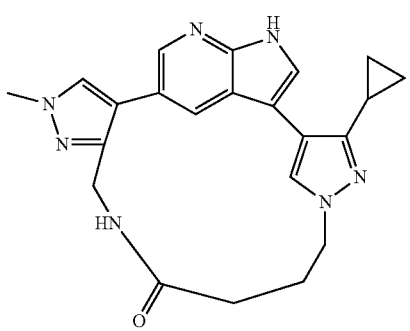
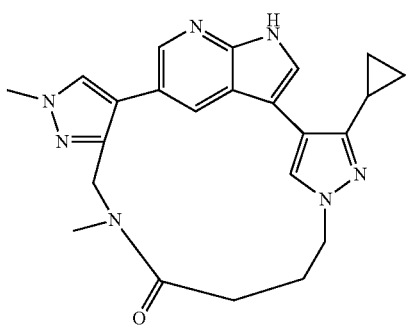
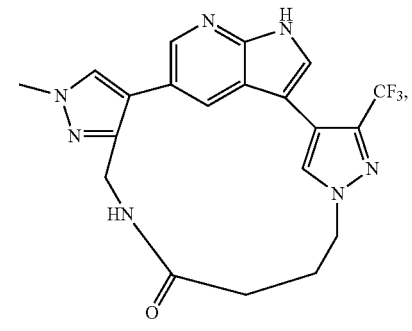
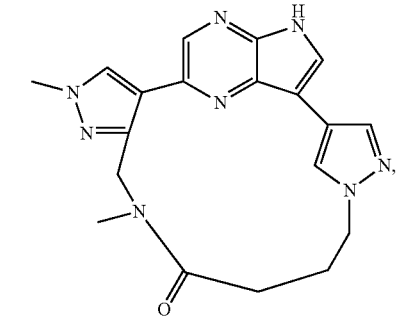

| 199 | 200 |
|---|---|
| -continued | -continued |
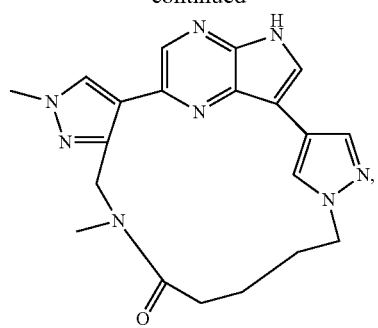
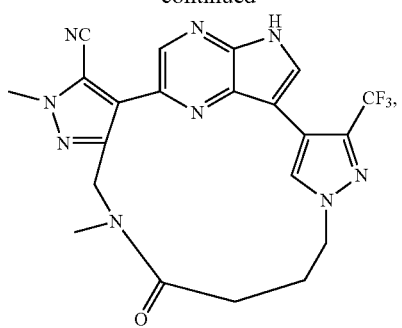
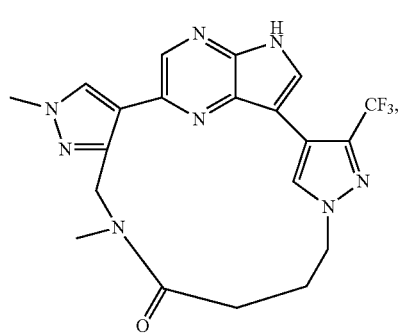
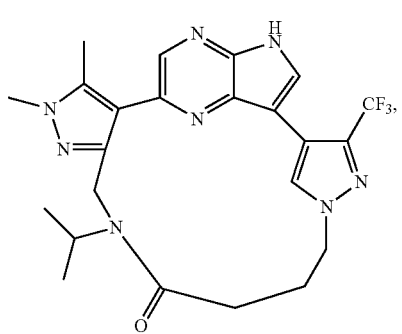
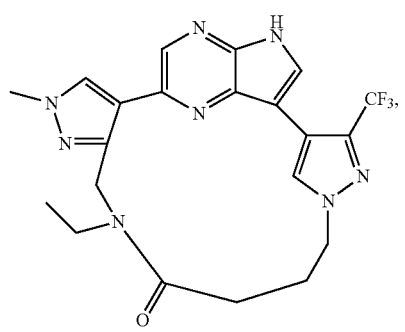
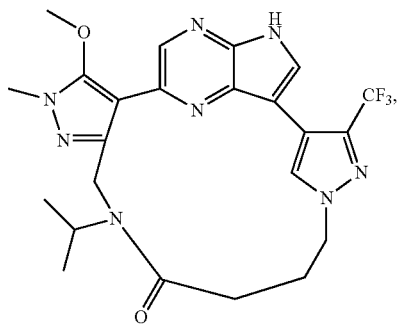
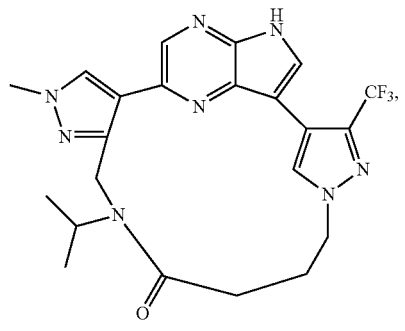
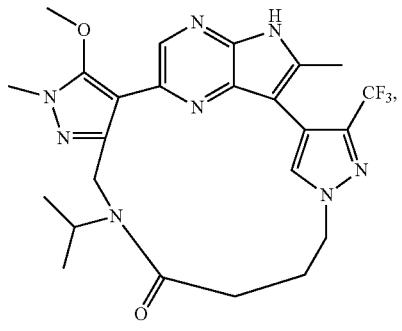
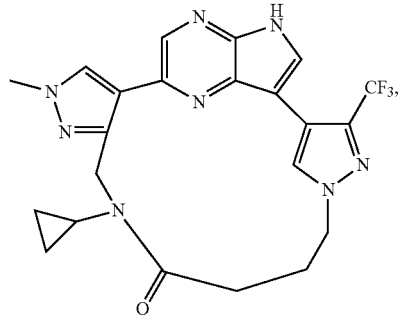
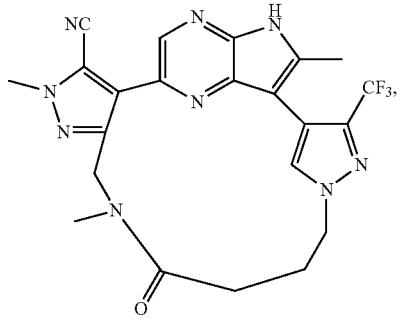

201
-continued
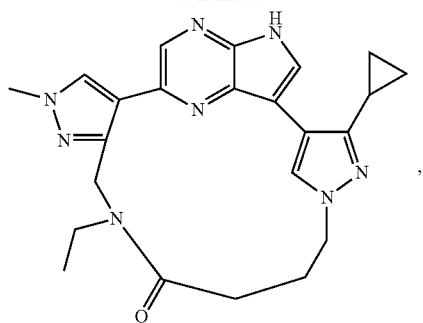
,
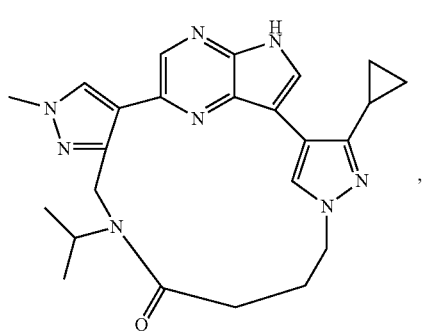
,
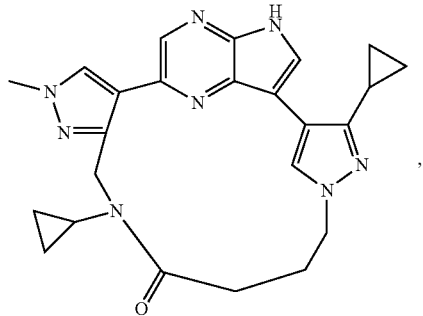
,
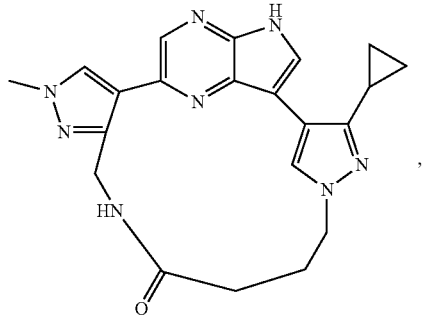
,
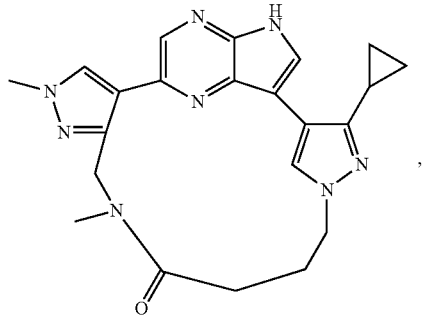
,
202
-continued
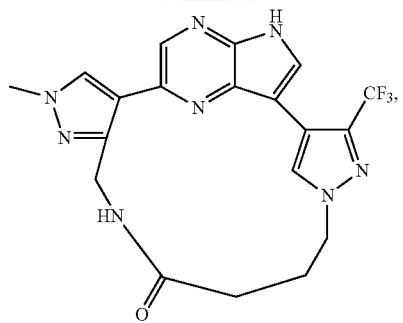
,
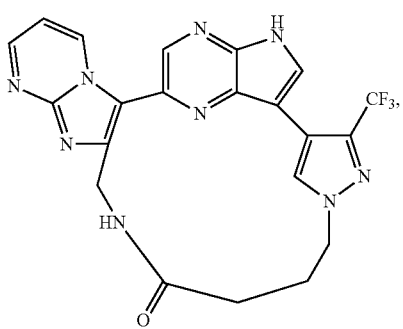
,
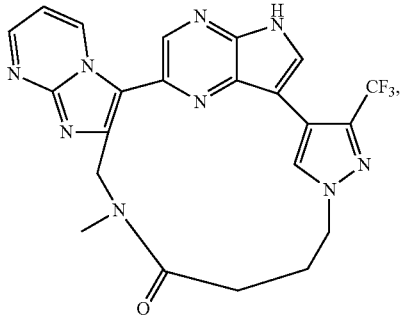
,
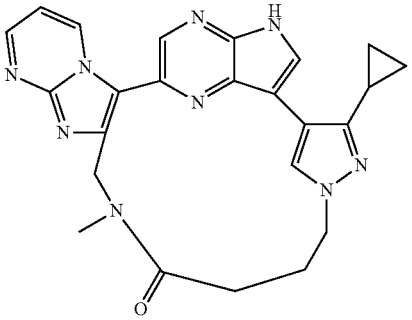
,
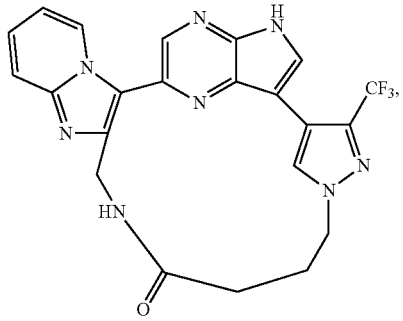
,

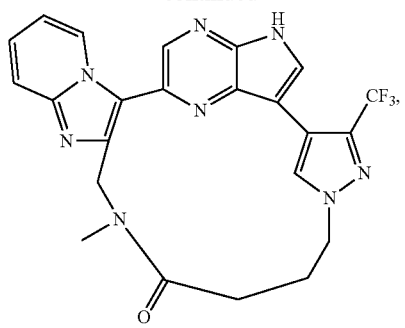
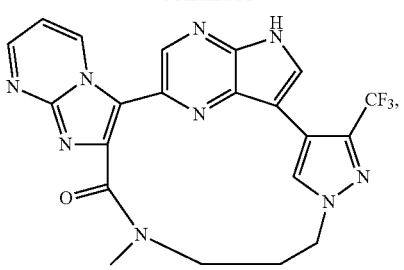
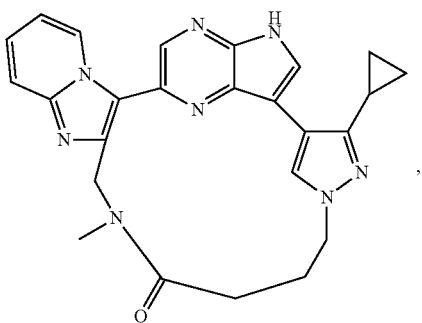
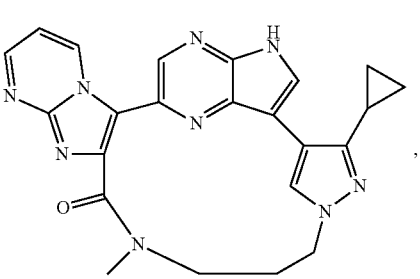
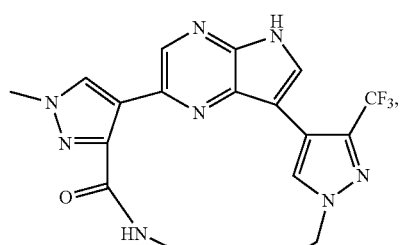
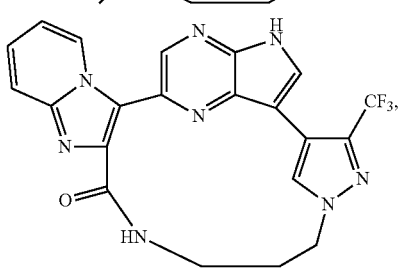
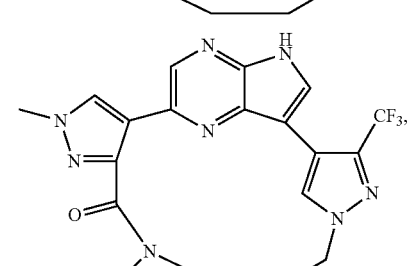
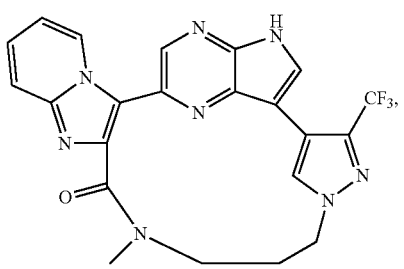
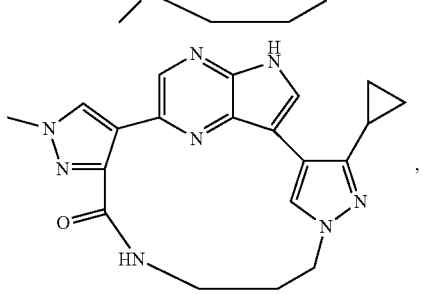
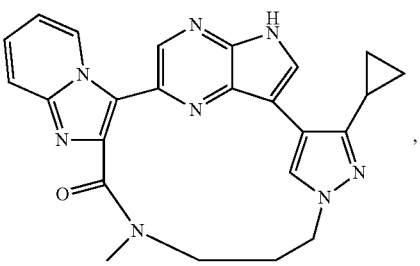
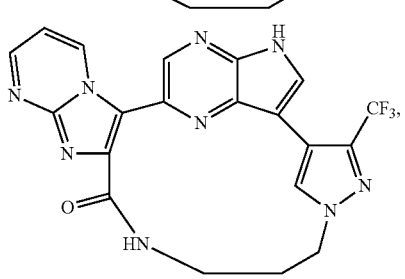
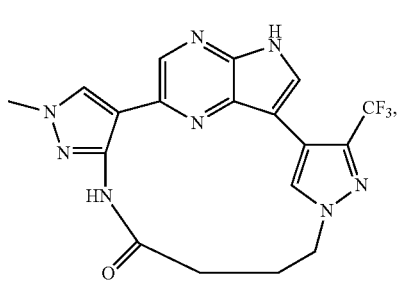

-continued
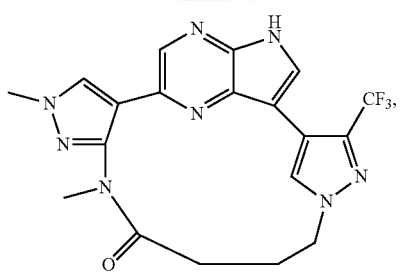
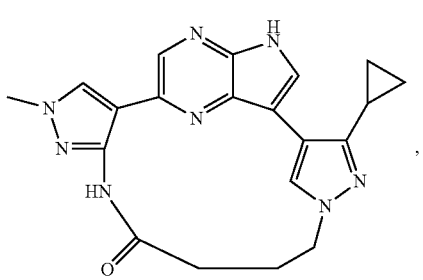
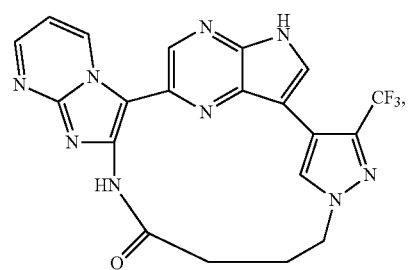
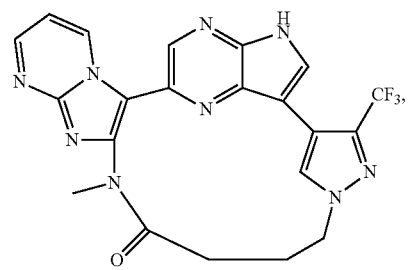
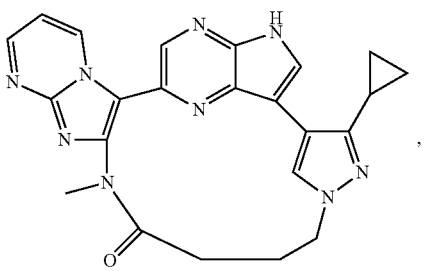
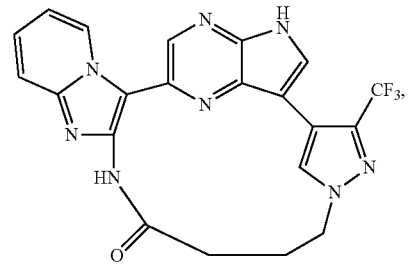
-continued
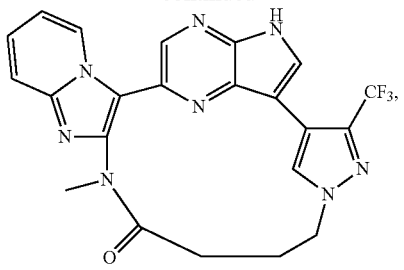
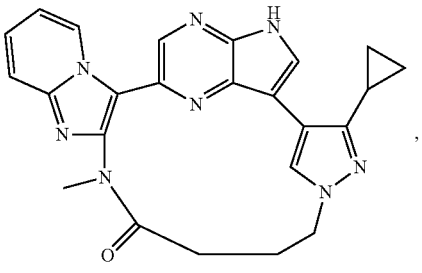
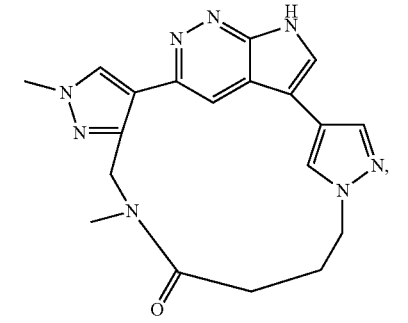
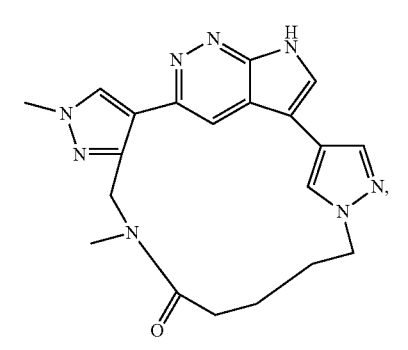
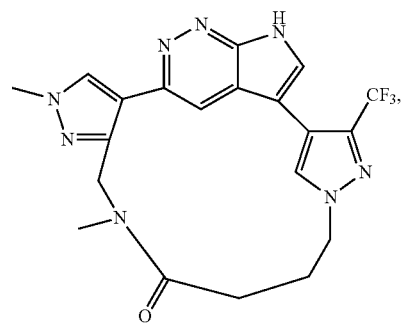

207
-continued
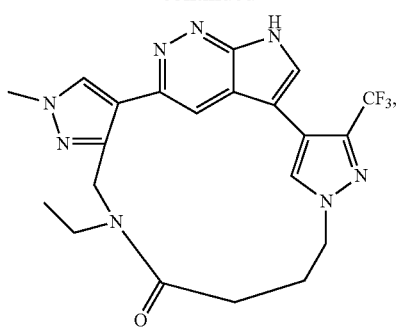
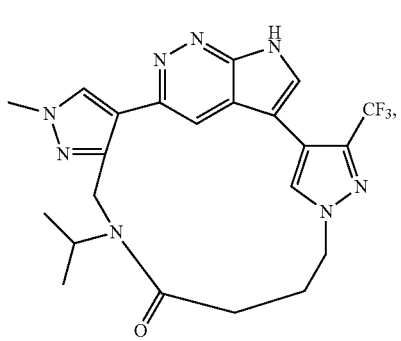
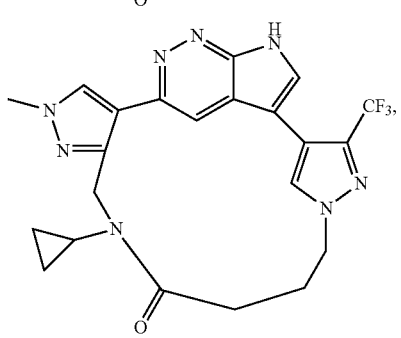
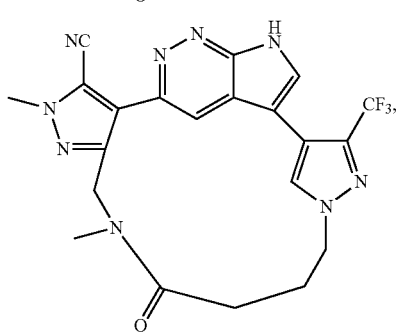
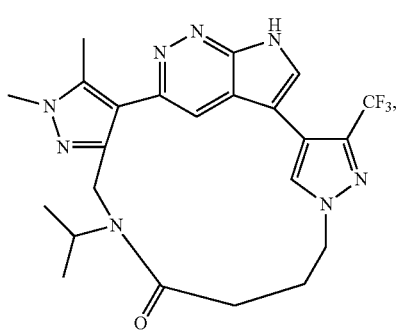
208
-continued
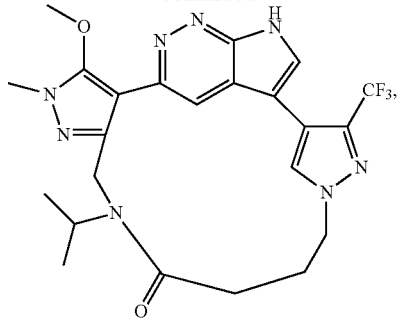
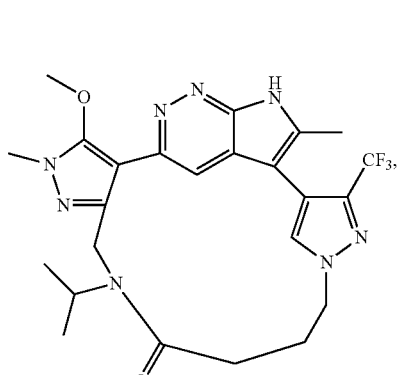
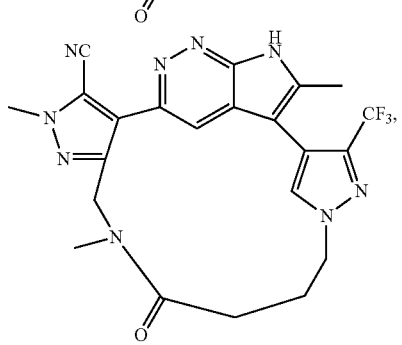
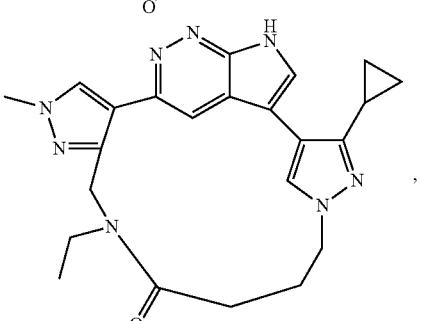
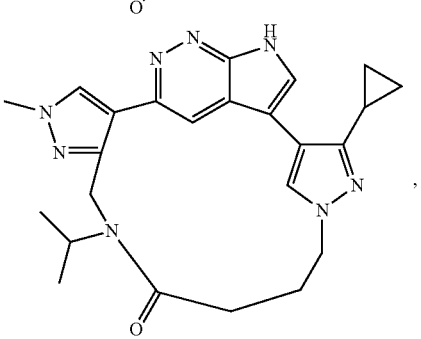

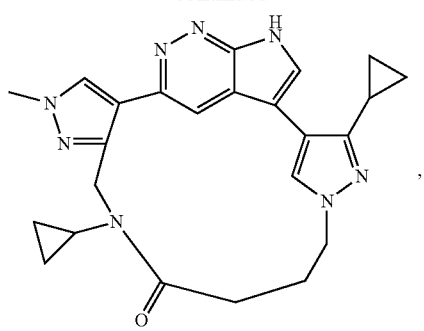
,
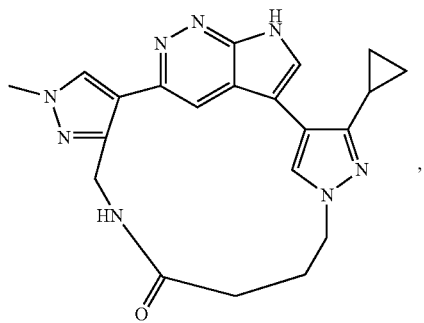
,
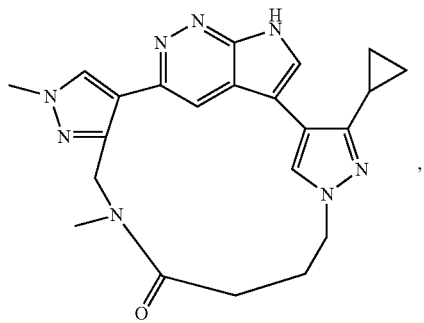
,
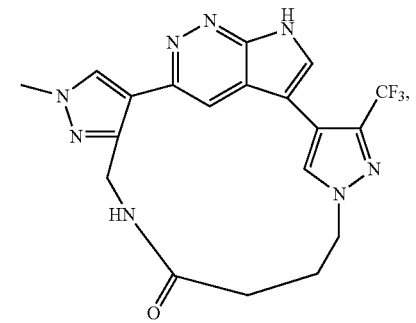
,
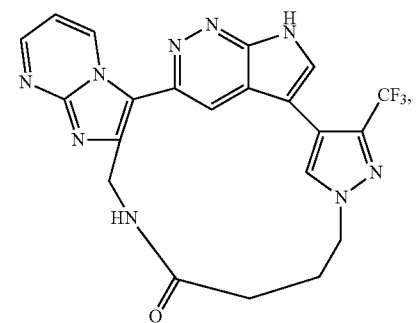
,
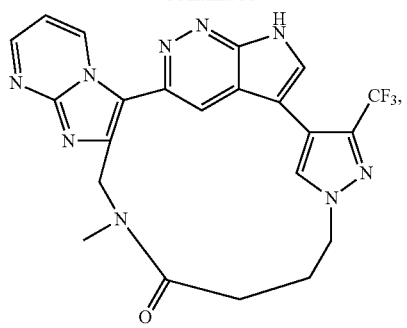
,
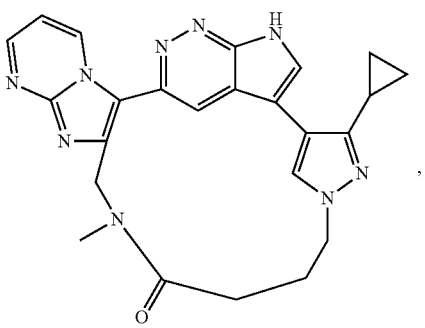
,
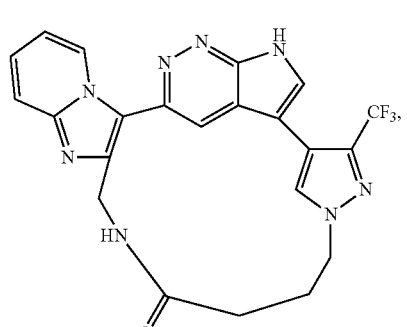
,
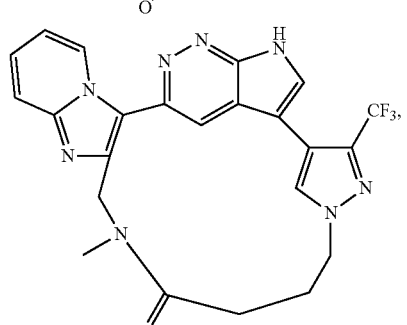
,
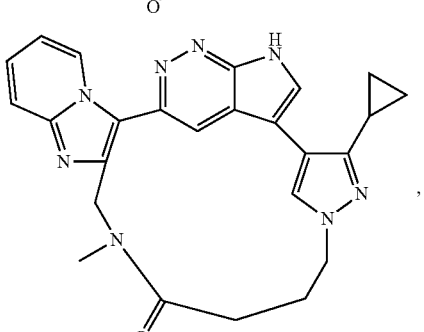
, 211
-continued
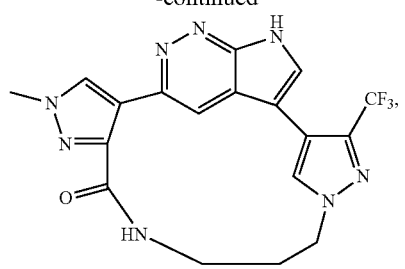
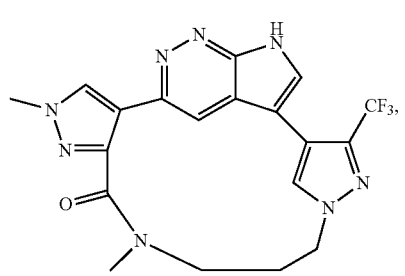
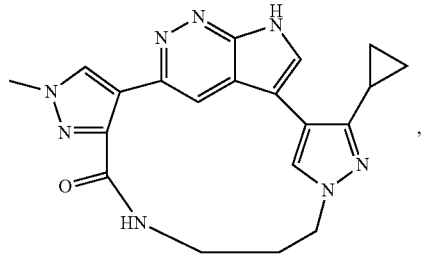
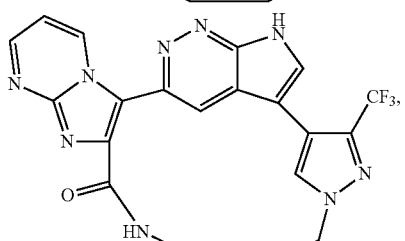
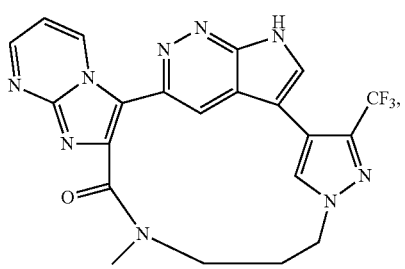
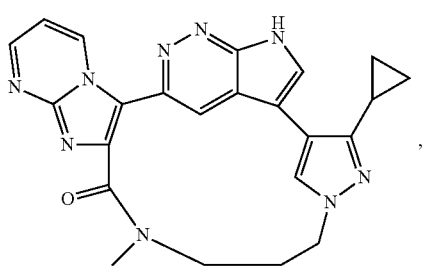
212
-continued
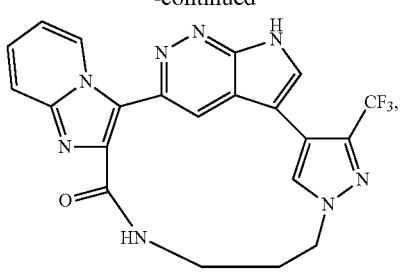
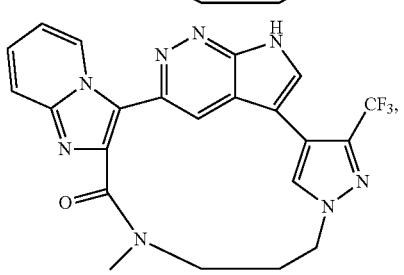
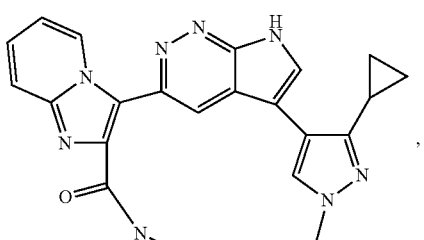
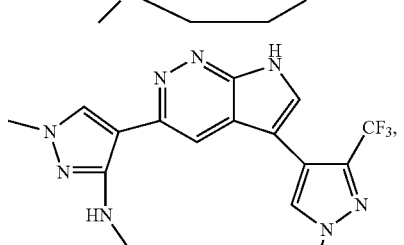
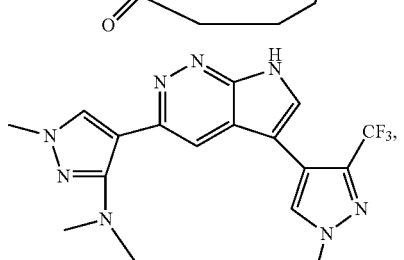
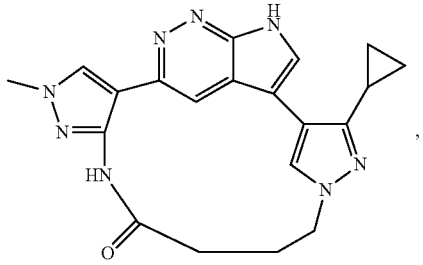

213
-continued
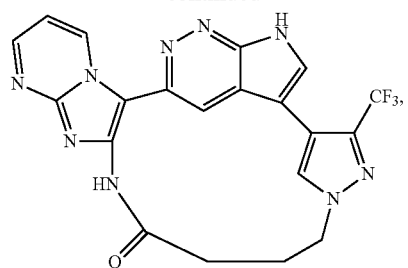
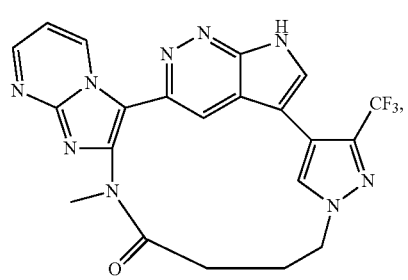
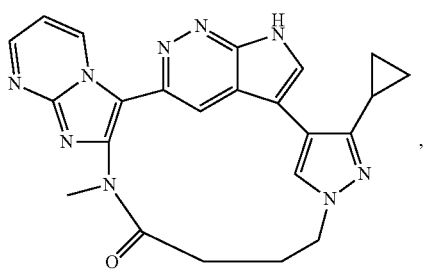
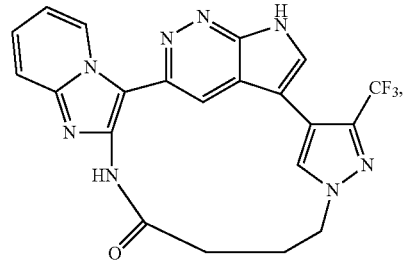
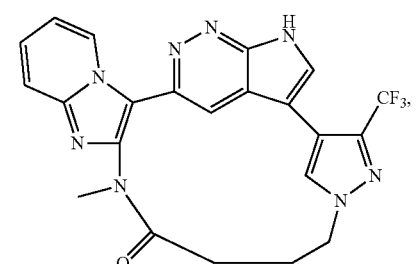
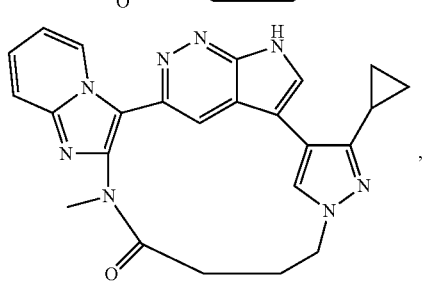
214
-continued
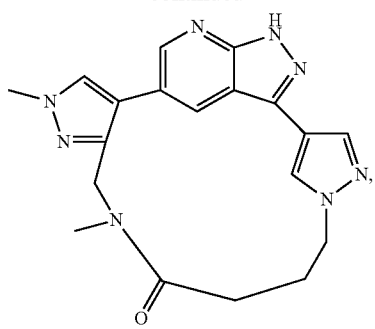
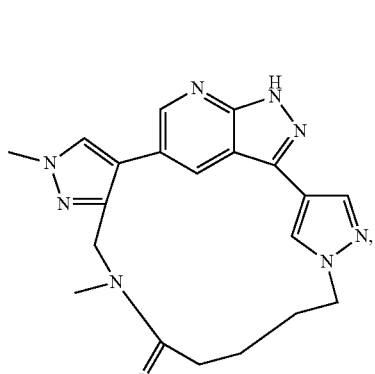
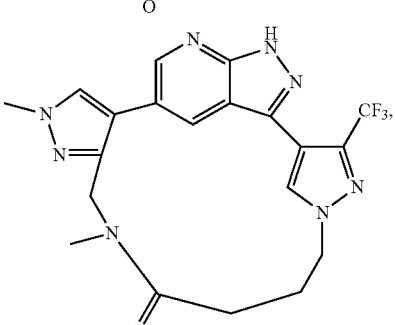
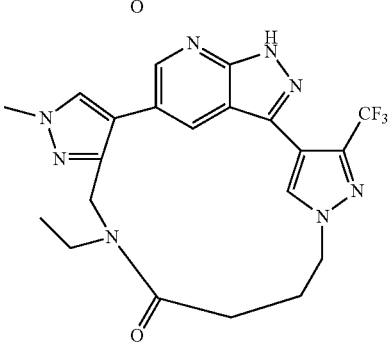
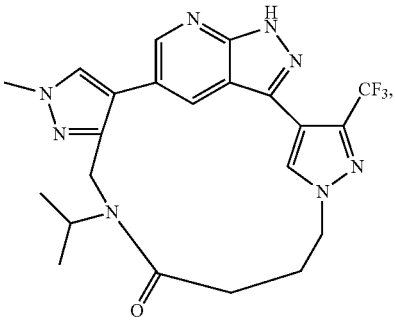

215
-continued
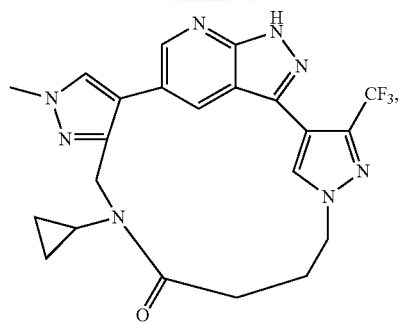
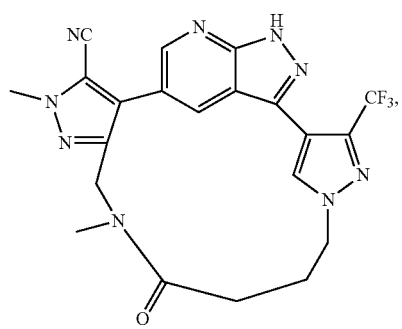
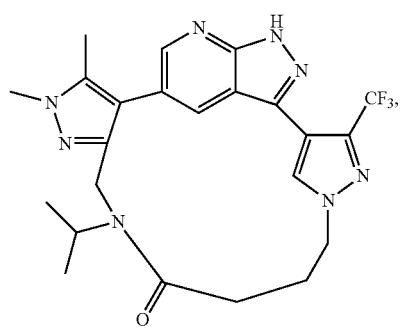
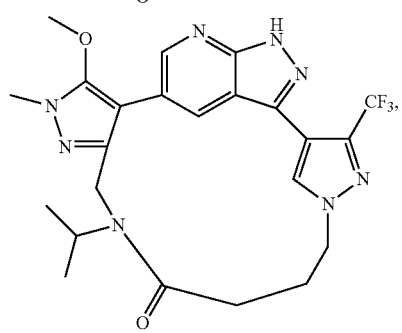
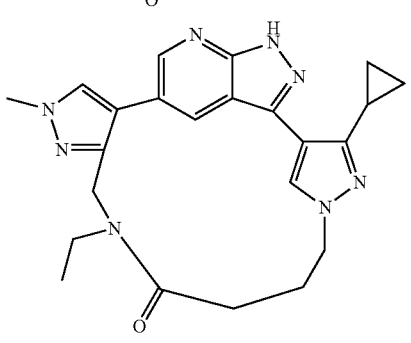
216
-continued
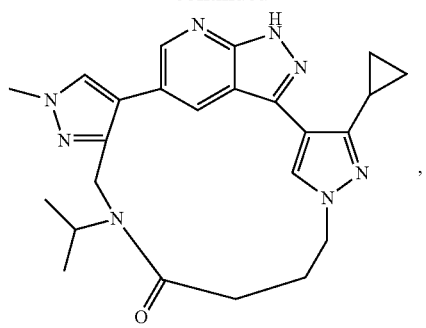
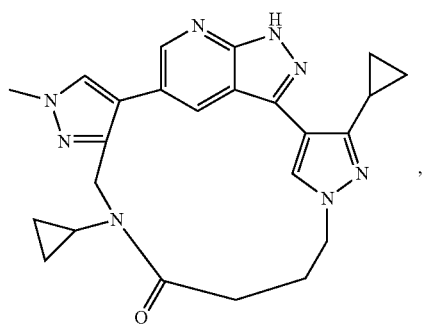

217
-continued
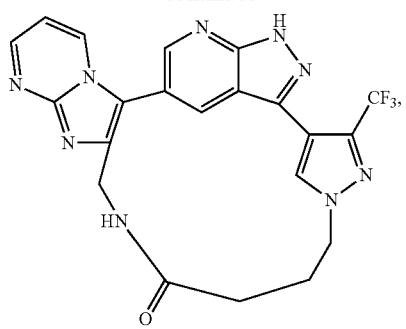
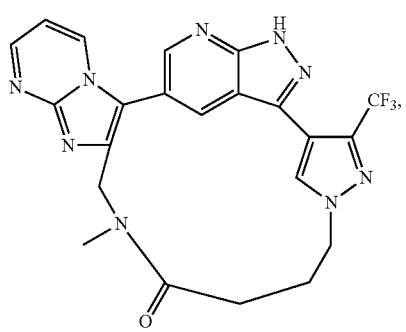
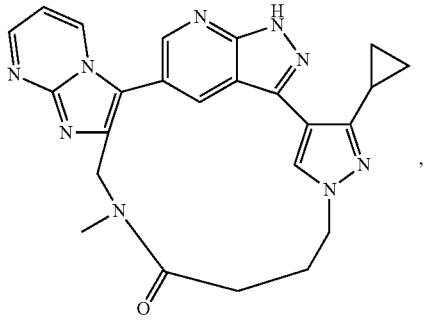
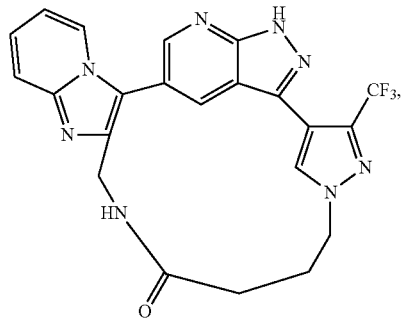
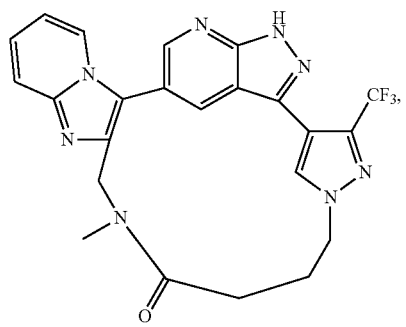
218
-continued
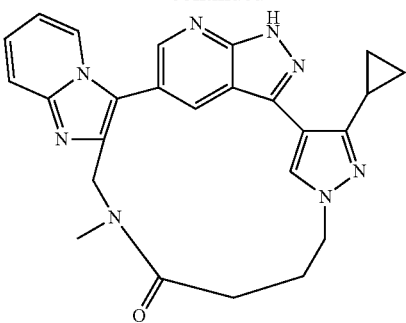
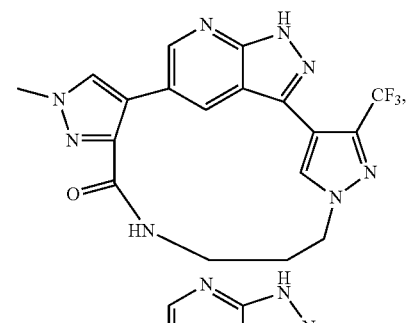
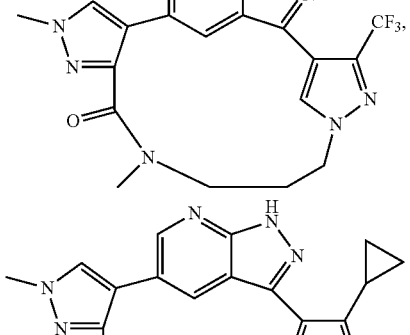
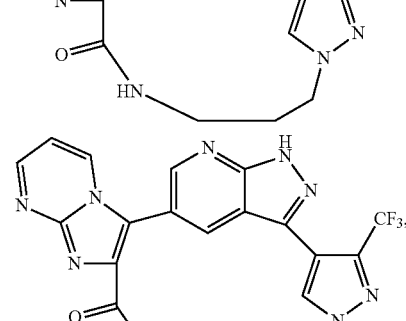
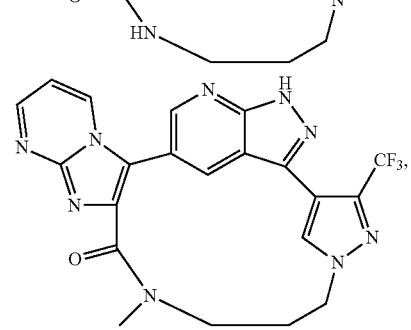

219
-continued
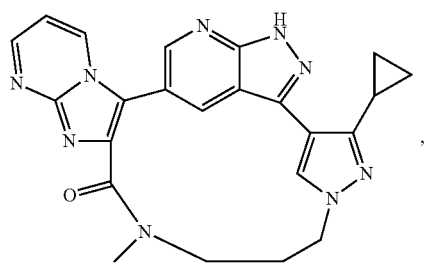
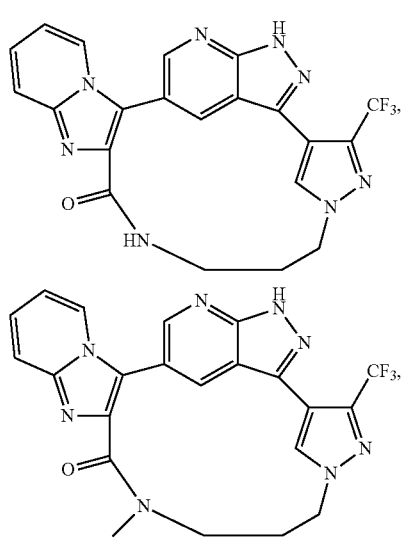
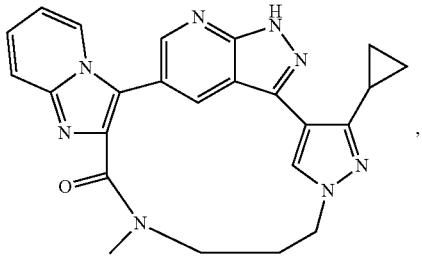
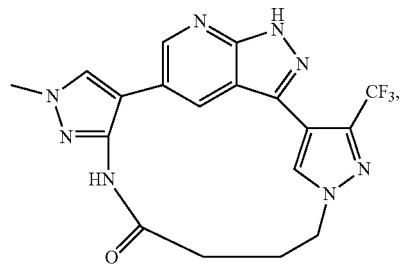
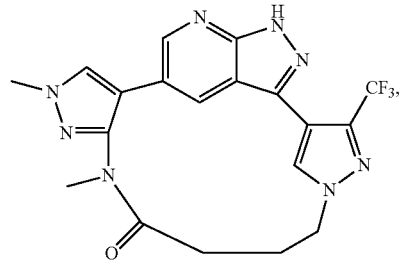
220
-continued
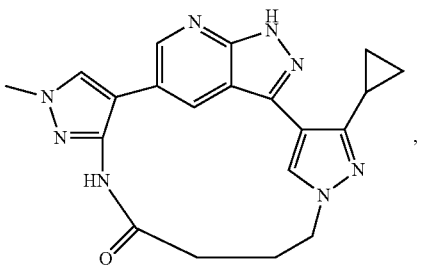
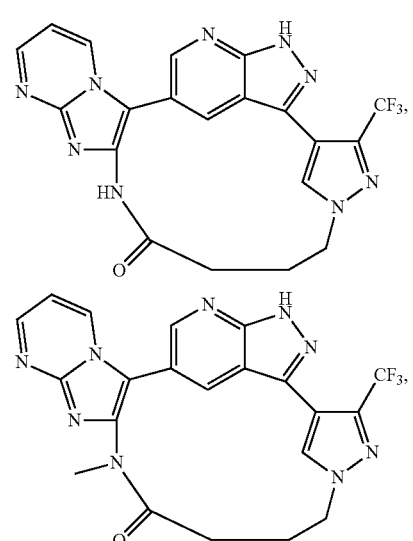
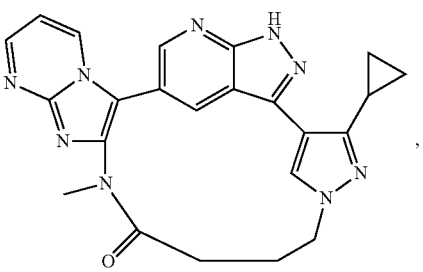
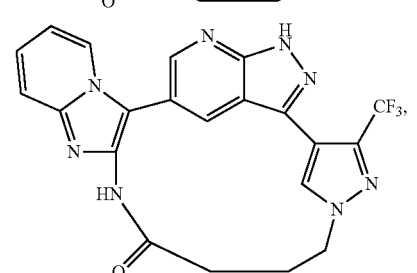
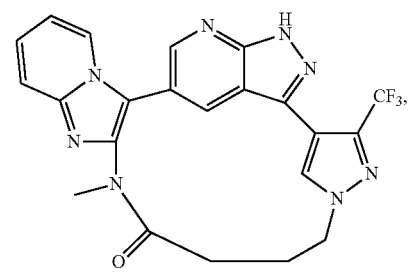

221
-continued
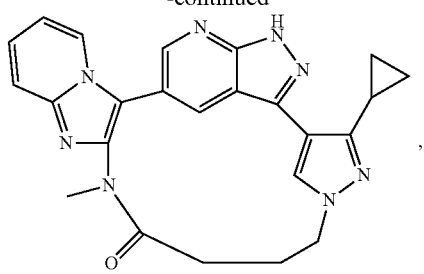
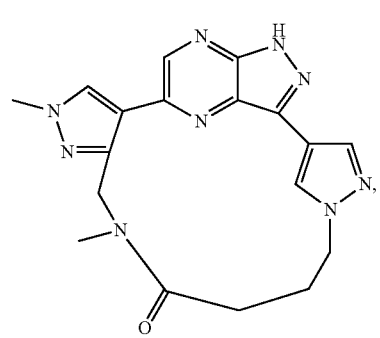
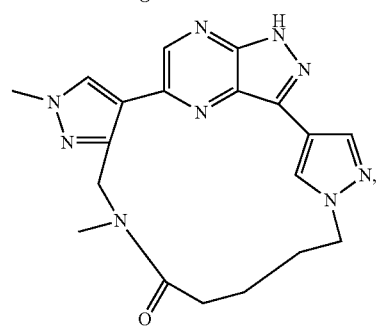
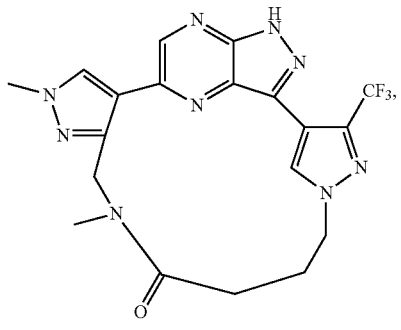
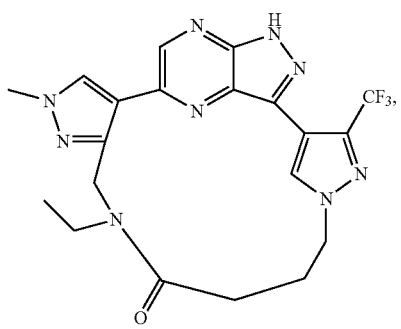
222
-continued
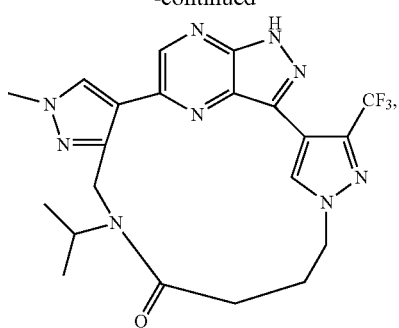
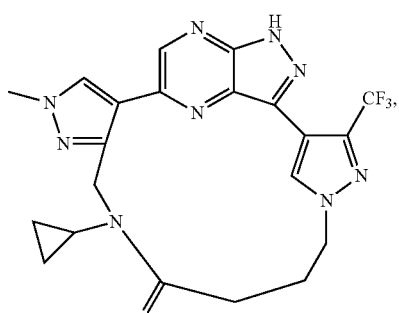
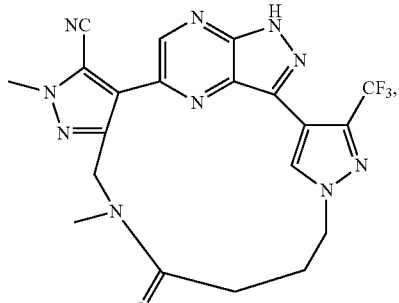
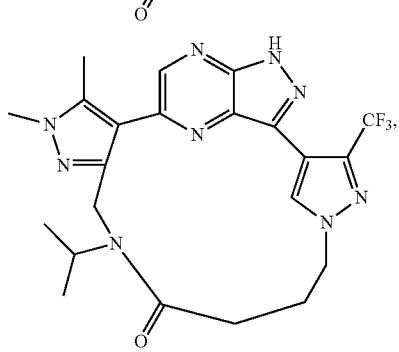
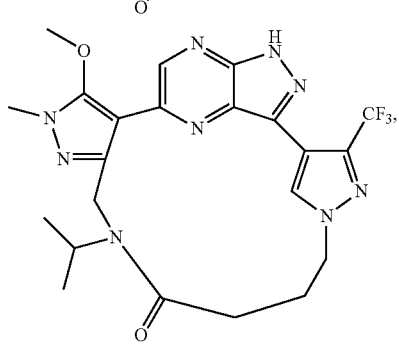

223
-continued
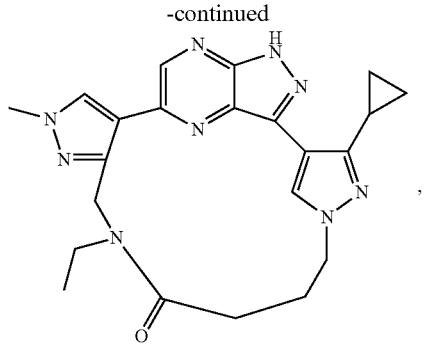
,
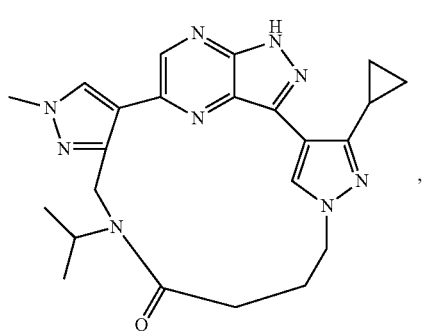
,
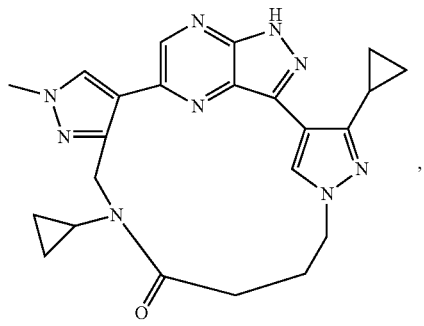
,
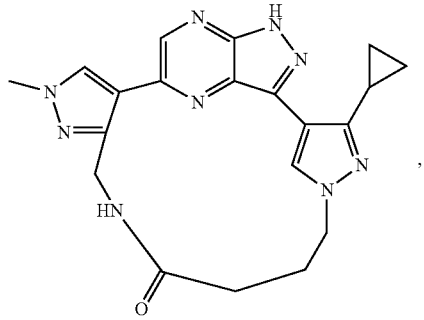
,
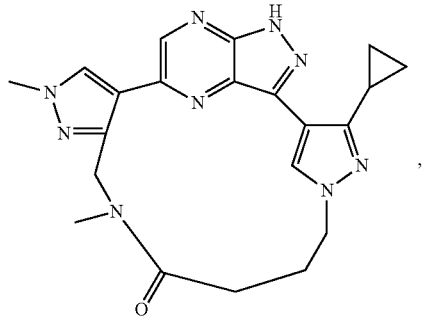
,
224
-continued
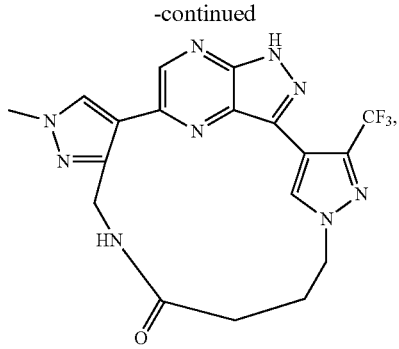
,
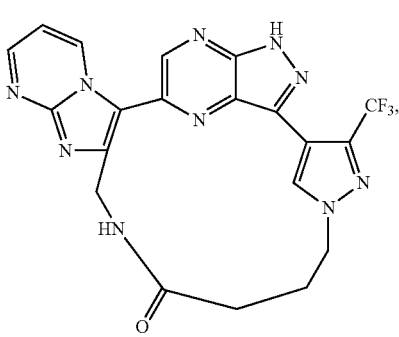
,
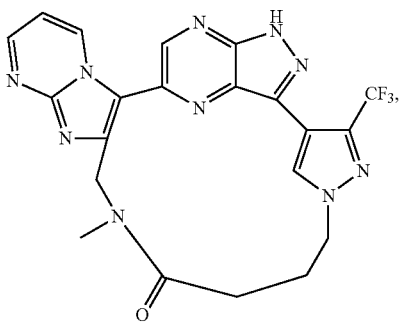
,
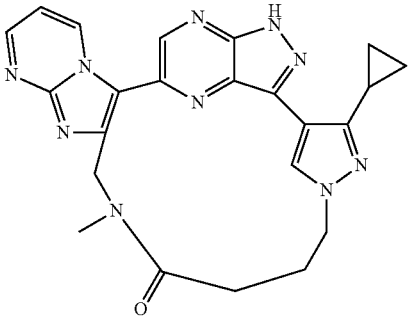
,
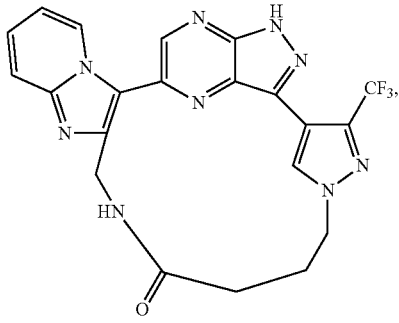
, 225
-continued
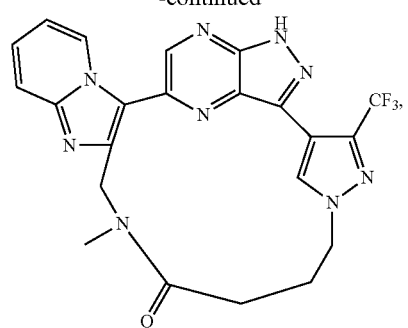
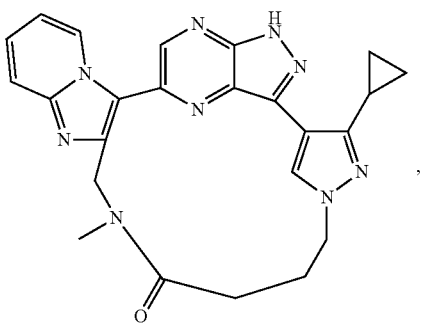
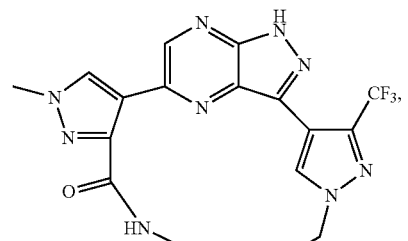
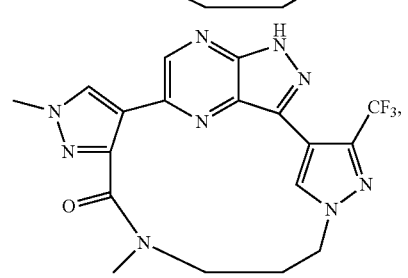
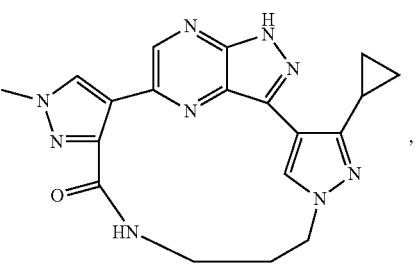
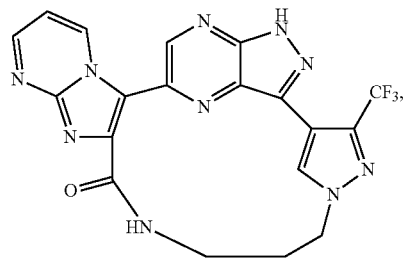
226
-continued
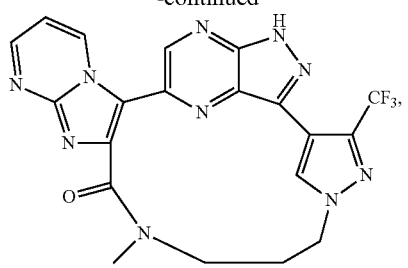
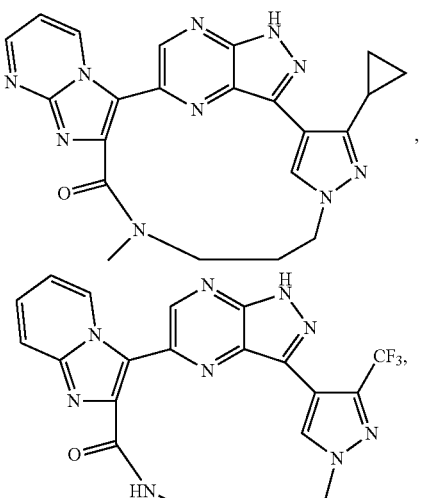
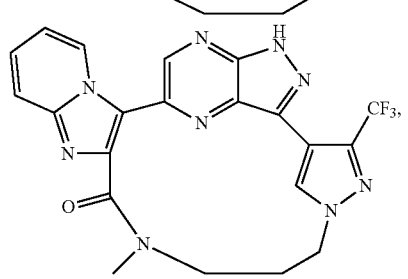
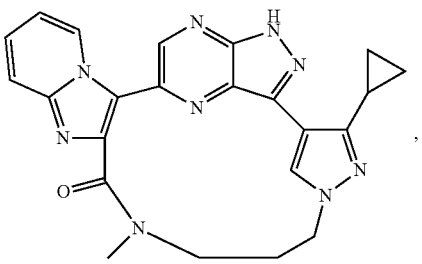
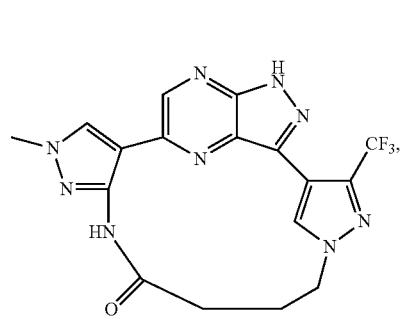

227
-continued
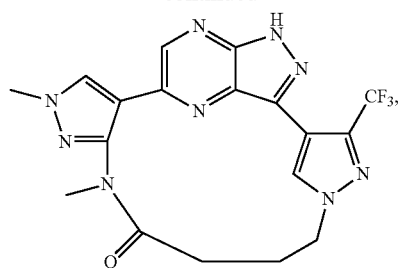
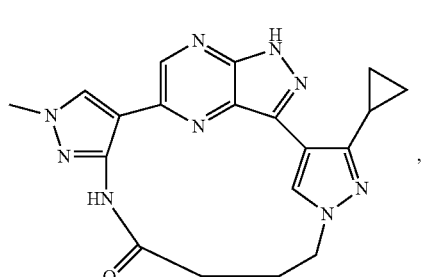,
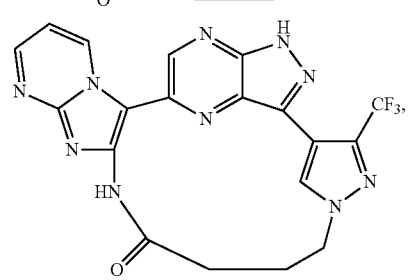
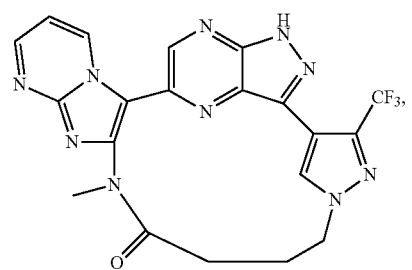
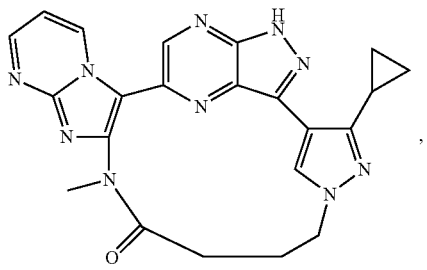,
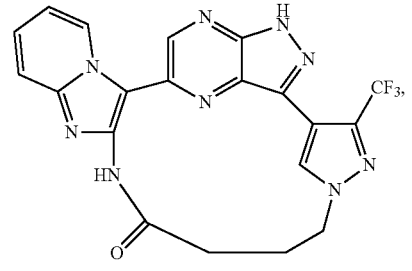
228
-continued
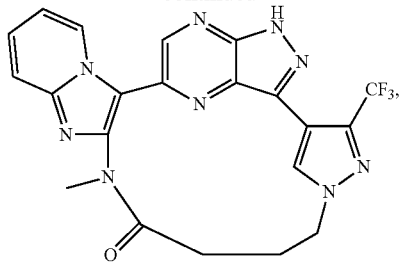
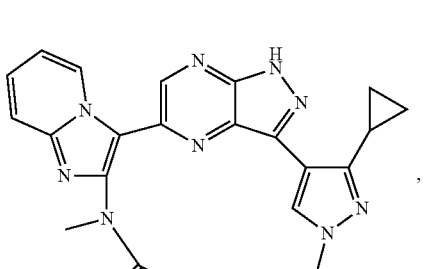,
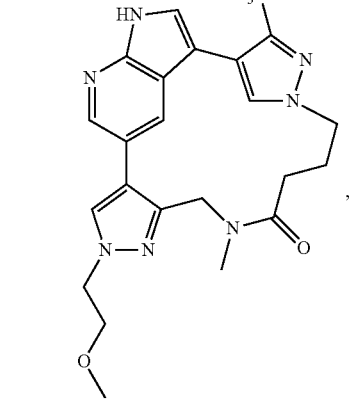,
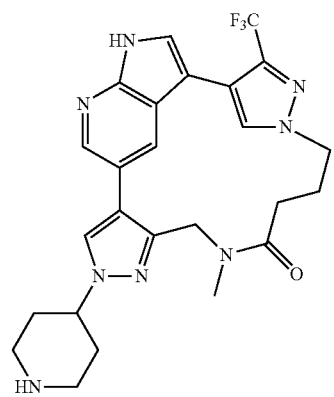, 229
-continued
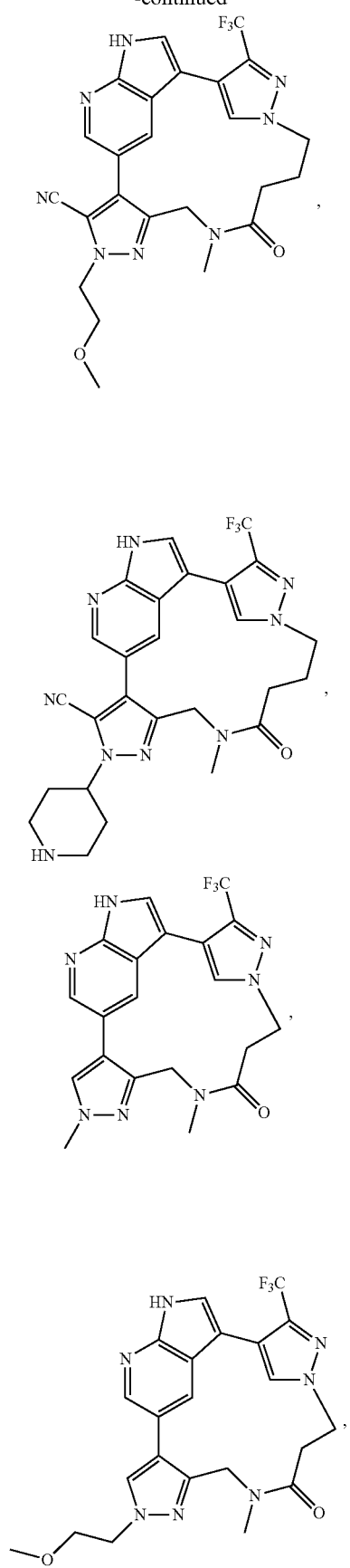
230
-continued
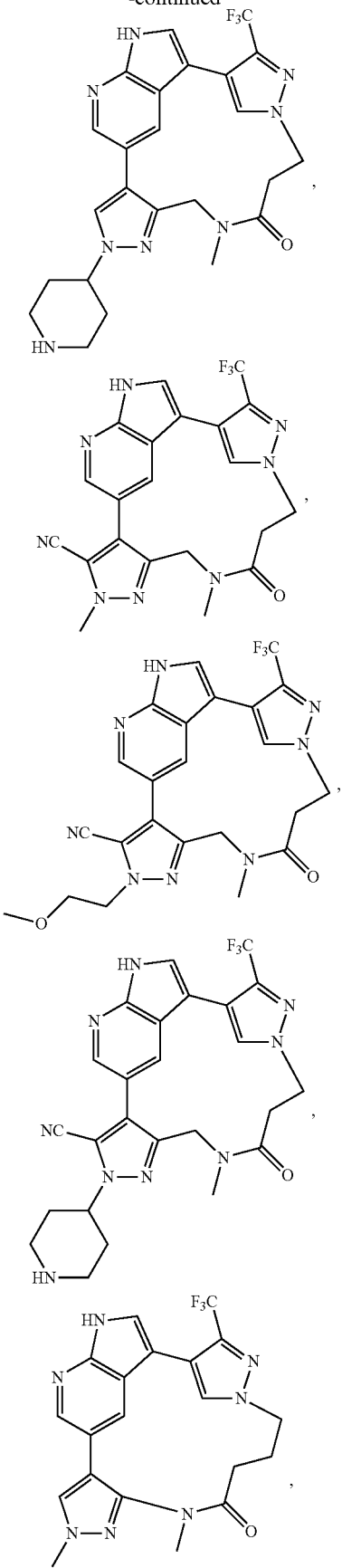

231

-continued

232

-continued

233
-continued
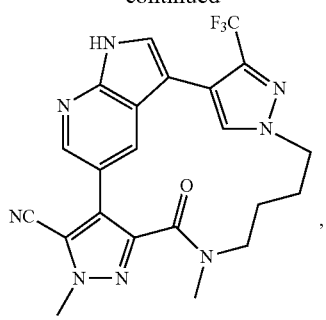
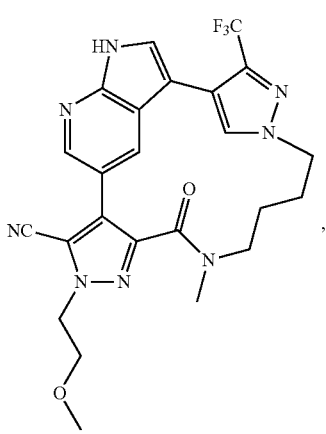
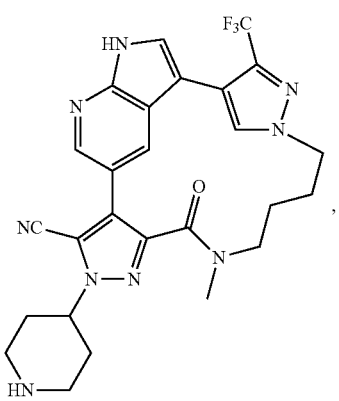
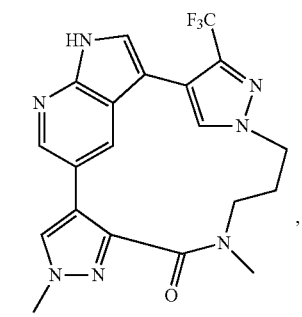
234
-continued
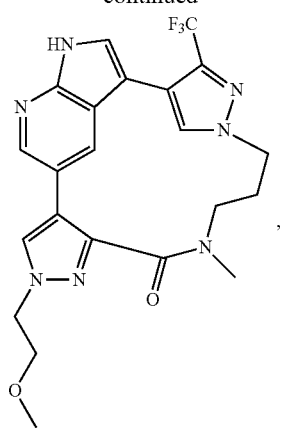
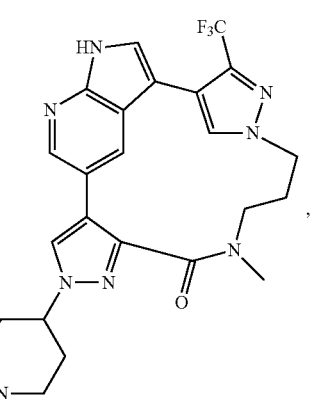
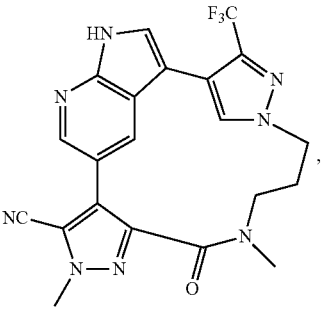
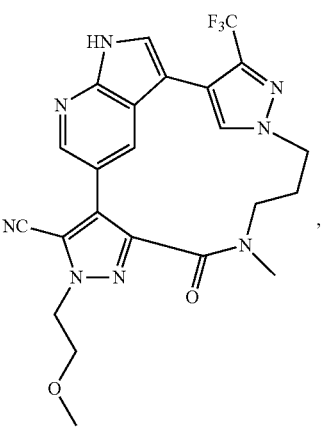

-continued

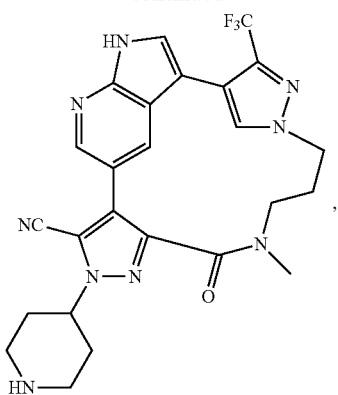

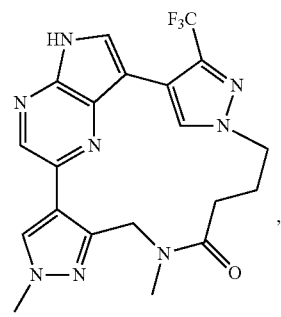

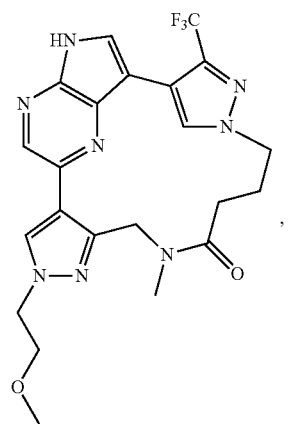

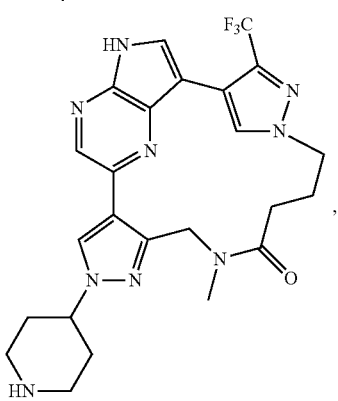

-continued

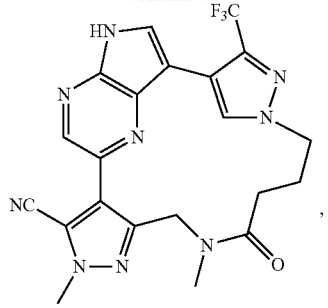

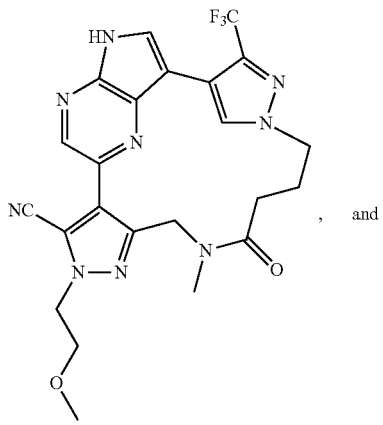, and

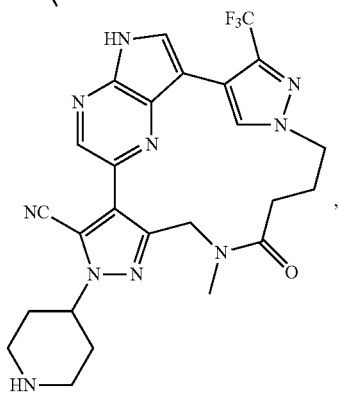

or a pharmaceutically acceptable salt or stereoisomer thereof.

30. A pharmaceutical composition, comprising a therapeutically effective amount of the compound of claim 1, or pharmaceutically acceptable salt or stereoisomer thereof, and a pharmaceutically acceptable carrier.

31. A method of treating a disease or disorder mediated by aberrant DYRK, TRK, TLK, and/or RET activity, comprising administering to a subject in need thereof a therapeutically effective amount of the compound of claim 1, or a pharmaceutically acceptable salt or stereoisomer thereof.

32. The method of claim 31, wherein the disease or disorder is selected from the group consisting of cancer, autoimmune diseases, neurodegenerative disorders, and genetic disorders.

33. The method of claim 32, wherein the disease or disorder is Parkinson's disease, Alzheimer's disease, Huntington's disease, Pick's syndrome, Down syndrome, diabetes mellitus, leukemia, brain cancer or glioma.

* * * * *

UNITED STATES PATENT AND TRADEMARK OFFICE
CERTIFICATE OF CORRECTION

| | | |
|---|---|---|
| PATENT NO. | : 12,157,741 B2 | Page 1 of 1 |
| APPLICATION NO. | : 17/293292 | |
| DATED | : December 3, 2024 | |
| INVENTOR(S) | : Nathanael S. Gray et al. | |

It is certified that error appears in the above-identified patent and that said Letters Patent is hereby corrected as shown below:

In the Claims

In Column 188, Lines 50-60:
Delete the following structure:

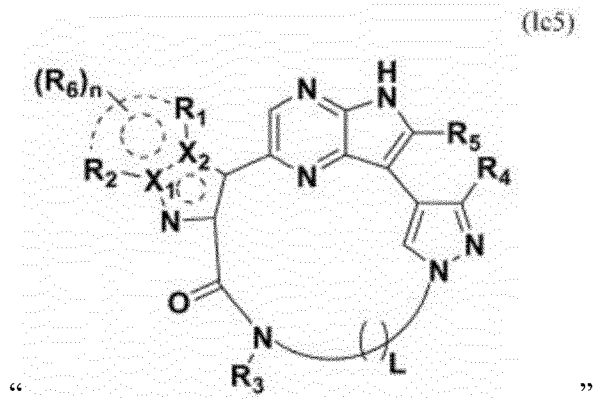

" "

Replace with the following structure:

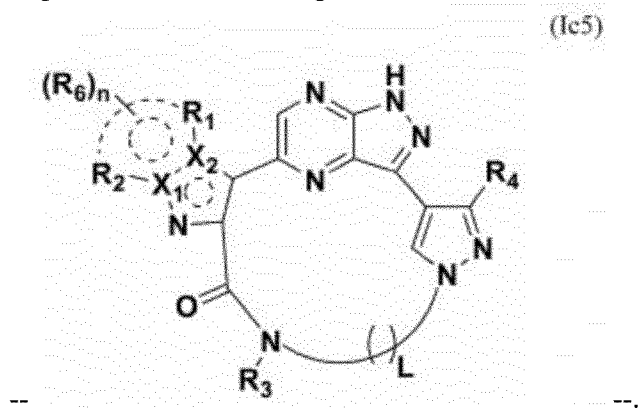

-- --.

Signed and Sealed this
Thirty-first Day of December, 2024

Derrick Brent
*Acting Director of the United States Patent and Trademark Office*